US009011860B2

(12) United States Patent
Dudler et al.

(10) Patent No.: US 9,011,860 B2
(45) Date of Patent: Apr. 21, 2015

(54) COMPOSITIONS FOR INHIBITING MASP-2 DEPENDENT COMPLEMENT ACTIVATION

(75) Inventors: Thomas Dudler, Bellevue, WA (US); Wayne R. Gombotz, Kenmore, WA (US); James Brian Parent, Bainbridge Island, WA (US); Clark E. Tedford, Poulsbo, WA (US); Anita Kavlie, Oslo (NO); Urs Beat Hagemann, Oslo (NO); Herald Reiersen, Sofiemyr (NO); Sergej Kiprijanov, Oslo (NO)

(73) Assignee: Omeros Corporation, Seattle, WA (US)

( * ) Notice: Subject to any disclaimer, the term of this patent is extended or adjusted under 35 U.S.C. 154(b) by 0 days.

(21) Appl. No.: 13/464,334

(22) Filed: May 4, 2012

(65) Prior Publication Data

US 2012/0282263 A1 Nov. 8, 2012

Related U.S. Application Data

(60) Provisional application No. 61/482,567, filed on May 4, 2011.

(51) Int. Cl.

| | |
|---|---|
| ***A61K 39/395*** | (2006.01) |
| ***C07K 16/40*** | (2006.01) |
| ***C12N 9/64*** | (2006.01) |
| *A61K 39/00* | (2006.01) |

(52) U.S. Cl.

CPC ........... *C07K 16/40* (2013.01); *A61K 2039/505* (2013.01); *C07K 2317/21* (2013.01); *C07K 2317/33* (2013.01); *C07K 2317/53* (2013.01); *C07K 2317/565* (2013.01); *C07K 2317/622* (2013.01); *C07K 2317/76* (2013.01); *C07K 2317/92* (2013.01); *C12N 9/6424* (2013.01); *C12Y 304/21104* (2013.01)

(58) Field of Classification Search

None

See application file for complete search history.

(56) References Cited

U.S. PATENT DOCUMENTS

| | | | |
|---|---|---|---|
| 4,816,567 A | 3/1989 | Cabilly et al. | |
| 5,211,657 A | 5/1993 | Yamada et al. | |
| 5,552,157 A | 9/1996 | Yagi et al. | |
| 5,565,213 A | 10/1996 | Nakamori et al. | |
| 5,567,434 A | 10/1996 | Szoka, Jr. | |
| 5,738,868 A | 4/1998 | Shinkarenko | |
| 5,741,516 A | 4/1998 | Webb et al. | |
| 5,795,587 A | 8/1998 | Gao et al. | |
| 5,859,205 A * | 1/1999 | Adair et al. | 530/387.3 |
| 6,420,432 B2 | 7/2002 | Demopulos et al. | |
| 6,645,168 B2 | 11/2003 | Demopulos et al. | |
| 6,969,601 B2 | 11/2005 | Jensenius et al. | |
| 7,060,267 B2 | 6/2006 | Jensenius et al. | |
| 7,083,786 B2 | 8/2006 | Jensenius et al. | |
| 7,396,915 B2 | 7/2008 | Hosokawa et al. | |
| 7,812,136 B2 | 10/2010 | Buettner et al. | |
| 7,919,094 B2 | 4/2011 | Schwaeble et al. | |
| 8,551,790 B2 | 10/2013 | Jensenius et al. | |
| 2002/0019369 A1 | 2/2002 | Li et al. | |
| 2002/0082209 A1 | 6/2002 | Jensenius et al. | |
| 2002/0098189 A1* | 7/2002 | Young et al. | 424/147.1 |
| 2003/0217373 A1* | 11/2003 | Green et al. | 800/6 |
| 2004/0038297 A1 | 2/2004 | Jensenius et al. | |
| 2006/0002937 A1 | 1/2006 | Schwaeble et al. | |
| 2007/0009528 A1 | 1/2007 | Larsen et al. | |
| 2007/0031420 A1 | 2/2007 | Jensenius et al. | |
| 2007/0172483 A1 | 7/2007 | Schwaeble et al. | |
| 2011/0020337 A1 | 1/2011 | Schwaeble et al. | |
| 2011/0091450 A1 | 4/2011 | Schwaeble et al. | |
| 2011/0311549 A1 | 12/2011 | Schwaeble et al. | |
| 2014/0134641 A1 | 5/2014 | Jensenius et al. | |

FOREIGN PATENT DOCUMENTS

| | | |
|---|---|---|
| JP | 07238100 | 9/1995 |
| WO | WO 00/35483 | 6/2000 |
| WO | WO 01/07067 A2 | 2/2001 |
| WO | WO 0206460 A2 * | 1/2002 |
| WO | WO 03/063799 | 8/2003 |
| WO | WO 2004/009664 | 1/2004 |
| WO | WO 2004106384 A1 * | 12/2004 |
| WO | WO 2005/120222 A2 | 12/2005 |
| WO | WO 2005/123128 A2 | 12/2005 |
| WO | WO 2005/123776 A1 | 12/2005 |
| WO | WO 2007/117996 | 10/2007 |
| WO | WO 2010/032060 A1 | 3/2010 |
| WO | WO 2010/054007 A1 | 5/2010 |

OTHER PUBLICATIONS

Vajdos et al. (J Mol Biol. Jul. 5, 2002;320(2):415-28).*

Colman (Research in Immunology, 145:33-36, 1994).*

Rudikoff et al. (Proc. Natl. Acad. Sci. USA, 79: 1979-1983, Mar. 1982).*

Eduardo Padlan, Mol Immunol. Feb. 1994;31(3):169-217.*

Portolano et al., J Immunol. Feb. 1, 1993;150(3):880-7.*

Harboe et al. (Clin Exp Immunol. Jun. 2006;144(3):512-20).*

Duncan et al. (Molecular Immunology, Aug. 2010, vol. 47, No. 13, Supp. 4, pp. 2265).*

Chen, C., et al., "Stoichiometry of Complexes between Mannose-binding Protein and its Associated Serine Proteases," *The Journal of Biological Chemistry* 276(28):25894-25902 (2001).

Lynch, N.J., et al., "L-Ficolin Specifically Binds to Lipoteichoic Acid, a Cell Wall Constituent of Gram-Positive Bacteria, and Activates the Lectin Pathway of Complement," *The Journal of Immunology* 172:1198-1202 (2004).

Stover, C.M., et al., "Two Constituents of the Initation Complex of the Mannan-Binding Lectin Activation Pathway of Complement are Encoded by a Single Structural Gene," *The Journal of Immunology* 162:3481-3490 (1999).

(Continued)

*Primary Examiner* — Zachary Skelding

(74) *Attorney, Agent, or Firm* — Tineka J. Quinton; Marcia S. Kelbon

(57) ABSTRACT

The present invention relates to anti-MASP-2 inhibitory antibodies and compositions comprising such antibodies for use in inhibiting the adverse effects of MASP-2 dependent complement activation.

24 Claims, 27 Drawing Sheets

(56) References Cited

OTHER PUBLICATIONS

Stover, C.M., et al., "The Rat and Mouse Homologues of MASP-2 and MAp19, components of the Lectin Activation Pathway of Complement," *The Journal of Immunology* 163:6848-6859 (1999).
Thiel, S., et al., "A second serine protease associated with mannan-binding lectin that activates complement," *Nature* 386:506-510 (1997).
Thiel, S., et al., "Interaction of C1q and Mannan-Binding Lectin (MBL) with C1r, C1s, MBL-Associated Serine Proteases 1 and 2, and the MBL-Associated Protein MAp19," *The Journal of Immunology* 165:878-887 (2000).
Vorup-Jensen, T., et al., "Distinct Pathways of Mannan-Binding Lectin (MBL)- and C1 Complex Autoactivation Revealed by Reconstitution of MBL with Recombinant MBL-Associated Serine Protease-2," *The Journal of Immunology* 165:2093-2100 (2000).
Thielens, N.M., et al,, "Interaction Properties of Human Mannan Binding Lectin (MBL)-Associated Serine Proteases-1 and -2, MBL-Associated Protein 19, and MBL," *The Journal of Immunology* 166:5068-5077 (2001).
Lachmann, P.J., et al,, "Initiation of Complement Activation," *Springer Semin Immunoptathol* 7:143-162 (1984).
Riedemarm, N.C., et al., "Complement in Ischemia Reperfusion Injury," *American Journal of Pathology* 162(2):363-367 (2003).
Matsushita, M. et al., "Activation of the Lectin Complement Pathway by H-Ficolin (Hakata Antigen)," *The Journal of Immunology* 168:3502-3506 (2002).
Stengaard-Pedersen, K., et al., "Inherited Deficiency of Mannan-Binding Lectin-Associated Serine Protease 2," *The New England Journal of Medicine* 349(6):554-560 (2003).
Takahashi, M., et al,, "A truncated form of mannose-binding lectin-associated serine protease (MASP)-2 expressed by alternative polyadenylation is a component of the lectin complement pathway," *International Immunology* 11(5):859-863 (1999).
Ambrus, G., et al., "Natural Substrates and Inhibitors of Mannan-Binding Lectin-Associated Serine Protease-1 and -2: A Study on Recombinant Catalytic Fragments," *The Journal of Immunology* 170:1374-1382 (2003).
Moller-Kristensen, M., et al., "Levels of mannan binding lectin-associated serine protease-2 in healthy individuals," *Journal of Immunological Methods* 282:159-167 (2003).
Dahl, M,R., et al., "MASP-3 and Its Association with Distinct Complexes of the Mannan-Binding Lectin Complement Activation Pathway," *Immunity* 15:127-135 (2001).
Liszewski, M.K., et al., "The Complement System," in *Fundamental Immunology, Third Edition*, Edited by William E. Paul, Raven Press, Chapter 26, pp. 917-939 (1993).
Collard, C.D., et al, "Complement Activation after Oxidative Stress: Role of the Lectin Complement Pathway," *American Journal of Pathology* 156(5):1549-1556 (2000).
Lu, J., et al., "Collectins and ficolins: sugar pattern recognition molecules of the mammalian innate immune system," *Biochimica et Biophysica Acta* 1572:387-400 (2002).
Jordan, J.E., et al., "Inhibition of Mannose-Binding Lectin Reduces Postischemic Myocardial Reperfusion Injury," *Circulation* 104:1413-1411 (2001).
Maynard, Y., et al., "Characterization of a Mannose and *N*-Acetylglucosamine-specific: Lectin Present in Rat Hepatocytes," *The Journal of Biological Chemistry* 257(7):3788-3794 (1982).
Lee, R.T., et al., "Multivalent Ligand Binding by Serum Mannose-Binding Protein," *Archives of Biochemistry and Biophysics* 299(1):129-136 (1992).
Collard, C.D., et al., "Endothelial Oxidative Stress Activates the Lectin Complement Pathway," *American Journal of Pathology* 159(3);1045-1054 (2001).
Ji, Y.H., et al., "Activation of the C4 and C3 Components of Complement by a Proteinase in Serum Bactericidal Factor, Ra Reactive Factor," *The Journal of Immunology* 150(2):571-578 (1993).
Kilpatrick, D.C., "Mannan-binding lectin: clinical significance and applications," *Biochimica et Biophysica Acta* 1572:401-413 (2002).
Weis, W.I., et al., "Structure of a C-type mannose-binding protein complexed with an oligosaccharide," *Nature* 360:127-134 (1992).
Kalli, K.R., et al., "Therapeutic uses of recombinant complement protein inhibitors," *Springer Seminol Immunopathology* 15:417-431 (1994).
Pangburn, M.K., et al., "Formation of the Initial C3 Convertase of the Alternative Complement Pathway: Acquisition of C3b-like Activities by Spontaneous Hydrolysis of the Putative Thioester in Native C3," *J. Exp. Med.* 154:856-867 (1981).
Wallis, R., et al., "Interaction of Mannose-binding Protein with Associated Serine Proteases: Effects of Naturally Occurring Mutations," *The Journal of Biolocical Chemistry* 275(40):30962-30969 (2000).
Sim, R.B., "Innate Immunity," *Biochemical Society Transactions* 28(5):545-550 (2000).
Clackson, T., et al., "Making antibody fragments using phage display libraries," *Nature* 352:624-628 (1991).
Makino, K., et al., "A Microcapsule Self-Regulating Delivery System for Insulin," *Journal of Controlled Release* 12:235-239 (1990).
Lee, V.H.L., "Protease inhibitors and Penetration Enhancers as Approaches to Modify Peptide Absorption," *Journal of Controlled Release* 13:213-223 (1990).
Hori, R., et al., "Enhanced Bioavailability of Subcutaneously injected Insulin Coadministered with Collagen in Rats and Humans," *Pharmaceutical Research* 6(9):813-816 (1989).
Flugelman, M.Y., et al., "Low Level In Vivo Gene Transfer Into the Arterial Wall Through a Perforated Balloon Catheter," *Circulation* 85:1110-1117 (1992).
De Boer, A.G., et al., "Rectal Absorption Enhancement of Peptide Drugs," *Journal of Controlled Release* 13:241-246 (1990).
Fuertges, R., et al., "The Clinical Efficacy of Poly(ethylene glycol)-Modified Proteins," *The Journal of Controlled Release* 11:139-148 (1990).
Schwaeble, W., et al., "The Mannan-Binding Lectin-Associated Serine Proteases (MASPs) and MAp19: Four Components of the Lectin Pathway Activation Complex Encoded by Two Genes," *Immunobiology* 205:455-466 (2002).
Rosenblatt, J., et al., "The Effect of Collagen Fiber Size Distribution on the Release Rate of Proteins from Collagen Matrices by Diffusion," *Journal of Controlled Release* 9:195-203 (1989).
Lee, V.H.L., "Enzymatic Barriers to Peptide and Protein Absorption," *CRC Critical Reviews in Therapeutic Drug Carrier Systems* 5(2):69-97 (1988).
Yamakawa, I., et al., "Sustained Release of Insulin by Double-Layered Implant Using Poly(D,L-Lactic Acid)," *Journal of Pharmaceutical Sciences* 79(6):505-509 (1990).
Takakura, Y. et al., "Control of Pharmaceutical Properties of Soybean Trypsin inhibitor by Conjugation with Dextran I: Synthsis and Characterization," *Journal of Pharmaceutical Sciences* 78(2):117-121 (1989).
Takakura, Y., et al., "Control of Pharmaceutical Properties of Soybean Trypsin Inhibitor by Conjugation with Dextran II: Biopharmaceutical and Pharmacological Properties," *Journal of Pharmaceutical Sciences* 78(3):219-222 (1989).
Ito, Y., et al., "An Insulin-releasing System that is Responisve to Glucose," *Journal of Controlled Release* 10:195-203 (1989).
Matsushita, M., et al., "Activation of the Classical Complement Pathway by Mannose-binding Protein in Association with a Novel C1s-like Serine Protease," *J. Exp. Med.* 176:1497-1502 (1992).
Morgan, B.R, et al., "Clinical complementology: recent progress and future trends," *European Journal of Clinical Investigation* 24:219-228 (1994).
Holmskov, U., et al., "Collectins and Ficolins: Humoral Lectins of the Innate Immune Defense," *Annu. Rev. Immunol.* 21:547-578 (2003).
Ikeda, K., et al., "Serum Lectin with Known Structure Activates Complement through the Classical Pathway," *The Journal of Biological Chemistry* 262(16):7451-7454 (1987).
Bae, Y.H., et al., "Insulin Permeation Through Thermo-Sensitive Hydrogels," *Journal of Controlled Release* 9:271-279 (1989).
Asano, M. et al., "In Vivo Characteristics of Low Molecular Weight Copoly(L-Lactic Acid/Glycolic Acid) Formulations with Controlled Release of Lutenizing Hormone-Releasing Hormone Agonist," *Journal of Controlled Release* 9:111-122 (1989).

(56) References Cited

OTHER PUBLICATIONS

Köhler, G., et al., "Continuous cultures of fused cells secreting antibody of predefined specificity," *Nature* 256:495-497 (1975).
Kuhlman, M., et al., "The Human Mannose-Binding Protein Functions as an Opsonin," *The Journal of Experimental Medicine* 169:1733-1745 (1989).
Marks, J.D., et al., "By-passing Immunization: Human Antibodies from V-gene Libraries Displayed on Phage," *J. Mol. Biol.* 222:581-597 (1991).
Matsushita, M., et al., "A Novel Human Serum Lectin with Collagen- and :Fibrinogen-like Domains that Functions as an Opsonin," *The Journal of Biological Chemistry* 271(5):2448-2454 (1996).
Matshushita, M., et al., "The Role of Ficolins in Innate Immunity," *Immunobiology* 205:490-497 (2002).
Takahashi, M., et al., "Essential Role of Mannose-Binding Lectin Associated Serine Protease-1 in Activation of the Complement Factor D," *Journal of Experimental Medicine* 207(1):29-37 (2010).
Labrijn, A., et al., "Therapeutic IgG4 Antibodies Engage in Fab-Arm Exchange with Endogenous Human IgG4 in vivo," *Nat. Biotechnol.* 27(8):767-771 (2009).
Teh, C., et al., "M-ficolin is Express on Monocytes and is a Lectin Binding N-acetyl-D-glucosamine and Mediates Monocyte Adhesion and Phagocytosis of *Escherichia coli," Immunology* 101(2):225-232 (2000).
Hansen, S., et al., "Collectin 11 (CL-K1) is a MASP—⅓-Associated Plasma Collectin with Microbial-Binding Activity," *J. Immunology* 185:6096-6104 (2010).
Jack, D.L., et al., "Mannose-Binding Lectin Enhances Phagocytosis and Killing of Neisseria Meningtidis by Human Macrophages," *J. Leukoc. Biol.* 77(3):328-336 (2005).
Aoyagi, Y., et al., Role of L-Ficolin/Mannose-Binding Lectin-Associated Serine Protease Complexes in the Opsonophagocytosis of Type III Group B Streptococci, *J. Immunology* 174(1):418-425 (2005).
Schwaeble, W., et al., "Does Properdin Crosslink the Cellular and the Humoral Immune Response," *Immunol. Today* 20(1):17-21 (1999).
Chothia, C., et al., "Canonical Structures for the Hypervariable Regions of Immunoglobulins," *J. Mol. Biol.* 196(4):901-917 (1987).
Ruiz, M., et al., "IMGT, the International ImMunoGeneTics Database," *Nucleic Acids Res.* 28(1):219-221 (2000).
Garavelli, J., "The RESID Database of Protein Structure Modifications: 2000 Update," *Nucleic Acids Res.* 28(1):209-211 (2000).
Graham, F.L., "Characteristics of a Human Cell Line Transformed by DNA from Human Adenovirus Type 5," *J. Gen. Virol.* 36(1):59-74 (1977).
Urlaub, G., et al., "Isolation of Chinese Hamster Cell Mutants Deficient in Dihydrofolate Reductase Activity," *Proc. Natl. Acad Sci. USA* 77(7):4216-4220 (1980).
Mather, J.P., "Establishment and Characterization of Two Distinct Mouse Testicular Epithelial Cell Lines," *Biol. Reprod.* 23(1):243-252 (1980).
Mather, J.P., et al., "Culture of Testicular Cells in Hormone-Supplemented Serum-Free Medium," *Ann. N.Y. Acad. Sci.* 383:44-68 (1982).
Logan, J., et al., "Adenovirus Tripartite Leader Sequence Enhances Translation of mRNAs Late After Infection," *Proc. Natl. Acad. Sci. USA* 81(12):3655-3659 (1984).
Kaufman, R.J., et al., "Improved Vectors for Stable Expression of Foreign Genes in Mammalian Cells by Use of the Untranslated Leader Sequence from EMC Virus," *Nucleic Acids Res.* 19(16):4485-4490 (1991).
Kaufman, R.J., "Selection and Coamplification of Heterologous Genes in Mammalian Cells," *Methods Enzymol.* 185:537-566 (1990).
Maniatis, A., et al., "Intermediate-Dose Melphalan for Refractory Myeloma," *Blood* 74:1177 (1989).
Peterson, S.V., et al., "Generation of antibodies Towards MASP-1 and MASP-2 Using Bacterial Expression Systems," *Molecular Immunology* 35(6-7):409 (1998).
Schwaeble, W., et al., "The mannan-binding lectin-associated serine proteases (MASPs) and MAp19: Four components of the lectin pathway activation complex encoded by two genes," *Immunobiol.* 205:455-466 (2002).
Lonberg, N., et al., "Antigen-specific human antibodies from mice comprising four distinct genetic modifications," *Nature* 368:856-859 (1994).
Schwaeble, W.J., et al., "Targeting of mannan-binding lectin-associated serine protease-2 confers protection from myocardial and gastrointestinal ischemia/reperfusion injury," *PNAS* 108(18):7523-7528 (2011).
Winter, G., et al., "Making antibodies by phage display technology," *Annu. Rev. Immunol.* 12:433-455 (1994).
McMullen, Meghan, E., et al., "Mannose-binding lectin binds IgM to activate the lectin complement pathway in vitro and in vivo," *Immunobiology* 2011:759-766 (2006).

* cited by examiner

```
                          (1) 1         10        20        30        40        51
BM 17N16md17N9    (1) QVQLQQSGPGLVKPSQTLSLTCAISGDSVSSTSAAWNWIRQSPSRGLEWLG
OD 17N16mc scFv   (1) QVQLQQSGPGLVKPSQTLSLTCAISGDSVSSTSAAWNWIRQSPSRGLEWLG
------------------------------------------------------------------- Section 2
                          (52) 52       60        70        80        90       102
BM 17N16md17N9   (52) RTYYRSKWYNDYAVSVKSRITINPDTSKNQFSLQLNSVTPEDTAVYYCARD
OD 17N16mc scFv  (52) RTYYRSKWYNDYAVSVKSRITINPDTSKNQFSLQLNSVTPEDTAVYYCARD
------------------------------------------------------------------- Section 3
                          (103) 103     110       120       130       140       153
BM 17N16md17N9  (103) PFGVPFSIWGQGTMVTVSSKLSGSASAPKLEEGEFSKARVSYELIQPPSVS
OD 17N16mc scFv (103) PFGVPFSIWGQGTMVTVSSKLSGSASAPKLEEGEFSKARVSYVLTQPPSVS
------------------------------------------------------------------- Section 4
                          (154) 154     160       170       180       190       204
BM 17N16md17N9  (154) VAPGQTATITCSGDNIGKKRVHWYQQKPGQAPVLVIYDDSDRPSGIPERFS
OD 17N16mc scFv (154) VAPGQTARITCGGNNIGSKRVHWYQQKPGQAPVLVIYDDSDRPSGIPERFS
------------------------------------------------------------------- Section 5
                          (205) 205     210       220       230       240       255
BM 17N16md17N9  (205) GSNSGNTATLTIRGEASSEADYYCQVWDIATDRVVFGGGTKLTVLAAAGS
OD 17N16mc scFv (205) GSNSGNTATLTIRVKASSEADYYCQVWDTTTDRVVFGGGTKLTVLAAAGS
------------------------------------------------------------------- Section 6
                          (256) 256     273
BM 17N16md17N9  (256) EQKLISEEDLNSHHHHH
OD 17N16mc scFv (256) EQKLISEEDLNSHHHHH
```

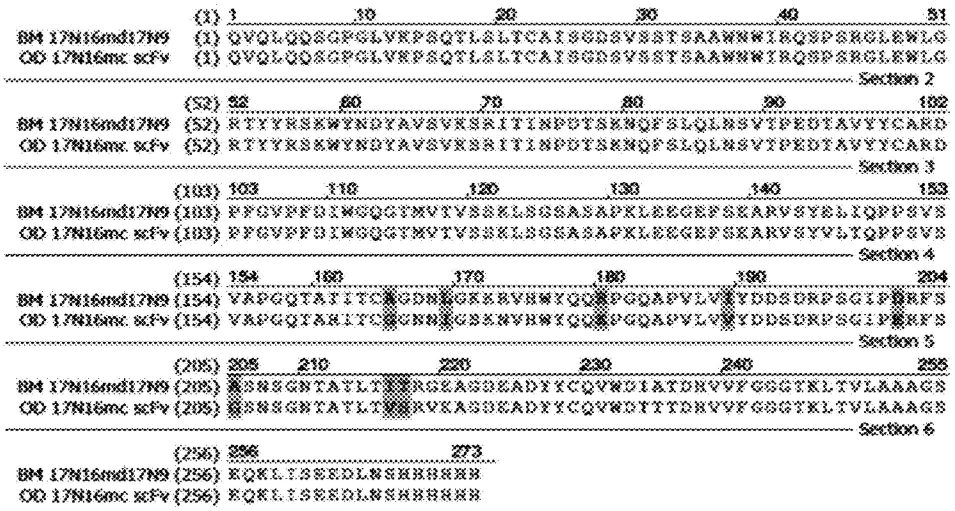

*Fig. 8.*

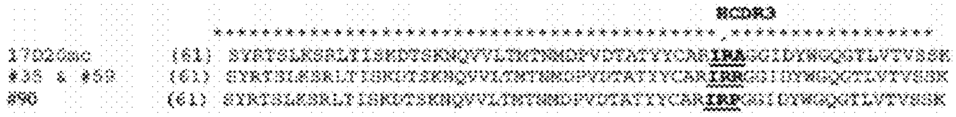

*Fig. 9.*

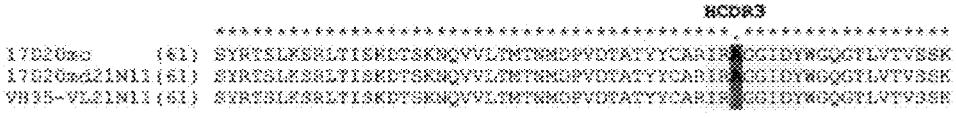

*Fig. 10A.*

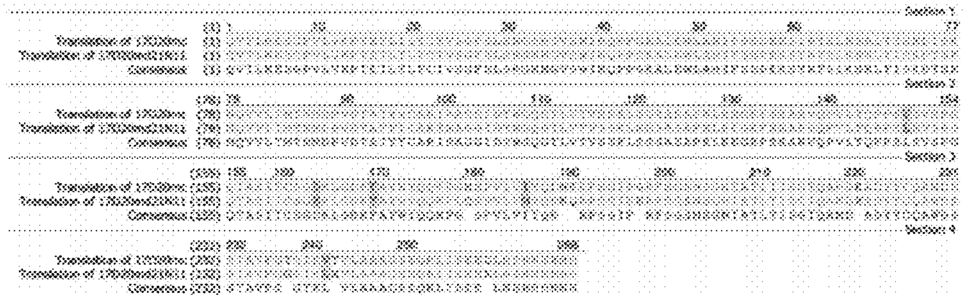

*Fig. 10B.*

COMPOSITIONS FOR INHIBITING MASP-2 DEPENDENT COMPLEMENT ACTIVATION

CROSS-REFERENCE TO RELATED APPLICATION

This application claims the benefit of U.S. Provisional Application No. 61/482,567 filed May 4, 2011, which is incorporated herein by reference in its entirety.

FIELD OF THE INVENTION

The present invention relates to anti-MASP-2 inhibitory antibodies and compositions comprising such antibodies for use in inhibiting the adverse effects of MASP-2 dependent complement activation.

STATEMENT REGARDING SEQUENCE LISTING

The sequence listing associated with this application is provided in text format in lieu of a paper copy and is hereby incorporated by reference into the specification. The name of the text file containing the sequence listing is MP_1__0115_US2_SequenceListingasFiled.20120504 ST25. The text file is 158 KB, was created on May 4, 2012; and is being submitted via EFS-Web with the filing of the specification.

BACKGROUND

The complement system provides an early acting mechanism to initiate, amplify and orchestrate the immune response to microbial infection and other acute insults (M. K. Liszewski and J. P. Atkinson, 1993, in *Fundamental Immunology*, Third Edition, edited by W. E. Paul, Raven Press, Ltd., New York) in humans and other vertebrates. While complement activation provides a valuable first-line defense against potential pathogens, the activities of complement that promote a protective immune response can also represent a potential threat to the host (K. R. Kalli, et al., *Springer Semin. Immunopathol.* 15:417-431, 1994; B. P. Morgan, *Eur. J. Clinical Investig.* 24:219-228, 1994). For example, the C3 and C5 proteolytic products recruit and activate neutrophils. While indispensable for host defense, activated neutrophils are indiscriminate in their release of destructive enzymes and may cause organ damage. In addition, complement activation may cause the deposition of lytic complement components on nearby host cells as well as on microbial targets, resulting in host cell lysis.

The complement system has also been implicated in the pathogenesis of numerous acute and chronic disease states, including: myocardial infarction, stroke, acute respiratory distress syndrome (ARDS), reperfusion injury, septic shock, capillary leakage following thermal burns, post cardiopulmonary bypass inflammation, transplant rejection, rheumatoid arthritis, multiple sclerosis, myasthenia gravis, and Alzheimer's disease. In almost all of these conditions, complement is not the cause but is one of several factors involved in pathogenesis. Nevertheless, complement activation may be a major pathological mechanism and represents an effective point for clinical control in many of these disease states.

The growing recognition of the importance of complement-mediated tissue injury in a variety of disease states underscores the need for effective complement inhibitory drugs. To date, Eculizumab (Soliris®), an antibody against C5, is the only complement-targeting drug that has been approved for human use. Yet, C5 is one of several effector molecules located "downstream" in the complement system, and blockade of C5 does not inhibit activation of the complement system. Therefore, an inhibitor of the initiation steps of complement activation would have significant advantages over a "downstream" complement inhibitor.

Currently, it is widely accepted that the complement system can be activated through three distinct pathways: the classical pathway, the lectin pathway, and the alternative pathway. The classical pathway is usually triggered by a complex composed of host antibodies bound to a foreign particle (i.e., an antigen) and thus requires prior exposure to an antigen for the generation of a specific antibody response. Since activation of the classical pathway depends on a prior adaptive immune response by the host, the classical pathway is part of the acquired immune system. In contrast, both the lectin and alternative pathways are independent of adaptive immunity and are part of the innate immune system.

The activation of the complement system results in the sequential activation of serine protease zymogens. The first step in activation of the classical pathway is the binding of a specific recognition molecule, C1q, to antigen-bound IgG and IgM complexes. C1q is associated with the C1r and C1s serine protease proenzymes as a complex called C1. Upon binding of C1q to an immune complex, autoproteolytic cleavage of the Arg-Ile site of C1r is followed by C1r-mediated cleavage and activation of C1s, which thereby acquires the ability to cleave C4 and C2. C4 is cleaved into two fragments, designated C4a and C4b, and, similarly, C2 is cleaved into C2a and C2b. C4b fragments are able to form covalent bonds with adjacent hydroxyl or amino groups and generate the C3 convertase (C4b2a) through noncovalent interaction with the C2a fragment of activated C2. C3 convertase (C4b2a) activates C3 by proteolytic cleavage into C3a and C3b subcomponents leading to generation of the C5 convertase (C4b2a3b), which, by cleaving C5 leads to the formation of the membrane attack complex (C5b combined with C6, C7, C8 and C9, also referred to as "MAC") that can disrupt cellular membranes leading to cell lysis. The activated forms of C3 and C4 (C3b and C4b) are covalently deposited on the foreign target surfaces, which are recognized by complement receptors on multiple phagocytes.

Independently, the first step in activation of the complement system through the lectin pathway is also the binding of specific recognition molecules, which is followed by the activation of associated serine protease proenzymes. However, rather than the binding of immune complexes by C1q, the recognition molecules in the lectin pathway comprise a group of carbohydrate-binding proteins (mannan-binding lectin (MBL), H-ficolin, M-ficolin, L-ficolin and C-type lectin CL-11), collectively referred to as lectins. See J. Lu et al., *Biochim. Biophys. Acta* 1572:387-400, 2002; Holmskov et al., *Annu. Rev. Immunol.* 21:547-578 (2003); Teh et al., *Immunology* 101:225-232 (2000)). See also J. Luet et al., *Biochim Biophys Acta* 1572:387-400 (2002); Holmskov et al, *Annu Rev Immunol* 21:547-578 (2003); Teh et al., *Immunology* 101:225-232 (2000); Hansen S. et al., *J. Immunol.* 185(10): 6096-6104 (2010).

Ikeda et al. first demonstrated that, like C1q, MBL could activate the complement system upon binding to yeast mannan-coated erythrocytes in a C4-dependent manner (Ikeda et al., *J. Biol. Chem.* 262:7 451-7454, 1987). MBL, a member of the collectin protein family, is a calcium-dependent lectin that binds carbohydrates with 3- and 4-hydroxy groups oriented in the equatorial plane of the pyranose ring. Prominent ligands for MBL are thus D-mannose and N-acetyl-D-glucosamine, while carbohydrates not fitting this steric requirement have undetectable affinity for MBL (Weis, W. I., et al., *Nature*

360:127-134, 1992). The interaction between MBL and monovalent sugars is extremely weak, with dissociation constants typically in the single-digit millimolar range. MBL achieves tight, specific binding to glycan ligands by avidity, i.e., by interacting simultaneously with multiple monosaccharide residues located in close proximity to each other (Lee, R. T., et al., *Archiv. Biochem. Biophys.* 299:129-136, 1992). MBL recognizes the carbohydrate patterns that commonly decorate microorganisms such as bacteria, yeast, parasites and certain viruses. In contrast, MBL does not recognize D-galactose and sialic acid, the penultimate and ultimate sugars that usually decorate "mature" complex glycoconjugates present on mammalian plasma and cell surface glycoproteins. This binding specificity is thought to promote recognition of "foreign" surfaces and help protect from "self-activation." However, MBL does bind with high affinity to clusters of high-mannose "precursor" glycans on N-linked glycoproteins and glycolipids sequestered in the endoplasmic reticulum and Golgi of mammalian cells (Maynard, Y., et al., *J. Biol. Chem.* 257:3788-3794, 1982). Therefore, damaged cells are potential targets for lectin pathway activation via MBL binding.

The ficolins possess a different type of lectin domain than MBL, called the fibrinogen-like domain. Ficolins bind sugar residues in a $Ca^{++}$-independent manner. In humans, three kinds of ficolins (L-ficolin, M-ficolin and H-ficolin), have been identified. The two serum ficolins, L-ficolin and H-ficolin, have in common a specificity for N-acetyl-D-glucosamine; however, H-ficolin also binds N-acetyl-D-galactosamine. The difference in sugar specificity of L-ficolin, H-ficolin, CL-11 and MBL means that the different lectins may be complementary and target different, though overlapping, glycoconjugates. This concept is supported by the recent report that, of the known lectins in the lectin pathway, only L-ficolin binds specifically to lipoteichoic acid, a cell wall glycoconjugate found on all Gram-positive bacteria (Lynch, N. J., et al., *J. Immunol.* 172:1198-1202, 2004). The collectins (i.e., MBL) and the ficolins bear no significant similarity in amino acid sequence. However, the two groups of proteins have similar domain organizations and, like C1q, assemble into oligomeric structures, which maximize the possibility of multisite binding.

The serum concentrations of MBL are highly variable in healthy populations and this is genetically controlled by the polymorphism/mutations in both the promoter and coding regions of the MBL gene. As an acute phase protein, the expression of MBL is further upregulated during inflammation. L-ficolin is present in serum at concentrations similar to those of MBL. Therefore, the L-ficolin branch of the lectin pathway is potentially comparable to the MBL arm in strength. MBL and ficolins can also function as opsonins, which allow phagocytes to target MBL- and ficolin-decorated surfaces (see Jack et al., *J Leukoc Biol.,* 77(3):328-36 (2004); Matsushita and Fujita, *Immunobiology,* 205(4-5):490-7 (2002); Aoyagi et al., *J Immunol* 174(1):418-25 (2005). This opsonization requires the interaction of these proteins with phagocyte receptors (Kuhlman, M., et al., *J. Exp. Med.* 169:1733, 1989; Matsushita, M., et al., *J. Biol. Chem.* 271:2448-54, 1996), the identity of which has not been established.

Human MBL forms a specific and high-affinity interaction through its collagen-like domain with unique C 1r/C1s-like serine proteases, termed MBL-associated serine proteases (MASPs). To date, three MASPs have been described. First, a single enzyme "MASP" was identified and characterized as the enzyme responsible for the initiation of the complement cascade (i.e., cleaving C2 and C4) (Matsushita M and Fujita T., *J Exp Med* 176(6):1497-1502 (1992), Ji, Y. H., et al., *J. Immunol.* 150:571-578, 1993). It was subsequently determined that the MASP activity was, in fact, a mixture of two proteases: MASP-1 and MASP-2 (Thiel, S., et al., *Nature* 386:506-510, 1997). However, it was demonstrated that the MBL-MASP-2 complex alone is sufficient for complement activation (Vorup-Jensen, T., et al., *J. Immunol.* 165:2093-2100, 2000). Furthermore, only MASP-2 cleaved C2 and C4 at high rates (Ambrus, G., et al., *J. Immunol.* 170:1374-1382, 2003). Therefore, MASP-2 is the protease responsible for activating C4 and C2 to generate the C3 convertase, C4b2a. This is a significant difference from the C1 complex of the classical pathway, where the coordinated action of two specific serine proteases (C1r and C1s) leads to the activation of the complement system. In addition, a third novel protease, MASP-3, has been isolated (Dahl, M. R., et al., *Immunity* 15:127-35, 2001). MASP-1 and MASP-3 are alternatively spliced products of the same gene.

MASPs share identical domain organizations with those of C1r and C1s, the enzymatic components of the C1 complex (Sim, R. B., et al., *Biochem. Soc. Trans.* 28:545, 2000). These domains include an N-terminal C1r/C1s/sea urchin VEGF/bone morphogenic protein (CUB) domain, an epidermal growth factor-like domain, a second CUB domain, a tandem of complement control protein domains, and a serine protease domain. As in the C1 proteases, activation of MASP-2 occurs through cleavage of an Arg-Ile bond adjacent to the serine protease domain, which splits the enzyme into disulfide-linked A and B chains, the latter consisting of the serine protease domain. Recently, a genetically determined deficiency of MASP-2 was described (Stengaard-Pedersen, K., et al., *New Eng. J. Med.* 349:554-560, 2003). The mutation of a single nucleotide leads to an Asp-Gly exchange in the CUB1 domain and renders MASP-2 incapable of binding to MBL.

MBL can also associated with an alternatively spliced form of MASP-2, known as MBL-associated protein of 19 kDa (MAp19) (Stover, C. M., *J. Immunol.* 162:3481-90, 1999) or small MBL-associated protein (sMAP) (Takahashi, M., et al., *Int. Immunol.* 11:859-863, 1999), which lacks the catalytic activity of MASP-2. MAp19 comprises the first two domains of MASP-2, followed by an extra sequence of four unique amino acids. The MASP 1 and MASP 2 genes are located on human chromosomes 3 and 1, respectively (Schwaeble, W., et al., *Immunobiology* 205:455-466, 2002).

Several lines of evidence suggest that there are different MBL-MASPs complexes and a large fraction of the MASPs in serum is not complexed with MBL (Thiel, S., et al., *J. Immunol.* 165:878-887, 2000). Both H- and L-ficolin bind to all MASPs and activate the lectin complement pathway, as does MBL (Dahl, M. R., et al., *Immunity* 15:127-35, 2001; Matsushita, M., et al., *J. Immunol.* 168:3502-3506, 2002). Both the lectin and classical pathways form a common C3 convertase (C4b2a) and the two pathways converge at this step.

The lectin pathway is widely thought to have a major role in host defense against infection in the naïve host. Strong evidence for the involvement of MBL in host defense comes from analysis of patients with decreased serum levels of functional MBL (Kilpatrick, D. C., *Biochim. Biophys. Acta* 1572:401-413, 2002). Such patients display susceptibility to recurrent bacterial and fungal infections. These symptoms are usually evident early in life, during an apparent window of vulnerability as maternally derived antibody titer wanes, but before a full repertoire of antibody responses develops. This syndrome often results from mutations at several sites in the collagenous portion of MBL, which interfere with proper formation of MBL oligomers. However, since MBL can function as an opsonin independent of complement, it is not known to what extent the increased susceptibility to infection is due to impaired complement activation.

In contrast to the classical and lectin pathways, no initiators of the alternative pathway have been found to fulfill the recognition functions that C1q and lectins perform in the other two pathways. Currently it is widely accepted that the alternative pathway spontaneously undergoes a low level of turnover activation, which can be readily amplified on foreign or other abnormal surfaces (bacteria, yeast, virally infected cells, or damaged tissue) that lack the proper molecular elements that keep spontaneous complement activation in check. There are four plasma proteins directly involved in the activation of the alternative pathway: C3, factors B and D, and properdin. Although there is extensive evidence implicating both the classical and alternative complement pathways in the pathogenesis of non-infectious human diseases, the role of the lectin pathway is just beginning to be evaluated. Recent studies provide evidence that activation of the lectin pathway can be responsible for complement activation and related inflammation in ischemia/reperfusion injury. Collard et al. (2000) reported that cultured endothelial cells subjected to oxidative stress bind MBL and show deposition of C3 upon exposure to human serum (Collard, C. D., et al., *Am. J. Pathol.* 156:1549-1556, 2000). In addition, treatment of human sera with blocking anti-MBL monoclonal antibodies inhibited MBL binding and complement activation. These findings were extended to a rat model of myocardial ischemia-reperfusion in which rats treated with a blocking antibody directed against rat MBL showed significantly less myocardial damage upon occlusion of a coronary artery than rats treated with a control antibody (Jordan, J. E., et al., *Circulation* 104:1413-1418, 2001). The molecular mechanism of MBL binding to the vascular endothelium after oxidative stress is unclear; a recent study suggests that activation of the lectin pathway after oxidative stress may be mediated by MBL binding to vascular endothelial cytokeratins, and not to glycoconjugates (Collard, C. D., et al., *Am. J. Pathol.* 159:1045-1054, 2001). Other studies have implicated the classical and alternative pathways in the pathogenesis of ischemia/reperfusion injury and the role of the lectin pathway in this disease remains controversial (Riedermann, N. C., et al., *Am. J. Pathol.* 162:363-367, 2003).

A recent study has shown that MASP-1 (and possibly also MASP-3) is required to convert the alternative pathway activation enzyme Factor D from its zymogen form into its enzymatically active form (See Takahashi M. et al., *J Exp Med* 207(1):29-37 (2010)). The physiological importance of this process is underlined by the absence of alternative pathway functional activity in plasma of MASP-1/3 deficient mice. Proteolytic generation of C3b from native C3 is required for the alternative pathway to function. Since the alternative pathway C3 convertase (C3bBb) contains C3b as an essential subunit, the question regarding the origin of the first C3b via the alternative pathway has presented a puzzling problem and has stimulated considerable research.

C3 belongs to a family of proteins (along with C4 and α-2 macroglobulin) that contain a rare posttranslational modification known as a thioester bond. The thioester group is composed of a glutamine whose terminal carbonyl group forms a covalent thioester linkage with the sulfhydryl group of a cysteine three amino acids away. This bond is unstable and the electrophilic glutamyl-thioester can react with nucleophilic moieties such as hydroxyl or amino groups and thus form a covalent bond with other molecules. The thioester bond is reasonably stable when sequestered within a hydrophobic pocket of intact C3. However, proteolytic cleavage of C3 to C3a and C3b results in exposure of the highly reactive thioester bond on C3b and, following nucleophilic attack by adjacent moieties comprising hydroxyl or amino groups, C3b becomes covalently linked to a target. In addition to its well-documented role in covalent attachment of C3b to complement targets, the C3 thioester is also thought to have a pivotal role in triggering the alternative pathway. According to the widely accepted "tick-over theory", the alternative pathway is initiated by the generation of a fluid-phase convertase, iC3Bb, which is formed from C3 with hydrolyzed thioester (iC3; $C3(H_2O)$) and factor B (Lachmann, P. J., et al., *Springer Semin. Immunopathol.* 7:143-162, 1984). The C3b-like $C3(H_2O)$ is generated from native C3 by a slow spontaneous hydrolysis of the internal thioester in the protein (Pangburn, M. K., et al., *J. Exp. Med.* 154:856-867, 1981). Through the activity of the C3 $(H_2O)$Bb convertase, C3b molecules are deposited on the target surface, thereby initiating the alternative pathway.

Very little is known about the initiators of activation of the alternative pathway. Activators are thought to include yeast cell walls (zymosan), many pure polysaccharides, rabbit erythrocytes, certain immunoglobulins, viruses, fungi, bacteria, animal tumor cells, parasites, and damaged cells. The only feature common to these activators is the presence of carbohydrate, but the complexity and variety of carbohydrate structures has made it difficult to establish the shared molecular determinants which are recognized. It is widely accepted that alternative pathway activation is controlled through the fine balance between inhibitory regulatory components of this pathway, such as Factor H, Factor I, DAF, CR1 and properdin, which is the only positive regulator of the alternative pathway. See Schwaeble W. J. and Reid K. B., *Immunol Today* 20(1):17-21 (1999)).

In addition to the apparently unregulated activation mechanism described above, the alternative pathway can also provide a powerful amplification loop for the lectin/classical pathway C3 convertase (C4b2a) since any C3b generated can participate with factor B in forming additional alternative pathway C3 convertase (C3bBb). The alternative pathway C3 convertase is stabilized by the binding of properdin. Properdin extends the alternative pathway C3 convertase half-life six to ten fold. Addition of C3b to the alternative pathway C3 convertase leads to the formation of the alternative pathway C5 convertase.

All three pathways (i.e., the classical, lectin and alternative) have been thought to converge at C5, which is cleaved to form products with multiple proinflammatory effects. The converged pathway has been referred to as the terminal complement pathway. C5a is the most potent anaphylatoxin, inducing alterations in smooth muscle and vascular tone, as well as vascular permeability. It is also a powerful chemotaxin and activator of both neutrophils and monocytes. C5a-mediated cellular activation can significantly amplify inflammatory responses by inducing the release of multiple additional inflammatory mediators, including cytokines, hydrolytic enzymes, arachidonic acid metabolites and reactive oxygen species. C5 cleavage leads to the formation of C5b-9, also known as the membrane attack complex (MAC). There is now strong evidence that sublytic MAC deposition may play an important role in inflammation in addition to its role as a lytic pore-forming complex.

In addition to its essential role in immune defense, the complement system contributes to tissue damage in many clinical conditions. Thus, there is a pressing need to develop therapeutically effective complement inhibitors to prevent these adverse effects.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, the invention provides an isolated human monoclonal antibody, or antigen binding fragment thereof, that binds to human MASP-2, comprising: (i) a heavy chain variable region comprising CDR-H1, CDR-H2 and CDR-H3 sequences; and (ii) a light chain variable region comprising CDR-L1, CDR-L2 and CDR-L3, wherein the heavy chain variable region CDR-H3 sequence comprises an amino acid sequence set forth as SEQ ID NO:38 or SEQ ID NO:90, and conservative sequence modifications thereof, wherein the light chain variable region CDR-L3 sequence comprises an amino acid sequence set forth as SEQ ID NO:51 or SEQ ID NO:94, and conservative sequence modifications thereof, and wherein the isolated antibody inhibits MASP-2 dependent complement activation.

In another aspect, the present invention provides a human antibody that binds human MASP-2, wherein the antibody comprises: I) a) a heavy chain variable region comprising: i) a heavy chain CDR-H1 comprising the amino acid sequence from 31-35 of SEQ ID NO:21; and ii) a heavy chain CDR-H2 comprising the amino acid sequence from 50-65 of SEQ ID NO:21; and iii) a heavy chain CDR-H3 comprising the amino acid sequence from 95-102 of SEQ ID NO:21; and b) a light chain variable region comprising: i) a light chain CDR-L1 comprising the amino acid sequence from 24-34 of either SEQ ID NO:25 or SEQ ID NO:27; and ii) a light chain CDR-L2 comprising the amino acid sequence from 50-56 of either SEQ ID NO:25 or SEQ ID NO:27; and iii) a light chain CDR-L3 comprising the amino acid sequence from 89-97 of either SEQ ID NO:25 or SEQ ID NO:27; or II) a variant thereof that is otherwise identical to said variable domains, except for up to a combined total of 10 amino acid substitutions within said CDR regions of said heavy chain variable region and up to a combined total of 10 amino acid substitutions within said CDR regions of said light chain variable region, wherein the antibody or variant thereof inhibits MASP-2 dependent complement activation.

In another aspect, the present invention provides an isolated human monoclonal antibody, or antigen binding fragment thereof, that binds human MASP-2, wherein the antibody comprises: I) a) a heavy chain variable region comprising: i) a heavy chain CDR-H1 comprising the amino acid sequence from 31-35 of SEQ ID NO:20; and ii) a heavy chain CDR-H2 comprising the amino acid sequence from 50-65 of SEQ ID NO:20; and iii) a heavy chain CDR-H3 comprising the amino acid sequence from 95-102 of either SEQ ID NO:18 or SEQ ID NO:20; and b) a light chain variable region comprising: i) a light chain CDR-L1 comprising the amino acid sequence from 24-34 of either SEQ ID NO:22 or SEQ ID NO:24; and ii) a light chain CDR-L2 comprising the amino acid sequence from 50-56 of either SEQ ID NO:22 or SEQ ID NO:24; and iii) a light chain CDR-L3 comprising the amino acid sequence from 89-97 of either SEQ ID NO:22 or SEQ ID NO:24; or II) a variant thereof, that is otherwise identical to said variable domains, except for up to a combined total of 10 amino acid substitutions within said CDR regions of said heavy chain and up to a combined total of 10 amino acid substitutions within said CDR regions of said light chain variable region, wherein the antibody or variant thereof inhibits MASP-2 dependent complement activation.

In another aspect, the present invention provides an isolated monoclonal antibody, or antigen-binding fragment thereof, that binds to human MASP-2, comprising a heavy chain variable region comprising any one of the amino acid sequences set forth in SEQ ID NO:18, SEQ ID NO:20 or SEQ ID NO:21.

In another aspect, the present invention provides an isolated monoclonal antibody, or antigen-binding fragment thereof, that binds to human MASP-2, comprising a light chain variable region comprising an one of the amino acid sequences set forth in SEQ ID NO:22, SEQ ID NO:24, SEQ ID NO:25 or SEQ ID NO:27.

In another aspect, the present invention provides nucleic acid molecules encoding the amino acid sequences of the anti-MASP-2 antibodies, or fragments thereof, of the present invention, such as those set forth in TABLE 2.

In another aspect, the present invention provides a cell comprising at least one of the nucleic acid molecules encoding the amino acid sequences of the anti-MASP-2 antibodies, or fragments thereof, of the present invention, such as those set forth in TABLE 2.

In another aspect, the invention provides a method of generating an isolated MASP-2 antibody comprising culturing cells comprising at least one of the nucleic acid molecules encoding the amino acid sequences of the anti-MASP-2 antibodies of the present invention under conditions allowing for expression of the nucleic acid molecules encoding the anti-MASP-2 antibody and isolating said anti-MASP-2 antibody.

In another aspect, the invention provides an isolated fully human monoclonal antibody or antigen-binding fragment thereof that dissociates from human MASP-2 with a $K_D$ of 10 nM or less as determined by surface plasmon resonance and inhibits C4 activation on a mannan-coated substrate with an $IC_{50}$ of 10 nM or less in 1% serum. In some embodiments, said antibody or antigen binding fragment thereof specifically recognizes at least part of an epitope recognized by a reference antibody, wherein said reference antibody comprises a heavy chain variable region as set forth in SEQ ID NO:20 and a light chain variable region as set forth in SEQ ID NO:24.

In another aspect, the present invention provides compositions comprising the fully human monoclonal anti-MASP-2 antibodies of the invention and a pharmaceutically acceptable excipient.

In another aspect, the present invention provides methods of inhibiting MASP-2 dependent complement activation in a human subject comprising administering a human monoclonal antibody of the invention in an amount sufficient to inhibit MASP-2 dependent complement activation in said human subject.

In another aspect, the present invention provides an article of manufacture comprising a unit dose of human monoclonal MASP-2 antibody of the invention suitable for therapeutic administration to a human subject, wherein the unit dose is the range of from 1 mg to 1000 mg.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIGS. 8 is a protein sequence alignment of the mother clone 17N16 (SEQ ID NO: 59) and the 17N9 daughter clone (SEQ ID NO :66) showing that the light chains (starting with SYE) has 17 amino acid residues that differ between the two clones, as described in Example 6;

FIG. 9 is a protein sequence alignment of the CDR-H3 region of the sequences of the Clones #35 (aa 61-119 of SEQ ID NO:20), #59 (aa 61-119 of SEQ ID NO:20) and #90 (substitution of P for A at position 102 of SEQ ID NO:18) resulting from mutagenesis in comparison with the 17D20 mother clone (aa 61-119 of SEQ ID NO: 18), as described in Example 7;

FIG. 10A is a protein sequence alignment of the CDR3 region of the 17D20 mother clone (aa 61-119 of SEQ NO:18), with the chain shuffled clone 17D20md21N11 (aa 61-119 of SEQ ID NO:18) and the mutagensis clone #35 CDR-H3 clone (aa 61-119 of SEQ ID NO:20) show in FIG. 9 combined with the VL of 17D20md21N11 (VH35-VL21N11), as described in Example 7;

FIG. 10B is a protein sequence alignment of the VL and VH regions of the 17D20 mother clone (SEQ ID NO:55) and the daughter clone 17D20md21N11 (SEQ ID NO:67), as described in Example 71;

FIG. 23A graphically illustrates the level of C3 deposition in the presence or absence of anti-MASP-2 antibody (OMS646) over a range of concentrations in 90% human serum under lectin pathway-specific conditions, demonstrating that OMS646 blocks C3 deposition under physiological conditions, as described in Example 12;

DESCRIPTION OF THE SEQUENCE LISTING

SEQ ID NO:1 human MASP-2 cDNA

Figure 1A:
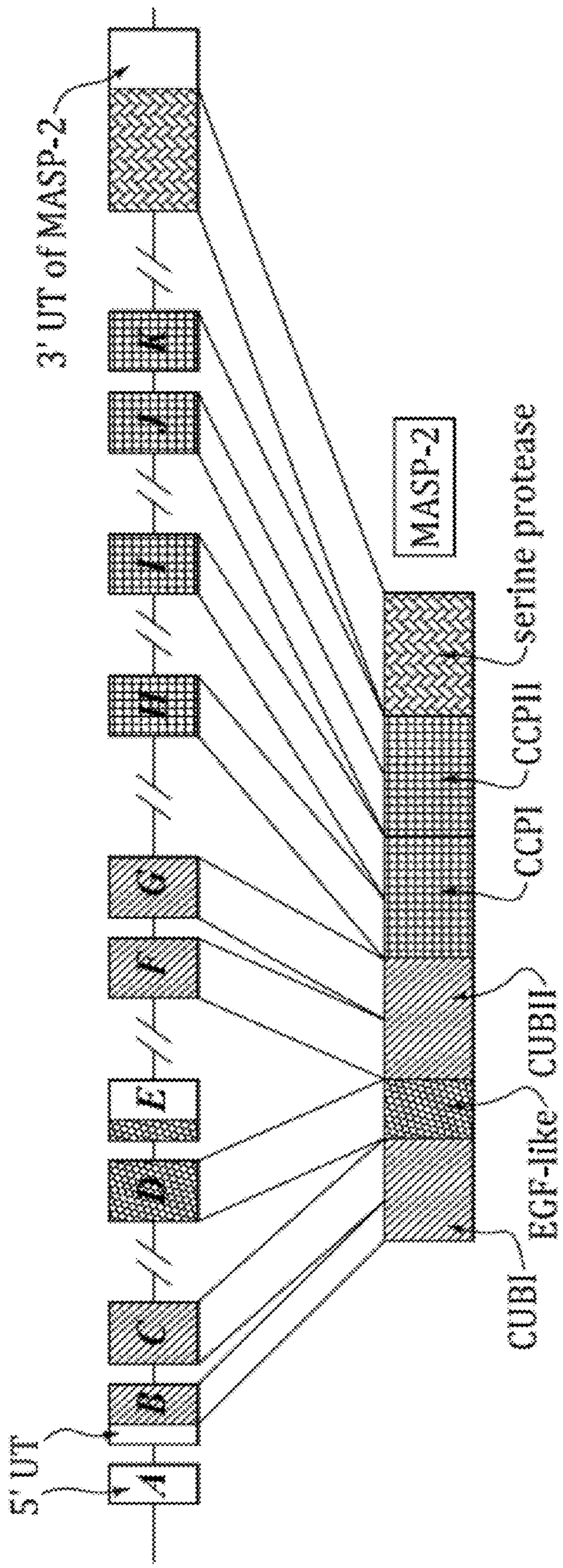
FIG. 1A is a diagram illustrating the genomic structure of human MASP-2.

SEQ ID NO:2 human MASP-2 protein (with leader)

SEQ ID NO:3 human MASP-2 protein (mature)

SEQ ID NO:4 rat MASP-2 cDNA

SEQ ID NO:5 rat MASP-2 protein (with leader)

SEQ ID NO:6 rat MASP-2 protein (mature)

Antigens (in Reference to Human MASP-2 Mature Protein)

SEQ ID NO:7 CUBI domain of human MASP-2 (aa 1-121)

SEQ ID NO:8 CUBI/EGF domains of human MASP-2 (aa 1-166)

SEQ ID NO:9 CUBI/EGF/CUBII domains of human MASP-2 (aa 1-277)

SEQ ID NO:10 EGF domain of human MASP-2 (aa 122-166)

SEQ ID NO:11 CCPI/CCPII/SP domains of human MASP-2 (aa 278-671)

SEQ ID NO:12 CCPI/CCPII domains of human MASP-2 (aa 278-429)

SEQ ID NO:13 CCPI domain of human MASP-2 (aa 278-347)

SEQ ID NO:14 CCPII/SP domain of human MASP-2 (aa348-671)

SEQ ID NO:15 CCPII domain of human MASP-2 (aa 348-429)

SEQ ID NO:16 SP domain of human MASP-2 (aa 429-671)

SEQ ID NO:17: Serine-protease inactivated mutant (aa 610-625 with mutated Ser 618)

Anti-MASP-2 Monoclonal Antibodies VH Chains

SEQ ID NO:18 17D20mc heavy chain variable region (VH) polypeptide

SEQ ID NO:19 DNA encoding 17D20_dc35VH21N11VL (OMS646) heavy chain variable region (VH) (without signal peptide)

SEQ ID NO:20 17D20_dc35VH21N11VL (OMS646) heavy chain variable region (VH) polypeptide SEQ ID NO:21 17N16mc heavy chain variable region (VH) polypeptide Anti-MASP-2 Monoclonal Antibodies VL Chains SEQ ID NO:22 17D20mc light chain variable region (VL) polypeptide SEQ ID NO:23 DNA encoding 17D20_dc21N11VL (OMS644) light chain variable region (VL) (without signal peptide)

SEQ ID NO:24 17D20_dc21N11VL (OMS644) light chain variable region (VL) polypeptide SEQ ID NO:25 17N16mc light chain variable region (VL) polypeptide SEQ ID NO:26 DNA encoding 17N16_dc17N9 (OMS641) light chain variable region (VL) (without signal peptide)

SEQ ID NO:27 17N16_dc17N9 (OMS641) light chain variable region (VL) polypeptide

Anti-MASP-2 Monoclonal Antibodies Heavy Chain CDRS

SEQ ID NOS:28-31 CDR-H1

SEQ ID NOS:32-35 CDR-H2

SEQ ID NOS:36-40 CDR-H3

Anti-MASP-2 Monoclonal Antibodies Light Chain CDRS

SEQ ID NOS:41-45 CDR-L1

SEQ ID NOS:46-50 CDR-L2

SEQ ID NOS:51-54 CDR-L3

MASP-2 Antibody Sequences

SEQ ID NO:55: scFv mother clone 17D20 full length polypeptide

SEQ ID NO:56: scFv mother clone 18L16 full length polypeptide

SEQ ID NO:57: scFv mother clone 4D9 full length polypeptide

SEQ ID NO:58: scFv mother clone 17L20 full length polypeptide

SEQ ID NO:59: scFv mother clone 17N16 full length polypeptide

SEQ ID NO:60: scFv mother clone 3F22 full length polypeptide

SEQ ID NO:61: scFv mother clone 9P13 full length polypeptide

SEQ ID NO:62: DNA encoding wild type IgG4 heavy chain constant region

SEQ ID NO:63: wild type IgG4 heavy chain constant region polypeptide

SEQ ID NO:64 DNA encoding IgG4 heavy chain constant region with mutant S228P

SEQ ID NO:65: IgG4 heavy chain constant region with mutant S228P polypeptide

SEQ ID NO:66: scFv daughter clone 17N16m_d17N9 full length polypeptide

SEQ ID NO:67: scFv daughter clone 17D20m_d21N11 full length polypeptide

SEQ ID NO:68: scFv daughter clone 17D20m_d3521N11 full length polypeptide

SEQ ID NO:69: DNA encoding wild type IgG2 heavy chain constant region

SEQ ID NO:70: wild type IgG2 heavy chain constant region polypeptide

SEQ ID NO:71: 17N16m_d17N9 light chain gene sequence (with signal peptide encoded by nt 1-57)

SEQ ID NO:72: 17N16m_d17N9 light chain protein sequence (with signal peptide aa1-19)

SEQ ID NO:73: 17N16m_d17N9 IgG2 heavy chain gene sequence (with signal peptide encoded by nt 1-57)

SEQ ID NO:74: 17N16m_d17N9 IgG2 heavy chain protein sequence (with signal peptide aa 1-19)

SEQ ID NO:75: 17N16m_d17N9 IgG4 heavy chain gene sequence (with signal peptide encoded by nt 1-57)

SEQ ID NO:76: 17N16m_d17N9 IgG4 heavy chain protein sequence (with signal peptide aa 1-19)

SEQ ID NO:77: 17N16m_d17N9 IgG4 mutated heavy chain gene sequence (with signal peptide encoded by nt 1-57)

SEQ ID NO:78: 17N17m_d17N9 IgG4 mutated heavy chain protein sequence (with signal peptide aa 1-19)

SEQ ID NO:79: 17D20_3521N11 light chain gene sequence (with signal peptide encoded by nt 1-57)

SEQ ID NO:80: 17D20_3521N11 light chain protein sequence (with signal peptide aa 1-19)

SEQ ID NO:81: 17D20_3521N11 IgG2 heavy chain gene sequence (with signal peptide encoded by nt 1-57)

SEQ ID NO:82: 17D20_3521N11 IgG2 heavy chain protein sequence (with signal peptide aa 1-19)

SEQ ID NO:83: 17D20_3521N11 IgG4 heavy chain gene sequence (with signal peptide encoded by nt 1-57)

SEQ ID NO:84: 17D20_3521N11 IgG4 heavy chain protein sequence (with signal peptide aa 1-19)

SEQ ID NO:85: 17D20_3521N11 IgG4 mutated heavy chain gene sequence (with signal peptide encoded by nt 1-57)

SEQ ID NO:86: 17D20_3521N11 IgG4 mutated heavy chain protein sequence (with signal peptide aa 1-19)

SEQ ID NO:87: scFv daughter clone 17N16m_d17N9 DNA encoding full length polypeptide (without signal peptide)

SEQ ID NO:88: scFv daughter clone 17D20m_d21N11 DNA encoding full length polypeptide (without signal peptide)

SEQ ID NO:89: scFv daughter clone 17D20m_d3521N11 DNA encoding full length polypeptide (without signal peptide)

SEQ ID NO:90: consensus heavy chain CDR-H3 of 17D20m and d3521N11

SEQ ID NO:91: consensus light chain CDR-L1 of 17D20m and d3521N11

SEQ ID NO:92: consensus light chain CDR-L1 of 17N16m and d17N9

SEQ ID NO:93: consensus light chain CDR-L2 of 17D20m, d3521N11, 17N16m and d17N9

SEQ ID NO:94: consensus light chain CDR-L3 of 17N16m and d17N9

DETAILED DESCRIPTION

The present invention provides fully human antibodies that bind to human MASP-2 and inhibit lectin-mediated complement activation while leaving the classical (C1q-dependent) pathway component of the immune system intact. The human anti-MASP-2 antibodies have been identified by screening a phage display library, as described in Examples 2-9. As described in Examples 10-12, high affinity anti-MASP-2 antibodies have been identified with the ability to inhibit lectin-mediated complement activation, as demonstrated in both in vitro assays and in vivo. The variable light and heavy chain fragments of the antibodies have been isolated in both a scFv format and in a full length IgG format. The human anti-MASP-2 antibodies are useful for inhibiting cellular injury associated with lectin-mediated complement pathway activation while leaving the classical (C1q-dependent) pathway component of the immune system intact.

I. Definitions

Unless specifically defined herein, all terms used herein have the same meaning as would be understood by those of ordinary skill in the art of the present invention. The following definitions are provided in order to provide clarity with respect to the terms as they are used in the specification and claims to describe the present invention.

As used herein, the term "MASP-2-dependent complement activation" comprises MASP-2-dependent activation of the lectin pathway, which occurs under physiological conditions (i.e., in the presence of $Ca^{++}$) leading to the formation of the lectin pathway C3 convertase C4b2a and upon accumulation of the C3 cleavage product C3b subsequently to the C5 convertase C4b2a(C3b)n.

As used herein, the term "alternative pathway" refers to complement activation that is triggered, for example, by zymosan from fungal and yeast cell walls, lipopolysaccharide (LPS) from Gram negative outer membranes, and rabbit erythrocytes, as well as from many pure polysaccharides, rabbit erythrocytes, viruses, bacteria, animal tumor cells, parasites and damaged cells, and which has traditionally been thought to arise from spontaneous proteolytic generation of C3b from complement factor C3.

As used herein, the term "lectin pathway" refers to complement activation that occurs via the specific binding of serum and non-serum carbohydrate-binding proteins including mannan-binding lectin (MBL), CL-11 and the ficolins (H-ficolin, M-ficolin, or L-ficolin).

As used herein, the term "classical pathway" refers to complement activation that is triggered by an antibody bound to a foreign particle and requires binding of the recognition molecule C1q.

As used herein, the term "MASP-2 inhibitory antibody" refers to any anti-MASP-2 antibody, or MASP-2 binding fragment thereof, that binds to or directly interacts with MASP-2 and effectively inhibits MASP-2-dependent complement activation. MASP-2 inhibitory antibodies useful in the method of the invention may reduce MASP-2-dependent complement activation by greater than 20%, such as greater than 30%, or greater than 40%, or greater than 50%, or greater than 60%, or greater than 70%, or greater than 80%, or greater than 90%, or greater than 95%.

As used herein, the term "MASP-2 blocking antibody" refers to MASP-2 inhibitory antibodies that reduce MASP-2-dependent complement activation by greater than 90%, such as greater than 95%, or greater than 98% (i.e., resulting in MASP-2 complement activation of only 10%, such as only 9%, or only 8%, or only 7%, or only 6%, such as only 5% or less, or only 4%, or only 4%, or only 3% or only 2% or only 1%).

The terms "antibody" and "immunoglobulin" are used interchangeably herein. These terms are well understood by those in the field, and refer to a protein consisting of one or more polypeptides that specifically binds an antigen. One form of antibody constitutes the basic structural unit of an antibody. This form is a tetramer and consists of two identical pairs of antibody chains, each pair having one light and one heavy chain. In each pair, the light and heavy chain variable regions are together responsible for binding to an antigen, and the constant regions are responsible for the antibody effector functions.

As used herein, the term "antibody" encompasses antibodies and antibody fragments thereof, derived from any antibody-producing mammal (e.g., mouse, rat, rabbit, and primate including human), or from a hybridoma, phage selection, recombinant expression or transgenic animals (or other methods of producing antibodies or antibody fragments), that specifically bind to MASP-2 polypeptides or portions thereof. It is not intended that the term "antibody" be limited as regards to the source of the antibody or manner in which it is made (e.g., by hybridoma, phage selection, recombinant expression, transgenic animal, peptide synthesis, etc). Exemplary antibodies include polyclonal, monoclonal and recombinant antibodies; multispecific antibodies (e.g., bispecific antibodies); humanized antibodies; murine antibodies; chimeric, mouse-human, mouse-primate, primate-human monoclonal antibodies; and anti-idiotype antibodies, and may be any intact molecule or fragment thereof. As used herein, the term "antibody" encompasses not only intact polyclonal or monoclonal antibodies, but also fragments thereof (such as dAb, Fab, Fab', $F(ab')_2$, Fv), single chain (ScFv), synthetic variants thereof, naturally occurring variants, fusion proteins comprising an antibody portion with an antigen-binding fragment of the required specificity, humanized antibodies, chimeric antibodies, and any other modified configuration of the immunoglobulin molecule that comprises an antigen-binding site or fragment (epitope recognition site) of the required specificity.

As used herein, the term "antigen-binding fragment" refers to a polypeptide fragment that contains at least one CDR of an immunoglobulin heavy and/or light chains that binds to human MASP-2. In this regard, an antigen-binding fragment of the herein described antibodies may comprise 1, 2, 3, 4, 5, or all 6 CDRs of a VH and VL sequence set forth herein from antibodies that bind MASP-2. An antigen-binding fragment of the herein described MASP-2-specific antibodies is capable of binding to MASP-2. In certain embodiments, an antigen-binding fragment or an antibody comprising an antigen-binding fragment, mediates inhibition of MASP-2 dependent complement activation.

As used herein the term "anti-MASP-2 monoclonal antibodies" refers to a homogenous antibody population, wherein the monoclonal antibody is comprised of amino acids that are involved in the selecting binding of an epitope on MASP-2. Anti-MASP-2 monoclonal antibodies are highly specific for the MASP-2 target antigen. The term "monoclonal antibody" encompasses not only intact monoclonal antibodies and full-length monoclonal antibodies, but also fragments thereof (such as Fab, Fab', $F(ab')_2$, Fv), single chain (ScFv), variants thereof, fusion proteins comprising an antigen-binding portion, humanized monoclonal antibodies, chimeric monoclonal antibodies, and any other modified configuration of the immunoglobulin molecule that comprises an antigen-binding fragment (epitope recognition site) of the required specificity and the ability to bind to an epitope.

As used herein, the modifier "monoclonal" indicates the character of the antibody as being obtained from a substantially homogenous population of antibodies, and is not. intended to be limited as regards the source of the antibody or the manner in which it is made (e.g., by hybridoma, phage selection, recombinant expression, transgenic animals, etc.). The term includes whole immunoglobulins as well as the fragments etc. described above under the definition of "antibody". Monoclonal antibodies can be obtained using any technique that provides for the production of antibody molecules by continuous cell lines in culture, such as the hybridoma method described by Kohler, G., et al., *Nature* 256:495, 1975, or they may be made by recombinant DNA methods (see, e.g., U.S. Pat. No. 4,816,567 to Cabilly). Monoclonal antibodies may also be isolated from phage antibody libraries using the techniques described in Clackson, T., et al., *Nature* 352:624-628, 1991, and Marks, J. D., et al., *J. Mol. Biol.* 222:581-597, 1991. Such antibodies can be of any immunoglobulin class including IgG, IgM, IgE, IgA, IgD and any subclass thereof.

The recognized immunoglobulin polypeptides include the kappa and lambda light chains and the alpha, gamma (IgG1, IgG2, IgG3, IgG4), delta, epsilon and mu heavy chains or equivalents in other species. Full-length immunoglobulin "light chains" (of about 25 kDa or about 214 amino acids) comprise a variable region of about 110 amino acids at the $NH_2$-terminus and a kappa or lambda constant region at the COOH-terminus. Full-length immunoglobulin "heavy chains" (of about 50 kDa or about 446 amino acids) similarly comprise a variable region (of about 116 amino acids) and one of the aforementioned heavy chain constant regions, e.g., gamma (of about 330 amino acids).

The basic four-chain antibody unit is a heterotetrameric glycoprotein composed of two identical light (L) chains and two identical heavy (H) chains. An IgM antibody consists of 5 of the basic heterotetramer units along with an additional polypeptide called the J chain, and therefore contains 10 antigen binding sites. Secreted IgA antibodies can polymerize to form polyvalent assemblages comprising 2-5 of the basic 4-chain units along with J chain. Each L chain is linked to an H chain by one covalent disulfide bond, while the two H chains are linked to each other by one or more by one or more disulfide bonds, depending on the H chain isotype. Each H and L chain also has regularly spaced intrachain disulfide bridges. The pairing of a VH and VL together forms a single antigen-binding site.

Each H chain has at the N-terminus, a variable domain (VH), followed by three constant domains (CH) for each of the $\alpha$ and $\gamma$ chains, and four CH domains (CH) for $\mu$ and $\epsilon$ isotypes.

Each L chain has at the N-terminus, a variable domain (VL) followed by a constant domain (CL) at its other end. The VL is aligned with the VH and the CL is aligned with the first constant domain of the heavy chain (CH1). The L chain from any vertebrate species can be assigned to one of two clearly distinct types, called kappa ($\kappa$) and lambda ($\lambda$), based on the amino acid sequences of their constant domains (CL).

Depending on the amino acid sequence of the constant domain of their heavy chains (CH), immunoglobulins can be assigned to different classes or isotypes. There are five classes of immunoglobulins: IgA, IgD, IgE, IgG and IgM, having heavy chains designated alpha ($\alpha$), delta ($\delta$), epsilon ($\epsilon$), gamma ($\gamma$) and mu ($\mu$), respectively. The $\gamma$ and $\alpha$ classes are further divided into subclasses on the basis of minor differences in CH sequence and function, for example, humans express the following subclasses: IgG1, IgG2, IgG3, IgG4, IgA1 and IgA2.

For the structure and properties of the different classes of antibodies, see, e.g., Basic and Clinical Immunology, 8th Edition, Daniel P. Stites, Abba I. Terr and Tristram G. Parslow (eds); Appleton and Lange, Norwalk, Conn., 1994, page 71 and Chapter 6.

The term "variable" refers to that fact that certain segments of the V domains differ extensively in sequence among antibodies. The V domain mediates antigen binding and defines specificity of a particular antibody for its particular antigen. However, the variability is not evenly distributed across the 110 amino acid span of the variable domains. Rather, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a beta-sheet configuration, connected by three hypervariable regions, which form loops connecting, and in some cases forming part of, the n-sheet structure. The hypervariable regions in each chain are held together in close proximity by the FRs and, with the hypervariable regions from the other chain, contribute to the formation of the antigen-binding site of antibodies (see Kabat, et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

As used herein, the term “hypervariable region” refers to the amino acid residues of an antibody that are responsible for antigen binding. The hypervariable region generally comprises amino acid residues from a “complementary determining region” or “CDR” (i.e., from around about residues 24-34 (L1), 50-56 (L2) and 89-97 (L3) in the light chain variable domain, and around about 31-35 (H1), 50-65 (H2) and 95-102 (H3) in the heavy chain variable domain when numbering in accordance with the Kabat numbering system as described in Kabat, et al., *Sequences of Proteins of Immunological Interest,* 5th Ed. Public Health Service, National Institutes of Health, Bethesda, Md. (1991)); and/or those residues from a “hypervariable loop” (i.e., residues 24-34 (L1), 50-56 (L2) and 89-97 (L3) in the light chain variable domain, and 26-32 (H1), 52-56 (H2) and 95-101 (H3) in the heavy chain variable domain when numbered in accordance with the Chothia numbering system, as described in Chothia and Lesk, *J. Mol. Biol.* 196:901-917 (1987)); and/or those residues from a “hypervariable loop”/CDR (e.g., residues 27-38 (L1), 56-65 (L2) and 105-120 (L3) in the VL, and 27-38 (H1), 56-65 (H2), and 105-120 (H3) in the VH when numbered in accordance with the IMGT numbering system as described in Lefranc, J. P., et al., *Nucleic Acids Res* 27:209-212; Ruiz, M., et al., *Nucleic Acids Res* 28:219-221 (2000)).

As used herein, the term “antibody fragment” refers to a portion derived from or related to a full-length anti-MASP-2 antibody, generally including the antigen binding or variable region thereof. Illustrative examples of antibody fragments include Fab, Fab', $F(ab)_2$, $F(ab')_2$ and Fv fragments, scFv fragments, diabodies, linear antibodies, single-chain antibody molecules, bispecific and multispecific antibodies formed from antibody fragments.

Where bispecific antibodies are to be used, these may be conventional bispecific antibodies, which can be manufactured in a variety of ways (Holliger, P. and Winter G. *Current Opinion Biotechnol.* 4, 446-449 (1993)), e.g. prepared chemically or from hybrid hybridomas, or may be any of the bispecific antibody fragments mentioned above.

As used herein, a “single-chain Fv” or “scFv” antibody fragment comprises the $V_H$ and $V_L$ domains of an antibody, wherein these domains are present in a single polypeptide chain. Generally, the Fv polypeptide further comprises a polypeptide linker between the $V_H$ and $V_L$ domains, which enables the scFv to form the desired structure for antigen binding. See Pluckthun in *The Pharmacology of Monoclonal Antibodies*, Vol. 113, Rosenburg and Moore eds., Springer-Verlag, New York, pp. 269-315 (1994). “Fv” is the minimum antibody fragment that contains a complete antigen-recognition and binding site. This fragment consists of a dimer of one heavy and one light chain variable region domain in tight, non-covalent association. From the folding of these two domains emanate six hypervariable loops (three loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

As used herein, the term “specific binding” refers to the ability of an antibody to preferentially bind to a particular analyte that is present in a homogeneous mixture of different analytes. In certain embodiments, a specific binding interaction will discriminate between desirable and undesirable analytes in a sample, in some embodiments more than about 10 to 100-fold or more (e.g., more than about 1000- or 10.000-fold). In certain embodiments, the affinity between a capture agent and analyte when they are specifically bound in a capture agent/analyte complex is characterized by a $K_D$ (dissociation constant) of less than about 100 nM, or less than about 50 nM, or less than about 25 nM, or less than about 10 nM, or less than about 5 nM, or less than about 1 nM.

As used herein, the term “variant” anti-MASP-2 antibody refers to a molecule which differs in amino acid sequence from a “parent” or reference antibody amino acid sequence by virtue of addition, deletion, and/or substitution of one or more amino acid residue(s) in the parent antibody sequence. In one embodiment, a variant anti-MASP-2 antibody refers to a molecule which contains variable regions that are identical to the parent variable domains, except for a combined total of 1, 2, 3, 4, 5, 6, 7, 8, 9 or 10 amino acid substitutions within the CDR regions of the heavy chain variable region, and/or up to a combined total of 1, 2, 3, 4, 5, 6, 7, 8, 9, or 10 amino acid substitutions with said CDR regions of the light chain variable region. In some embodiments, the amino acid substitutions are conservative sequence modifications.

As used herein, the term “parent antibody” refers to an antibody which is encoded by an amino acid sequence used for the preparation of the variant. Preferably, the parent antibody has a human framework region and, if present, has human antibody constant region(s). For example, the parent antibody may be a humanized or fully human antibody.

As used herein, the term “isolated antibody” refers to an antibody that has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight; (2) to a degree sufficient to obtain at least 15 residues of N-terminal or internal amino acid sequence by use of a spinning cup sequenator; or (3) to homogeneity by SDS-PAGE under reducing or nonreducing conditions using Coomassie blue or, preferably, silver stain. Isolated antibody includes the antibody in situ within recombinant cells since at least one component of the antibody’s natural environment will not be present. Ordinarily, however, isolated antibody will be prepared by at least one purification step.

As used herein, the term “epitope” refers to the portion of an antigen to which a monoclonal antibody specifically binds. Epitopic determinants usually consist of chemically active surface groupings of molecules such as amino acids or sugar side chains and usually have specific three dimensional structural characteristics, as well as specific charge characteristics. More specifically, the term “MASP-2 epitope,” as used herein refers to a portion of the corresponding polypeptide to which an antibody immunospecifically binds as determined by any method well known in the art, for example, by immunoassays. Antigenic epitopes need not necessarily be immunogenic. Such epitopes can be linear in nature or can be a discontinuous epitope. Thus, as used herein, the term “conformational epitope” refers to a discontinuous epitope formed by a spatial relationship between amino acids of an antigen other than an unbroken series of amino acids.

As used herein, the term "mannan-binding lectin" ("MBL") is equivalent to mannan-binding protein ("MBP").

As used herein, the "membrane attack complex" ("MAC") refers to a complex of the terminal five complement components (C5-C9) that inserts into and disrupts membranes. Also referred to as C5b-9.

As used herein, "a subject" includes all mammals, including without limitation, humans, non-human primates, dogs, cats, horses, sheep, goats, cows, rabbits, pigs and rodents.

As used herein, the amino acid residues are abbreviated as follows: alanine (Ala;A), asparagine (Asn;N), aspartic acid (Asp;D), arginine (Arg;R), cysteine (Cys;C), glutamic acid (Glu;E), glutamine (Gln;Q), glycine (Gly;G), histidine (His;H), isoleucine (Ile;I), leucine (Leu;L), lysine (Lys;K), methionine (Met;M), phenylalanine (Phe;F), proline (Pro;P), serine (Ser;S), threonine (Thr;T), tryptophan (Trp;W), tyrosine (Tyr;Y), and valine (Val;V).

In the broadest sense, the naturally occurring amino acids can be divided into groups based upon the chemical characteristic of the side chain of the respective amino acids. By "hydrophobic" amino acid is meant either Ile, Leu, Met, Phe, Trp, Tyr, Val, Ala, Cys or Pro. By "hydrophilic" amino acid is meant either Gly, Asn, Gln, Ser, Thr, Asp, Glu, Lys, Arg or His. This grouping of amino acids can be further subclassed as follows. By "uncharged hydrophilic" amino acid is meant either Ser, Thr, Asn or Gln. By "acidic" amino acid is meant either Glu or Asp. By "basic" amino acid is meant either Lys, Arg or His.

As used herein the term "conservative amino acid substitution" is illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine.

As used herein, an "isolated nucleic acid molecule" is a nucleic acid molecule (e.g., a polynucleotide) that is not integrated in the genomic DNA of an organism. For example, a DNA molecule that encodes a growth factor that has been separated from the genomic DNA of a cell is an isolated DNA molecule. Another example of an isolated nucleic acid molecule is a chemically-synthesized nucleic acid molecule that is not integrated in the genome of an organism. A nucleic acid molecule that has been isolated from a particular species is smaller than the complete DNA molecule of a chromosome from that species.

As used herein, a "nucleic acid molecule construct" is a nucleic acid molecule, either single- or double-stranded, that has been modified through human intervention to contain segments of nucleic acid combined and juxtaposed in an arrangement not existing in nature.

As used herein, an "expression vector" is a nucleic acid molecule encoding a gene that is expressed in a host cell. Typically, an expression vector comprises a transcription promoter, a gene, and a transcription terminator. Gene expression is usually placed under the control of a promoter, and such a gene is said to be "operably linked to" the promoter. Similarly, a regulatory element and a core promoter are operably linked if the regulatory element modulates the activity of the core promoter.

As used herein, the terms "approximately" or "about" in reference to a number are generally taken to include numbers that fall within a range of 5% in either direction (greater than or less than) of the number unless otherwise stated or otherwise evident from the context (except where such number would exceed 100% of a possible value). Where ranges are stated, the endpoints are included within the range unless otherwise stated or otherwise evident from the context.

As used herein the singular forms "a", "an" and "the" include plural aspects unless the context clearly dictates otherwise. Thus, for example, reference to "a cell" includes a single cell, as well as two or more cells; reference to "an agent" includes one agent, as well as two or more agents; reference to "an antibody" includes a plurality of such antibodies and reference to "a framework region" includes reference to one or more framework regions and equivalents thereof known to those skilled in the art, and so forth.

Each embodiment in this specification is to be applied mutatis mutandis to every other embodiment unless expressly stated otherwise.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. These and related techniques and procedures may be generally performed according to conventional methods well known in the art and as described in various general and more specific references that are cited and discussed throughout the present specification. See e.g., Sambrook et al., 2001, MOLECULAR CLONING: A LABORATORY MANUAL, 3d ed., Cold Spring Harbor Laboratory Press, Cold Spring Harbor, N.Y.; Current Protocols in Molecular Biology (Greene Publ. Assoc. Inc. & John Wiley & Sons, Inc., NY, N.Y.); Current Protocols in Immunology (Edited by: John E. Coligan, Ada M. Kruisbeek, David H. Margulies, Ethan M. Shevach, Warren Strober 2001 John Wiley & Sons, NY, N.Y.); or other relevant Current Protocol publications and other like references. Unless specific definitions are provided, the nomenclature utilized in connection with, and the laboratory procedures and techniques of, molecular biology, analytical chemistry, synthetic organic chemistry, and medicinal and pharmaceutical chemistry described herein are those well known and commonly used in the art. Standard techniques may be used for recombinant technology, molecular biological, microbiological, chemical syntheses, chemical analyses, pharmaceutical preparation, formulation, and delivery, and treatment of patients.

It is contemplated that any embodiment discussed in this specification can be implemented with respect to any method, kit, reagent, or composition of the invention, and vice versa. Furthermore, compositions of the invention can be used to achieve methods of the invention.

II. Overview

Lectins (MBL, M-ficolin, H-ficolin, L-ficolin and CL-11) are the specific recognition molecules that trigger the innate complement system and the system includes the lectin initiation pathway and the associated terminal pathway amplification loop that amplifies lectin-initiated activation of terminal complement effector molecules. C1q is the specific recognition molecule that triggers the acquired complement system and the system includes the classical initiation pathway and associated terminal pathway amplification loop that amplifies C1q-initiated activation of terminal complement effector molecules. We refer to these two major complement activation systems as the lectin-dependent complement system and the C1q-dependent complement system, respectively.

In addition to its essential role in immune defense, the complement system contributes to tissue damage in many clinical conditions. Thus, there is a pressing need to develop therapeutically effective complement inhibitors to prevent these adverse effects.

As described in U.S. Pat. No. 7,919,094, co-pending U.S. patent application Ser. No. 12/905,972 (published as US 2011/0091450), and co-pending U.S. patent application Ser. No. 13/083,441 (published as US2011/0311549), each of which is assigned to Omeros Corporation, the assignee of the instant application, and each of which is hereby incorporated by reference, it was determined through the use of a MASP-2−/− mouse model that it is possible to inhibit the lectin mediated MASP-2 pathway while leaving the classical pathway intact. With the recognition that it is possible to inhibit the lectin mediated MASP-2 pathway while leaving the classical pathway intact comes the realization that it would be highly desirable to specifically inhibit only the complement activation system causing a particular pathology without completely shutting down the immune defense capabilities of complement. For example, in disease states in which complement activation is mediated predominantly by the lectin-dependent complement system, it would be advantageous to specifically inhibit only this system. This would leave the C1q-dependent complement activation system intact to handle immune complex processing and to aid in host defense against infection.

The preferred protein component to target in the development of therapeutic agents to specifically inhibit the lectin-dependent complement system is MASP-2. Of all the known protein components of the lectin-dependent complement system (MBL, H-ficolin, M-ficolin, L-ficolin, MASP-2, C2-C9, Factor B, Factor D, and properdin), only MASP-2 is both unique to the lectin-dependent complement system and required for the system to function. The lectins (MBL, H-ficolin, M-ficolin, L-ficolin and CL-11) are also unique components in the lectin-dependent complement system. However, loss of any one of the lectin components would not necessarily inhibit activation of the system due to lectin redundancy. It would be necessary to inhibit all five lectins in order to guarantee inhibition of the lectin-dependent complement activation system. Furthermore, since MBL and the ficolins are also known to have opsonic activity independent of complement, inhibition of lectin function would result in the loss of this beneficial host defense mechanism against infection. In contrast, this complement-independent lectin opsonic activity would remain intact if MASP-2 was the inhibitory target. An added benefit of MASP-2 as the therapeutic target to inhibit the lectin-dependent complement activation system is that the plasma concentration of MASP-2 is among the lowest of any complement protein (≈500 ng/ml); therefore, correspondingly low concentrations of high-affinity inhibitors of MASP-2 is sufficient to obtain full inhibition, as demonstrated in the Examples herein.

In accordance with the foregoing, as described herein, the present invention provides monoclonal fully human anti-MASP-2 antibodies that bind to human MASP-2 with high affinity and are capable of inhibiting lectin-mediated complement pathway activation.

III. MASP-2 Inhibitory Antibodies

In one aspect, the invention provides a monoclonal fully human anti-MASP-2 antibody, or antigen binding fragment thereof, that specifically binds to human MASP-2 and inhibits or blocks MASP-2-dependent complement activation. MASP-2 inhibitory antibodies may effectively inhibit or effectively block the MASP-2-dependent complement activation system by inhibiting or blocking the biological function of MASP-2. For example, an inhibitory antibody may effectively inhibit or block MASP-2 protein-to-protein interactions, interfere with MASP-2 dimerization or assembly, block $Ca^{2+}$ binding, or interfere with the MASP-2 serine protease active site.

MASP-2 Epitopes

The invention provides fully human antibodies that specifically bind to human MASP-2. The MASP-2 polypeptide exhibits a molecular structure similar to MASP-1, MASP-3, and C1r and C1s, the proteases of the C1 complement system. The cDNA molecule set forth in SEQ ID NO:1 encodes a representative example of MASP-2 (consisting of the amino acid sequence set forth in SEQ ID NO:2) and provides the human MASP-2 polypeptide with a leader sequence (aa 1-15) that is cleaved after secretion, resulting in the mature form of human MASP-2 (SEQ ID NO:3). As shown in FIG. 1A, the human MASP 2 gene encompasses twelve exons. The human MASP-2 cDNA is encoded by exons B, C, D, F, G, H, I, J, K and L. The cDNA molecule set forth in SEQ ID NO:4 encodes the rat MASP-2 (consisting of the amino acid sequence set forth in SEQ ID NO:5) and provides the rat MASP-2 polypeptide with a leader sequence that is cleaved after secretion, resulting in the mature form of rat MASP-2 (SEQ ID NO:6).

Those skilled in the art will recognize that the sequences disclosed in SEQ ID NO:1 and SEQ ID NO:4 represent single alleles of human and rat MASP-2, respectively, and that allelic variation and alternative splicing are expected to occur. Allelic variants of the nucleotide sequences shown in SEQ ID NO:1 and SEQ ID NO:4, including those containing silent mutations and those in which mutations result in amino acid sequence changes, are within the scope of the present invention. Allelic variants of the MASP-2 sequence can be cloned by probing cDNA or genomic libraries from different individuals according to standard procedures.

Figure 1B:
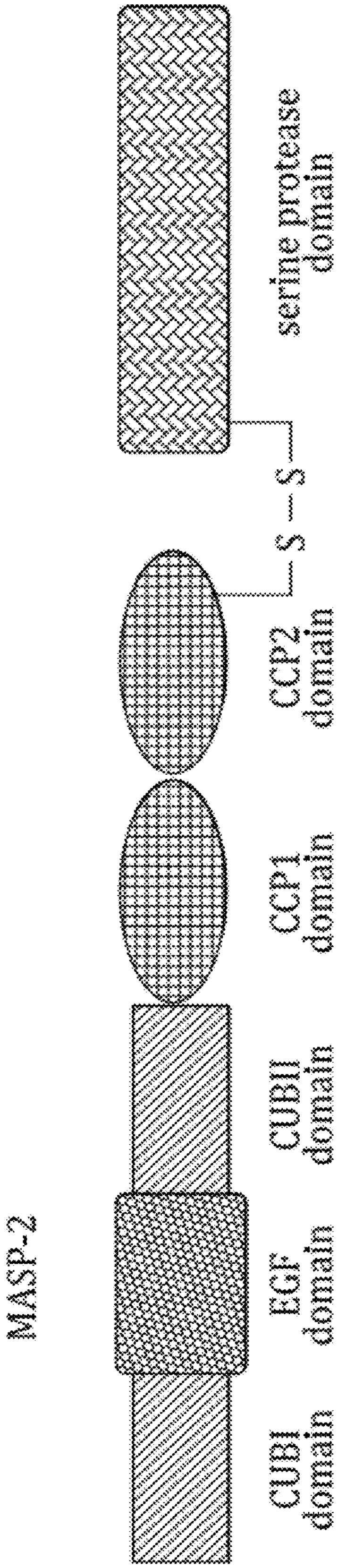
FIG. 1B is a diagram illustrating the domain structure of human MASP-2 protein.

The domains of the human MASP-2 protein (SEQ ID NO:3) are shown in FIG. 1B and TABLE 1 below, and include an N-terminal C1r/C1s/sea urchin VEGF/bone morphogenic protein (CUBI) domain, an epidermal growth factor-like domain, a second CUB domain (CUBII), as well as a tandem of complement control protein domains CCP1 and CCP2, and a serine protease domain. Alternative splicing of the MASP-2 gene results in MAp 19. MAp 19 is a nonenzymatic protein containing the N-terminal CUB1-EGF region of MASP-2 with four additional residues (EQSL).

Several proteins have been shown to bind to, or interact with MASP-2 through protein-to-protein interactions. For example, MASP-2 is known to bind to, and form $Ca^{2+}$ dependent complexes with, the lectin proteins MBL, H-ficolin and L-ficolin. Each MASP-2/lectin complex has been shown to activate complement through the MASP-2-dependent cleavage of proteins C4 and C2 (Ikeda, K., et al., *J. Biol. Chem.* 262:7451-7454, 1987; Matsushita, M., et al., *J. Exp. Med.* 176:1497-2284, 2000; Matsushita, M., et al., *J. Immunol.* 168:3502-3506, 2002). Studies have shown that the CUB1-EGF domains of MASP-2 are essential for the association of MASP-2 with MBL (Thielens, N. M., et al., *J. Immunol.* 166:5068, 2001). It has also been shown that the CUB1EGFCUBII domains mediate dimerization of MASP-2, which is required for formation of an active MBL complex (Wallis, R., et al., *J. Biol. Chem.* 275:30962-30969, 2000). Therefore, MASP-2 inhibitory antibodies can be identified that bind to or interfere with MASP-2 target regions known to be important for MASP-2-dependent complement activation.

TABLE 1

MASP-2 Polypeptide Domains

| SEQ ID NO: | Amino Acid Sequence |
|---|---|
| SEQ ID NO: 2 | human MASP-2 protein (w/leader) |
| SEQ ID NO: 3 | human MASP-2 mature protein |

TABLE 1-continued

| MASP-2 Polypeptide Domains | |
|---|---|
| SEQ ID NO: | Amino Acid Sequence |
| SEQ ID NO: 5 | rat MASP-2 protein (w/leader) |
| SEQ ID NO: 6 | rat MASP-2 mature protein |
| SEQ ID NO: 7 | CUBI domain of human MASP-2 (aa 1-121 of SEQ ID NO: 3) |
| SEQ ID NO: 8 | CUBI/EGF domains of human MASP-2 (aa 1-166 of SEQ ID NO: 3) |
| SEQ ID NO: 9 | CUBI/EGF/CUBII domains of human MASP-2 (aa 1-277 of SEQ ID NO: 3) |
| SEQ ID NO: 10 | EGF domain of human MASP-2 (aa 122-166 of SEQ ID NO: 3) |
| SEQ ID NO: 11 | CCPI/CCPII/SP domains of human MASP-2 (aa 278-671 aa of SEQ ID NO: 3) |
| SEQ ID NO: 12 | CCPI/CCPII domains of human MASP-2 (aa 278-429 of SEQ ID NO: 3) |
| SEQ ID NO: 13 | CCPI domain of human MASP-2 (aa 278-347 of SEQ ID NO: 3) |
| SEQ ID NO: 14 | CCPII/SP domains of human MASP-2 (aa 348-671 of SEQ ID NO: 3) |
| SEQ ID NO: 15 | CCPII domain of human MASP-2 (aa 348-429 of SEQ ID NO: 3) |
| SEQ ID NO: 16 | SP domain of human MASP-2 (aa 429-671 of SEQ ID NO: 3) |
| SEQ ID NO: 17 (GKDSCRGDAGGA LVFL) | Serine-protease inactivated mutant form (aa 610-625 of SEQ ID NO: 3 with mutated Ser 618) |

In one embodiment, the anti-MASP-2 inhibitory antibodies of the invention bind to a portion of the full length human MASP-2 protein (SEQ ID NO:3), such as CUBI, EGF, CUBII, CCPI, CCPII, or SP domain of MASP-2. In some embodiments, the anti-MASP-2 inhibitory antibodies of the invention bind to an epitope in the CCP1 domain (SEQ ID NO:13 (aa 278-347 of SEQ ID NO:3)). For example, anti-MASP-2 antibodies (e.g., OMS646) have been identified that only bind to MASP-2 fragments containing the CCP1 domain and inhibit MASP-2 dependent complement activation, as described in Example 9.

Binding Affinity of MASP-2 Inhibitory Antibodies

The anti-MASP-2 inhibitory antibodies specifically bind to human MASP-2 (set forth as SEQ ID NO:3, encoded by SEQ ID NO:1), with an affinity of at least ten times greater than to other antigens in the complement system. In some embodiments, the MASP-2 inhibitory antibodies specifically bind to human MASP-2 with a binding affinity of at least 100 times greater than to other antigens in the complement system.

In some embodiments, the MASP-2 inhibitory antibodies specifically bind to human MASP-2 with a $K_D$ (dissociation constant) of less than about 100 nM, or less than about 50 nM, or less than about 25 nM, or less than about 10 nM, or less than about 5 nM, or less than or equal to about 1 nM, or less than or equal to 0.1 nM. The binding affinity of the MASP-2 inhibitory antibodies can be determined using a suitable binding assay known in the art, such as an ELISA assay, as described in Examples 3-5 herein.

Potency of MASP-2 Inhibitory Antibodies

In one embodiment, a MASP-2 inhibitory antibody is sufficiently potent to inhibit MASP-2 dependent complement activation at an $IC_{50}\leq 30$ nM, preferably less than or about 20 nM, or less than about 10 nM or less than about 5 nM, or less than or equal to about 3 nM, or less than or equal to about 1 nM when measured in 1% serum.

In one embodiment, a MASP-2 inhibitory antibody is sufficiently potent to inhibit MASP-2 dependent complement activation at an $IC_{50}\leq 30$ nM, preferably less than or about 20 nM, or less than about 10 nM or less than about 5 nM, or less than or equal to about 3 nM, or less than or equal to about 1 nM, when measured in 90% serum.

The inhibition of MASP-2-dependent complement activation is characterized by at least one of the following changes in a component of the complement system that occurs as a result of administration of a MASP-2 inhibitory antibody: the inhibition of the generation or production of MASP-2-dependent complement activation system products C4a, C3a, C5a and/or C5b-9 (MAC) (measured, for example, as described in Example 2 of U.S. Pat. No. 7,919,094) as well as their catabolic degradation products (e.g., C3desArg), the reduction of C4 cleavage and C4b deposition (measured, for example, as described in Example 5) and its subsequent catabolic degradation products (e.g., C4bc or C4d), or the reduction of C3 cleavage and C3b deposition (measured, for example, as described in Example 5), or its subsequent catabolic degradation products (e.g., C3bc, C3d, etc).

In some embodiments, the MASP-2 inhibitory antibodies of the invention are capable of inhibiting C3 deposition in full serum to less than 80%, such as less than 70%, such as less than 60%, such as less than 50%, such as less than 40%, such as less than 30%, such as less than 20%, such as less than 15%, such as less than 10% of control C3 deposition.

In some embodiments, the MASP-2 inhibitory antibodies of the invention are capable of inhibiting C4 deposition in full serum to less than 80%, such as less than 70%, such as less than 60%, such as less than 50%, such as less than 40%, such as less than 30%, such as less than 20%, such as less than 15%, such as less than 10% of control C4 deposition.

In some embodiments, the anti-MASP-2 inhibitory antibodies selectively inhibit MASP-2 complement activation (i.e., bind to MASP-2 with at least 100-fold or greater affinity than to C1r or C1s), leaving the C1 q-dependent complement activation system functionally intact (i.e., at least 80%, or at least 90%, or at least 95%, or at least 98%, or 100% of the classical pathway activity is retained).

In some embodiments, the subject anti-MASP-2 inhibitory antibodies have the following characteristics: (a) high affinity for human MASP-2 (e.g., a $K_D$ of 10 nM or less, preferably a $K_D$ of 1 nM or less), and (b) inhibit MASP-2 dependent complement activity in 90% human serum with an $IC_{50}$ of 30 nM or less, preferably an $IC_{50}$ of 10 nM or less).

Figure 5A:
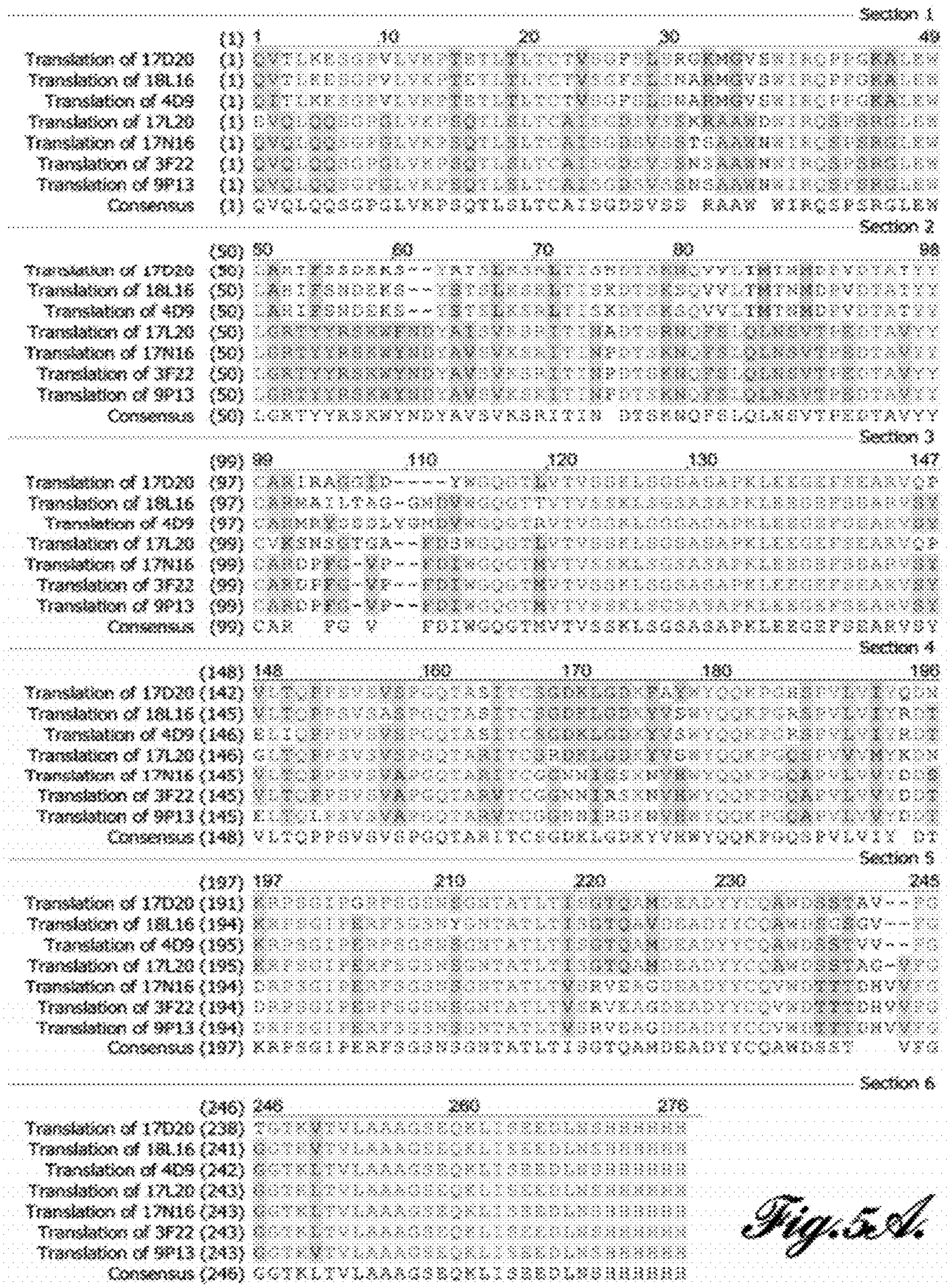
FIG. 5A is an amino acid sequence alignment of full length scFv clones 17D20 (SEQ ID NO;55), 18L16 (SEQ ID NO:56)4D9 (SEQ ID NO:57), 17L20 (SEQ ID NO:58), 17N16 (SEQ ID NO:59), 3F22 (SEQ ID NO:60) and 9P13 (SEQ ID NO:61) wherein a comparison of the heavy chain region (residues 1-120) of the most active clones reveals two distinct groups belonging to VH2 and VH6 gene family, respectively, as described in Example 4.
Figure 5B:
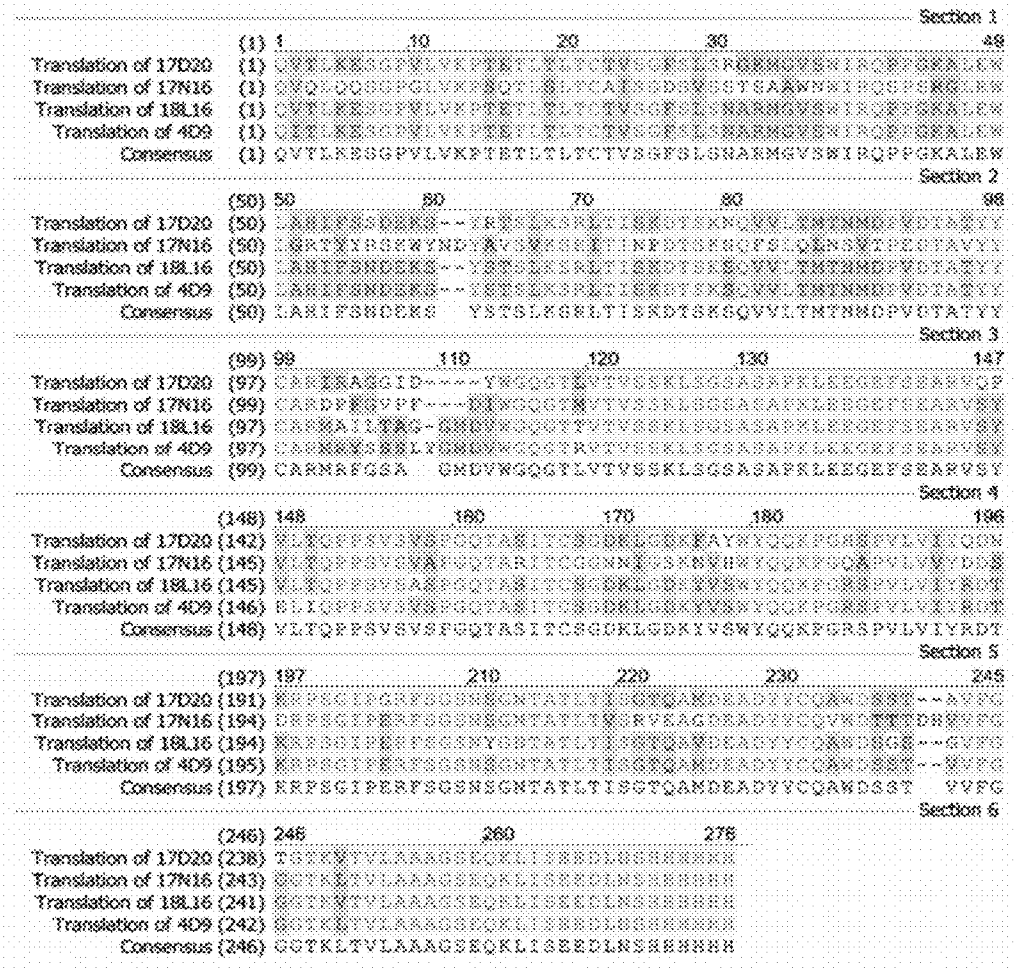
FIG. 5B is an amino acid sequence alignment of the say clones 17D20 (SEQ ID NO:55), 17N16 (SEQ ID NO:59), 18L16 (SEQ ID NO:56) and 4D9 (SEQ ID NO:57), as described in Example 4.

As described in Examples 2-12, fully human antibodies have been identified that bind with high affinity to MASP-2 and inhibit lectin-mediated complement activation while leaving the classical (C1q-dependent) pathway component of the immune system intact. The variable light and heavy chain fragments of the antibodies have been sequenced, isolated and analyzed in both a scFv format and in a full length IgG format. FIG. 5A is an amino acid sequence alignment of seven scFv anti-MASP-2 clones that were identified as having high binding affinity to MASP-2 and the ability to inhibit MASP-2 dependent activity. FIG. 5B is an amino acid sequence alignment of four of the scFv mother clones 17D20, 17N16, 18L16 and 4D9, showing the framework regions and the CDR regions. The scFv mother clones 17D20 and 17N16 were subjected to affinity maturation, leading to the generation of daughter clones with higher affinity and increased potency as compared to the mother clones, as described in Examples 6 and 7. The amino acid sequences of the heavy chain variable regions (VH) (aa 1-120) and the light chain variable regions (VL) (aa 148-250) of the scFv clones shown in FIGS. 5A and 5B and the resulting daughter clones, is provided below in TABLE 2.

Substitutable positions of a human anti-MASP-2 inhibitory antibody, as well the choice of amino acids that may be substituted into those positions, are revealed by aligning the heavy and light chain amino acid sequences of the anti-MASP-2 inhibitory antibodies discussed above, and determining which amino acids occur at which positions of those antibodies. In one exemplary embodiment, the heavy and light chain amino acid sequences of FIGS. 5A and 5B are aligned, and the identity of amino acids at each position of the exemplary antibodies is determined. As illustrated in FIGS. 5A and 5B (illustrating the amino acids present at each position of the heavy and light chains of the exemplary MASP-2 inhibitory antibodies), several substitutable positions, as well as the amino acid residues that can be substituted into those positions, are readily identified. In another exemplary embodiment, the light chain amino acid sequences of the mother and daughter clones are aligned and the identity of amino acids at each position of the exemplary antibodies is determined in order to determine substitutable positions, as well as the amino acid residues that can be substituted into these positions.

TABLE 2

Sequences of representative anti-MASP-2 antibodies

| ID Reference: | mother/daughter | VH | VL | antibody type |
|---|---|---|---|---|
| 17D20 | mother clone | SEQ ID NO: 18 | SEQ ID NO: 22 | scFv |
| 17D20_35VH-21N11VL (OMS644) | daughter clone | SEQ ID NO: 20 (one aa change in VH (A to R) at position 102 of SEQ ID NO: 18) | SEQ ID NO: 24 (10 aa changes from parent VL) | IgG2 |
| 17D20_35VH-21N11VL (OMS645) | daughter clone | SEQ ID NO: 20 (one aa change in VH (A to R) at position 102 of SEQ ID NO: 18) | SEQ ID NO: 24 | IgG4 |
| 17D20_35VH-21N11VL (OMS646) | daughter clone | SEQ ID NO: 20 (one aa change in VH (A to R) at position 102 of SEQ ID NO: 18) | SEQ ID NO: 24 | IgG4 (mutant IgG4 hinge region) |
| 17N16 | mother | SEQ ID NO: 21, | SEQ ID NO: 25 | scFv |
| 17N16_17N9 (OMS641) | daughter | SEQ ID NO: 21 | SEQ ID NO: 27 (17aa changes from SEQ ID NO: 25) | IgG2 |
| 17N16_17N9 (OMS642) | daughter | SEQ ID NO: 21 | SEQ ID NO: 27 | IgG4 |
| 17N16_17N9 (OMS643) | daughter | SEQ ID NO: 21 | SEQ ID NO: 27 | IgG4 (mutant IgG4 hinge region) |

In certain embodiments, a subject human anti-MASP-2 monoclonal inhibitory antibody has a heavy chain variable domain that is substantially identical (e.g., at least about 70%, at least 75%, at least about 80%, at least about 85%, at least about 90%, at least about 95%, or at least about 96% identical, or at least about 97% identical, or at least about 98% identical, or at least 99% identical), to that of any of the heavy chain variable domain sequences set forth in TABLE 2.

In some embodiments, a subject human anti-MASP-2 monoclonal inhibitory antibody has a heavy chain variable domain that is substantially identical (e.g., at least about 70%, at least 75%, at least about 80%, at least about 85%, at least about 90%, at least about 95%, or at least about 96% identical, or at least about 97% identical, or at least about 98% identical, or at least 99% identical) to 17D20 (VH), set forth as SEQ ID NO:18. In some embodiments, the subject human anti-MASP-2 monoclonal inhibitory antibody has a heavy chain variable domain that comprises, or consists of SEQ ID NO:18.

In some embodiments, a subject human anti-MASP-2 monoclonal inhibitory antibody has a heavy chain variable domain that is substantially identical (e.g. at least about 70%, at least 75%, at least about 80%, at least about 85%, at least about 90%, at least about 95%, at least about 96% identical, at least about 97% identical, at least about 98% identical, or at least 99% identical) to 17D20_cd35VH2N11 (VH), set forth as SEQ ID NO:20. In some embodiments, the subject human anti-MASP-2 monoclonal inhibitory antibody has a heavy chain variable domain that comprises, or consists of SEQ ID NO:20.

In some embodiments, a subject human anti-MASP-2 monoclonal inhibitory antibody has a heavy chain variable domain that is substantially identical (e.g., at least about 70%, at least 75%, at least about 80%, at least about 85%, at least about 90%, at least about 95%, or at least about 96% identical, or at least about 97% identical, or at least about 98% identical, or at least 99% identical) to 17N16 (VH), set forth as SEQ ID NO:21. In some embodiments, the subject human anti-MASP-2 monoclonal inhibitory antibody has a heavy chain variable domain that comprises, or consists of SEQ ID NO:21.

In some embodiments, a subject human anti-MASP-2 monoclonal inhibitory antibody has a light chain variable domain that is substantially identical (e.g., at least about 70%, at least 75%, at least about 80%, at least about 85%, at least about 90%, at least about 95%, or at least about 96% identical, or at least about 97% identical, or at least about 98% identical, or at least 99% identical), to that of any of the light chain variable domain sequences set forth in TABLE 2.

In some embodiments, a subject human anti-MASP-2 monoclonal inhibitory antibody has a light chain variable domain that is substantially identical (e.g., at least about 70%, at least 75%, at least about 80%, at least about 85%, at least about 90%, at least about 95%, or at least about 96% identical, or at least about 97% identical, or at least about 98% identical, or at least 99% identical) to 17D20 (VL), set forth as SEQ ID NO:22. In some embodiments, the subject human anti-MASP-2 monoclonal inhibitory antibody has a light chain that comprises, or consists of SEQ ID NO:22.

In some embodiments, a subject human anti-MASP-2 monoclonal inhibitory antibody has a light chain variable domain that is substantially identical (e.g., at least about 70%, at least 75%, at least about 80%, at least about 85%, at least about 90%, at least about 95%, or at least about 96% identical, or at least about 97% identical, or at least about 98% identical, or at least 99% identical) to 17D20_35VH-21N11VL (VL), set forth as SEQ ID NO:24. In some embodiments, the subject human anti-MASP-2 monoclonal inhibitory antibody has a light chain that comprises, or consists of SEQ ID NO:24.

In some embodiments, a subject human anti-MASP-2 monoclonal inhibitory antibody has a light chain variable domain that is substantially identical (e.g., at least about 70%, at least 75%, at least about 80%, at least about 85%, at least about 90%, at least about 95%, or at least about 96% identical, or at least about 97% identical, or at least about 98% identical, or at least 99% identical) to 17N16 (VL), set forth as SEQ ID NO:25. In some embodiments, the subject human anti-MASP-2 monoclonal inhibitory antibody has a light chain that comprises, or consists of SEQ ID NO:25.

In some embodiments, a subject human anti-MASP-2 monoclonal inhibitory antibody has a light chain variable domain that is substantially identical (e.g., at least about 70%, at least 75%, at least about 80%, at least about 85%, at least about 90%, at least about 95%, or at least about 96% identical, or at least about 97% identical, or at least about 98% identical, or at least 99% identical) to 17N16_17N9 (VL), set forth as SEQ ID NO:27. In some embodiments, the subject human anti-MASP-2 monoclonal inhibitory antibody has a light chain that comprises, or consists of SEQ ID NO:27.

In some embodiments, the anti-MASP-2 antibodies of the invention contain a heavy or light chain that is encoded by a nucleotide sequence that hybridizes under high stringency conditions to a nucleotide sequence encoding a heavy or light chain, as set forth in TABLE 2. High stringency conditions include incubation at 50° C. or higher in 0.1xSSC (15 mM saline/0.15 mM sodium citrate).

In some embodiments, the anti-MASP-2 inhibitory antibodies of the invention have a heavy chain variable region comprising one or more CDRs (CDR1, CDR2 and/or CDR3) that are substantially identical (e.g., at least about 70%, at least 75%, at least about 80%, at least about 85%, at least about 90%, at least about 95%, or at least about 96% identical, or at least about 97% identical, or at least about 98% identical, or at least 99% identical), or comprise or consist of the identical sequence as compared to the amino acid sequence of the CDRs of any of the heavy chain variable sequences shown in FIG. 5A or 5B, or described below in TABLES 3A-F and TABLE 4.

In some embodiments, the anti-MASP-2 inhibitory antibodies of the invention have a light chain variable region comprising one or more CDRs (CDR1, CDR2 and/or CDR3) that are substantially identical (e.g., at least about 70%, at least 75%, at least about 80%, at least about 85%, at least about 90%, at least about 95%, or at least about 96% identical, or at least about 97% identical, or at least about 98% identical, or at least 99% identical), or comprise or consist of the identical sequence as compared to the amino acid sequence of the CDRs of any of the light chain variable sequences shown in FIGS. 5A or 5B, or described below in TABLES 4A-F and TABLE 5.

Heavy Chain Variable Region

TABLE 3A

| Heavy chain (aa 1-20) Heavy chain | | | | | | | | | | | | | | | | | | | | |
|---|---|---|---|---|---|---|---|---|---|---|---|---|---|---|---|---|---|---|---|---|
| aa | 1 | 2 | 3 | 4 | 5 | 6 | 7 | 8 | 9 | 10 | 11 | 12 | 13 | 14 | 15 | 16 | 17 | 18 | 19 | 20 |
| 17D20m (SEQ: 18) | Q | V | T | L | K | E | S | G | P | V | L | V | K | P | T | E | T | L | T | L |
| d3521N11 (SEQ: 20) | Q | V | T | L | K | E | S | G | P | V | L | V | K | P | T | E | T | L | T | L |
| 17N16m (SEQ: 21) | Q | V | Q | L | Q | Q | S | G | P | G | L | V | K | P | S | Q | T | L | S | L |
| d17N9 (SEQ: 21) | Q | V | Q | L | Q | Q | S | G | P | G | L | V | K | P | S | Q | T | L | S | L |

TABLE 3B

| Heavy chain (aa 21-40) Heavy chain | | | | | | | | | | | | | | | | | | | | |
|---|---|---|---|---|---|---|---|---|---|---|---|---|---|---|---|---|---|---|---|---|
| | | | | | | CDR-H1 | | | | | | | | | | | | | | |
| aa | 21 | 22 | 23 | 24 | 25 | 26 | 27 | 28 | 29 | 30 | 31 | 32 | 33 | 34 | 35 | 36 | 37 | 38 | 39 | 40 |
| 17D20m (SEQ: 18) | T | C | T | V | S | G | F | S | L | S | **R** | **G** | **K** | **M** | **G** | V | S | W | I | R |
| d3521N11 (SEQ: 20) | T | C | T | V | S | G | F | S | L | S | **R** | **G** | **K** | **M** | **G** | V | S | W | I | R |
| 17N16m (SEQ: 21) | T | C | A | I | S | G | D | S | V | S | **S** | **T** | **S** | **A** | **A** | W | N | W | I | R |

TABLE 3B-continued

| Heavy chain (aa 21-40) | | | | | | | | | | | | | | | | | | | | |
|---|---|---|---|---|---|---|---|---|---|---|---|---|---|---|---|---|---|---|---|---|
| | | | | | | CDR-H1 | | | | | | | | | | | | | | |
| aa | 21 | 22 | 23 | 24 | 25 | 26 | 27 | 28 | 29 | 30 | 31 | 32 | 33 | 34 | 35 | 36 | 37 | 38 | 39 | 40 |
| d17N9 (SEQ: 21) | T | C | A | I | S | G | D | S | V | S | **S** | **T** | **S** | **A** | **A** | W | N | W | I | R |

TABLE 3C

| Heavy chain (aa 41-60) | | | | | | | | | | | | | | | | | | | | |
|---|---|---|---|---|---|---|---|---|---|---|---|---|---|---|---|---|---|---|---|---|
| | | | | | | | | | | CDR-H2 | | | | | | | | | | |
| aa | 41 | 42 | 43 | 44 | 45 | 46 | 47 | 48 | 49 | 50 | 51 | 52 | 53 | 54 | 55 | 56 | 57 | 58 | 59 | 60 |
| 17D20m (SEQ: 18) | Q | P | P | G | K | A | L | E | W | **L** | **A** | **H** | **I** | **F** | **S** | **S** | **D** | **E** | **K** | **S** |
| d3521N11 (SEQ: 20) | Q | P | P | G | K | A | L | E | W | **L** | **A** | **H** | **I** | **F** | **S** | **S** | **D** | **E** | **K** | **S** |
| 17N16m (SEQ: 21) | Q | S | P | S | R | G | L | E | W | **L** | **G** | **R** | **T** | **Y** | **Y** | **R** | **S** | **K** | **W** | **Y** |
| d17N9 (SEQ: 21) | Q | S | P | S | R | G | L | E | W | **L** | **G** | **R** | **T** | **Y** | **Y** | **R** | **S** | **K** | **W** | **Y** |

TABLE 3D

| Heavy chain (aa 61-80) | | | | | | | | | | | | | | | | | | | | |
|---|---|---|---|---|---|---|---|---|---|---|---|---|---|---|---|---|---|---|---|---|
| | CDR-H2 (cont'd) | | | | | | | | | | | | | | | | | | | |
| aa | 61 | 62 | 63 | 64 | 65 | 66 | 67 | 68 | 69 | 70 | 71 | 72 | 73 | 74 | 75 | 76 | 77 | 78 | 79 | 80 |
| 17D20m (SEQ: 18) | **Y** | **R** | **T** | **S** | **L** | K | S | R | L | T | I | S | K | D | T | S | K | N | Q | V |
| d3521N11 (SEQ: 20) | **Y** | **R** | **T** | **S** | **L** | K | S | R | L | T | I | S | K | D | T | S | K | N | Q | V |
| 17N16m (SEQ: 21) | **N** | **D** | **Y** | **A** | **V** | S | V | K | S | R | I | T | I | N | P | D | T | S | K | N |
| d17N9 (SEQ: 21) | **N** | **D** | **Y** | **A** | **V** | S | V | K | S | R | I | T | I | N | P | D | T | S | K | N |

TABLE 3E

| Heavy chain (aa 81-100) | | | | | | | | | | | | | | | | | | | | |
|---|---|---|---|---|---|---|---|---|---|---|---|---|---|---|---|---|---|---|---|---|
| | | | | | | | | | | | | | | | CDR-H3 | | | | | |
| aa | 81 | 82 | 83 | 84 | 85 | 86 | 87 | 88 | 89 | 90 | 91 | 92 | 93 | 94 | 95 | 96 | 97 | 98 | 99 | 100 |
| 17D20m (SEQ: 18) | V | L | T | M | T | N | M | D | P | V | D | T | A | T | **Y** | **Y** | **C** | **A** | **R** | **I** |
| d3521N11 (SEQ: 20) | V | L | T | M | T | N | M | D | P | V | D | T | A | T | **Y** | **Y** | **C** | **A** | **R** | **I** |
| 17N16m (SEQ: 21) | Q | F | S | L | Q | L | N | S | V | T | P | E | D | T | **A** | **V** | **Y** | **Y** | **C** | **A** |
| d17N9 (SEQ: 21) | Q | F | S | L | Q | L | N | S | V | T | P | E | D | T | **A** | **V** | **Y** | **Y** | **C** | **A** |

TABLE 3F

| | heavy chain (aa 101-118) Heavy chain | | | | | | | | | |
|---|---|---|---|---|---|---|---|---|---|---|
| | CDR-H3 (cont'd) | | | | | | | | | |
| aa | 101 | 102 | 103 | 104 | 105 | 106 | 107 | 108 | 109 | 110 |
| 17D20m (SEQ: 19) | **R** | **A** | G | G | I | D | Y | W | G | Q |
| d3521N11 (SEQ: 20) | **R** | **R** | G | G | I | D | Y | W | G | Q |
| 17N16m (SEQ: 21) | **R** | **D** | P | F | G | V | P | F | D | I |
| d17N9 (SEQ: 21) | **R** | **D** | P | F | G | V | P | F | D | I |

| | CDR-H3 (cont'd) | | | | | | | | | |
|---|---|---|---|---|---|---|---|---|---|---|
| aa | 111 | 112 | 113 | 114 | 115 | 116 | 117 | 118 | 119 | 120 |
| 17D20m (SEQ: 19) | G | T | L | V | T | V | S | S | | |
| d3521N11 (SEQ: 20) | G | T | L | V | T | V | S | S | | |
| 17N16m (SEQ: 21) | W | G | Q | G | T | M | V | T | V | S |
| d17N9 (SEQ: 21) | W | G | Q | G | T | M | V | T | V | S |

Presented below are the heavy chain variable region (VH) sequences for the mother clones and daughter clones listed above in TABLE 2 and TABLES 3A-F.

The Kabat CDRs (31-35 (H1), 50-65 (H2) and 95-102 (H3)) are bolded; and the Chothia CDRs (26-32 (H1), 52-56 (H2) and 95-101 (H3)) are underlined.

```
17D20 heavy chain variable region (VH)
(SEQ ID NO: 18):
QVTLKESGPVLVKPTETLTLTCTVSGFSLSRGKMGVSWIRQPPGKALEWLA

HIFSSDEKSYRTSLKSRLTISKDTSKNQVVLTMTNMDPVDTATYYCARIRA

GGIDYWGQGTLVTVSS

17D20_35VH-21N11VL heavy chain variable region (VH)
(SEQ ID NO: 20)
QVTLKESGPVLVKPTETLTLTCTVSGFSLSRGKMGVSWIRQPPGKALEWLA

HIFSSDEKSYRTSLKSRLTISKDTSKNQVVLTMTNMDPVDTATYYCARIRR

GGIDYWGQGTLVTVSS

17N16 heavy chain variable region (VH)
(SEQ ID NO: 21)
QVQLQQSGPGLVKPSQTLSLTCAISGDSVSSTSAAWNWIRQSPSRGLEWL

GRTYYRSKWYNDYAVSVKSRITINPDTSKNQFSLQLNSVTPEDTAVYYCA

RDPFGVPFDIWGQGTMVTVSS
```

TABLE 4

| Heavy Chain CDRs | | | |
|---|---|---|---|
| Clone Reference | CDR | aa Sequence | SEQ ID NO: |
| 17D20m | CDR-H1 (kabat) | RGKMG | 28 |
| d3521N11 | CDR-H1 (kabat) | RGKMG | 28 |
| 17N16m | CDR-H1 (kabat) | STSAA | 29 |
| d17N9 | CDR-H1 (kabat) | STSAA | 29 |
| 17D20m | CDR-H1 (chothia) | GFSLSRG | 30 |
| d3521N11 | CDR-H1 (chothia) | GFSLSRG | 30 |
| 17N16m | CDR-H1 (chothia) | GDSVSST | 31 |
| d17N9 | CDR-H1 (chothia) | GDSVSST | 31 |
| 17D20m | CDR-H2 (kabat) | LAHIFSSDEKSYRTSL | 32 |
| d3521N11 | CDR-H2 (kabat) | LAHIFSSDEKSYRTSL | 32 |
| 17N16m | CDR-H2 (kabat) | LGRTYYRSKWYNDYAV | 33 |
| d17N9 | CDR-H2 (chothia) | LGRTYYRSKWYNDYAV | 33 |

TABLE 4-continued

| Heavy Chain CDRs | | | |
|---|---|---|---|
| Clone Reference | CDR | aa Sequence | SEQ ID NO: |
| 17D20m | CDR-H2 (chothia) | HIFSS | 34 |
| d3521N11 | CDR-H2 (chothia) | HIFSS | 34 |
| 17N16m | CDR-H2 (chothia) | RTYYR | 35 |
| d17N9 | CDR-H2 (chothia) | RTYYR | 35 |
| 17D20m | CDR-H3 (kabat) | YYCARIRA | 36 |
| d3521N11 | CDR-H3 (kabat) | YYCARIRR | 37 |
| 17D20m and d3521N11 consensus | CDR-H3 (kabat) | YYCARIRX (wherein X at position 8 is A (Ala) or R (Arg)) | 90 |
| 17N16m | CDR-H3 (kabat) | AVYYCARD | 38 |
| d17N9 | CDR-H3 (kabat) | AVYYCARD | 38 |
| 17D20m | CDR-H3 (chothia) | YYCARIR | 39 |
| d3521N11 | CDR-H3 (chothia) | YYCARIR | 39 |
| 17N16m | CDR-H3 (chothia) | AVYYCAR | 40 |
| d17N9 | CDR-H3 (chothia) | AVYYCAR | 40 |

Light Chain Variable Regions

TABLE 5A

| Light chain (aa 1-20) Light chain | | | | | | | | | | | | | | | | | | | | |
|---|---|---|---|---|---|---|---|---|---|---|---|---|---|---|---|---|---|---|---|---|
| aa | 1 | 2 | 3 | 4 | 5 | 6 | 7 | 8 | 9 | 10 | 11 | 12 | 13 | 14 | 15 | 16 | 17 | 18 | 19 | 20 |
| 17D20m (SEQ: 22) | Q | P | V | L | T | Q | P | P | S | V | S | V | S | P | G | Q | T | A | S | I |
| d3521N11 (SEQ: 24) | Q | P | V | L | T | Q | P | P | S | **L** | S | V | S | P | G | Q | T | A | S | I |
| 17N16m (SEQ: 25) | S | Y | V | L | T | Q | P | P | S | V | S | V | A | P | G | Q | T | A | R | I |
| d17N9 (SEQ: 27) | S | Y | **E** | L | **I** | Q | P | P | S | V | S | V | A | P | G | Q | T | A | **T** | I |

TABLE 5B

| Light chain (aa 21-40) Light chain | | | | | | | | | | | | | | | | | | | | |
|---|---|---|---|---|---|---|---|---|---|---|---|---|---|---|---|---|---|---|---|---|
| | | | | CDR-L1 | | | | | | | | | | | | | | | | |
| aa | 21 | 22 | 23 | 24 | 25 | 26 | 27 | 28 | 29 | 30 | 31 | 32 | 33 | 34 | 35 | 36 | 37 | 38 | 39 | 40 |
| 17D20m (SEQ: 22) | T | C | S | G | D | K | L | G | D | K | F | A | Y | W | Y | Q | Q | K | P | G |
| d3521N11 (SEQ: 24) | T | C | S | G | **E** | K | L | G | D | K | **Y** | **A** | Y | W | Y | Q | Q | K | P | G |
| 17N16m (SEQ: 25) | T | C | G | G | N | N | I | G | S | K | N | V | H | W | Y | Q | Q | K | P | G |
| d17N9 (SEQ: 27) | T | C | **A** | G | **D** | N | **L** | G | **K** | K | **R** | V | H | W | Y | Q | Q | **R** | P | G |

TABLE 5C

| Light chain (aa 41-60) Light chain | | | | | | | | | | | | | | | | | | | | |
|---|---|---|---|---|---|---|---|---|---|---|---|---|---|---|---|---|---|---|---|---|
| | | | | | | | | | | CDR-L2 | | | | | | | | | | |
| aa | 41 | 42 | 43 | 44 | 45 | 46 | 47 | 48 | 49 | 50 | 51 | 52 | 53 | 54 | 55 | 56 | 57 | 58 | 59 | 60 |
| 17D20m (SEQ: 22) | H | S | P | V | L | V | I | Y | Q | D | N | K | R | P | S | G | I | P | G | R |
| d3521N11 (SEQ: 24) | **Q** | S | P | V | L | V | **M** | Y | Q | D | **K** | **Q** | R | P | S | G | I | P | **E** | R |
| 17N16m (SEQ: 25) | Q | A | P | V | L | V | V | Y | D | D | S | D | R | P | S | G | I | P | E | R |
| d17N9 (SEQ: 27) | Q | A | P | V | L | V | **I** | Y | D | D | S | D | R | P | S | G | I | P | **D** | R |

TABLE 5D

| Light chain (aa 61-80) Light chain | | | | | | | | | | | | | | | | | | | | |
|---|---|---|---|---|---|---|---|---|---|---|---|---|---|---|---|---|---|---|---|---|
| | CDR-L2 (cont'd) | | | | | | | | | | | | | | | | | | | |
| aa | 61 | 62 | 63 | 64 | 65 | 66 | 67 | 68 | 69 | 70 | 71 | 72 | 73 | 74 | 75 | 76 | 77 | 78 | 79 | 80 |
| 17D20m (SEQ: 22) | F | S | G | S | N | S | G | N | T | A | T | L | T | I | S | G | T | Q | A | M |
| d3521N11 (SEQ: 24) | F | S | G | S | N | S | G | N | T | A | T | L | T | I | S | G | T | Q | A | M |
| 17N16m (SEQ: 25) | F | S | G | S | N | S | G | N | T | A | T | L | T | V | S | R | V | E | A | G |
| d17N9 (SEQ: 27) | F | S | **A** | S | N | S | G | N | T | A | T | L | T | **I** | **T** | R | **G** | E | A | G |

TABLE 5E

| Light chain (aa 81-100) Light chain | | | | | | | | | | | | | | | | | | | | |
|---|---|---|---|---|---|---|---|---|---|---|---|---|---|---|---|---|---|---|---|---|
| | | | | | | | | | CDR-L3 | | | | | | | | | | | |
| aa | 81 | 82 | 83 | 84 | 85 | 86 | 87 | 88 | 89 | 90 | 91 | 92 | 93 | 94 | 95 | 96 | 97 | 98 | 99 | 100 |
| 17D20m (SEQ: 22) | D | E | A | D | Y | Y | C | Q | A | W | D | S | S | T | A | V | F | G | T | G |
| d3521N11 (SEQ: 24) | D | **X** | A | D | Y | Y | C | Q | A | W | D | S | S | T | A | V | F | G | **G** | G |
| 17N16m (SEQ: 25) | D | E | A | D | Y | Y | C | Q | V | W | D | T | T | T | D | H | V | V | F | G |
| d17N9 (SEQ: 27) | D | E | A | D | Y | Y | C | Q | V | W | D | **I** | **A** | T | D | H | V | V | F | G |

TABLE 5F

| Light chain (aa 101-120) Light chain | | | | | | | | | | |
|---|---|---|---|---|---|---|---|---|---|---|
| | CDR-L3 (cont'd) | | | | | | | | | |
| aa | 101 | 102 | 103 | 104 | 105 | 106 | 107 | 108 | 109 | 110 |
| 17D20m (SEQ: 22) | T | K | V | T | V | L | A | A | A | G |
| d3521N11 (SEQ: 24) | T | K | **L** | T | V | L | A | A | A | G |
| 17N16m (SEQ: 25) | G | G | T | K | L | T | V | L | A | A |

TABLE 5F-continued

| Light chain (aa 101-120) Light chain | | | | | | | | | | |
|---|---|---|---|---|---|---|---|---|---|---|
| d17N9 (SEQ: 27) | G | G | T | K | L | T | V | L | A | A |
| | CDR-L3 (cont'd) | | | | | | | | | |
| aa | 111 | 112 | 113 | 114 | 115 | 116 | 117 | 118 | 119 | 120 |
| 17D20m (SEQ: 22) | S | E | Q | K | L | I | S | E | E | D |
| d3521N11 (SEQ: 24) | S | E | Q | K | L | I | S | E | E | D |
| 17N16m (SEQ: 25) | A | G | S | E | Q | K | L | I | S | E |
| d17N9 (SEQ: 27) | A | G | S | E | Q | K | L | I | S | E |

Presented below are the light chain variable region (VL) sequences for the mother clones and daughter clones listed above in TABLE 2 and TABLES 5A-F.

The Kabat CDRs (24-34 (L1); 50-56 (L2); and 89-97 (L3) are bolded; and the Chothia CDRs (24-34 (L1); 50-56 (L2) and 89-97 (L3) are underlined. These regions are the same whether numbered by the Kabat or Chothia system.

17D20m light chain variable region (VL) (SEQ ID NO: 22)

QPVLTQPPSVSVSPGQTASITCSGDKLGDKFAYWYQQKPGHSPVLVIYQD
NKRPSGIPGRFSGSNSGNTATLTISGTQAMDEADYYCQAWDSSTAVFGTG
TKVTVLA

17D20m_d3521N11 light chain variable region (VL) (SEQ ID NO: 24)

QPVLTQPPSLSVSPGQTASITCSGEKLGDKYAYWYQQKPGQSPVLVMYQD

-continued

KQRPSGIPERFSGSNSGNTATLTISGTQAMDEADYYCQAWDSSTAVFGGG
TKLTVL

17N16m light chain variable region (VL) (SEQ ID NO: 25)

SYVLTQPPSVSVAPGQTARITCGGNNIGSKNVHWYQQKPGQAPVLVVYDD
SDRPSGIPERFSGSNSGNTATLTVSRVEAGDEADYYCQVWDTTTDHVVFG
GGTKLTVLAAAGSEQKLISE

17N16m_d17N9 light chain variable region (VL) (SEQ ID NO: 27)

SYELIQPPSVSVAPGQTATITCAGDNLGKKRVHWYQQRPGQAPVLVIYDD
SDRPSGIPDRFSASNSGNTATLTITRGEAGDEADYYCQVWDIATDHVVFG
GGTKLTVLAAAGSEQKLISE

TABLE 6

| Light Chain CDRs (Kabat/chothia) | | | |
|---|---|---|---|
| Reference | CDR | aa Sequence | SEQ ID NO: |
| 17D20m | CDR-L1 | GDKLGDKFAYW | 41 |
| d3521N11 | CDR-L1 | G**E**KLGDK**Y**AYW | 42 |
| 17D20m and d3521N11 consensus | CDR-L1 | GXKLGDKXAYW (wherein X at position 2 is D (Asp) or E (Glu); and wherein X at position 8 is F (Phe) or Y (Tyr) | 91 |
| 17N16m | CDR-L1 | GNNIGSKNVHW | 43 |
| d17N9 | CDR-L1 | G**D**N**L**G**K**K**R**VHW | 44 |
| 17N16m and d17N9 consensus | CDR-L1 | GXNXGXKXVHW (wherein X at position 2 is N (Asn) or D (Asp); wherein X at position 4 is I (Ile) or L (Leu); wherein X at position 6 is S (Ser) or K (Lys); and wherein X at position 8 is N (Asn) or R (Arg)) | 92 |
| d17N9 | CDR-L1 (aa23-38) | **A**G**D**N**L**G**K**K**R**VHWYQQ**R** | 45 |
| 17D20m | CDR-L2 | DNKRPSG | 46 |
| d3521N11 | CDR-L2 | D**KQ**RPSG | 47 |

TABLE 6-continued

| Light Chain CDRs (Kabat/chothia) | | | |
|---|---|---|---|
| Reference | CDR | aa Sequence | SEQ ID NO: |
| d3521N11 | CDR-L2 (aa50-60) | D**KQ**RPSGIP**E**R | 48 |
| 17N16m | CDR-L2 | DSDRPSG | 49 |
| d17N9 | CDR-L2 | DSDRPSG | 49 |
| 17D20m, d3521N11, 17N16m, d17N9 consensus | CDR-L2 | DXXRPSG (wherein X at position 2 is N (Asn), K (Lys) or S (Ser); and wherein X at position 3 is K (Lys), Q (Gln) or D (Asp)) | 93 |
| d17N9 | CDR-L2 (aa 50-63) | DSDRPSGIP**D**RFS**A** | 50 |
| 17D20m | CDR-L3 | AWDSSTAVF | 51 |
| d3521N11 | CDR-L3 | AWDSSTAVF | 51 |
| d3521N11 | CDR-L3 (aa 89-104) | AWDSSTAVFG**G**GTK**L**T | 52 |
| 17N16m | CDR-L3 | VWDTTTDHV | 53 |
| d17N9 | CDR-L3 | VWD**IA**TDHV | 54 |
| 17N16m and d17N9 consensus | CDR-L3 | VWDXXTDHV (wherein X at position 4 is T (Thr) or I (Ile); and wherein X at position 5 is T (Thr) or A (Ala)) | 94 |

In one aspect, the invention provides an isolated human monoclonal antibody, or antigen binding fragment thereof, that binds to human MASP-2, comprising:

(i) a heavy chain variable region comprising CDR-H1, CDR-H2 and CDR-H3 sequences; and (ii) a light chain variable region comprising CDR-L1, CDR-L2 and CDR-L3, wherein the heavy chain variable region CDR-H3 sequence comprises an amino acid sequence set forth as SEQ ID NO:38 or SEQ ID NO:90, and conservative sequence modifications thereof, wherein the light chain variable region CDR-L3 sequence comprises an amino acid sequence set forth as SEQ ID NO:51 or SEQ ID NO:94, and conservative sequence modifications thereof, and wherein the isolated antibody inhibits MASP-2 dependent complement activation.

In one embodiment, the heavy chain variable region CDR-H2 sequence comprises an amino acid sequence set forth as SEQ ID NO:32 or 33, and conservative sequence modifications thereof. In one embodiment, the heavy chain variable region CDR-H1 sequence comprises an amino acid sequence set forth as SEQ ID NO:28 or SEQ ID NO:29, and conservative modifications thereof. In one embodiment, the light chain variable region CDR-L2 sequence comprises an amino acid sequence set forth as SEQ ID NO:93 and conservative modifications thereof. In one embodiment, the light chain variable region CDR-L1 sequence comprises an amino acid sequence set forth as SEQ ID NO:91 or SEQ ID NO:92 and conservative modifications thereof. In one embodiment, the CDR-H1 of the heavy chain variable region comprises SEQ ID NO:28.

In one embodiment, the CDR-H2 of the heavy chain variable region comprises SEQ ID NO:32. In one embodiment, the CDR-H3 of the heavy chain variable region comprises SEQ ID NO:90, (as shown in TABLE 4). In one embodiment, the amino acid sequence set forth in SEQ ID NO:90 contains an R (Arg) at position 8.

In one embodiment, the CDR-L1 of the light chain variable region comprises SEQ ID NO:91 (as shown in TABLE 6). In one embodiment, the amino acid set forth in SEQ ID NO:91 contains an E (Glu) at position 2. In one embodiment, the amino acid sequence set forth in SEQ ID NO:91 contains a Y (Tyr) at position 8.

In one embodiment, the CDR-L2 of the light chain variable region comprises SEQ ID NO: 93 (as shown in TABLE 6), and wherein the amino acid sequence set forth in SEQ ID NO:93 contains a K (Lys) at position 2. In one embodiment, the amino acid sequence set forth in SEQ ID NO:93 contains a Q (Gln) at position 3.

In one embodiment, the CDR-L3 of the light chain variable region comprises SEQ ID NO:51.

In one embodiment, said antibody or antigen binding fragment thereof binds human MASP-2 with a $K_D$ of 10 nM or less. In one embodiment, said antibody or antigen binding fragment thereof inhibits C4 activation in an in vitro assay in 1% human serum at an $IC_{50}$ of 10 nM or less. In one embodiment, said antibody or antigen binding fragment thereof inhibits C4 activation in 90% human serum with an $IC_{50}$ of 30 nM or less. In one embodiment, the conservative sequence modifications thereof comprise or consist of a molecule which contains variable regions that are identical to the recited variable domain(s), except for a combined total of 1, 2, 3, 4, 5, 6, 7, 8, 9 or 10 amino acid substitutions within the CDR regions of the heavy chain variable region, and/or up to a combined total of 1, 2, 3, 4, 5, 6, 7, 8, 9, or 10 amino acid substitutions with said CDR regions of the light chain variable region.

In another aspect, the invention provides an isolated human antibody, or antigen binding fragment thereof, that binds to human MASP-2 wherein the antibody comprises: I) a) a heavy chain variable region comprising: i) a heavy chain CDR-H1 comprising the amino acid sequence from 31-35 of SEQ ID NO:21; and ii) a heavy chain CDR-H2 comprising the amino acid sequence from 50-65 of SEQ ID NO:21; and iii) a heavy chain CDR-H3 comprising the amino acid sequence from 95-102 of SEQ ID NO:21; and b) a light chain variable region comprising: i) a light chain CDR-L1 comprising the amino acid sequence from 24-34 of either SEQ ID NO:25 or SEQ ID NO:27; and ii) a light chain CDR-L2 comprising the amino acid sequence from 50-56 of either SEQ ID NO:25 or SEQ ID NO:27; and iii) a light chain CDR-L3 comprising the amino acid sequence from 89-97 of either SEQ ID NO:25 or SEQ ID NO:27; or II) a variant thereof that is otherwise identical to said variable domains, except for up to a combined total of 1, 2, 3, 4, 5, 6, 7, 8, 9 or 10 amino acid substitutions within said CDR regions of said heavy chain variable region and up to a combined total of 1, 2, 3, 4, 5, 6, 7, 8, 9, or 10 amino acid substitutions within said CDR regions of said light chain variable region, wherein the antibody or variant thereof inhibits MASP-2 dependent complement activation. In one embodiment, said variant comprises an amino acid substitution at one or more positions selected from the group consisting of position 31, 32, 33, 34, 35, 51, 52, 53, 54, 55, 56, 57, 58, 59, 60, 61, 62, 63, 64, 65, 95, 96, 97, 98, 99, 100 or 102 of said heavy chain variable region. In one embodiment, said variant comprises an amino acid substitution at one or more positions selected from the group consisting of position 25, 26, 27, 29, 31, 32, 33, 51, 52, 89, 92, 93, 95, 96 or 97 of said light chain variable region. In one embodiment, the heavy chain of said antibody comprises SEQ ID NO:21. In one embodiment, the light chain of said antibody comprises SEQ ID NO:25. In one embodiment, the light chain of said antibody comprises SEQ ID NO:27.

In another aspect, the invention provides an isolated human monoclonal antibody that binds to human MASP-2, wherein the antibody comprises: I) a) a heavy chain variable region comprising: i) a heavy chain CDR-H1 comprising the amino acid sequence from 31-35 of SEQ ID NO:20; and ii) a heavy chain CDRH-2 comprising the amino acid sequence from 50-65 of SEQ ID NO:20; and iii) a heavy chain CDR-H3 comprising the amino acid sequence from 95-102 of either SEQ ID NO:18 or SEQ ID NO:20; and b) a light chain variable region comprising: i) a light chain CDR-L1 comprising the amino acid sequence from 24-34 of either SEQ ID NO:22 or SEQ ID NO:24; and ii) a light chain CDR-L2 comprising the amino acid sequence from 50-56 of either SEQ ID NO:22 or SEQ ID NO:24; and iii) a light chain CDR-L3 comprising the amino acid sequence from 89-97 of either SEQ ID NO:22 or SEQ ID NO:24; or II) a variant thereof that is otherwise identical to said variable domains, except for up to a combined total of 1, 2, 3, 4, 5, 6, 7, 8, 9, or 10 amino acid substitutions within said CDR regions of said heavy chain variable region and up to a combined total of 1, 2, 3, 4, 5, 6, 7, 8, 9, or 10 amino acid substitutions within said CDR regions of said light chain variable region, wherein the antibody or variant thereof inhibits MASP-2 dependent complement activation. In one embodiment, said variant comprises an amino acid substitution at one or more positions selected from the group consisting of position 31, 32, 33, 34, 35, 51, 52, 53, 54, 55, 56, 57, 58, 59, 60, 61, 62, 63, 64, 65, 95, 96, 97, 98, 99, 100 or 102 of said heavy chain variable region. In one embodiment, said variant comprises an amino acid substitution at one or more positions selected from the group consisting of position 25, 26, 27, 29, 31, 32, 33, 51, 52, 89, 92, 93, 95, 96 or 97 of said light chain variable region. In one embodiment, the heavy chain of said antibody comprises SEQ ID NO:20, or a variant thereof comprising at least 80% identity to SEQ ID NO:20 (e.g., at least 85%, at least 90%, at least 95% or at least 98% identity to SEQ ID NO:20). In one embodiment, the heavy chain of said antibody comprises SEQ ID NO:18, or a variant thereof comprising at least 80% identity to SEQ ID NO:18 (e.g., at least 85%, at least 90%, at least 95% or at least 98% identity to SEQ ID NO:18). In one embodiment, the light chain of said antibody comprises SEQ ID NO:22, or a variant thereof comprising at least 80% identity to SEQ ID NO:22 (e.g., at least 85%, at least 90%, at least 95% or at least 98% identity to SEQ ID NO:22). In one embodiment, the light chain of said antibody comprises SEQ ID NO:24, or a variant thereof comprising at least 80% identity to SEQ ID NO:24 (e.g., at least 85%, at least 90%, at least 95% or at least 98% identity to SEQ ID NO:24).

In one embodiment, said antibody binds to an epitope in the CCP1 domain of MASP-2.

In one embodiment, said antibody binds human MASP-2 with a $K_D$ of 10 nM or less. In one embodiment, said antibody inhibits C3b deposition in an in vitro assay in 1% human serum at an $IC_{50}$ of 10 nM or less. In one embodiment, said antibody inhibits C3b deposition in 90% human serum with an $IC_{50}$ of 30 nM or less.

In one embodiment, said antibody is an antibody fragment selected from the group consisting of Fv, Fab, Fab', $F(ab)_2$ and $F(ab')_2$. In one embodiment, said antibody is a single chain molecule. In one embodiment, said antibody is an IgG2 molecule. In one embodiment, said antibody is an IgG1 molecule. In one embodiment, said antibody is an IgG4 molecule. In one embodiment, said IgG4 molecule comprises a S228P mutation.

In one embodiment, said antibody does not substantially inhibit the classical pathway (i.e., the classical pathway activity is at least 80%, or at least 90% or at least 95%, or at least 95% intact).

In another aspect, the invention provides an isolated fully human monoclonal antibody or antigen-binding fragment thereof that dissociates from human MASP-2 with a $K_D$ of 10 nM or less as determined by surface plasmon resonance and inhibits C4 activation on a mannan-coated substrate with an $IC_{50}$ of 10 nM or less in 1% serum. In some embodiments, said antibody or antigen binding fragment thereof specifically recognizes at least part of an epitope recognized by a reference antibody comprising a heavy chain variable region as set forth in SEQ ID NO:20 and a light chain variable region as set forth in SEQ ID NO:24, such as reference antibody OMS646 (see TABLE 22). In accordance with the foregoing, an antibody or antigen-binding fragment thereof according to certain preferred embodiments of the present application may be one that competes for binding to human MASP-2 with any antibody described herein which both (i) specifically binds to the antigen and (ii) comprises a VH and/or VL domain disclosed herein, or comprises a CDR-H3 disclosed herein, or a variant of any of these. Competition between binding members may be assayed easily in vitro, for example using ELISA and/or by tagging a specific reporter molecule to one binding member which can be detected in the presence of other untagged binding member(s), to enable identification of specific binding members which bind the same epitope or an overlapping epitope. Thus, there is presently provided a specific antibody or antigen-binding fragment thereof, comprising a human antibody antigen-binding site which competes with an antibody described herein that binds to human MASP-2, such as any one of OMS641 to OMS646 as set forth in TABLE 24, for binding to human MASP-2.

Variant MASP-2 Inhibitory Antibodies

The above-described human monoclonal antibodies may be modified to provide variant antibodies that inhibit MASP-2 dependent complement activation. The variant antibodies may be made by substituting, adding, or deleting at least one amino acid of an above-described human monoclonal antibody. In general, these variant antibodies have the general characteristics of the above-described human antibodies and contain at least the CDRs of an above-described human antibody, or, in certain embodiments, CDRs that are very similar to the CDRs of an above-described human antibody.

In the preferred embodiment, the variant comprises one or more amino acid substitution(s) in one or more hypervariable region(s) of the parent antibody. For example, the variant may comprise at least one, e.g., from about one to about ten, such as at least 1, at least 2, at least 3, at least 4, at least 5, at least 6, at least 7, at least 8, at least 9 or at least 10 substitutions, and preferably from about two to about six, substitutions in one or more CDR regions of the parent antibody. In one embodiment, said variant comprises an amino acid substitution at one or more positions selected from the group consisting of position 31, 32, 33, 34, 35, 51, 52, 53, 54, 55, 56, 57, 58, 59, 60, 61, 62, 63, 64, 65, 95, 96, 97, 98, 99, 100 or 102 of said heavy chain variable region. In one embodiment, said variant comprises an amino acid substitution at one or more positions selected from the group consisting of position 25, 26, 27, 29, 31, 32, 33, 51, 52, 89, 92, 93, 95, 96 or 97 of said light chain variable region.

In some embodiments, the variant antibodies have an amino acid sequence that is otherwise identical to the variable domain of a subject antibody set forth in TABLE 2, except for up to a combined total of 1, 2, 3, 4, 5 or 6 amino acid substitutions within said CDR regions of said heavy chain variable region and/or up to a combined total of 1, 2, 3, 4, 5 or 6 amino acid substitutions within said CDR regions of said light chain variable region, wherein the antibody or variant thereof inhibits MASP-2 dependent complement activation.

Ordinarily, the variant will have an amino acid sequence having at least 75% amino acid sequence identity with the parent antibody heavy or light chain variable domain sequences, more preferably at least 80%, more preferably at least 85%, more preferably at least 90%, and most preferably at least 95%, or at least 96%, or at least 97%, or at least 98%, or at least 99% identity. Identity or homology with respect to this sequence is defined herein as the percentage of amino acid residues in the candidate sequence that are identical with the parent antibody residues, after aligning the sequences and introducing gaps, if necessary, to achieve the maximum percent sequence identity. None of N-terminal, C-terminal, or internal extensions, deletions, or insertions into the antibody sequence (such as, for example, signal peptide sequences, linker sequences, or tags, such as HIS tags) shall be construed as affecting sequence identity or homology. The variant retains the ability to bind human MASP-2 and preferably has properties which are superior to those of the parent antibody. For example, the variant may have a stronger binding affinity and/or an enhanced ability to inhibit or block MASP-2 dependent complement activation.

To analyze such properties, one should compare a Fab form of the variant to a Fab form of the parent antibody or a full length form of the variant to a full length form of the parent antibody, for example, since it has been found that the format of the anti-MASP-2 antibody impacts its activity in the biological activity assays disclosed herein. The variant antibody of particular interest herein is one which displays at least about 10-fold, preferably at least about 20-fold, and most preferably at least about 50-fold, enhancement in biological activity when compared to the parent antibody.

The antibodies of the invention may be modified to enhance desirable properties, such as it may be desirable to control serum half-life of the antibody. In general, complete antibody molecules have a very long serum persistence, whereas fragments (<60-80 kDa) are filtered very rapidly through the kidney. Hence, if long-term action of the MASP-2 antibody is desirable, the MASP-2 antibody is preferably a complete full length IgG antibody (such as IgG2 or IgG4), whereas if shorter action of the MASP-2 antibody is desirable, an antibody fragment may be preferred. As described in Example 5, it has been determined that an S228P substitution in the hinge region of IgG4 increases serum stability. Accordingly, in some embodiments, the subject MASP-2 antibody is a full length IgG4 antibody with an S228P substitution.

Single Chain Antibodies

In one embodiment of the present invention, the MASP-2 inhibitory antibody is a single chain antibody, defined as a genetically engineered molecule containing the variable region of the light chain, the variable region of the heavy chain, linked by a suitable polypeptide linker as a genetically fused single chain molecule. Such single chain antibodies are also referred to as "single-chain Fv" or "scFv" antibody fragments. Generally, the Fv polypeptide further comprises a polypeptide linker between the VH and VL domains that enables the scFv to form the desired structure for antigen binding. The scFv antibodies that bind MASP-2 can be oriented with the variable light region either amino terminal to the variable heavy region or carboxyl terminal to it. Exemplary scFv antibodies of the invention are set forth herein as SEQ ID NOS: 55-61 and SEQ ID NOS: 66-68.

Methods for Producing Antibodies

In many embodiments, the nucleic acids encoding a subject monoclonal antibody are introduced directly into a host cell, and the cell incubated under conditions sufficient to induce expression of the encoded antibody.

In some embodiments, the invention provides a nucleic acid molecule encoding an anti-MASP-2 antibody, or fragment thereof, of the invention, such as an antibody or fragment thereof set forth in TABLE 2. In some embodiments the invention provides a nucleic acid molecule comprising a nucleic acid sequence selected from the group consisting of SEQ ID NO:19, SEQ ID NO:23, SEQ ID NO:26, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:97, SEQ ID NO:88 and SEQ ID NO:89.

In some embodiments, the invention provides a cell comprising a nucleic acid molecule encoding an anti-MASP-2 antibody of the invention.

In some embodiments, the invention provides an expression cassette comprising a nucleic acid molecule encoding an anti-MASP-2 antibody of the invention.

In some embodiments, the invention provides a method of producing anti-MASP-2 antibodies comprising culturing a cell comprising a nucleic acid molecule encoding an anti-MASP-2 antibody of the invention.

According to certain related embodiments there is provided a recombinant host cell which comprises one or more constructs as described herein; a nucleic acid encoding any antibody, CDR, VH or VL domain, or antigen-binding fragment thereof; and a method of production of the encoded product, which method comprises expression from encoding nucleic acid therefor. Expression may conveniently be achieved by culturing under appropriate conditions recombinant host cells containing the nucleic acid. Following production by expression, an antibody or antigen-binding fragment thereof, may be isolated and/or purified using any suitable technique, and then used as desired.

For example, any cell suitable for expression of expression cassettes may be used as a host cell, for example, yeast, insect, plant, etc., cells. In many embodiments, a mammalian host cell line that does not ordinarily produce antibodies is used, examples of which are as follows: monkey kidney cells (COS cells), monkey kidney CVI cells transformed by SV40 (COS-7, ATCC CRL 165 1); human embryonic kidney cells (HEK-293, Graham et al., *J. Gen Virol.* 36:59 (1977)); baby hamster kidney cells (BHK, ATCC CCL 10); Chinese hamster ovary-cells (CHO, Urlaub and Chasin, *Proc. Natl. Acad. Sci.* (*USA*) 77:4216, (1980); mouse sertoli cells (TM4, Mather, *Biol. Reprod.* 23:243-251 (1980)); monkey kidney cells (CVI ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (hep G2, HB 8065); mouse mammary tumor (MMT 060562, ATCC CCL 51); TR1 cells (Mather et al., *Annals N.Y. Acad. Sci.* 383:44-68 (1982)); NIH/3T3 cells (ATCC CRL-1658); and mouse L cells (ATCC CCL-1). Additional cell lines will become apparent to those of ordinary skill in the art. A wide variety of cell lines are available from the American Type Culture Collection, 10801 University Boulevard, Manassas, Va. 20110-2209.

Methods of introducing nucleic acids into cells are well known in the art. Suitable methods include electroporation, particle gun technology, calcium phosphate precipitation, direct microinjection, and the like. The choice of method is generally dependent on the type of cell being transformed and the circumstances under which the transformation is taking place (i.e., in vitro, ex vivo, or in vivo). A general discussion of these methods can be found in Ausubel, et al., *Short Protocols in Molecular Biology,* 3d ed., Wiley & Sons, 1995. In some embodiments, lipofectamine and calcium mediated gene transfer technologies are used.

After the subject nucleic acids have been introduced into a cell, the cell is typically incubated, normally at 37° C., sometimes under selection, for a suitable time to allow for the expression of the antibody. In most embodiments, the antibody is typically secreted into the supernatant of the media in which the cell is growing in.

In mammalian host cells, a number of viral-based expression systems may be utilized to express a subject antibody. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, *Proc. Natl. Acad. Sci. USA* 81:355-359 (1984)). The efficiency of expression may be enhanced by the inclusion of appropriate transcription enhancer elements, transcription terminators, etc. (see Bittner et al., *Methods in Enzymol.* 153:51-544 (1987)).

For long-term, high-yield production of recombinant antibodies, stable expression may be used. For example, cell lines, which stably express the antibody molecule, may be engineered. Rather than using expression vectors which contain viral origins of replication, host cells can be transformed with immunoglobulin expression cassettes and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into a chromosome and grow to form foci which in turn can be cloned and expanded into cell lines. Such engineered cell lines may be particularly useful in screening and evaluation of compounds that interact directly or indirectly with the antibody molecule.

Once an antibody molecule of the invention has been produced, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In many embodiments, antibodies are secreted from the cell into culture medium and harvested from the culture medium. For example, a nucleic acid sequence encoding a signal peptide may be included adjacent the coding region of the antibody or fragment, for example as provided in nucleotides 1-57 of SEQ ID NO:71, encoding the signal peptide as provided in amino acids 1-19 of SEQ ID NO:72. Such a signal peptide may be incorporated adjacent to the 5' end of the amino acid sequences set forth herein for the subject antibodies in order to facilitate production of the subject antibodies.

Pharmaceutical Carriers and Delivery Vehicles

In another aspect, the invention provides compositions for inhibiting the adverse effects of MASP-2-dependent complement activation comprising a therapeutically effective amount of a human anti-MASP-2 inhibitory antibody and a pharmaceutically acceptable carrier.

In general, the human MASP-2 inhibitory antibody compositions of the present invention, combined with any other selected therapeutic agents, are suitably contained in a pharmaceutically acceptable carrier. The carrier is non-toxic, biocompatible and is selected so as not to detrimentally affect the biological activity of the MASP-2 inhibitory antibody (and any other therapeutic agents combined therewith). Exemplary pharmaceutically acceptable carriers for polypeptides are described in U.S. Pat. No. 5,211,657 to Yamada. The anti-MASP-2 antibodies may be formulated into preparations in solid, semi-solid, gel, liquid or gaseous forms such as tablets, capsules, powders, granules, ointments, solutions, depositories, inhalants and injections allowing for oral, parenteral or surgical administration. The invention also contemplates local administration of the compositions by coating medical devices and the like.

Suitable carriers for parenteral delivery via injectable, infusion or irrigation and topical delivery include distilled water, physiological phosphate-buffered saline, normal or lactated Ringer's solutions, dextrose solution, Hank's solution, or propanediol. In addition, sterile, fixed oils may be employed as a solvent or suspending medium. For this purpose, any biocompatible oil may be employed including synthetic mono- or diglycerides. In addition, fatty acids such as oleic acid find use in the preparation of injectables. The carrier and agent may be compounded as a liquid, suspension, polymerizable or non-polymerizable gel, paste or salve.

The carrier may also comprise a delivery vehicle to sustain (i.e., extend, delay or regulate) the delivery of the agent(s) or to enhance the delivery, uptake, stability or pharmacokinetics of the therapeutic agent(s). Such a delivery vehicle may include, by way of non-limiting example, microparticles, microspheres, nanospheres or nanoparticles composed of proteins, liposomes, carbohydrates, synthetic organic compounds, inorganic compounds, polymeric or copolymeric hydrogels and polymeric micelles. Suitable hydrogel and micelle delivery systems include the PEO:PHB:PEO copolymers and copolymer/cyclodextrin complexes disclosed in WO 2004/009664 A2 and the PEO and PEO/cyclodextrin complexes disclosed in U.S. Patent Application Publication No. 2002/0019369 A1. Such hydrogels may be injected locally at the site of intended action, or subcutaneously or intramuscularly to form a sustained release depot.

For intra-articular delivery, the MASP-2 inhibitory antibody may be carried in above-described liquid or gel carriers that are injectable, above-described sustained-release delivery vehicles that are injectable, or a hyaluronic acid or hyaluronic acid derivative.

For intrathecal (IT) or intracerebroventricular (ICV) delivery, appropriately sterile delivery systems (e.g., liquids; gels, suspensions, etc.) can be used to administer the present invention.

The compositions of the present invention may also include biocompatible excipients, such as dispersing or wetting agents, suspending agents, diluents, buffers, penetration enhancers, emulsifiers, binders, thickeners, flavoring agents (for oral administration).

To achieve high concentrations of anti-MASP-2 antibodies for local delivery, the antibodies may be formulated as a suspension of particulates or crystals in solution for subsequent injection, such as for intramuscular injection of a depot.

More specifically with respect to anti-MASP-2 antibodies, exemplary formulations can be parenterally administered as injectable dosages of a solution or suspension of the compound in a physiologically acceptable diluent with a pharmaceutical carrier that can be a sterile liquid such as water, oils, saline, glycerol or ethanol. Additionally, auxiliary substances such as wetting or emulsifying agents, surfactants, pH buffering substances and the like can be present in compositions comprising anti-MASP-2 antibodies. Additional components of pharmaceutical compositions include petroleum (such as of animal, vegetable or synthetic origin), for example, soybean oil and mineral oil. In general, glycols such as propylene glycol or polyethylene glycol are preferred liquid carriers for injectable solutions.

The anti-MASP-2 antibodies can also be administered in the form of a depot injection or implant preparation that can be formulated in such a manner as to permit a sustained or pulsatile release of the active agents.

The pharmaceutical compositions comprising MASP-2 inhibitory antibodies may be administered in a number of ways depending on whether a local or systemic mode of administration is most appropriate for the condition being treated. Additionally, as described herein above with respect to extracorporeal reperfusion procedures, MASP-2 inhibitory antibodies can be administered via introduction of the compositions of the present invention to recirculating blood or plasma. Further, the compositions of the present invention can be delivered by coating or incorporating the compositions on or into an implantable medical device.

Systemic Delivery

As used herein, the terms "systemic delivery" and "systemic administration" are intended to include but are not limited to oral and parenteral routes including intramuscular (IM), subcutaneous, intravenous (IV), intra-arterial, inhalational, sublingual, buccal, topical, transdermal, nasal, rectal, vaginal and other routes of administration that effectively result in dispersal of the delivered antibody to a single or multiple sites of intended therapeutic action. Preferred routes of systemic delivery for the present compositions include intravenous, intramuscular, subcutaneous and inhalational. It will be appreciated that the exact systemic administration route for selected agents utilized in particular compositions of the present invention will be determined in part to account for the agent's susceptibility to metabolic transformation pathways associated with a given route of administration.

MASP-2 inhibitory antibodies and polypeptides can be delivered into a subject in need thereof by any suitable means. Methods of delivery of MASP-2 antibodies and polypeptides include administration by oral, pulmonary, parenteral (e.g., intramuscular, intraperitoneal, intravenous (IV) or subcutaneous injection), inhalation (such as via a fine powder formulation), transdermal, nasal, vaginal, rectal, or sublingual routes of administration, and can be formulated in dosage forms appropriate for each route of administration.

By way of representative example, MASP-2 inhibitory antibodies and peptides can be introduced into a living body by application to a bodily membrane capable of absorbing the polypeptides, for example the nasal, gastrointestinal and rectal membranes. The polypeptides are typically applied to the absorptive membrane in conjunction with a permeation enhancer. (See, e.g., Lee, V. H. L., *Crit. Rev. Ther. Drug Carrier Sys.* 5:69, 1988; Lee, V. H. L., *J. Controlled Release* 13:213, 1990; Lee, V. H. L., Ed., *Peptide and Protein Drug Delivery*, Marcel Dekker, New York (1991); DeBoer, A. G., et al., *J. Controlled Release* 13:241, 1990.) For example, STDHF is a synthetic derivative of fusidic acid, a steroidal surfactant that is similar in structure to the bile salts, and has been used as a permeation enhancer for nasal delivery. (Lee, W. A., *Biopharm.* 22, November/December 1990.)

The MASP-2 inhibitory antibodies and polypeptides may be introduced in association with another molecule, such as a lipid, to protect the polypeptides from enzymatic degradation. For example, the covalent attachment of polymers, especially polyethylene glycol (PEG), has been used to protect certain proteins from enzymatic hydrolysis in the body and thus prolong half-life (Fuertges, F., et al., *J. Controlled Release* 11:139, 1990). Many polymer systems have been reported for protein delivery (Bae, Y. H., et al., *J. Controlled Release* 9:271, 1989; Hori, R., et al., *Pharm. Res.* 6:813, 1989; Yamakawa, I., et al., *J. Pharm. Sci.* 79:505, 1990; Yoshihiro, I., et al., *J. Controlled Release* 10:195, 1989; Asano, M., et al., *J. Controlled Release* 9:111, 1989; Rosenblatt, J., et al., *J. Controlled Release* 9:195, 1989; Makino, K., *J. Controlled Release* 12:235, 1990; Takakura, Y., et al., *J. Pharm. Sci.* 78:117, 1989; Takakura, Y., et al., *J. Pharm. Sci.* 78:219, 1989).

Recently, liposomes have been developed with improved serum stability and circulation half-times (see, e.g., U.S. Pat. No. 5,741,516, to Webb). Furthermore, various methods of liposome and liposome-like preparations as potential drug carriers have been reviewed (see, e.g., U.S. Pat. No. 5,567,434, to Szoka; U.S. Pat. No. 5,552,157, to Yagi; U.S. Pat. No. 5,565,213, to Nakamori; U.S. Pat. No. 5,738,868, to Shinkarenko; and U.S. Pat. No. 5,795,587, to Gao).

For transdermal applications, the MASP-2 inhibitory antibodies and polypeptides may be combined with other suitable ingredients, such as carriers and/or adjuvants. There are no limitations on the nature of such other ingredients, except that they must be pharmaceutically acceptable for their intended administration, and cannot degrade the activity of the active ingredients of the composition. Examples of suitable vehicles include ointments, creams, gels, or suspensions, with or without purified collagen. The MASP-2 inhibitory antibodies and polypeptides may also be impregnated into transdermal patches, plasters, and bandages, preferably in liquid or semi-liquid form.

The compositions of the present invention may be systemically administered on a periodic basis at intervals determined to maintain a desired level of therapeutic effect. For example, compositions may be administered, such as by subcutaneous injection, every two to four weeks or at less frequent intervals. The dosage regimen will be determined by the physician considering various factors that may influence the action of the combination of agents. These factors will include the extent of progress of the condition being treated, the patient's age, sex and weight, and other clinical factors. The dosage for each individual agent will vary as a function of the MASP-2 inhibitory antibody that is included in the composition, as well as the presence and nature of any drug delivery vehicle (e.g., a sustained release delivery vehicle). In addition, the dosage quantity may be adjusted to account for variation in the frequency of administration and the pharmacokinetic behavior of the delivered agent(s).

Local Delivery

As used herein, the term "local" encompasses application of a drug in or around a site of intended localized action, and may include for example topical delivery to the skin or other affected tissues, ophthalmic delivery, intrathecal (IT), intracerebroventricular (ICV), intra-articular, intracavity, intracranial or intravesicular administration, placement or irrigation. Local administration may be preferred to enable administration of a lower dose, to avoid systemic side effects, and for more accurate control of the timing of delivery and concentration of the active agents at the site of local delivery. Local administration provides a known concentration at the target site, regardless of interpatient variability in metabolism, blood flow, etc. Improved dosage control is also provided by the direct mode of delivery.

Local delivery of a MASP-2 inhibitory antibody may be achieved in the context of surgical methods for treating a disease or condition, such as for example during procedures such as arterial bypass surgery, atherectomy, laser procedures, ultrasonic procedures, balloon angioplasty and stent placement. For example, a MASP-2 inhibitor can be administered to a subject in conjunction with a balloon angioplasty procedure. A balloon angioplasty procedure involves inserting a catheter having a deflated balloon into an artery. The deflated balloon is positioned in proximity to the atherosclerotic plaque and is inflated such that the plaque is compressed against the vascular wall. As a result, the balloon surface is in contact with the layer of vascular endothelial cells on the surface of the blood vessel. The MASP-2 inhibitory antibody may be attached to the balloon angioplasty catheter in a manner that permits release of the agent at the site of the atherosclerotic plaque. The agent may be attached to the balloon catheter in accordance with standard procedures known in the art. For example, the agent may be stored in a compartment of the balloon catheter until the balloon is inflated, at which point it is released into the local environment. Alternatively, the agent may be impregnated on the balloon surface, such that it contacts the cells of the arterial wall as the balloon is inflated. The agent may also be delivered in a perforated balloon catheter such as those disclosed in Flugelman, M. Y., et al., *Circulation* 85:1110-1117, 1992. See also published PCT Application WO 95/23161 for an exemplary procedure for attaching a therapeutic protein to a balloon angioplasty catheter. Likewise, the MASP-2 inhibitory antibody may be included in a gel or polymeric coating applied to a stent, or may be incorporated into the material of the stent, such that the stent elutes the MASP-2 inhibitory antibody after vascular placement.

Treatment Regimes

MASP-2 inhibitory antibody compositions used in the treatment of arthritides and other musculoskeletal disorders may be locally delivered by intra-articular injection. Such compositions may suitably include a sustained release delivery vehicle. As a further example of instances in which local delivery may be desired, MASP-2 inhibitory antibody compositions used in the treatment of urogenital conditions may be suitably instilled intravesically or within another urogenital structure.

In prophylactic applications, the pharmaceutical compositions are administered to a subject susceptible to, or otherwise at risk of, a condition associated with MASP-2-dependent complement activation in an amount sufficient to eliminate or reduce the risk of developing symptoms of the condition. In therapeutic applications, the pharmaceutical compositions are administered to a subject suspected of, or already suffering from, a condition associated with MASP-2-dependent complement activation in a therapeutically effective amount sufficient to relieve, or at least partially reduce, the symptoms of the condition. In both prophylactic and therapeutic regimens, compositions comprising MASP-2 inhibitory antibodies may be administered in several dosages until a sufficient therapeutic outcome has been achieved in the subject. Application of the MASP-2 inhibitory antibody compositions of the present invention may be carried out by a single administration of the composition, or a limited sequence of administrations, for treatment of an acute condition, e.g., reperfusion injury or other traumatic injury. Alternatively, the composition may be administered at periodic intervals over an extended period of time for treatment of chronic conditions, e.g., arthritides or psoriasis.

MASP-2 inhibitory compositions used in the present invention may be delivered immediately or soon after an acute event that results in activation of the lectin pathway, such as following an ischemic event and reperfusion of the ischemic tissue. Examples include myocardial ischemia reperfusion, renal ischemia reperfusion, cerebral ischemia reperfusion, organ transplant and digit/extremity reattachment. Other acute examples include sepsis. A MASP-2 inhibitory composition of the present invention may be administered as soon as possible following an acute event that activates the lectin pathway, preferably within twelve hours and more preferably within two to three hours of a triggering event, such as through systemic delivery of the MASP-2 inhibitory composition.

The methods and compositions of the present invention may be used to inhibit inflammation and related processes that typically result from diagnostic and therapeutic medical and surgical procedures. To inhibit such processes, the MASP-2 inhibitory composition of the present invention may be applied periprocedurally. As used herein "periprocedurally" refers to administration of the inhibitory composition preprocedurally and/or intraprocedurally and/or postprocedurally, i.e., before the procedure, before and during the procedure, before and after the procedure, before, during and after the procedure, during the procedure, during and after the procedure, or after the procedure. Periprocedural application may be carried out by local administration of the composition to the surgical or procedural site, such as by injection or continuous or intermittent irrigation of the site or by systemic administration. Suitable methods for local perioperative delivery of MASP-2 inhibitory antibody solutions are disclosed in U.S. Pat. Nos. 6,420,432 to Demopulos and 6,645,168 to Demopulos. Suitable methods for local delivery of chondroprotective compositions including MASP-2 inhibitory antibodies are disclosed in International PCT Patent Application WO 01/07067 A2. Suitable methods and compositions for targeted systemic delivery of chondroprotective compositions including MASP-2 inhibitory antibodies are disclosed in International PCT Patent Application WO 03/063799 A2.

Dosages

The MASP-2 inhibitory antibodies can be administered to a subject in need thereof, at therapeutically effective doses to treat or ameliorate conditions associated with MASP-2-dependent complement activation. A therapeutically effective dose refers to the amount of the MASP-2 inhibitory antibody sufficient to result in amelioration of symptoms of the condition.

Toxicity and therapeutic efficacy of MASP-2 inhibitory antibodies can be determined by standard pharmaceutical procedures employing experimental animal models, such as the African Green Monkey, as described herein. Using such animal models, the NOAEL (no observed adverse effect level) and the MED (the minimally effective dose) can be determined using standard methods. The dose ratio between NOAEL and MED effects is the therapeutic ratio, which is expressed as the ratio NOAEL/MED. MASP-2 inhibitory antibodies that exhibit large therapeutic ratios or indices are most preferred. The data obtained from the cell culture assays and animal studies can be used in formulating a range of dosages for use in humans. The dosage of the MASP-2 inhibitory antibody preferably lies within a range of circulating concentrations that include the MED with little or no toxicity. The dosage may vary within this range depending upon the dosage form employed and the route of administration utilized.

For any compound formulation, the therapeutically effective dose can be estimated using animal models. For example, a dose may be formulated in an animal model to achieve a circulating plasma concentration range that includes the MED. Quantitative levels of the MASP-2 inhibitory antibody in plasma may also be measured, for example, by high performance liquid chromatography.

In addition to toxicity studies, effective dosage may also be estimated based on the amount of MASP-2 protein present in a living subject and the binding affinity of the MASP-2 inhibitory antibody. It has been shown that MASP-2 levels in normal human subjects is present in serum in low levels in the range of 500 ng/ml, and MASP-2 levels in a particular subject can be determined using a quantitative assay for MASP-2 described in Moller-Kristensen M., et al., *J. Immunol. Methods* 282:159-167, 2003, hereby incorporated herein by reference.

Generally, the dosage of administered compositions comprising MASP-2 inhibitory antibodies varies depending on such factors as the subject's age, weight, height, sex, general medical condition, and previous medical history. As an illustration, MASP-2 inhibitory antibodies, can be administered in dosage ranges from about 0.010 to 10.0 mg/kg, preferably 0.010 to 1.0 mg/kg, more preferably 0.010 to 0.1 mg/kg of the subject body weight.

Therapeutic efficacy of MASP-2 inhibitory compositions and methods of the present invention in a given subject, and appropriate dosages, can be determined in accordance with complement assays well known to those of skill in the art. Complement generates numerous specific products. During the last decade, sensitive and specific assays have been developed and are available commercially for most of these activation products, including the small activation fragments C3a, C4a, and C5a and the large activation fragments iC3b, C4d, Bb, and sC5b-9. Most of these assays utilize antibodies that react with new antigens (neoantigens) exposed on the fragment, but not on the native proteins from which they are formed, making these assays very simple and specific. Most rely on ELISA technology, although radioimmunoassay is still sometimes used for C3a and C5a. These latter assays measure both the unprocessed fragments and their 'desArg' fragments, which are the major forms found in the circulation. Unprocessed fragments and $C5a_{desArg}$ are rapidly cleared by binding to cell surface receptors and are hence present in very low concentrations, whereas $C3a_{desArg}$ does not bind to cells and accumulates in plasma. Measurement of C3a provides a sensitive, pathway-independent indicator of complement activation. Alternative pathway activation can be assessed by measuring the Bb fragment. Detection of the fluid-phase product of membrane attack pathway activation, sC5b-9, provides evidence that complement is being activated to completion. Because both the lectin and classical pathways generate the same activation products, C4a and C4d, measurement of these two fragments does not provide any information about which of these two pathways has generated the activation products.

The inhibition of MASP-2-dependent complement activation is characterized by at least one of the following changes in a component of the complement system that occurs as a result of administration of an anti-MASP-2 antibody in accordance with the present invention: the inhibition of the generation or production of MASP-2-dependent complement activation system products C4b, C3a, C5a and/or C5b-9 (MAC), the reduction of C4 cleavage and C4b deposition, or the reduction of C3 cleavage and C3b deposition.

Articles of Manufacture

In another aspect, the present invention provides an article of manufacture containing a human MASP-2 inhibitory antibody, or antigen binding fragment thereof, as described herein in a unit dosage form suitable for therapeutic administration to a human subject, such as, for example, a unit dosage in the range of 1 mg to 5000 mg, such as from 1 mg to 2000 mg, such as from 1 mg to 1000 mg, such as 5 mg, 10 mg, 50 mg, 100 mg, 200 mg, 500 mg, or 1000 mg. In some embodiments, the article of manufacture comprises a container and a label or package insert on or associated with the container. Suitable containers include, for example, bottles, vials, syringes, etc. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). At least one active agent in the composition is the MASP-2 inhibitory antibody or antigen binding fragment thereof of the invention. The label or package insert indicates that the composition is used for treating the particular condition. The label or package insert will further comprise instructions for administering the antibody composition to the patient. Articles of manufacture and kits comprising combinatorial therapies described herein are also contemplated.

Therapeutic Uses of the Anti-MASP-2 Inhibitory Antibodies

In another aspect, the invention provides a method of inhibiting MASP-2 dependent complement activation in a human subject comprising administering a human monoclonal anti-MASP-2 inhibitory antibody of the invention in an amount sufficient to inhibit MASP-2 dependent complement activation in said human subject.

In accordance with this aspect of the invention, as described in Example 10, the MASP-2 inhibitory antibodies of the present invention are capable of inhibiting the lectin pathway in African Green Monkeys following intravenous administration. As shown in Table 24, Example 8, the antibody used in this study, OMS646, was found to be more potent in human serum. As known by those of skill in the art, non-human primates are often used as a model for evaluating antibody therapeutics.

As described in U.S. Pat. No. 7,919,094, co-pending U.S. patent application Ser. No. 13/083,441, and co-pending U.S. patent application Ser. No. 12/905,972 (each of which is assigned to Omeros Corporation, the assignee of the instant application), each of which is hereby incorporated by reference, MASP-2 dependent complement activation has been implicated as contributing to the pathogenesis of numerous acute and chronic disease states, including MASP-2-dependent complement mediated vascular condition, an ischemia reperfusion injury, atherosclerosis, inflammatory gastrointestinal disorder, a pulmonary condition, an extracorporeal reperfusion procedure, a musculoskeletal condition, a renal condition, a skin condition, organ or tissue transplant, nervous system disorder or injury, a blood disorder, a urogenital condition, diabetes, chemotherapy or radiation therapy, malignancy, an endocrine disorder, a coagulation disorder, or an ophthalmologic condition. Therefore, the MASP-2 inhibitory antibodies of the present invention may be used to treat the above-referenced diseases and conditions.

As further described in Example 11, the MASP-2 inhibitory antibodies of the present invention are effective in treating a mammalian subject at risk for, or suffering from the detrimental effects of acute radiation syndrome, thereby demonstrating therapeutic efficacy in vivo.

The following examples merely illustrate the best mode now contemplated for practicing the invention, but should not be construed to limit the invention.

EXAMPLE 1

This Example describes the recombinant expression and protein production of recombinant full-length human, rat and murine MASP-2, MASP-2 derived polypeptides, and catalytically inactivated mutant forms of MASP-2.

Expression of Full-Length Human and Rat MASP-2:

The full length cDNA sequence of human MASP-2 (SEQ ID NO: 1), encoding the human MASP-2 polypeptide with leader sequence (SEQ ID NO:2) was subcloned into the mammalian expression vector pCI-Neo (Promega), which drives eukaryotic expression under the control of the CMV enhancer/promoter region (described in Kaufman R. J. et al., *Nucleic Acids Research* 19:4485-90, 1991; Kaufman, *Methods in Enzymology,* 185:537-66 (1991)). The full length rat MASP-2 cDNA (SEQ ID NO:4), encoding the rat MASP-2 polypeptide with leader sequence (SEQ ID NO:5) was subcloned into the pED expression vector. The MASP-2 expression vectors were then transfected into the adherent Chinese hamster ovary cell line DXB1 using the standard calcium phosphate transfection procedure described in Maniatis et al., 1989. Cells transfected with these constructs grew very slowly, implying that the encoded protease is cytotoxic. The mature form of the human MASP-2 protein (SEQ ID NO:3) and the mature form of the rat MASP-2 protein (SEQ ID NO:6) were secreted into the culture media and isolated as described below.

Expression of Full-Length Catalytically Inactive MASP-2:

Rationale:

MASP-2 is activated by autocatalytic cleavage after the recognition subcomponents MBL, C-type lectin CL-11, or ficolins (either L-ficolin, H-ficolin or M-ficolin), collectively referred to as lectins, bind to their respective carbohydrate pattern. Autocatalytic cleavage resulting in activation of MASP-2 often occurs during the isolation procedure of MASP-2 from serum, or during the purification following recombinant expression. In order to obtain a more stable protein preparation for use as an antigen, a catalytically inactive form of MASP-2, designed as MASP-2A, was created by replacing the serine residue that is present in the catalytic triad of the protease domain with an alanine residue in the mature rat MASP-2 protein (SEQ ID NO:6 Ser617 to Ala617); or in mature human MASP-2 protein (SEQ ID NO:3 Ser618 to Ala618).

In order to generate catalytically inactive human and rat MASP-2A proteins, site-directed mutagenesis was carried out as described in US2007/0172483, hereby incorporated herein by reference. The PCR products were purified after agarose gel electrophoresis and band preparation and single adenosine overlaps were generated using a standard tailing procedure. The adenosine tailed MASP-2A was then cloned into the pGEM-T easy vector, transformed into *E. coli*. The human and rat MASP-2A were each further subcloned into either of the mammalian expression vectors pED or pCI-Neo and transfected into the Chinese Hamster ovary cell line DXB1 as described below.

Construction of Expression Plasmids Containing Polypeptide Regions Derived from Human Masp-2.

The following constructs were produced using the MASP-2 signal peptide (residues 1-15 of SEQ ID NO:2) to secrete various domains of MASP-2. A construct expressing the human MASP-2 CUBI domain (SEQ ID NO:7) was made by PCR amplifying the region encoding residues 1-121 of MASP-2 (SEQ ID NO:3) (corresponding to the N-terminal CUB 1 domain). A construct expressing the human MASP-2 CUBI/EGF domain (SEQ ID NO:8) was made by PCR amplifying the region encoding residues 1-166 of MASP-2 (SEQ ID NO:3) (corresponding to the N-terminal CUB1/EGF domain). A construct expressing the human MASP-2 CUBI/EGF/CUBII domain (SEQ ID NO:9) was made by PCR amplifying the region encoding aa residues 1-277 of MASP-2 (SEQ ID NO:3) (corresponding to the N-terminal CUBIEGFCUBII domain). A construct expressing the human MASP-2 EGF domain (SEQ ID NO:10) was made by PCR amplifying the region encoding aa residues 122-166 of MASP-2 (SEQ ID NO:3) (corresponding to the EGF domain). A construct expressing the human MASP-2 CCPI/CCPII/SP domains (SEQ ID NO:11) was made by PCR amplifying the region encoding aa residues 278-671 of MASP-2 (SEQ ID NO:3) (corresponding to the CCPI/CCPII/SP domains). A construct expressing the human MASP-2 CCPI/CCPII domains (SEQ ID NO:12) was made by PCR amplifying the region encoding aa residues 278-429 of MASP-2 (SEQ ID NO:3) (corresponding to the CCPI/CCPII domains). A construct expressing the CCPI domain of MASP-2 (SEQ ID NO:13) was made by PCR amplifying the region encoding aa residues 278-347 of MASP-2 (SEQ ID NO:3) (corresponding to the CCPI domain). A construct expressing the CCPII/SP domains of MASP-2 (SEQ ID NO:14) was made by PCR amplifying the region encoding aa residues 348-671 of MASP-2 (SEQ ID NO:3) (corresponding to the CCPII/SP domains). A construct expressing the CCPII domain of MASP-2 (SEQ ID NO:15) was made by PCR amplifying the region encoding aa residues 348-429 of MASP-2 (SEQ ID NO:3) (corresponding to the CCPII domain). A construct expressing the SP domain of MASP-2 (SEQ ID NO:16) was made by PCR amplifying the region encoding aa residues 429-671 of MASP-2 (SEQ ID NO:3) (corresponding to the SP domain).

The above mentioned MASP-2 domains were amplified by PCR using $Vent_R$ polymerase and pBS-MASP-2 as a template, according to established PCR methods. The 5' primer sequence of the sense primer introduced a BamHI restriction site (underlined) at the 5' end of the PCR products. Antisense primers for each of the MASP-2 domains were designed to introduce a stop codon followed by an EcoRI site at the end of each PCR product. Once amplified, the DNA fragments were digested with BamHI and EcoRI and cloned into the corresponding sites of the pFastBac1 vector. The resulting constructs were characterized by restriction mapping and confirmed by dsDNA sequencing.

Recombinant Eukaryotic Expression of MASP-2 and Protein Production of Enzymatically Inactive Rat and Human MASP-2A.

The MASP-2 and MASP-2A expression constructs described above were transfected into DXB1 cells using the standard calcium phosphate transfection procedure (Maniatis et al., 1989). MASP-2A was produced in serum-free medium to ensure that preparations were not contaminated with other serum proteins. Media was harvested from confluent cells every second day (four times in total). The level of recombinant MASP-2A averaged approximately 1.5 mg/liter of culture medium for each of the two species.

MASP-2A Protein Purification: The MASP-2A (Ser-Ala mutant described above) was purified by affinity chromatography on MBP-A-agarose columns. This strategy enabled rapid purification without the use of extraneous tags. MASP-2A (100-200 ml of medium diluted with an equal volume of loading buffer (50 mM Tris-C1, pH 7.5, containing 150 mM NaCl and 25 mM $CaCl_2$) was loaded onto an MBP-agarose affinity column (4 ml) pre-equilibrated with 10 ml of loading buffer. Following washing with a further 10 ml of loading buffer, protein was eluted in 1 ml fractions with 50 mM Tris-C1, pH 7.5, containing 1.25 M NaCl and 10 mM EDTA. Fractions containing the MASP-2A were identified by SDS-polyacrylamide gel electrophoresis. Where necessary, MASP-2A was purified further by ion-exchange chromatography on a MonoQ column (HR 5/5). Protein was dialysed with 50 mM Tris-C1 pH 7.5, containing 50 mM NaC1 and loaded onto the column equilibrated in the same buffer. Following washing, bound MASP-2A was eluted with a 0.05-1 M NaCl gradient over 10 ml.

Results: Yields of 0.25-0.5 mg of MASP-2A protein were obtained from 200 ml of medium. The molecular mass of 77.5 kDa determined by MALDI-MS is greater than the calculated value of the unmodified polypeptide (73.5 kDa) due to glycosylation. Attachment of glycans at each of the N-glycosylation sites accounts for the observed mass. MASP-2A migrates as a single band on SDS-polyacrylamide gels, demonstrating that it is not proteolytically processed during biosynthesis. The weight-average molecular mass determined by equilibrium ultracentrifugation is in agreement with the calculated value for homodimers of the glycosylated polypeptide.

EXAMPLE 2

This Example describes the screening method used to identify high affinity fully human anti-MASP-2 scFv antibody candidates that block MASP-2 functional activity for progression into affinity maturation.

Background and Rationale:

MASP-2 is a complex protein with many separate functional domains, including: binding site(s) for MBL and ficolins, a serine protease catalytic site, a binding site for proteolytic substrate C2, a binding site for proteolytic substrate C4, a MASP-2 cleavage site for autoactivation of MASP-2 zymogen, and two $Ca^{++}$ binding sites. scFv antibody fragments were identified that bind with high affinity to MASP-2, and the identified Fab2 fragments were tested in a functional assay to determine if they were able to block MASP-2 functional activity.

To block MASP-2 functional activity, an antibody or scFv or Fab2 antibody fragment must bind and interfere with a structural epitope on MASP-2 that is required for MASP-2 functional activity. Therefore, many or all of the high affinity binding anti-MASP-2 scFvs or Fab2s may not inhibit MASP-2 functional activity unless they bind to structural epitopes on MASP-2 that are directly involved in MASP-2 functional activity.

A functional assay that measures inhibition of lectin pathway C3 convertase formation was used to evaluate the "blocking activity" of anti-MASP-2 scFvs. It is known that the primary physiological role of MASP-2 in the lectin pathway is to generate the next functional component of the lectin-mediated complement pathway, namely the lectin pathway C3 convertase. The lectin pathway C3 convertase is a critical enzymatic complex (C4b2a) that proteolytically cleaves C3 into C3a and C3b. MASP-2 is not a structural component of the lectin pathway C3 convertase (C4b2a); however, MASP-2 functional activity is required in order to generate the two protein components (C4b, C2a) that comprise the lectin pathway C3 convertase. Furthermore, all of the separate functional activities of MASP-2 listed above appear to be required in order for MASP-2 to generate the lectin pathway C3 convertase. For these reasons, a preferred assay to use in evaluating the "blocking activity" of anti-MASP-2 Fab2s and scFv antibody fragments is believed to be a functional assay that measures inhibition of lectin pathway C3 convertase formation.

The target profile for therapeutic anti-MASP-2 antibodies predicted to yield >90% lectin pathway ablation in vivo following administration of 1 mg/kg to a human is an $IC_{50}$<5 nM in 90% plasma. The relationship between in vitro pharmacological activity in these assay formats and in vivo pharmacodynamics was validated experimentally using anti-rodent MASP-2 antibodies.

The criteria for selection of first generation MASP-2 blocking antibodies for therapeutic use were as follows: high affinity to MASP-2 and functional $IC_{50}$ values up to ~25 nM. In addition, candidates were screened for cross-reactivity with non-human primate serum, and with rat serum.

Methods:

Screening of scFv Phagemid Library Against MASP-2 Antigen

Antigens:

Human MASP-2A with an N-terminal 5×His tag, and rat MASP-2A with an N-terminal 6×His tags were generated using the reagents described in Example 1 and purified from culture supernatants by nickel-affinity chromatograph, as previously described (Chen et al., *J. Biol. Chem.* 276:25894-02 (2001)).

OMS100, a human anti-MASP-2 antibody in Fab2 format, was used as a positive control for binding MASP-2.

Phagemid Library Description:

A phage display library of human immunoglobulin light and heavy chain variable region sequences was subjected to antigen panning followed by automated antibody screening and selection to identify high affinity scFv antibodies to rat MASP-2 protein and human MASP-2 protein.

Panning Methods:

Overview: Two panning strategies were used to isolate phages from the phagemid library that bound to MASP-2 in a total of three rounds of panning. Both strategies involved panning in solution and fishing out phage bound to MASP-2. MASP-2 was immobilized on magnetic beads either via the His-tag (using NiNTA beads) or via a biotin (using Streptavidin beads) on the target.

The first two panning rounds involved alkaline elution (TEA), and the third panning round was first eluted competitively with MBL before a conventional alkaline (TEA) elution step. Negative selection was carried out before rounds 2 and 3, and this was against the functional analogs, C1s and C1r of the classical complement pathway. After panning, specific enrichment of phages with scFv fragments against MASP-2A was monitored, and it was determined that the panning strategy had been successful (data not shown).

The scFv genes from panning round 3 were cloned into a pHOG expression vector, and run in a small-scale filter screening to look for specific clones against MASP-2A, as further described below.

TABLE 7

Phage Panning Methods (biotin/streptavidin)

| Panning Round | Antigen (μg) | magnetic beads | block | prepanning | elution |
|---|---|---|---|---|---|
| 1 | biotin human MASP-2A (10 μg) | streptavidin | 4% blot block | nothing | TEA (alkaline) |
| 2 | biotin rat MASP-2A (10 μg) | streptavidin | 4% blot block | C1s/C1r | TEA (alkaline) |
| 3 | biotin human MASP-2A (1 μg) | streptavidin | 4% blot block | C1s/C1r | Competition w/MBL, followed by TEA (alkaline) |

TABLE 8

Phage Panning Methods (HIS/NiNTA)

| Panning Round | Antigen (μg) | magnetic beads | block | prepanning | elution |
|---|---|---|---|---|---|
| 1 | human MASP-2A His tagged (10 μg) | NiNTA | 4% milk in PBS | nothing | TEA (alkaline) |
| 2 | rat MASP-2A His tagged (10 μg) | NiNTA | 4% milk in PBS | C1s/C1r | TEA (alkaline) |
| 3 | biotin human MASP-2A (10 μg) | NiNTA | 4% milk in PBS | C1s/C1r | Competitively with MBL + TEA (alkaline) |

Panning Reagents:

Human MASP-2A

OMS100 antibody (positive control)

Goat anti-human IgG (H+L) (Pierce #31412)

NiNTA beads (Qiagen #LB13267)

Dynabeads® M-280 Streptavidin, 10 mg/ml (LB12321)

Normal human serum (LB 13294)

Polyclonal rabbit anti-human C3c (LB13137)

Goat anti-rabbit IgG, HRP (American Qualex #A102PU)

To test the tagged MASP-2A antigen, an experiment was carried out to capture the positive control OMS100 antibody (200 ng/ml) preincubated with biotin-tagged MASP-2A or HIS-tagged MASP-2A antigen (10 μg), with 50 μl NiNTA beads in 4% milk PBS or 200 μL Streptavidin beads, respectively. Bound MASP-2A-OMS100 antibody was detected with Goat-anti-human IgG (H+L) HRP (1:5000) and TMB (3,3',5,5'-tetramethylbenzidine) substrate.

NiNTA Beads ELISA Assay

50 μl NiNTA beads were blocked with 1 ml 4% milk in phosphate buffered saline (PBS) and incubated on a rotator wheel for 1 hour at room temperature. In parallel, 10 μg of MASP-2A and OMS100 antibody (diluted to 200 ng/ml in 4% milk-PBS) were pre-incubated for one hour. The beads were then washed three times with 1 ml PBS-T using a magnet between each step. The MASP-2A pre-incubated with OMS100 antibody was added to the washed beads. The mixture was incubated on a rotator wheel for 1 h at RT, then washed three times with 1 ml PBS-T using a magnet as described above. The tubes were incubated for 1 hr at RT with Goat anti-human IgG (H+L) HRP diluted 1:5000 in 4% milk in PBS. For negative controls, Goat-anti-human IgG (H+L) HRP (1:5000) was added to washed and blocked Ni-NTA beads in a separate tube.

The samples were incubated on rotator wheel for 1 hour at room temperature, then washed three times with 1 ml PBS-T and once with 1×PBS using the magnet as described above. 100 μl TMB substrate was added and incubated for 3 min at room temperature. The tubes were placed in a magnetic rack for 2 min to concentrate the beads, then the TMB solution was transferred to a microtiter plate and the reaction was stopped with 100 μl 2M $H_2SO_4$. Absorbance at 450 nm was read in the ELISA reader.

Streptavidin Beads ELISA Assay

This assay was carried out as described above for the NiNTA beads ELISA Assay, but using 200 μl Streptavidin beads per sample instead, and non-biotinylated antigens.

Results: The His-tagged and biotin-tagged MASP-2A antigen, preincubated with the positive control OMS100 antibody, were each successfully captured with NiNTA beads, or Streptavidin beads, respectively.

Panning

Three rounds of panning the scFv phage library against HIS-tagged or biotin-tagged MASP-2A was carried out as shown in TABLE 7 or TABLE 8, respectively. The third round of panning was eluted first with MBL, then with TEA (alkaline). To monitor the specific enrichment of phages displaying scFv fragments against the target MASP-2A, a polyclonal phage ELISA against immobilized MASP-2A was carried out as described below.

MASP-2A ELISA on Polyclonal Phage Enriched After Panning

After three rounds of panning the scFv phage library against human MASP-2 as described above, specific enrichment of phages with scFv fragments against the target MASP-2A was monitored by carrying out an ELISA assay on the enriched polyclonal phage populations generated by panning against immobilized MASP-2A as described below.

Methods:

5 ng/ml MASP-2A was immobilized on maxisorp ELISA plates in PBS overnight at 4° C. The packaged phages from all three panning rounds were diluted 1:3 in 4% Milk-PBS and titrated with 3-fold dilutions. The negative control was M13 helper phage.

The block was 4% Milk in PBS. The plates were washed 3× in 200 μl PBS-Tween 0.05% (v/v) between every step. The primary antibody was Rabbit α-fd (M13 coat protein), 1:5000 in 4% Milk-PBS (w/v). The conjugate was Rabbit α-Goat—HRP at 1:10.000 in 4% Milk-PBS (w/v). The substrate was ABTS. All volumes, except washes and blocking, were 100 μl/well. All incubations were for 1 hour with shaking at room temperature.

Figure 2:
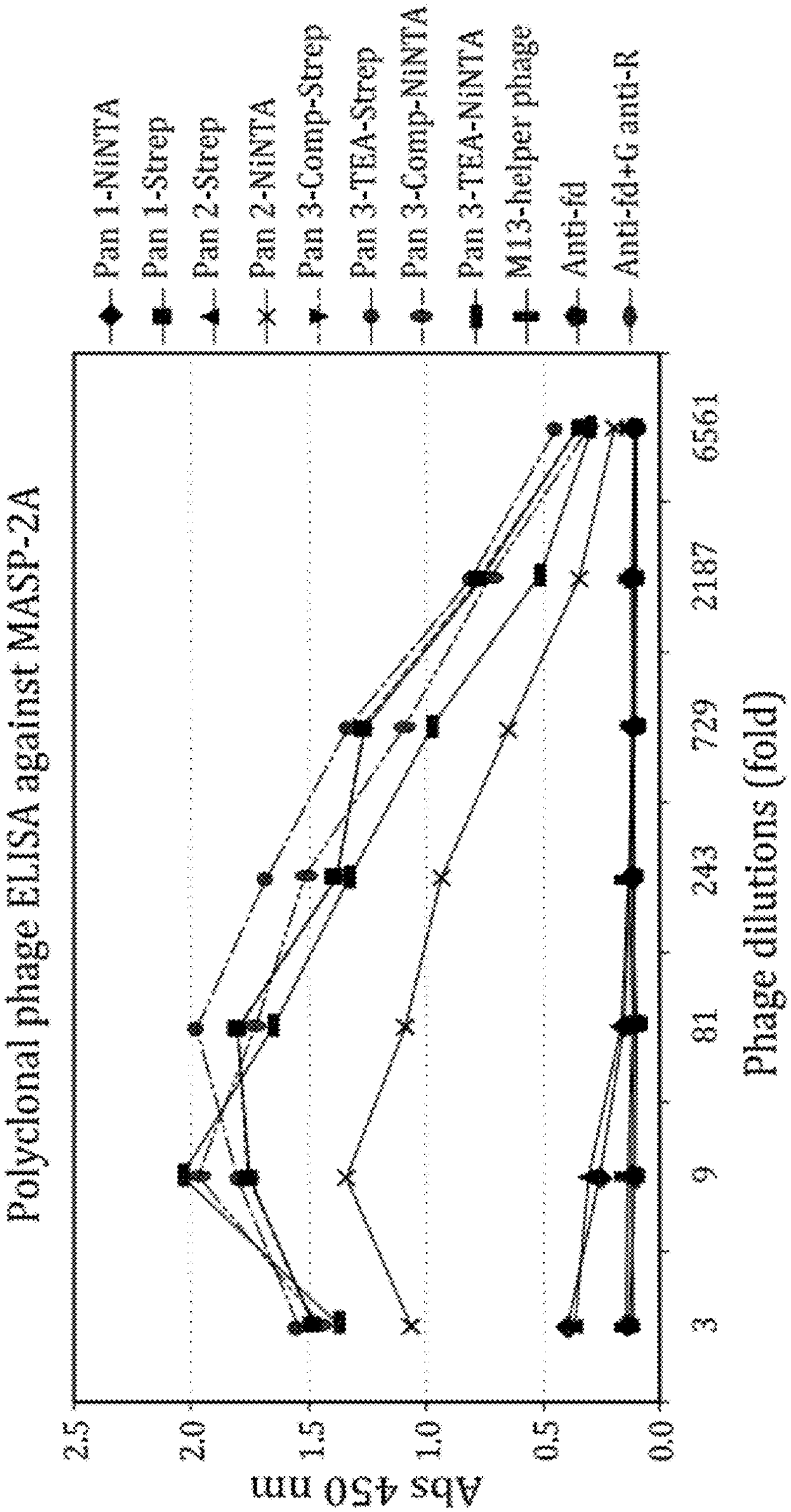
FIG. 2 graphically illustrates the results of an ELISA assay carried out on polyclonal populations selected from a scFcv phage library panned against various MASP-2 antigens, as described in Example 2.

Results:

The results of the phage ELISA showed a specific enrichment of scFv's against MASP-2A for both panning strategies. See FIG. 2. As shown in FIG. 2, the strategy involving capture by NiNTA magnetic beads gave enrichment of scFv on phages against MASP-2A after two rounds of panning, whereas both strategies had good enrichments both in competitive and TEA elution, after the third round of panning. The negative control phage was M13 helper phage, which showed no cross reaction against MASP-2A at its lowest dilution. These results demonstrate that the signal observed is due to scFv specifically binding to MASP-2A.

Filter Screening:

Bacterial colonies containing plasmids encoding scFv fragments from the third round of panning were picked, gridded onto nitrocellulose membranes and grown overnight on non-inducing medium to produce master plates. A total of 18,000 colonies were picked and analyzed from the third panning round, half from the competitive elution and half from the subsequent TEA elution.

The nitrocellulose membranes with bacterial colonies were induced with IPTG to express and secrete a soluble scFv protein and were brought into contact with a secondary nitrocellulose membrane coated with MASP-2A antigen along with a parallel membrane coated with 4% milk in PBS (blocking solution).

ScFvs that bound to MASP-2A were detected via their c-Myc tag with Mouse α-cMyc mAb and Rabbit α-Mouse HRP. Hits corresponding to scFv clones that were positive on MASP-2A and negative on Milk-PBS were selected for further expression, and subsequent ELISA analysis.

Results: Panning of the scFv phagemid library against MASP-2A followed by scFv conversion and a filter screen yielded 137 positive clones. The majority of the positive clones came from competitive elution with MBL, using both NiNTA and Streptavidin strategies. All the positive clones were continued with micro expression (200 μl scale) and subsequent extraction. ScFv were isolated from the periplasma of the bacteria by incubating the bacteria suspension with sucrose lysis buffer and lysozyme for one hour, after which the supernatant was isolated by a centrifugation step. The supernatant containing scFv secreted into the medium together with the contents of the periplasma was analyzed by two assays: ELISA using physically adsorbed MASP-2A, and binding analysis using amine coupled MASP-2A to a CM5 chip on the Biocore, as described in more detail below.

MASP-2A ELISA on ScFv Candidate Clones Identified by Panning/scFv Conversion and Filter Screening Methods:

4 μg/ml MASP-2A was immobilized on maxisorp ELISA plates (Nunc) in PBS overnight at 4° C. The next day, the plates were blocked by washing three times with PBS-Tween (0.05%). Crude scFv material (100 μl medium-periplasma extract) from each of the 137 scFv candidates (generated as described above) was added per well to the plate. Next, anti-cMyc was added, and in the final step HRP-conjugated Rabbit anti-Mouse was applied to detect bound scFv. The reaction was developed in peroxidase substrate 1-step ABTS (Calbiochem). The positive control was OMS100 (an anti-MASP-2 antibody in Fab2 format) diluted to 10 μg/ml in PBS-Tween 0.05%. The negative control was medium-periplasma from XL1-Blue without plasmid.

Washes of 3×200 μl PBS-Tween 0.05% (v/v) were carried out between every step.

The primary antibody was murine α-cMyc, 1:5000 in PBS-Tween 0.05% (w/v).

The conjugate was rabbit α-Goat-HRP at 1:5000 in PBS-Tween 0.05% (w/v) or Goat anti-human IgG (H+L, Pierce 31412). The substrate was ABTS, with 15 minutes incubation at room temperature. All volumes, except washes and blocking, were 100 μl/well. All incubations were for 1 hour with shaking at room temperature.

Results: 108/137 clones were positive in this ELISA assay (data not shown), of which 45 clones were further analyzed as described below. The positive control was OMS100 Fab2 diluted to 10 μg/ml in PBS-Tween, and this clone was positive. The negative control was medium-periplasma from XL1-Blue without plasmid, which was negative.

EXAMPLE 3

This Example describes the MASP-2 functional screening method used to analyze the high affinity fully human anti-MASP-2 scFv antibody candidates for the ability to block MASP-2 activity in normal human serum.

Rationale/Background

Assay to Measure Inhibition of Formation of Lectin Pathway C3 Convertase:

A functional assay that measures inhibition of lectin pathway C3 convertase formation was used to evaluate the "blocking activity" of the anti-MASP-2 scFv candidate clones. The lectin pathway C3 convertase is the enzymatic complex (C4b2a) that proteolytically cleaves C3 into the two potent proinflammatory fragments, anaphylatoxin C3a and opsonic C3b. Formation of C3 convertase appears to a key step in the lectin pathway in terms of mediating inflammation. MASP-2 is not a structural component of the lectin pathway C3 convertase (C4b2a); therefore anti-MASP-2 antibodies (or Fab2) will not directly inhibit activity of preexisting C3 convertase. However, MASP-2 serine protease activity is required in order to generate the two protein components (C4b, C2a) that comprise the lectin pathway C3 convertase. Therefore, anti-MASP-2 scFv which inhibit MASP-2 functional activity (i.e., blocking anti-MASP-2 scFv) will inhibit de novo formation of lectin pathway C3 convertase. C3 contains an unusual and highly reactive thioester group as part of its structure. Upon cleavage of C3 by C3 convertase in this assay, the thioester group on C3b can form a covalent bond with hydroxyl or amino groups on macromolecules immobilized on the bottom of the plastic wells via ester or amide linkages, thus facilitating detection of C3b in the ELISA assay.

Yeast mannan is a known activator of the lectin pathway. In the following method to measure formation of C3 convertase, plastic wells coated with mannan were incubated with diluted human serum to activate the lectin pathway. The wells were then washed and assayed for C3b immobilized onto the wells using standard ELISA methods. The amount of C3b generated in this assay is a direct reflection of the de novo formation of lectin pathway C3 convertase. Anti-MASP-2 scFv's at selected concentrations were tested in this assay for their ability to inhibit C3 convertase formation and consequent C3b generation.

Methods:

The 45 candidate clones identified as described in Example 2 were expressed, purified and diluted to the same stock concentration, which was again diluted in $Ca^{++}$ and $Mg^{++}$ containing GVB buffer (4.0 mM barbital, 141 mM NaCl, 1.0 mM $MgCl_2$, 2.0 mM $CaCl_2$, 0.1% gelatin, pH 7.4) to assure that all clones had the same amount of buffer. The scFv clones were each tested in triplicate at the concentration of 2 μg/ml. The positive control was OMS100 Fab2 and was tested at 0.4 μg/ml. C3c formation was monitored in the presence and absence of the scFv/IgG clones.

Mannan was diluted to a concentration of 20 μg/ml (1 μg/well) in 50 mM carbonate buffer (15 mM $Na_2CO_3$+35 mM $NaHCO_3$+1.5 mM $NaN_3$), pH 9.5 and coated on an ELISA plate overnight at 4° C. The next day, the mannan coated plates were washed 3× with 200 μl PBS. 100 μl of 1% HSA blocking solution was then added to the wells and incubated for 1 hour at room temperature. The plates were washed 3× with 200 μl PBS, and stored on ice with 200 μl PBS until addition of the samples.

Normal human serum was diluted to 0.5% in CaMgGVB buffer, and scFv clones or the OMS100 Fab2 positive control were added in triplicates at 0.01 μg/ml; 1 μg/ml (only OMS100 control) and 10 μg/ml to this buffer and preincubated 45 minutes on ice before addition to the blocked ELISA plate. The reaction was initiated by incubation for one hour at 37° C. and was stopped by transferring the plates to an ice bath. C3b deposition was detected with a Rabbit α-Mouse C3c antibody followed by Goat α-Rabbit HRP. The negative control was buffer without antibody (no OMS100=maximum C3b deposition), and the positive control was buffer with EDTA (no C3b deposition). The background was determined by carrying out the same assay, but in mannan negative wells. The background signal against plates without mannan was subtracted from the mannan positive signals. A cut-off criterion was set at half of the activity of an irrelevant scFv clone (VZV) and buffer alone.

Figure 3A:
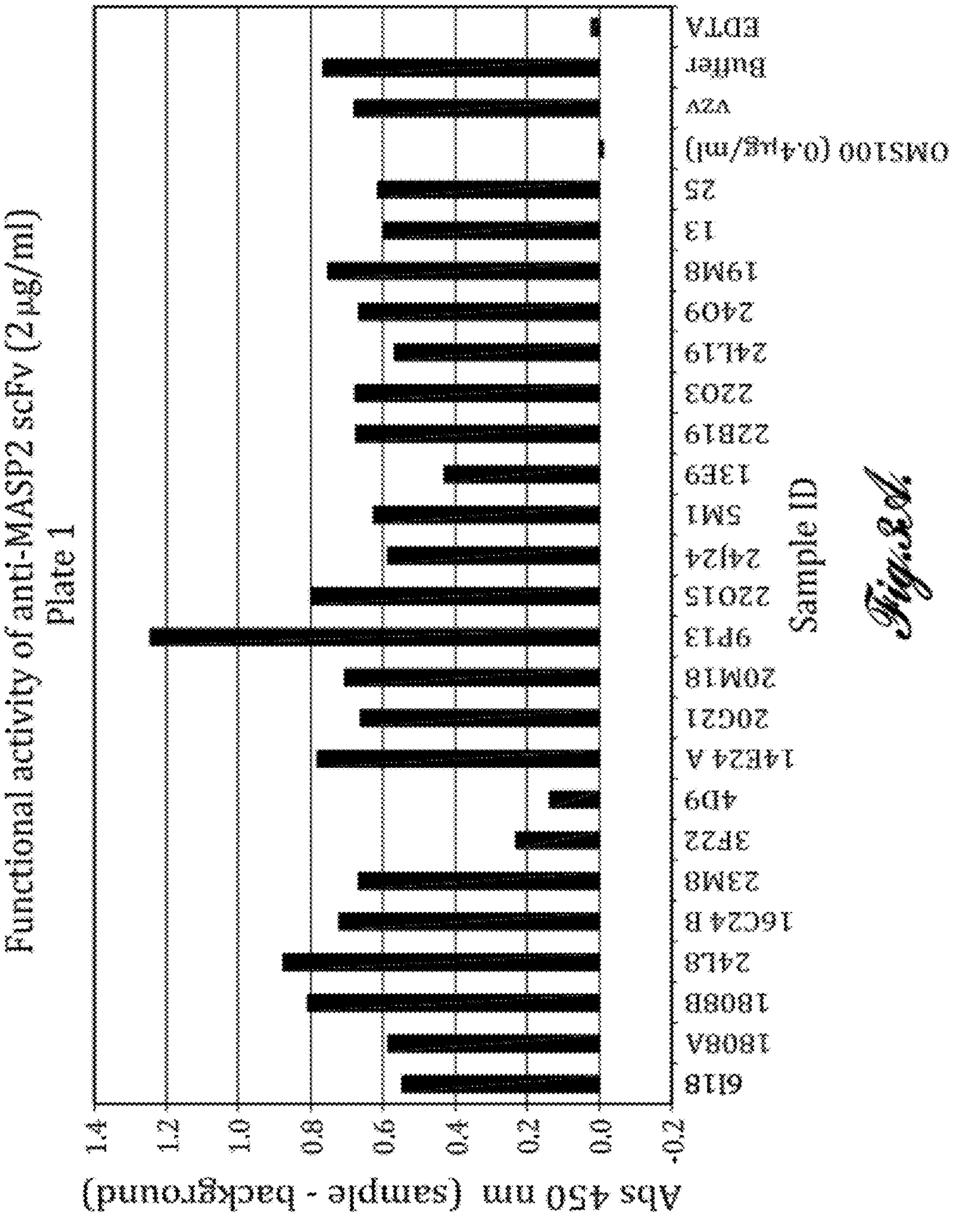
FIGS. 3A and 3B show results of testing of 45 candidate scFv clones for functional activity in the complement assay, as described in Example 3.
Figure 3B:
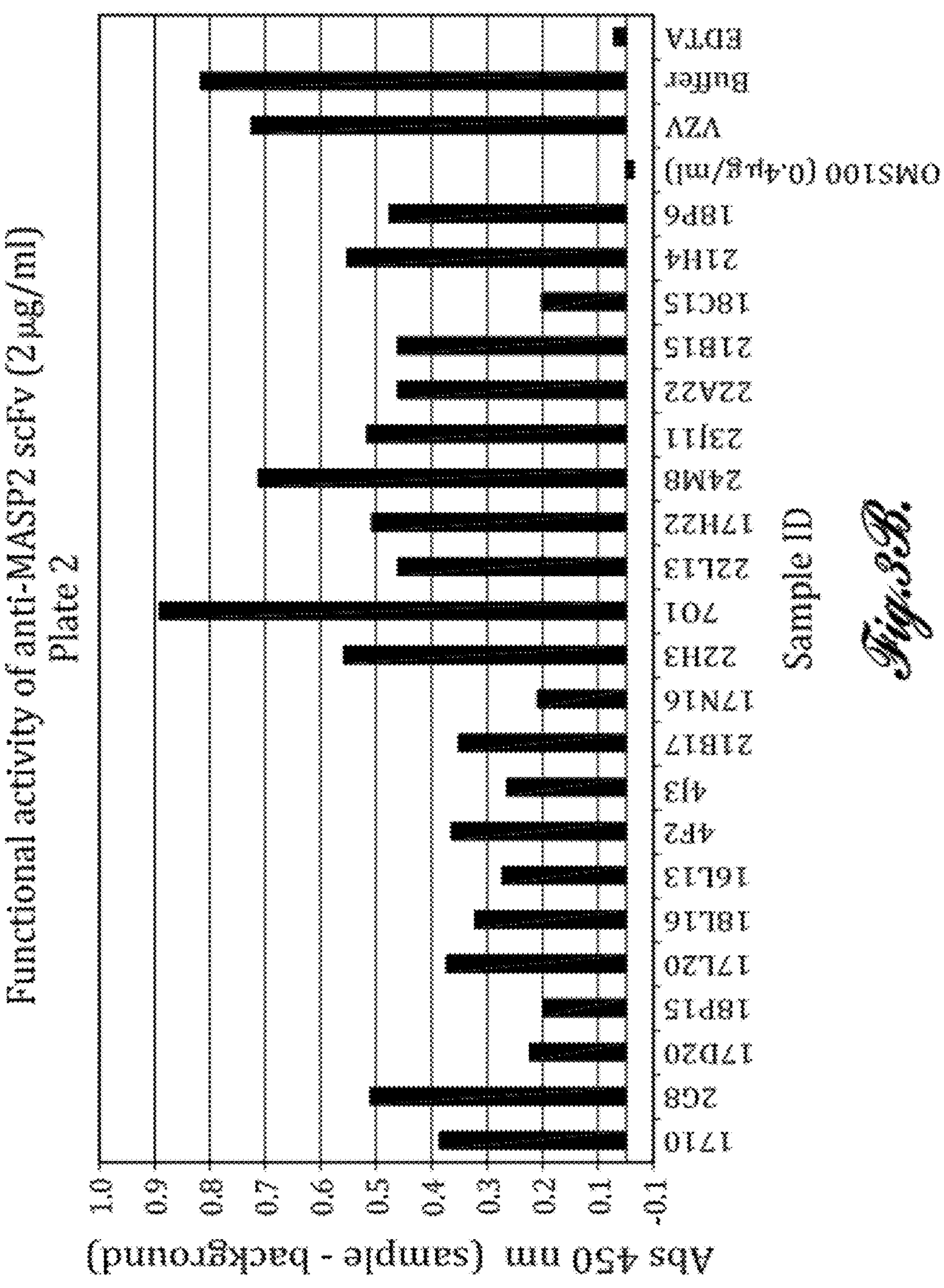

Results: Based on the cut-off criteria, a total of 13 clones were found to block the activity of MASP-2 as shown in FIGS. 3A and 3B. All 13 clones producing >50% pathway suppression were selected and sequenced, yielding 10 unique clones, as shown below in TABLE 9. The ten different clones shown in TABLE 9 were found to result in acceptable functional activity in the complement assay. All ten clones were found to have the same light chain subclass, λ3, but three different heavy chain subclasses, VH2, VH3 and VH6. The sequence identity of the clones to germline sequences is also shown in TABLE 9.

TABLE 9

10 Unique Clones with Functional anti-MASP-2 Activity

| Clone name | ELISA | Bio-core | Panning | Elution | VH subclass | Germline identity (%) | VL subclass | Germline identity (%) |
|---|---|---|---|---|---|---|---|---|
| 18P15 (13C24/6I18) | + | + | Streptavidin | Comp/TEA | VH6 | 95.62 | λ3 | 94.27 |
| 4D9 (18L16) | + | + | Streptavidin | TEA/Comp | VH2 | 99.66 | λ3 | 95.34 |
| 17D20 (17P10) | + | + | Streptavidin | Comp | VH2 | 96.56 | λ3 | 94.98 |
| 17L20 | + | + | Streptavidin | Comp | VH6 | 96.3 | λ3 | 93.55 |
| 4J3 (16L13/4F2) | + | + | Streptavidin | Comp/TEA | VH2 | 98.97 | λ3 | 98.21 |
| 18L16 | + | + | Streptavidin | Comp | VH2 | 100 | λ3 | 93.55 |
| 21B17 | + | − | NiNTA | TEA | VH3 | 99.31 | λ3 | 96.42 |
| 9P13 | + | − | NiNTA | Comp | VH6 | 100 | λ3 | 95.34 |
| 17N16 | + | − | Streptavidin | TEA/Comp | VH6 | 99.66 | λ3 | 97.85 |
| 3F22 (18C15) | + | − | Streptavidin | | VH6 | 100 | λ3 | 96.42 |

As shown above in TABLE 9, 10 different clones with acceptable functional activity and unique sequences were chosen for further analysis. As noted in TABLE 9, some of the clones were detected two or three times, based on identical sequences (see first column of TABLE 9 with clone names).

Expression and Purification of Ten svFc Candidate Clones

The ten candidate clones shown in TABLE 9 were expressed in one liter scale and purified via ion exchange in Nickel chromatography. After that a sample of each clone was run on a size exclusion chromatography column to assess the monomer and dimer content. As shown below in TABLE 10, nearly all of the scFv clones were present in the monomer form, and this monomer fraction was isolated for further testing and ranking.

TABLE 10

Analysis of Monomer Content

| Clone Name | Monomer |
|---|---|
| 4D9 | 97% |
| 18P15 | 98% |
| 17D20 | 95% |
| 17N16 | 93% |
| 3F22 | 86% |
| 4J3 | 81% |
| 17L20 | 98% |
| 18L16 | 92% |
| 9P13 | 89% |
| 21B17 | 91% |

Testing Monomer Fraction for Binding and Functional Activity

The clones shown in TABLE 10 were expressed in 1 L scale, purified on metal chromatography and ion exchange, separated into monomer fraction by size exclusion chromatography (SEC) and functional assays were repeated to determine $IC_{50}$ values and cross-reactivity.

Functional Assay on Monomer Fractions:

The monomer fraction of the top ten clones, shown in TABLE 10, was purified and tested for functional $IC_{50}$ nM in a dilution series in which each received the same concentration of GVB buffer with Calcium and Magnesium and human serum. The scFv clones were tested in 12 dilutions in triplicate. The positive control was OMS100 Fab2. C3b deposition was monitored in the presence and absence of antibody. The results are shown below in TABLE 11.

Binding Assay:

Binding affinity $K_D$ was determined in two different ways for purified monomer fractions of the ten candidate scFv clones. MASP-2A was either immobilized by amine coupling to a CM5 chip, or a fixed concentration of scFv (50 nM) was first captured with amine coupled high affinity α-cMyc antibody, and next a concentration series of MASP-2A in solution was passed over the chip. The results are shown below in TABLE 11.

Results:

TABLE 11

Summary of functional inhibitory activity ($IC_{50}$) and MASP-2 binding affinity ($K_D$) for the ten candidate scFv clones assayed in the monomer state

| Clone name | Inhibitory activity in Human Serum $IC_{50}$ (nM) | Binding Affinity to human MASP-2 (immobilized) $K_D$ (nM) | Binding Affinity human MASP-2 in solution $K_D$ (nM) |
|---|---|---|---|
| 18P15 (13C24/6118) | 123.1 | 39.8 | 5.88 |
| 4D9 (18L16) | 22.0 | 8.4 | 2.0E−11 |
| 17D20 (17P10) | 156.6 | 11.3 | 0.76 |
| 17L20 | ND | 28.8 | 21.3 |
| 4J3 (16L13/4F2) | 54.9 | 55.5 | 5.72 |
| 18L16 | 6.1 | 39.0 | 5.48 |
| 21B17 | ND | ND | 4.0 |
| 9P13 | 28.9 | 220.0 | 2.4E−11 |
| 17N16 | 15.4 | 3560.0 | 1.68 |
| 3F22 (18C15) | 20.6 | ND | 2.8E−12 |

Discussion of Results:

As shown in TABLE 11, in the functional assay, five out of the ten candidate scFv clones gave $IC_{50}$ nM values less than the 25 nM target criteria using 0.5% human serum. As described below, these clones were further tested in the presence of non-human primate serum and rat serum to determine functional activity in other species. With regard to binding affinity, in solution, all binding affinities were in the range of low nM or better, whereas in the conventional assay with immobilized MASP-2, only two clones (4D9 and 17D20) had affinities in the low nM range. The observation of higher affinities in the solution based assay is likely a result of the fact that the antigen multimerizes when in solution. Also, when the target is immobilized on the chip (via oriented coupling) the epitope may be masked, thereby reducing the observed affinities in the immobilized assay.

EXAMPLE 4

This Example describes the results of testing the ten candidate human anti-MASP-2 scFv clones for cross-reactivity with rat MASP-2 and determining the $IC_{50}$ values of these scFv clones in a functional assay to determine their ability to inhibit MASP-2 dependent complement activation in human serum, non-human primate serum, and rat serum.

Methods:

Cross-Reactivity with Rat MASP-2

The ten candidate scFv clones, shown in TABLE 9 of Example 3, were tested for cross-reactivity against rat MASP-2A in a conventional ELISA assay against adsorbed rat MASP-2A. Rat MASP-2A was diluted to 4 μg/ml in PBS and coated on a Maxisorp ELISA plate (Nunc) overnight at 4° C. The next day, the plate was blocked by washing three times in PBS-Tween (0.05%). The ScFv clones (100 μl) diluted in 20 μg/ml in PBS-Tween were added to the plate, and further titrated with 4-fold dilutions three times. MASP-2A specific svFc clones (wells containing bound scFv) were detected with anti-cMyc and rabbit anti-mouse HRP secondary antibody. The reaction was developed in peroxidase substrate TMB (Pierce). The positive control was OMS100 Fab2 diluted to 10 μg/ml in PBS-Tween. All the tested clones showed cross reaction with rat MASP-2A, which was expected since the second panning round was with rat MASP-2 (data not shown).

Functional Characterization of the Ten Candidate scFv Clones in Human Serum, Non-Human Primate (NHP) Serum and Rat Serum Determination of Baseline C3c Levels in Different Sera First, an experiment was carried out to compare the baseline C3b levels in the three sera (human, rat and NHP) as follows.

Mannan was diluted to 20 μg/ml and coated on an ELISA plate overnight at 4° C. The next day wells were blocked with 1% HSA. Normal human, rat and African Green Monkey serum (non-human primate "NHP") serum was diluted starting at 2% with two-fold dilutions in CaMgGVB buffer. The reaction was initiated by incubation for one hour at 37° C., and was stopped by transferring the plate to an ice bath. C3b deposition was detected with a rabbit anti-mouse C3c antibody, followed by goat anti-rabbit HRP. The negative control was buffer without antibody (no OMS100 results in maximum C3b deposition) and the positive control for inhibition was buffer with EDTA (no C3b deposition).

Figure 4:
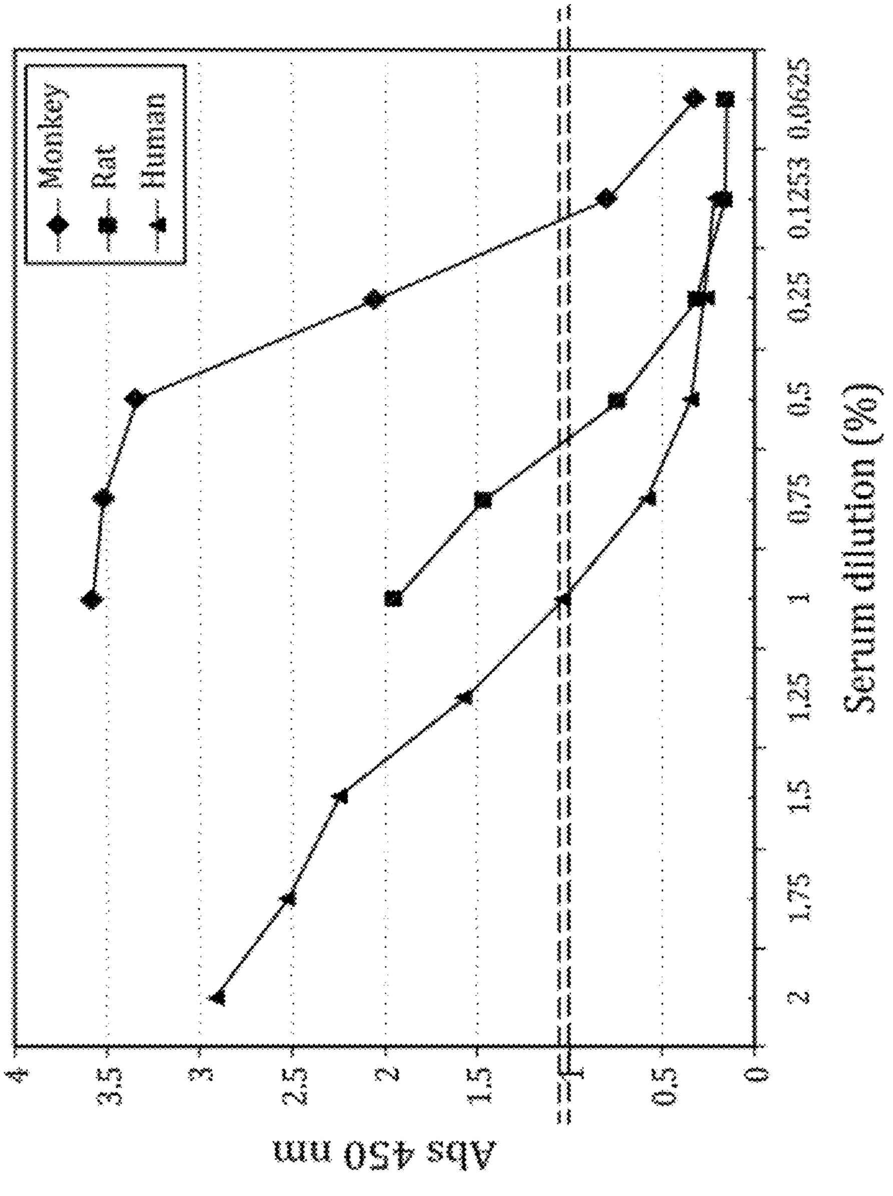
FIG. 4 graphically illustrates the results of an experiment that was carried out to compare C3c levels in the three sera (human, rat and NHP), as described in Example 4.

FIG. 4 graphically illustrates the baseline C3c levels in the three sera (human, rat and NHP). As shown in FIG. 4, the C3c levels were very different in the different sera tested. When comparing the C3c levels, it appeared that 1% human serum gave equivalent levels as 0.2% NHP and 0.375% rat serum. Based on these results, the concentrations of sera were normalized so that the scFv results could be directly compared in the three different types of sera.

Functional Assay of the ScFv Clones in Different Sera

Purified monomer fractions of the ten candidate scFv clones were then tested for functional $IC_{50}$ nM in human serum, rat serum and African green monkey serum (non-human primate "NHP"). The assay was performed as described in Example 3, using 1000 nM scFv purified protein and either normal human serum that was diluted to 0.9% in CaMgGVB buffer; African Green Monkey serum diluted to 0.2% in CaMgGVB buffer; or Rat serum diluted to 0.375% in CaMgGVB buffer. All ten scFv clones were tested in a dilution series in which they received the same concentration of GVB buffer with calcium and magnesium and serum. The scFv clones were tested in twelve dilutions in triplicates. The positive control was OMS100 Fab2 at 100 ng/ml or addition of EDTA to the reaction. The negative control was an irrelevant scFv control or PBS with no scFv. C3b deposition was monitored in the presence and absence of scFv or Fab2 antibody. The background signal of OMS100 at 100 ng/ml was subtracted from all signals. TABLE 12 summarizes the results of the functional assays in all three sera.

TABLE 12

Functional $IC_{50}$ (nM) activity of the scFv clones in three different types of sera.

| Clone name | human serum Exp #1* | human serum Exp #2 | human serum Exp #3 | human serum Exp #4 | Non-human primate Exp #1 | Non-human primate Exp #2 | rat serum Exp #1 |
|---|---|---|---|---|---|---|---|
| 18P15 (13C24/6I18) | 123.1 | 207.5 | 198.9 | 81.92 | 407.1 | 249.6 | ND |
| 4D9 (18L16) | 22.0 | 46.31 | 62.16 | 38.37 | 114.6 | 203.1 | ND |
| 17D20 (17P10) | 156.6 | 39.93 | 24.05 | 23.74 | 94.75 | 71.85 | 434.1 |
| 17L20 | ND | 104.3 | 308.1 | 198.9 | ambiguous | 71.74 | 40.97 |
| 4J3 (16L13/4F2) | 54.9 | 105.6 | 123.8 | 41.64 | 180.9 | 168.3 | ND |
| 18L16 | 6.1 | 96.85 | 52.32 | 53.51 | 65.60 | 127.6 | ND |
| 21B17 | ND | 93.73 | 325.4 | 434.7 | 338.3 | 366.4 | ND |
| 9P13 | 28.9 | 120.5 | 17.28 | 24.26 | 99.29 | 77.1 | ND |
| 17N16 | 15.4 | 65.42 | 24.78 | 19.16 | 95.57 | 58.78 | ND |
| 3F22 (18C15) | 20.6 | 36.73 | 41.40 | 68.81 | 114.2 | 172.8 | ND |

Note:
*the first set of data on human serum (Exp #1) was done on scFv samples that were not concentrated, therefore, clones with low concentration could not be titrated fully.

In the remaining experiments, all clones were concentrated and titrations started at identical concentrations.

Summary of Results for Functional Activity in scFv Candidate Clones in Different Sera:

All ten of the scFv clones showed function in both human and non-human primate (NHP) serum after the sera had been normalized with respect to C3b deposition levels. The six most active clones in human serum were: 9P13>17N16>17D20>4D9>3F22>18L16, when ranked from best to worst. In NHP serum, the clones ranked (best to worst): 17L20>17N16>17D20>9P13>18L16>3F22. Both 17N16 and 17D20 ranked in the top three for both human and NHP sera. 17D20 also showed some activity in rat serum.

Based on these results, the top three scFv clones were determined to be: 18L16, 17D20 and 17N16. These three clones were further analyzed in dilute human serum (1% serum) as shown below in TABLE 13.

TABLE 13

C3 Assay of the three candidate clones: ($IC_{50}$ nM) in dilute serum (1%)

| | 17D20 | 17N16 | 18L16 |
|---|---|---|---|
| human serum | | | |
| Exp #1 | 24 nM | 19 nM | 53 nM |
| Exp #2 | 24 nM | 24 nM | 52 nM |
| Exp #3 | 40 nM | 65 nM | 97 nM |
| mean | 29 +/- 5 | 36 +/- 15 | 67 +/- 15 |
| non-human primate serum | | | |
| Exp #1 | 94 nM | 95 nM | 65 nM |
| Exp #2 | 74 nM | 58 nM | 154 nM |
| mean | 84 nM | 76 nM | 110 nM |

FIG. 5A is an amino acid sequence alignment of the full length scFv clones 17D20, 18L16, 4D9, 17L20, 17N16, 3F22 and 9P13. The scFv clones comprise a heavy chain variable region (aa1-120), a linker region (aa121-145), and a light chain variable region (aa 146-250). As shown in FIG. 5A, alignment of the heavy chain region (residues 1-120) of the most active clones reveals two distinct groups belonging to VH2 and VH6 gene family, respectively. As shown in FIG. 5A, the VH region with respect to the clones of the VH2 class: 17D20, 18L16 and 4D9 has a variability in 20 aa positions in the total 120 amino acid region (i.e. 83% identity).

As further shown in FIG. 5A, the VH region with respect to the clones of the VH6 class: 17L20, 17N16, 3F22, and 9P13, has a variability in 18 aa positions in the total 120 amino acid region (i.e. 85% identity).

FIG. 5B is a sequence alignment of the scFv clones 17D20, 17N16, 18L16 and 4D9.

TABLE 14

Sequence of ScFv Candidate clones shown in FIG. 5A and 5B

| Clone Reference ID | full length AA sequence |
|---|---|
| 17D20 | SEQ ID NO: 55 |
| 18L16 | SEQ ID NO: 56 |
| 4D9 | SEQ ID NO: 57 |
| 17L20 | SEQ ID NO: 58 |
| 17N16 | SEQ ID NO: 59 |
| 3F22 | SEQ ID NO: 60 |
| 9P13 | SEQ ID NO: 61 |

The ranking priorities were (1) human serum functional potency and full blockage; (2) NHP cross-reactivity and (3) sequence diversity. 17D20 and 17N16 were selected as the best representatives from each gene family. 18L16 was selected as the third candidate with appreciable CDR3 sequence diversity.

17N16 and 17D20 were the top two choices due to complete functional blockage, with the best functional potencies against human; appreciable monkey cross-reactivity and different VH gene families. 3F22 and 9P13 were eliminated due to VH sequences nearly identical to 17N16. 18P15, 4J9 and 21B17 were eliminated due to modest potency. 17L20 was not pursued because it was only partially blocking.

18L16 and 4D9 had similar activities and appreciable diversity compared to 17D20. 18L16 was chosen due to greater primate cross-reactivity than 4D9.

Therefore, based on these criteria: the following three mother clones: 17D20, 17N16 and 18L16 were advanced into affinity maturation as further described below.

EXAMPLE 5

This Example describes the cloning of three mother clones 17D20, 17N16 and 18L16 (identified as described in Examples 2-4) into wild-type IgG4 format, and assessing the functionality of three mother clones as full length IgGs.

Rationale:

Fully human anti-MASP-2 scFv antibodies with moderate functional potency were identified using phage display as described in Examples 2-4. Three such mother clones, 17D20, 17N16 and 18L16 were selected for affinity maturation. To assess the functionality of these mother clones as full length IgGs, IgG4 wild-type and S228P hinge region IgG4 mutant forms of these antibodies were produced. The S228P hinge region mutant was included to increase serum stability (see Labrijn A. F. et al., *Nature Biotechnology* 27:767 (2009)).

The amino acid sequence of IgG4 wild-type is set forth as SEQ ID NO:63, encoded by SEQ ID NO:62.

The amino acid sequence of IgG4 S228P is set forth as SEQ ID NO:65, encoded by SEQ ID NO:64.

The IgG4 molecules were also cleaved into F(ab')2 formats with pepsin digestion and fractionated by size exclusion chromatography in order to compare the mother clones directly to the OMS100 control antibody, which is a F(ab)2 molecule.

Methods:

Generating the Clones into Full Length Format

The three mother clones were converted into wild type IgG4 format and into IgG4 mutant S228P format. This was accomplished by PCR isolation of the appropriate VH and VL regions from the above-referenced mother clones and cloning them into pcDNA3 expression vectors harboring the appropriate heavy chain constant regions to create in-frame fusions to produce the desired antibody. The three mother clones in mutant IgG4 format were then cleaved with pepsin to generate F(ab')2 fragments and the latter were purified by fractionation on a size exclusion chromatography column.

Binding Assay

The candidate mother clones converted into IgG4 format were transiently transfected into HEK 293 cells and supernatants from the transient transfection were titrated in an ELISA assay. The clones showed excellent reactivity with physically adsorbed human MASP-2A, and ranked in the following order: 17N16>17D20>18L16 (data not shown).

The clones were then purified and re-tested in an ELISA and activity assay as follows. Human MASP-2A was coated at 3 μg/ml in PBS on a maxisorp plate, IgG (45 μg/ml) and Fab'2 (30 μg/ml) were diluted in PBS-Tween to a starting concentration of 300 nM, and further with 3-fold dilutions. IgGs were detected with HRP conjugated Goat α-Human IgG (Southern Biotech) and the F(ab')2 were detected with HRP-conjugated Goat α-Human IgG H+L (Pierce 31412). The reaction was developed with TMB substrate and stopped with 2M $H_2SO_4$. The results are shown below in TABLE 15.

TABLE 15

Binding affinity to human MASP-2

| Antibody Clone Reference | IgG4 mutated format (pM) | F(ab')2 (pM) | scFv (nM) |
|---|---|---|---|
| OMS100 control | ND | 92.5 | ND |
| 18L16 | 96.2 | 178.7 | ND |
| 17N16 | 20.6 | 95.9 | 18.9 |
| 17D20 | 28.4 | 181.5 | ND |

Functional Assay

The C3 convertase assay using 1% normal human serum (NHS), as described in Example 4, was used to compare the functional activity of the mother scFv clones and full length IgG4 counterparts in 1% NHS. Mannan was diluted to a concentration of 20 μg/ml and coated on ELISA plate overnight at 4° C. The next day, the wells were blocked with 1% human serum. Human serum was diluted to 1% in CaMgGVB buffer and the purified antibodies; scFv (900 nM), F(ab')2 (300 nM), IgG (300 nM) were added in duplicates at a series of different dilutions to the same amount of buffer, and pre-incubated for 45 minutes on ice before adding to the blocked ELISA plate. The reaction was initiated by incubation at 37° C. for one hour and was stopped by placing the plate on ice. C3b deposition was determined with a Rabbit α-Mouse C3c antibody followed by a Goat α-Rabbit HRP. The background of OMS100 at 50 nM on mannan positive plates was subtracted from the curves. A summary of the results of this analysis are shown below in TABLE 16.

TABLE 16

C3 convertase assay using 1% human serum ($IC_{50}$ nM)

| scFv clone ID# | wt IgG4 ($IC_{50}$ nM) | F(ab')2 ($IC_{50}$ nM) | scFv ($IC_{50}$ nM) | Fold improvement (scFv to divalent form) |
|---|---|---|---|---|
| 17D20 | 7.392/10.32 | 7.305/13.54 | 98.27/151.0 | ~13.5x/~12.6x |
| 17N16 | 5.447/3.088 | 5.701/5.092 | 36.18/77.60 | ~6.6x/~19.3x |
| 18L16 | 33.93/22.0 | NA | 160.2/193.0 | ~4.7x/~8.7x |

Note:
The two values shown in columns 2-4 of Table 16 refer to the results of two separate experiments.

The functional potency of the IgG4 mother clones were also compared to the IgG4 hinge mutant (S228P) format for each clone. The numeric $IC_{50}$ values for the C3b deposition assay using 1% NHS are shown below in TABLE 17.

TABLE 17

Wild type (IgG4) versus Hinge Mutant format (S228P) in C3b deposition assay in 1% human serum ($IC_{50}$ nM)

| Clone ID | WT format (IgG4) | IgG4 hinge mutant (S228P) |
|---|---|---|
| 17D20 | 22 nM | 11/27 nM |
| 17N16 | ≈20 nM | agonist |
| 18L16 | 59 nM | partial/mixed |

As shown above in TABLE 17, in some cases, unexpected agonist pharmacology was noted for IgG's derived from antagonistic scFv's. The mechanistic basis for this observation is not understood.

The activities of IgG4 converted mother clones with inhibitory function in 1% NHS were further evaluated under more stringent assay conditions that more closely mimic physiological conditions. To estimate antibody activity under physiological conditions, testing of mother clone IgG4 preparations was conducted for their ability to inhibit Lectin-pathway (LP) dependent C3b deposition onto Mannan-coated plates under stringent assay conditions using minimally diluted (90%) human plasma.

Figure 6:
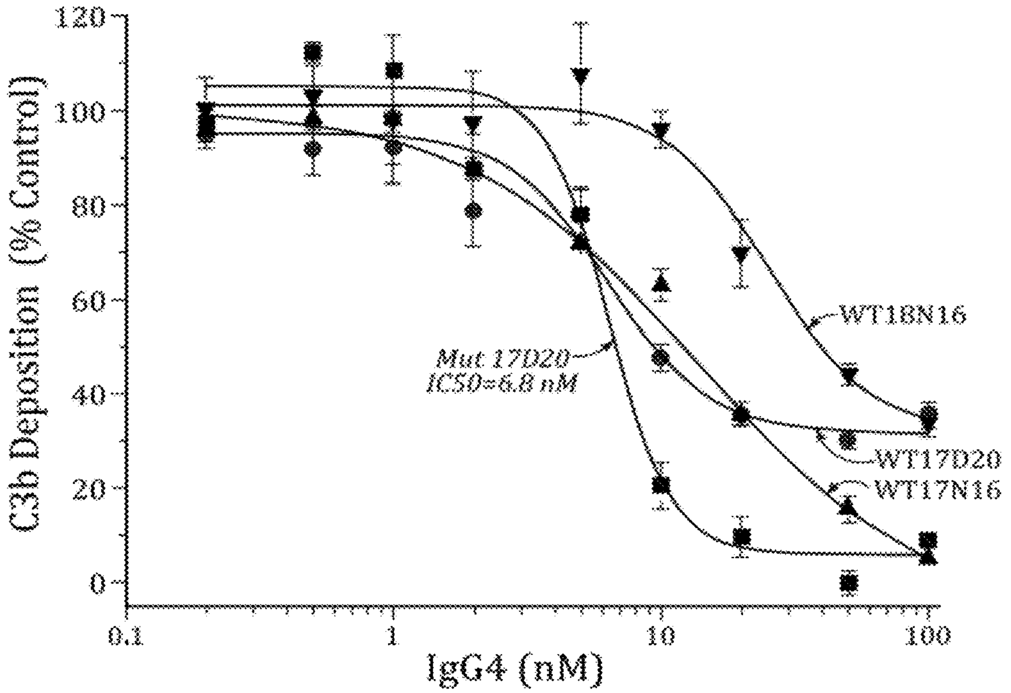
FIG. 6 graphically illustrates the inhibitory activities of preparations of IgG4 converted mother clones in a C3b deposition assay using 90% human plasma, as described in Example 5.

The results of the C3b deposition assay in 90% human plasma are shown in FIG. 6. Since MASP-2 and its substrates are present in the assay mixture at approximately 100-fold higher concentration than in the dilute serum assay using 1% normal human serum, a right-shift of the antagonist dose-response curve is generally expected. As shown in FIG. 6, as expected, a right-shift to lower apparent potencies was observed for OMS100 and all the MASP-2 antibodies tested. However, surprisingly, no reduction in apparent potency was observed for the hinge region mutant (S228P) of 17D20, and the potency in this format was comparable to that measured in 1% plasma (see TABLE 17). In the 90% NHS assay format the functional potency of 17D20 IgG4 (S228) was found to be modestly lower than OMS100 Fab2, which is in contrast to the assay results in 1% NHS where OMS100 was 50 to 100-fold more potent than 17D20 IgG4 S228P (data not shown). The wild type IgG4 form of 17N16 also showed full inhibition in 90% NHS but was somewhat less potent in this assay format ($IC_{50}$ of 15 nM) while the wild type IgG4 form of 18L16 was less potent and only partially inhibitory, as shown in FIG. 6.

Based on these findings, the activity of IgG4 converted mother clones was further evaluated by examining C4b deposition under stringent assay conditions (90% NHS). This assay format provides for a direct measure of antibody activity on the enzymatic reaction catalyzed by MASP-2.

Assay to Measure Inhibition of MASP-2-Dependent C4 Cleavage

Background: The serine protease activity of MASP-2 is highly specific and only two protein substrates for MASP-2 have been identified; C2 and C4. Cleavage of C4 generates C4a and C4b. Anti-MASP-2 Fab2 may bind to structural epitopes on MASP-2 that are directly involved in C4 cleavage (e.g., MASP-2 binding site for C4; MASP-2 serine protease catalytic site) and thereby inhibit the C4 cleavage functional activity of MASP-2.

Yeast mannan is a known activator of the lectin pathway. In the following method to measure the C4 cleavage activity of MASP-2, plastic wells coated with mannan were incubated for 90 minutes at 4° C. with 90% human serum to activate the lectin pathway. The wells were then washed and assayed for human C4b immobilized onto the wells using standard ELISA methods. The amount of C4b generated in this assay is a measure of MASP-2 dependent C4 cleavage activity. Anti-MASP-2 antibodies at selected concentrations were tested in this assay for their ability to inhibit C4 cleavage.

Methods: 96-well Costar Medium Binding plates were incubated overnight at 5° C. with mannan diluted in 50 mM carbonate buffer, pH 9.5 at 1.0 μg/50 μL/well. Each well was washed 3× with 200 μL PBS. The wells were then blocked with 100 μL/well of 1% bovine serum albumin in PBS and incubated for one hour at room temperature with gentle mixing. Each well was washed 3× with 200 μL of PBS. Anti-MASP-2 antibody samples were diluted to selected concentrations in $Ca^{++}$ and $Mg^{++}$ containing GVB buffer (4.0 mM barbital, 141 mM NaCl, 1.0 mM $MgCl_2$, 2.0 mM $CaCl_2$, 0.1% gelatin, pH 7.4) at 5° C. 90% human serum was added to the above samples at 5° C. and 100 μL was transferred to each well. The plates were covered and incubated for 90 min in an ice waterbath to allow complement activation. The reaction was stopped by adding EDTA to the reaction mixture. Each well was washed 5×200 μL with PBS-Tween 20 (0.05% Tween 20 in PBS), then each well was washed with 2× with 200 μL PBS. 100 μL/well of 1:700 dilution of biotin-conjugated chicken anti-human C4c (Immunsystem AB, Uppsala, Sweden) was added in PBS containing 2.0 mg/ml bovine serum albumin (BSA) and incubated one hour at room temperature with gentle mixing. Each well was washed 5×200 μL PBS. 100 μL/well of 0.1 μg/ml of peroxidase-conjugated streptavidin (Pierce Chemical #21126) was added in PBS containing 2.0 mg/ml BSA and incubated for one hour at room temperature on a shaker with gentle mixing. Each well was washed 5×200 μL with PBS. 100 μL/well of the peroxidase substrate TMB (Kirkegaard & Perry Laboratories) was added and incubated at room temperature for 16 min. The peroxidase reaction was stopped by adding 100 μL/well of 1.0 M $H_3PO_4$ and the $OD_{450}$ was measured.

Results:

In this format, both IgG4 forms of 17D20 inhibited Lectin pathway driven C4b deposition, although the $IC_{50}$ values were ≈3 fold higher compared to the C3b deposition assay. Interestingly, 17N16 IgG4 wild type showed good activity in this assay with an $IC_{50}$ value and dose-response profile comparable to the C3b deposition assay. 18L16 was considerably less potent and did not achieve complete inhibition in this format (data not shown).

Discussion:

As described in Examples 2-5, fully human anti-MASP-2 scFv antibodies with functional blocking activity were identified using phage display. Three such clones, 17N16, 17D20 and 18L16, were selected for affinity maturation and further testing. To assess the functionality of these mother clones as full length IgGs, IgG4 wild type and IgG4 S228P hinge region mutant forms of these antibodies were produced. As described in this Example, the majority of full length IgGs had improved functional activity as compared to their scFv counterparts when tested in a standard functional assay format with 1% human plasma. To estimate antibody activity under physiological conditions, testing of mother clone IgG4 preparations was conducted under stringent assay conditions using 90% human plasma. Under these conditions, several antibodies revealed functional potencies which were substantially better than expected based on their performance in standard (1%) plasma functional assays.

EXAMPLE 6

This Example describes the chain shuffling and affinity maturation of mother clones 17D20, 17N16 and 18L16, and analysis of the resulting daughter clones.

Methods:

To identify antibodies with improved potency, the three mother scFv clones, 17D20, 17N16 and 18L16, identified as described in Examples 2-5, were subjected to light chain shuffling. This process involved the generation of a combinatorial library consisting of the VH of each of the mother clones paired up with a library of naïve, human lambda light chains (VL) derived from six healthy donors. This library was then screened for scFv clones with improved binding affinity and/or functionality.

9,000 light chain shuffled daughter clones were analyzed per mother clone, for a total of 27,000 clones. Each daughter clone was induced to express and secrete soluble scFv, and was screened for the ability to bind to human MASP-2A. ScFvs that bound to human MASP-2A were detected via their c-Myc tag. This initial screen resulted in the selection of a total of 119 clones, which included 107 daughter clones from the 17N16 library, 8 daughter clones from the 17D20 library, and 4 daughter clones from the 18L16 library.

The 119 clones were expressed in small scale, purified on NiNTA columns, and tested for binding affinity in an ELISA assay against physically adsorbed human MASP-2A.

Figure 7A:
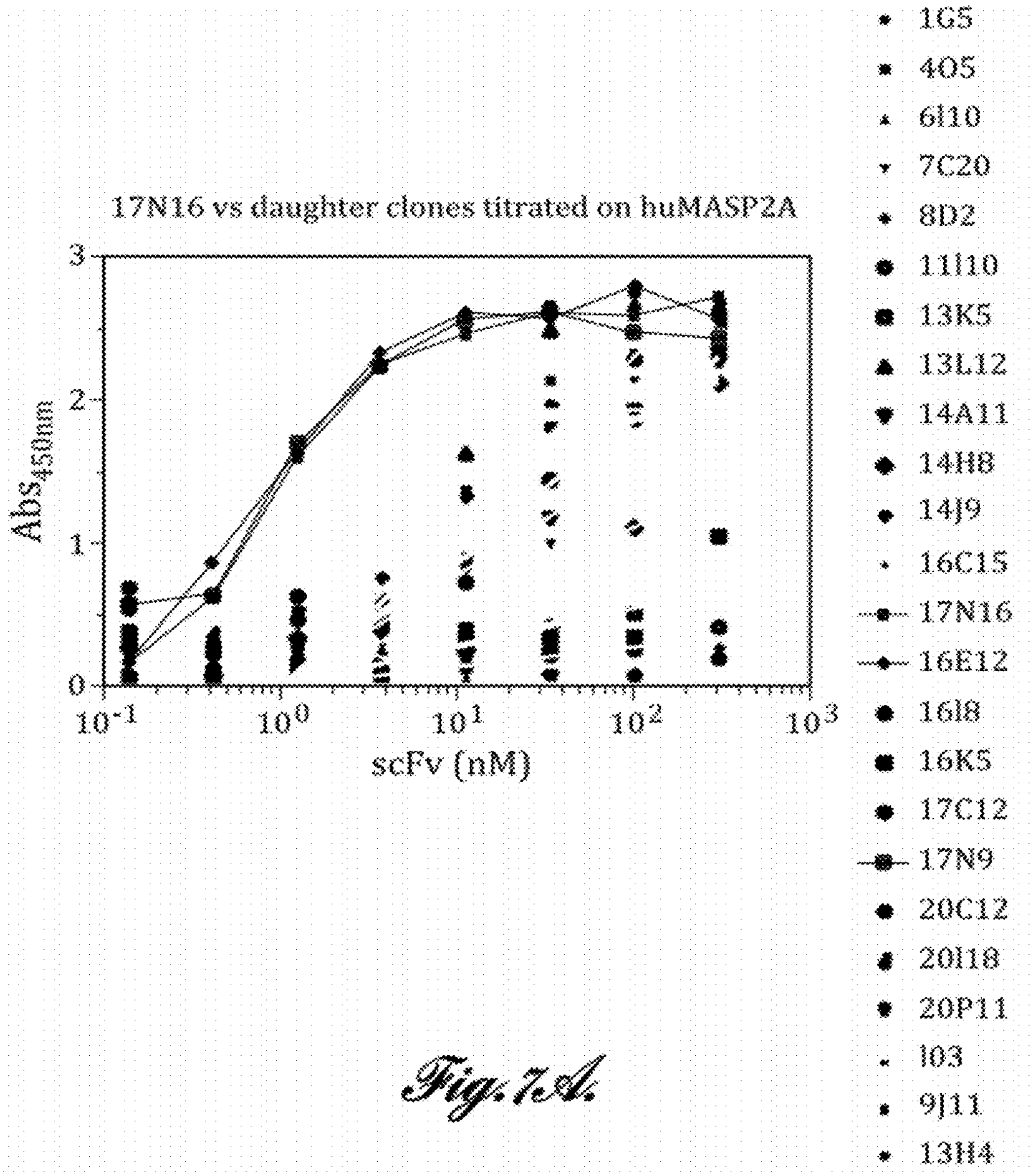
FIG. 7A graphically illustrates the results of the ELISA assay on the 17N16 mother clone versus daughter clones titrated on huMASP2A, as described in Example 6.
Figure 7B:
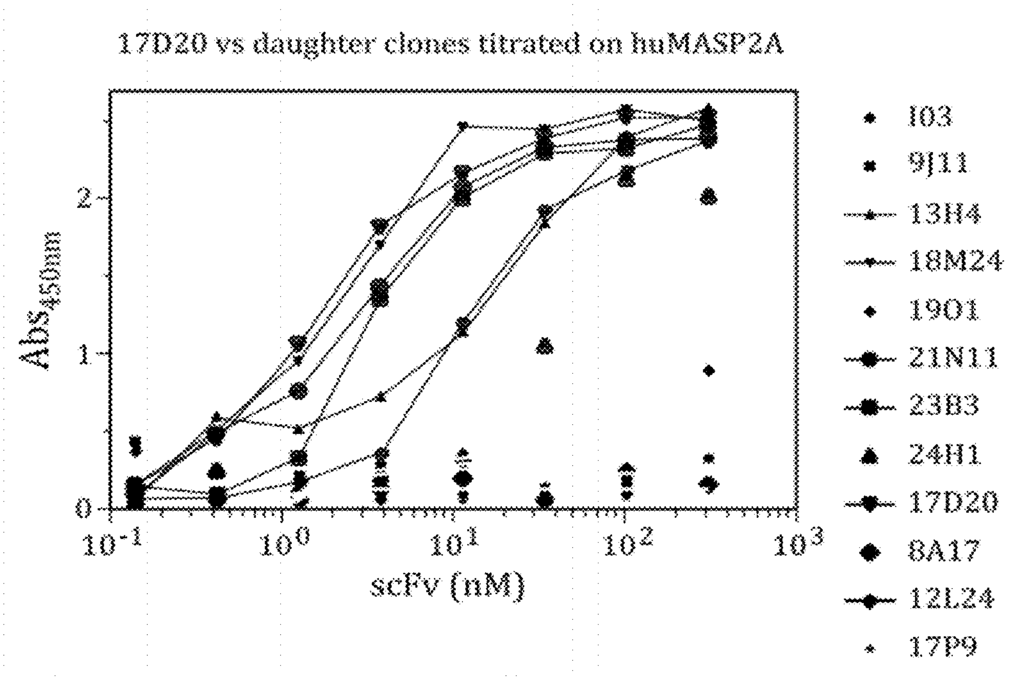
FIG. 7B graphically illustrates the results of the ELISA assay on the 17D20 mother clone versus daughter clones titrated on huMASP2A, as described in Example 6.

Results:

The results of the ELISA assay on a representative subset of the 119 daughter clones is shown in FIGS. 7A and B. FIG. 7A graphically illustrates the results of the ELISA assay on the 17N16 mother clone versus daughter clones titrated on huMASP-2A. FIG. 7B graphically illustrates the results of the ELISA assay on the 17D20 mother clone versus daughter clones titrated on huMASP-2A.

As shown in FIG. 7A, daughter clones 17N16m_d16E12 and 17N16m_d17N9, derived from the 17N16 mother clone had affinities that were higher than the mother clone. Also, as shown in FIG. 7B, one clone derived from the 17D20 mother clone, 17D20m_d18M24, had a higher affinity that the mother clone. These three clones, and an additional three clones: 17N16m_d13L12, 17N16m_d16K5, 17N16m_d1G5, and 17D20m_d1824 that had a low expression level were expressed in 0.5 L scale, purified into monomer fraction by size exclusion chromatography and were retested in an ELISA and functional assay. The 18L16 library did not produce any daughter clones with the desired binding affinity.

After purification, the six daughter clones were tested in a complement assay for inhibitory activity. The results are shown in TABLE 18.

TABLE 18

Complement assay of mother and daughter clones

| scFv clone ID# | $IC_{50}$ nM | $K_D$ nM |
|---|---|---|
| 17N16mc | 8.8 | 18.9 |
| 17N16m_d17N9 | 10.3 | 48.6 |
| 17N16m_d16E12 | 103.2 | |
| 17D20m_d18M24 | 172.3 | |

As shown above in TABLE 18, only one of the clones, 17N16m_d17N9, had affinity and activity in the same range as the mother clone.

FIG. 8 is a amino acid sequence alignment of the full length scFv mother clone 17N16 (SEQ ID NO:59) and the 17N16m_d17N9 daughter clone (SEQ ID NO:66), showing that the light chains (starting with SYE) have 17 amino acid residues that differ between the two clones.

Rescreening of the 17N16 lambda library resulted in several additional candidate daughter clones, of which 17N16m_d27E13 was identified in an ELISA and complement assay, and was included in the set of candidate daughter clones for further analysis.

Assaying Daughter Clones in Different Sera

The candidate daughter clones were analyzed in different sera as follows. Mannan was diluted to 20 μg/ml and coated on an ELISA plate overnight at 4° C. The next day, the wells were blocked with 1% HSA. African Green monkey serum was diluted to 0.2%, rat serum was diluted to 0.375% and human serum was diluted to 1% in CaMgGVB buffer. Purified scFv from each of the candidate daughter clones was added in duplicates at a series of different concentrations to the same amount of buffer and preincubated for 45 minutes on ice prior to addition to the blocked ELISA plate. The reaction was initiated by incubation for one hour at 37° C., and was stopped by transferring the plate to an ice bath. C3c release was detected with a Rabbit α-Mouse C3c antibody followed by a Goat α-Rabbit HRP. The background of OMS100 at 0.1 μg/ml on mannan negative plates was subtracted from these curves. The results are summarized below in TABLE 19.

TABLE 19

$IC_{50}$ values for mother clone 17N16 and daughter clones 17N16m_d17N9 and 17N16m_d27E13 in different sera.

| ScFv Clones | African Green Serum $IC_{50}$ (nM) | Human Serum $IC_{50}$ (nM) | Rat Serum $IC_{50}$ (nM) |
|---|---|---|---|
| 17N16mc | 92.93/81.37 | 65.31/73.54 | ND/195.8 |
| 17N16m_d17N9 | 63.82/81.11 | 39.90/57.67 | 79.32/140.6 |
| 17N16m_d27E13 | ND/430.9 | 389.1/NA | NA |

Note:
The two values shown in columns 2-4 of Table 19 refer to the results of two separate experiments.

Discussion of Results:

As shown in TABLE 19, daughter clone 17N16m_d17N9 has higher functional activity than the mother clone. The improved function in rat serum in addition to the seventeen amino acid sequence difference in the light chain as compared to the mother clone makes this clone a positive candidate. Based on this data, daughter clone 17N16m_d17N9 was selected for further analysis.

EXAMPLE 7

This Example describes the generation and analysis of daughter clone 17D20m_d3521N11, derived from mother clone 17D20.

Background/Rationale:

To improve on affinity of the mother clone candidate 17D20mc, an additional "look-through-mutagenesis" was performed on the first three amino acids in the CDR3 of the heavy chain (CDR-H3). This was a mutagenesis campaign in parallel with the normal light chain shuffling of 17D20mc. Therefore, three different scFv libraries were constructed by PCR where the amino acid positions 1, 2 and 3 were randomized to the set of all possible 20 amino acids using degenerate codons. After cloning the libraries, microscale expression was performed and scFv binding was monitored on a MASP-2A coated CM5 chip (not shown). BIAcore analysis of microscale expression was carried out on the three different libraries on chips coated with MASP-2A, randomized at position 1, 2, or 3 and potentially interesting daughter clones were identified.

It was observed that for the amino acid positions 1 and 2 of CDR-H3, no clone was found having an improved off-rate in comparison with the mother candidate clone 17D20m. However, a few candidates with mutations in amino acid position 3 in the CDR-H3 demonstrated improved off-rates in comparison with the mother clone 17D20m. These clones (#35, #59 and #90) were sequenced to identify the mutation. Sequences of two "look-through-mutagenesis" derived clones are compared with 17D20mc (original sequence). Interestingly, all sequenced clones except one (#90), harbored an Ala-Arg substitution in comparison with the mother candidate.

FIG. 9 is a sequence comparison of the amino acid sequence of the heavy chain region of the scFv mother clone 17D20m (aa 61-119 of SEQ ID NO:18) and the amino acid sequence of the CRD-H3 region of scFv clones with mutations in CDR-H3, clone #35 (aa 61-119 of SEQ ID NO:20, having a substitution of R for A at position 102 of SEQ ID NO:18), clone #59 (same sequence as clone #35), and clone #90 (substitution of P for A at position 102 of SEQ ID NO:18).

Analysis of Mutant Clones #35 and #59

The mutant clones #35 and #59 were expressed in small scale and further tested in comparison with the mother candidate clone 17D20 in a titration-ELISA on immobilized MASP-2A (10 μg/ml). The scFvs were serially diluted 5-fold starting from 20 μg/ml and binding was detected using anti-Myc (mouse)/anti-mouse HRP. Slightly improved binding was observed in the ELISA assay for the candidate clones #35 and #59 in comparison with the mother candidate clone 17D20 (data not shown).

The improved clone #35 was combined with the best light chain shuffled clone 17D20m_d21N11. The mutation in the VH of the candidate 17D20md35 (Ala-Arg) was combined with the light chain of the candidate 17D20m_d21N11, thus resulting in the clone termed VH35-VL21N11, otherwise referred to as 3521N11.

FIG. 10A is an amino acid sequence alignment of sequence of the CDR3 region of mother clone 17D20 (aa 61-119 of SEQ ID NO:18), the same region of daughter clone 17D20m_d21N11, having the same sequence, and the same region of the mutagenesis clone #35 combined with the VL of 17D20m_d21N11, referred to as "3521N11" (aa 61-119 of SEQ ID NO:20). The highlighted VH sequence regions comprise the CDRH3, and mutated target residue region is underlined.

FIG. 10B is a protein sequence alignment of the full length scFv including VL and VH regions of the 17D20 mother clone (SEQ ID NO:55) and the daughter clone 17D20m_d21N11 (SEQ ID NO:67). scFv daughter clone 17D20m_d3521N11 is set forth as SEQ ID NO:68. Note: it has been determined that the X residue in FIG. 10B at position 220 is an "E", as set forth in SEQ ID NO:68.

A titration ELISA assay of the set of scFvs shown in FIG. 10 was run on MASP-2 (10 μg/ml). The results are shown in TABLE 20.

TABLE 20

ELISA on human MASP-2

| Clone ID | $K_D$ (nM) |
|---|---|
| 17D20m_d21N11 | 10 |
| 17D20m_d3521N11 | 1.6 |
| 17D20mc (monomer) | 1.9 |
| 17D20md#35 (monomer) | 1.2 |

The 17D20m_d3521N11 daughter clone was further analyzed for functional activity as described below in Example 8.

EXAMPLE 8

This Example describes the conversion and analysis of the candidate daughter clones 17N16m_d17N9 and 17D20m_d3521N11 into IgG4, IgG4/S228P and IgG2 format.

Rationale/Background

The antibody screening methods described in Examples 2-7 have identified two mother clones, 17N16 and 17D20, with suitable functionality. Affinity maturation of these mother clones has yielded daughter clones that showed approximately 2-fold improvements in potency as compared to the mother clones in surrogate functional assays at the scFv level. The daughter clones with the best activities are 17N16m_d17N9 and 17D20m_d3521N11. As described in Example 6, in a comparison of functional activity of 17N16 mother clone with light chain shuffled daughter clones (scFv format, 1% NHS assay) it was determined that 17N16m_d17N9 is slightly more potent than the mother clone and has the best functional potency of all daughter clones tested in this assay.

Methods:

A comparison of the functional potency of the candidate scFv clones was carried out in the C3 conversion assay (1% human serum and 90% human serum), and in a C4 conversion assay (90% human serum), carried out as described in Example 5. The results are shown below in TABLE 21.

TABLE 21

Comparison of functional potency in $IC_{50}$ (nM) of the lead daughter clones and their respective mother clones (all in scFv format)

| scFv clone | 1% human serum C3 assay ($IC_{50}$ nM) | 90% human serum C3 assay ($IC_{50}$ nM) | 90% human serum C4 assay ($IC_{50}$ nM) |
|---|---|---|---|
| 17D20mc | 38 | nd | nd |
| 17D20m_d21N11 | 360 | nd | ~500 |
| 17D20m_d3521N11 | 26 | >1000 | 140 |
| 17N16mc | 68 | nd | nd |
| 17N16m_d17N9 | 48 | 15 | 230 |
| 17N16m_d27E13 | 390 | >1000 | nd |

As shown above in TABLE 21, 17N16m_d17N9 has good activity when assayed in 90% normal human serum (NHS) in the C3 assay and is more potent that the other daughter clones in this format.

Conversion of Candidate Clones into IgG4, IgG4/S228P and IgG2 format

All of these candidate clones were converted to IgG4, IgG4/S228P and IgG2 format for further analysis.

SEQ ID NO:62: cDNA encoding wild type IgG4

SEQ ID NO:63: wild type IgG4 polypeptide

SEQ ID NO:64 cDNA encoding IgG4 mutant S228P

SEQ ID NO:65: IgG4 mutant S228P polypeptide

SEQ ID NO:69: cDNA encoding wild type IgG2

SEQ ID NO: 70: wild type IgG2 polypeptide

TABLE 22

Summary of candidate clones:

| clone reference | daughter clone | Ig format | VH | VL |
|---|---|---|---|---|
| #1 (OMS641) | 17N16m_d17N9 | IgG2 | SEQ ID NO: 21 | SEQ ID NO: 27 |
| #2 (OMS642) | 17N16m_d17N9 | IgG4 | SEQ ID NO: 21 | SEQ ID NO: 27 |
| #3 (OMS643) | 17N16m_d17N9 | IgG4 (mutant) | SEQ ID NO: 21 | SEQ ID NO: 27 |
| #4 (OMS644) | 17D20_3521N11 | IgG2 | SEQ ID NO: 20 | SEQ ID NO: 24 |
| #5 (OMS645) | 17D20_3521N11 | IgG4 | SEQ ID NO: 20 | SEQ ID NO: 24 |
| #6 (OMS646) | 17D20_3521N11 | IgG4 mutant | SEQ ID NO: 20 | SEQ ID NO: 24 |

Monoclonal antibodies #1-6 were tested for the ability to cross-react with a non-human MASP-2 protein (African Green (AG) monkey) in a C3 assay to determine if these antibodies could be used to test for toxicity in an animal model that would be predictive for humans. Monoclonal antibodies #1-6 were also tested in a C3b deposition assay and a C4 assay in 90% human serum. The results are shown below in TABLE 23.

TABLE 23

| Human anti-MASP-2 MoAbs ($IC_{50}$ nM) in 90% human serum | | | | | | |
|---|---|---|---|---|---|---|
| Assay | MoAb#1 | MoAb#2 | MoAb#3 | MoAb#4 | MoAb#5 | MoAb#6 |
| Human C3 Assay | 20 | 3 | 12 | 2 | 3 | 2 |
| Human C4 assay | 30 | 30 | 30 | 5 | 5 | 4 |
| African Green Monkey C3 assay | nd | 26 | nd | 18 | 16 | 14 |

Figure 11A:
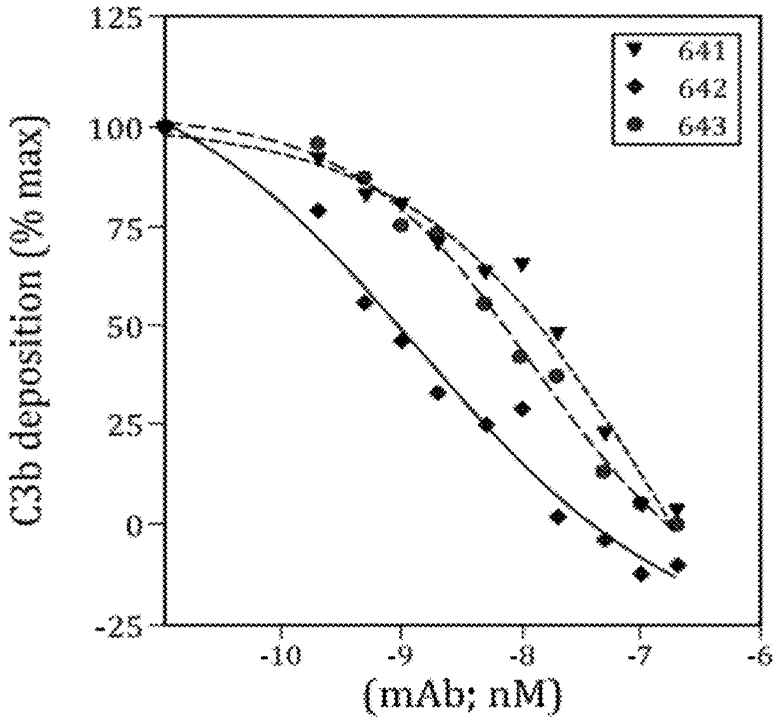
FIG. 11A graphically illustrates the results of the C3b deposition assay carried out for the daughter clone isotype variants (MoAb#1-3), derived from the human anti-MASP-2 monoclonal antibody mother clone 17N16, as described in Example 8.

FIG. 11A graphically illustrates the results of the C3b deposition assay carried out for the daughter clone isotype variants (MoAb#1-3), derived from the human anti-MASP-2 monoclonal antibody mother clone 17N16.

Figure 11B:
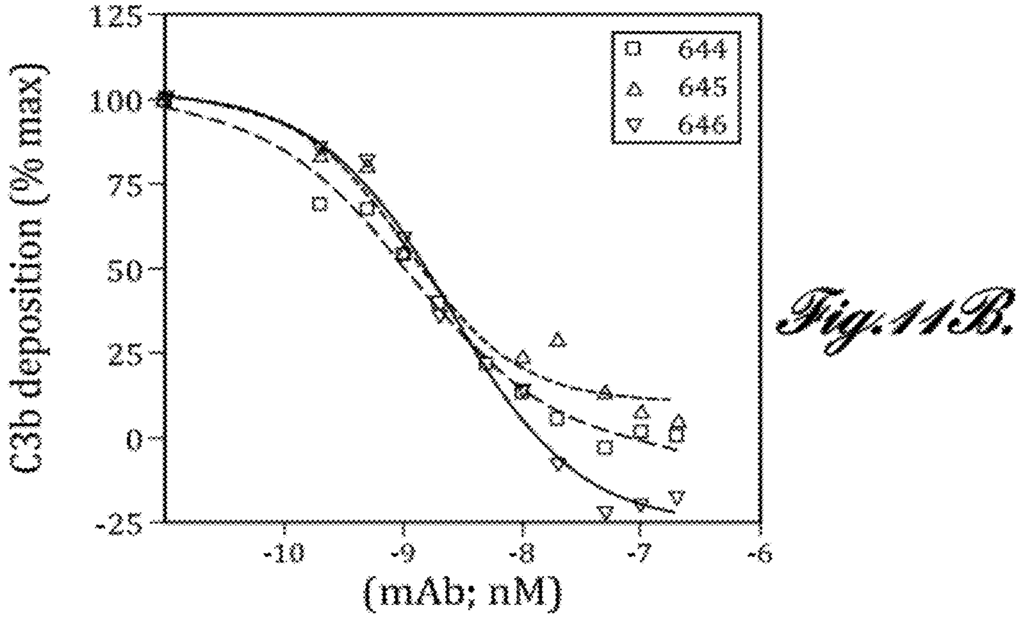
FIG. 11B graphically illustrates the results of the C3b deposition assay carried out for the daughter clone isotype variants (MoAb#4-6), derived from the human anti-MASP-2 monoclonal antibody mother clone 17D20, as described in Example 8.

FIG. 11B graphically illustrates the results of the C3b deposition assay carried out for the daughter clone isotype variants (MoAb#4-6), derived from the human anti-MASP-2 monoclonal antibody mother clone 17D20.

As shown in TABLE 23 and FIGS. 11A and 11B, the human anti-MASP-2 monoclonal antibodies (MoAb#1-6) bind MASP-2 with high affinity, and inhibit the function of C3 and C4 activity in 90% human serum. It is also noted that the human anti-MASP-2 MoAbs cross-react with the non-human MASP-2 protein (African Green monkey), which provides an animal model for toxicity studies that would be predictive for humans.

The MoAb#1-6 were further analyzed in 95% human serum, 95% African Green serum. The results are summarized below in TABLE 24.

TABLE 24

| Antibody ID | Binding to immobilized hMASP-2 (average Kd) | Functional inhibition of C3 deposition in 95% human serum (Average $IC_{50}$; Average $IC_{90}$) nM | Functional inhibition of C3 deposition in 95% African Green Serum (Average $IC_{50}$) nM | Functional inhibition of C4 deposition in 95% human serum (Average $IC_{50}$) nM |
|---|---|---|---|---|
| 17N16 (IgG4) | 0.067 | 4.9; 60.3 | 17.0 | 3.3 |
| MoAb#1 (IgG2) | 0.291 | 10; 104.1 | nd | 25.6 |
| MoAb#2 (IgG4) | 0.314 | 11.9; 118.0 | 17.4 | 19.5 |
| MoAb#3 (IgG4 mutant) | 0.323 | 9.4; 61.0 | 9.2 | 19.8 |
| 17D20 (IgG4) | 0.073 | 2.6; 19.0 | 25.0 | 8.5 |
| MoAb#4 (IgG2) | 0.085 | 0.9; 9.5 | 31.0 | 12.4 |
| MoAb#5 (IgG4) | 0.067 | 2.6; 122.0 | 17.0 | 7.2 |
| MoAb#6 (IgG4 mutant) | 0.067 | 1.5; 7.0 | 13.2 | 4.5 |

Figure 12A:
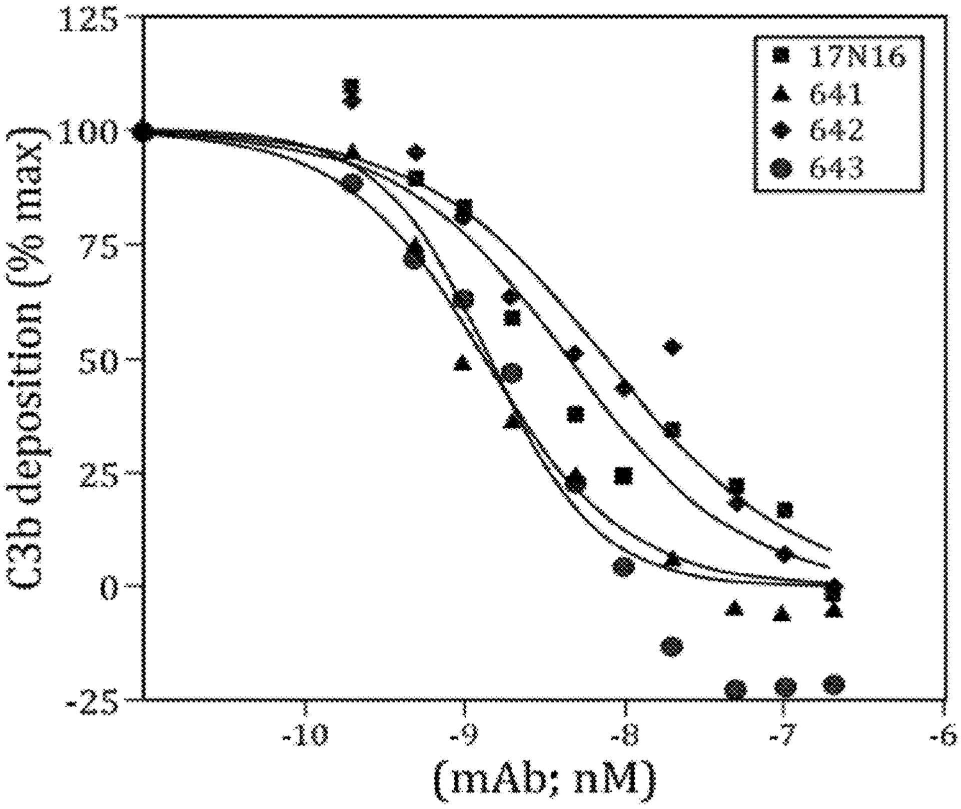
FIGS. 12A and 12B graphically illustrate the testing of the mother clones and MoAb#1-6 in a C3b deposition assay in 95% serum, as described in Example 8.
Figure 12B:
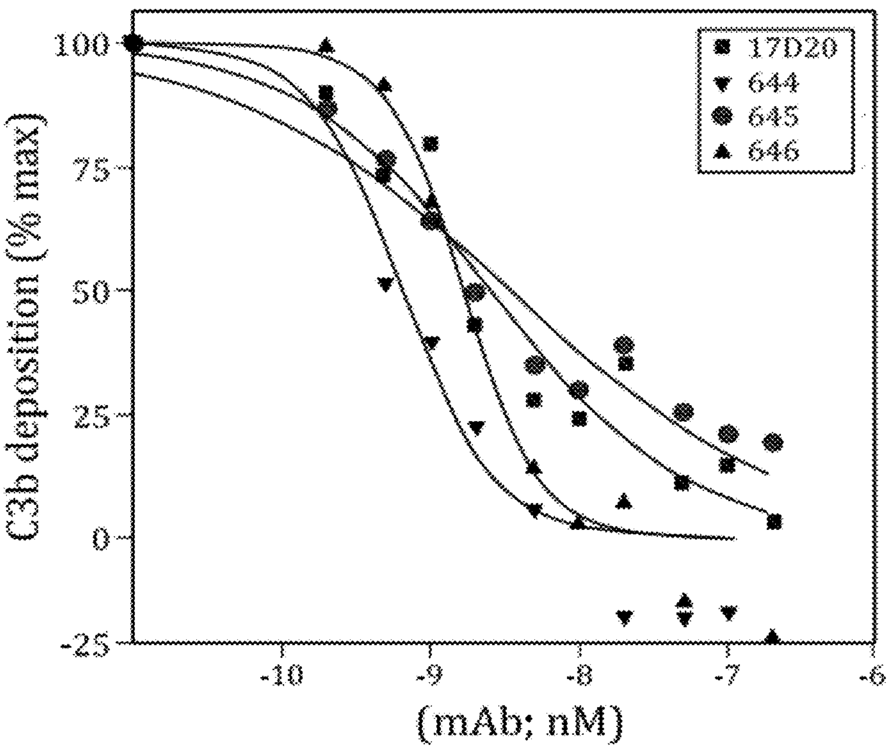

FIGS. 12A and 12B graphically illustrate the testing of the mother clones and MoAb#1-6 in a C3b deposition assay in 95% normal human serum.

Figure 13:
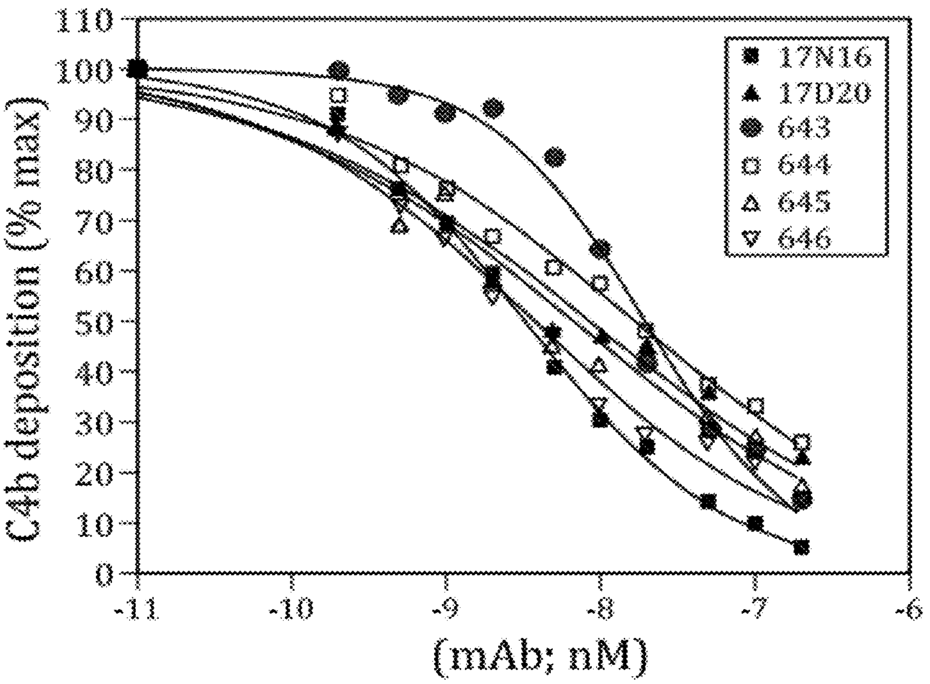
FIG. 13 graphically illustrates the inhibition of C4b deposition in 95% normal human serum, as described in Example 8.

FIG. 13 graphically illustrates the inhibition of C4b deposition in 95% normal human serum.

Figure 14:
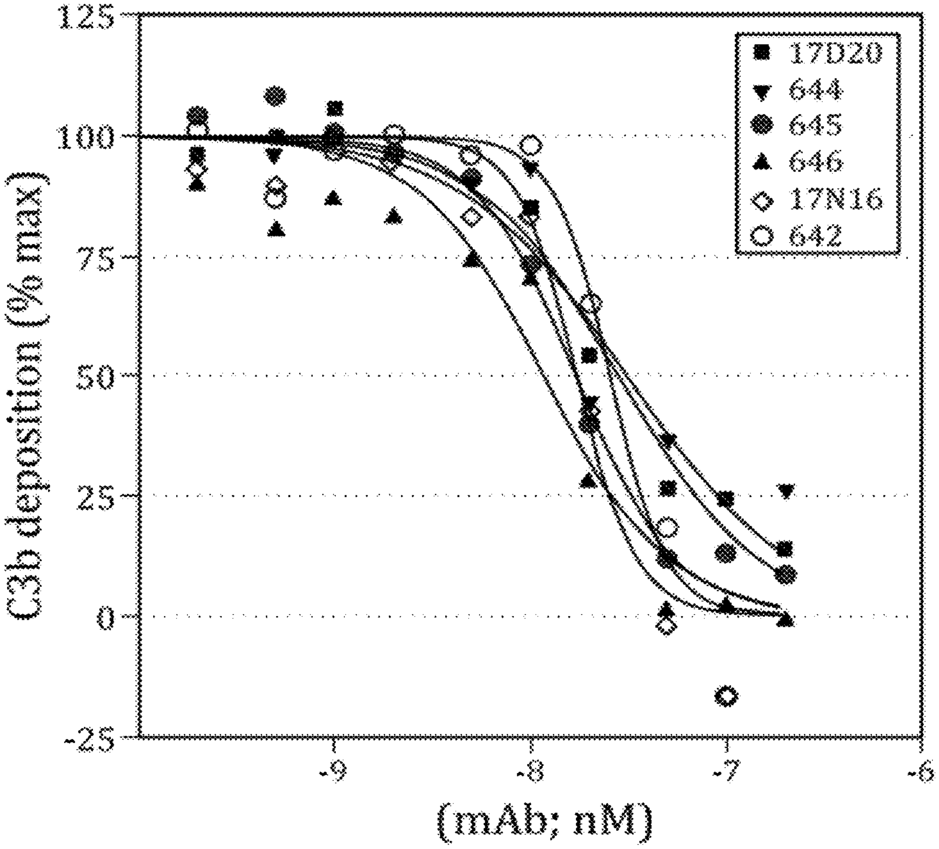
FIG. 14 graphically illustrates the inhibition of C3b deposition in 95% African Green monkey serum, as described in Example 8.

FIG. 14 graphically illustrates the inhibition of C3b deposition in 95% African Green monkey serum.

The MoAb#1-6 were further tested for the ability to selectively inhibit the lectin pathway by assaying for inhibition of Rat C3b, inhibition of preassembled MBL-MASP-2 complexes; classical pathway inhibition, and selectivity over C1s. The results are summarized in TABLE 25.

TABLE 25

| Summary of functional assay results | | | | |
|---|---|---|---|---|
| Antibody ID | Inhibition of Rat C3b ($IC_{50}$ nM) | Inhibition of preassembled MBL-MASP-2 complexes $IC_{50}$ (nM) | Classical Pathway inhibition $IC_{50}$ (nM) | Selectivity over C1s |
| 17N16 (IgG4) | nd | nd | nd | nd |
| MoAb#1 (IgG2) | nd | nd | nd | >5000x |
| MoAb#2 (IgG4) | 100 | not detected (@200 nM) | not detected | >5000x |
| MoAb#3 (IgG4 mutant) | 200 | not detected (@200 nM) | not detected | >5000x |
| 17D20 (IgG4) | nd | nd | nd | nd |
| MoAb#4 (IgG2) | nd | nd | nd | >5000x |
| MoAb#5 (IgG4) | 500 | Yes, $IC_{50}$ = 17 nM | not detected | >5000x |

TABLE 25-continued

| Summary of functional assay results | | | | |
|---|---|---|---|---|
| Antibody ID | Inhibition of Rat C3b ($IC_{50}$ nM) | Inhibition of preassembled MBL-MASP-2 complexes $IC_{50}$ (nM) | Classical Pathway inhibition $IC_{50}$ (nM) | Selectivity over C1s |
| MoAb#6 (IgG4 mutant) | >500 | Yes, $IC_{50}$ = 24.1 nM | not detected | >5000x |

Figure 15:
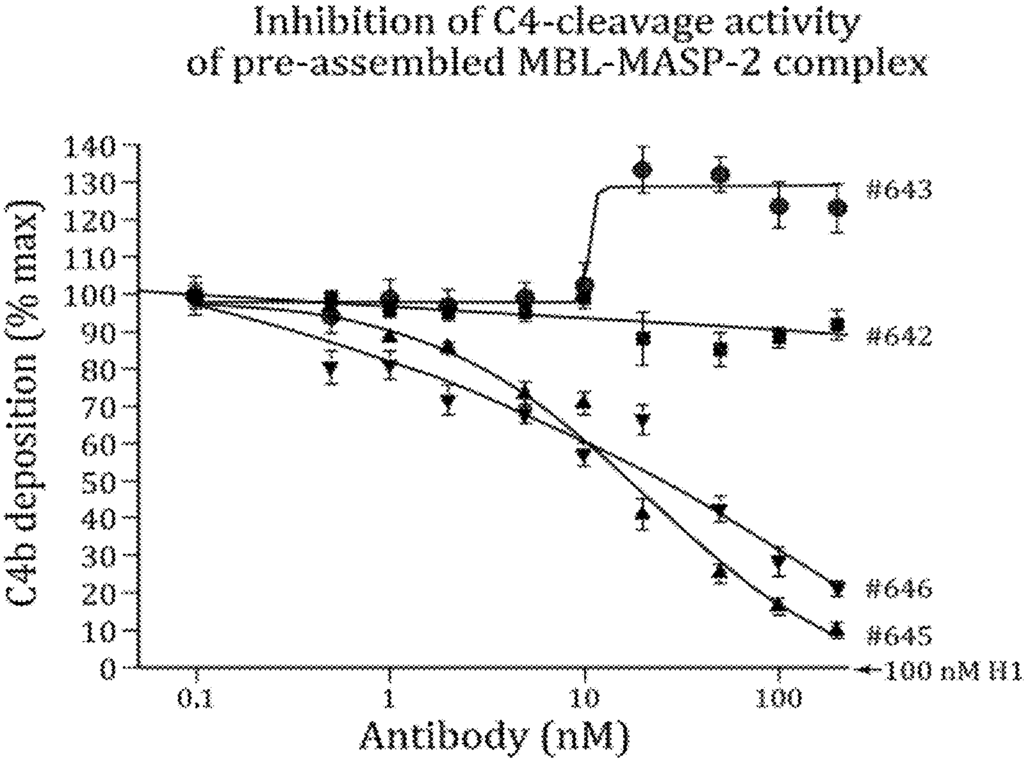
FIG. 15 graphically illustrates the inhibition of C4 cleavage activity of pre-assembled MBL-MASP2 complex by MoAb#2-6, as described in Example 8.

FIG. 15 graphically illustrates the inhibition of C4 cleavage activity of pre-assembled MBL-MASP-2 complex by MoAb#2, 3, 5 and 6.

Figure 16:
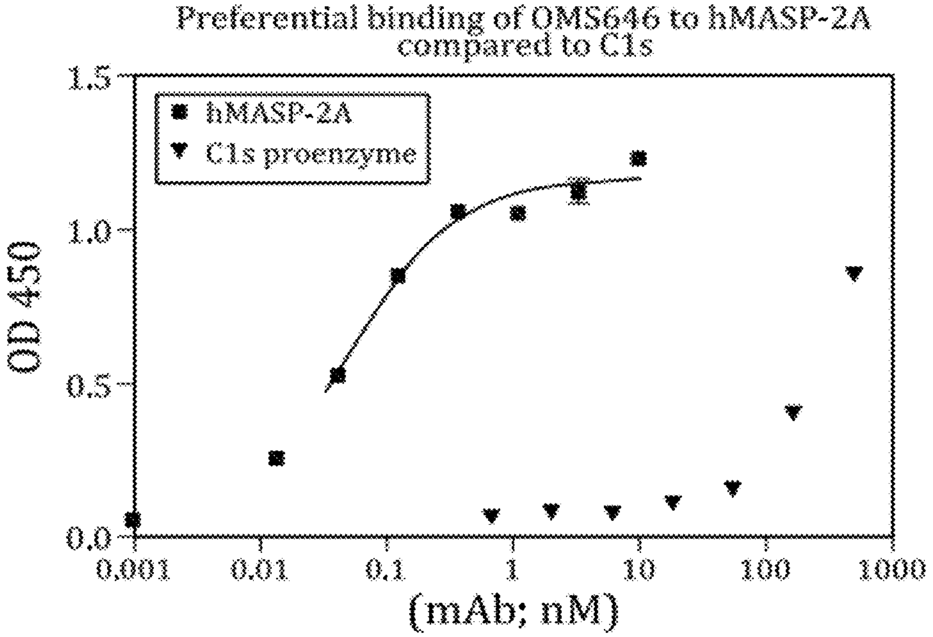
FIG. 16 graphically illustrates the preferential binding of MoAb#6 to human MASP2 as compared to C1s, as described in Example 8.

FIG. 16 graphically illustrates the preferential binding of MoAb#6 to human MASP-2 as compared to C1s.

TABLE 26

Summary of sequences of daughter clones in various formats:

| Clone ID | Description | SEQ ID NO: |
|---|---|---|
| 17N16m__d17N9 | light chain gene sequence | 71 |
| 17N16m__d17N9 | light chain protein sequence | 72 |
| 17N16m__d17N9 | IgG2 heavy chain gene sequence | 73 |
| 17N16m__d17N9 | IgG2 heavy chain protein sequence | 74 |
| 17N16m__d17N9 | IgG4 heavy chain gene sequence | 75 |
| 17N16m__d17N9 | IgG4 heavy chain protein sequence | 76 |
| 17N16m__d17N9 | IgG4 mutated heavy chain gene sequence | 77 |
| 17N17m__d17N9 | IgG4 mutated heavy chain protein sequence | 78 |
| 17D20__3521N11 | light chain gene sequence | 79 |
| 17D20__3521N11 | light chain protein sequence | 80 |
| 17D20__3521N11 | IgG2 heavy chain gene sequence | 81 |
| 17D20__3521N11 | IgG2 heavy chain protein sequence | 82 |
| 17D20__3521N11 | IgG4 heavy chain gene sequence | 83 |
| 17D20__3521N11 | IgG4 heavy chain protein sequence | 84 |
| 17D20__3521N11 | IgG4 mutated heavy chain gene sequence | 85 |
| 17D20__3521N11 | IgG4 mutated heavy chain protein sequence | 86 |
| 17N16m__d17N9 | cDNA encoding full length scFv polypeptide | 87 |
| 17D20m__d21N11 | cDNA encoding full length scFv polypeptide | 88 |
| 17D20m__d3521N11 | cDNA encoding full length scFv polypeptide | 89 |

EXAMPLE 9

This Example describes the epitope mapping that was carried out for several of the blocking human anti-MASP-2 MoAbs.

Methods:

The following recombinant proteins were produced as described in Example 1:

Human MAp 19

Human MASP2A

Human MASP-2 SP

Human MASP-2 CCP2-SP

Human MASP-2 CCP1-CCP2-SP

Human MASP-1/3 CUB1-EGF-CUB2

Human MASP-1 CCP1-CCP2-SP

The anti-MASP-2 antibodies OMS100 and MoAb#6 (35VH-21N11VL), which have both been demonstrated to bind to human MASP-2 with high affinity and have the ability to block functional complement activity (see Examples 6-8) were analyzed with regard to epitope binding by dot blot analysis.

Dot Blot Analysis

Serial dilutions of the recombinant MASP-2 polypeptides described above were spotted onto a nitrocellulose membrane. The amount of protein spotted ranged from 50 ng to 5 pg, in ten-fold steps. In later experiments, the amount of protein spotted ranged from 50 ng down to 16 pg, again in five-fold steps. Membranes were blocked with 5% skimmed milk powder in TBS (blocking buffer) then incubated with 1.0 μg/ml anti-MASP-2 Fab2s in blocking buffer (containing 5.0 mM $Ca^{2+}$). Bound Fab2s were detected using HRP-conjugated anti-human Fab (AbD/Serotec; diluted 1/10,000) and an ECL detection kit (Amersham). One membrane was incubated with polyclonal rabbit-anti human MASP-2 Ab (described in Stover et al., *J Immunol* 163:6848-59 (1999)) as a positive control. In this case, bound Ab was detected using HRP-conjugated goat anti-rabbit IgG (Dako; diluted 1/2,000).

Results:

The results are summarized in TABLE 27.

TABLE 27

Epitope Mapping

| Expression construct | MoAb #6 | OMS100 |
|---|---|---|
| human MAp19 | – | – |
| human MASP-2A | + | + |
| Human MASP-2 SP | – | – |
| human MASP-2 CCP2-SP | – | – |
| human MASP-2 CCP1-CCP2-SP | + | + |
| human MASP-1/3 CUB-EGF-CUBII | – | – |
| human MASP-1 CCP1-CCP2-SP | – | – |
| human MBL/MASP2 complexes | + | + |

The results show that MoAb#6 and OMS100 antibodies are highly specific for MASP-2 and do not bind to MASP-1 or MASP-3. Neither antibody bound to Map19 and MASP-2 fragments not containing the CCP1 domain of MASP-2, leading to the conclusion that the binding sites encompass the CCP1 domain.

EXAMPLE 10

This Example demonstrates that human anti-MASP-2 MoAb#6 inhibits the lectin pathway in African Green Monkeys following intravenous administration.

Methods:

MoAb#6 was administered intravenously to a first group of three African Green Monkeys at a dosage of 1 mg/kg and to a second group of three African Green Monkeys at a dosage of 3 mg/kg. Blood samples were obtained 2, 4, 8, 10, 24, 48, 72 and 98 hours after administration and were tested for the presence of lectin pathway activity.

Figure 17:
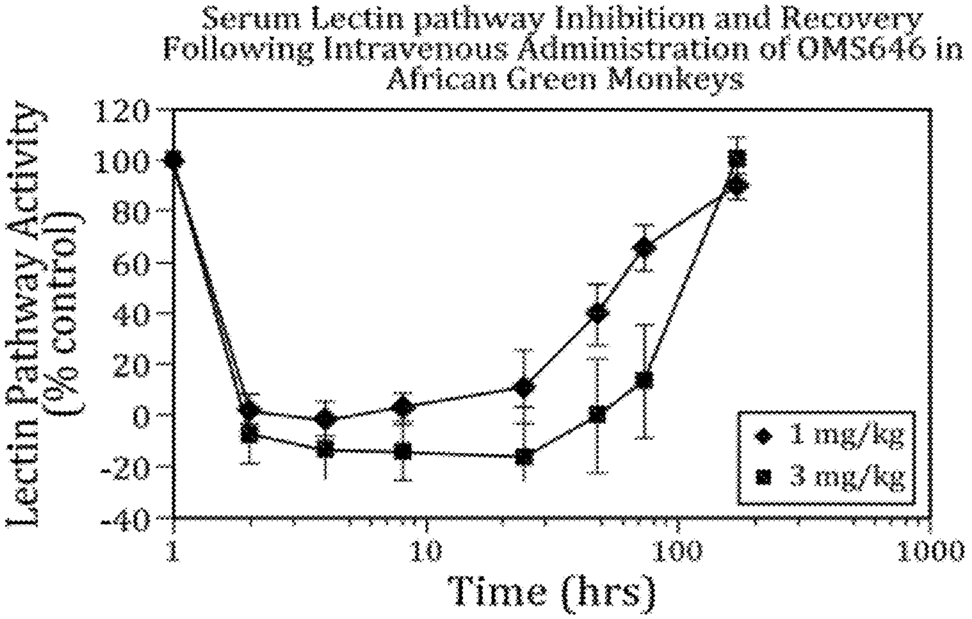
FIG. 17 graphically illustrates that the lectin pathway was completely inhibited following intravenous administration of anti-human MoAb#OMS646 into African Green Monkeys, as described in Example 10.

As shown in FIG. 17, the lectin pathway was completely inhibited following intravenous administration of anti-human MoAb#6.

EXAMPLE 11

This Example demonstrates that a MASP-2 inhibitor, such as an anti-MASP-2 antibody, is effective for the treatment of radiation exposure and/or for the treatment, amelioration or prevention of acute radiation syndrome.

Rationale:

Exposure to high doses of ionizing radiation causes mortality by two main mechanisms: toxicity to the bone marrow and gastrointestinal syndrome. Bone marrow toxicity results in a drop in all hematologic cells, predisposing the organism to death by infection and hemorrhage. The gastrointestinal syndrome is more severe and is driven by a loss of intestinal barrier function due to disintegration of the gut epithelial layer and a loss of intestinal endocrine function. This leads to sepsis and associated systemic inflammatory response syndrome which can result in death.

The lectin pathway of complement is an innate immune mechanism that initiates inflammation in response to tissue injury and exposure to foreign surfaces (i.e., bacteria). Blockade of this pathway leads to better outcomes in mouse models of ischemic intestinal tissue injury or septic shock. It is hypothesized that the lectin pathway may trigger excessive and harmful inflammation in response to radiation-induced tissue injury. Blockade of the lectin pathway may thus reduce secondary injury and increase survival following acute radiation exposure.

The objective of the study carried out as described in this Example was to assess the effect of lectin pathway blockade on survival in a mouse model of radiation injury by administering anti-murine MASP-2 antibodies.

Study #1

Methods and Materials:

Materials.

The test articles used in this study were (i) a high affinity anti-murine MASP-2 antibody (mAbM11) and (ii) a high affinity anti-human MASP-2 antibody (mAbOMS646) that block the MASP-2 protein component of the lectin complement pathway which were produced in transfected mammalian cells. Dosing concentrations were 1 mg/kg of anti-murine MASP-2 antibody (mAbM11), 5 mg/kg of anti-human MASP-2 antibody (mAbOMS646), or sterile saline. For each dosing session, an adequate volume of fresh dosing solutions were prepared.

Animals. Young adult male Swiss-Webster mice were obtained from Harlan Laboratories (Houston, Tex.). Animals were housed in solid-bottom cages with Alpha-Dri bedding and provided certified PMI 5002 Rodent Diet (Animal Specialties, Inc., Hubbard Oreg.) and water ad libitum. Temperature was monitored and the animal holding room operated with a 12 hour light/12 hour dark light cycle.

Irradiation. After a 2-week acclimation in the facility, mice were irradiated at 6.5, 7.0 and 8.0 Gy by whole-body exposure in groups of 10 at a dose rate of 0.78 Gy/min using a Therapax X-RAD 320 system equipped with a 320-kV high stability X-ray generator, metal ceramic X-ray tube, variable x-ray beam collimator and filter (Precision X-ray Incorporated, East Haven, Conn.).

Drug Formulation and Administration. The appropriate volume of concentrated stock solutions were diluted with ice cold saline to prepare dosing solutions of 0.2 mg/ml anti-murine MASP-2 antibody (mAbM11) or 0.5 mg/ml anti-human MASP-2 antibody (mAbOMS646) according to protocol. Administration of anti-MASP-2 antibody mAbM11 and mAbOMS646 was via IP injection using a 25-gauge needle base on animal weight to deliver 1 mg/kg mAbM11, 5 mg/kg mAbOMS646, or saline vehicle.

Study Design. Mice were randomly assigned to the groups as described in Table 28. Body weight and temperature were measured and recorded daily. Mice in Groups 7, 11 and 13 were sacrificed at post-irradiation day 7 and blood collected by cardiac puncture under deep anesthesia. Surviving animals at post-irradiation day 30 were sacrificed in the same manner and blood collected. Plasma was prepared from collected blood samples according to protocol and returned to Sponsor for analysis.

TABLE 28

Study Groups

| Group ID | N | Irradiation Level (Gy) | Treatment | Dose Schedule |
|---|---|---|---|---|
| 1 | 20 | 6.5 | Vehicle | 18 hr prior to irradiation, 2 hr post irradiation, weekly booster |
| 2 | 20 | 6.5 | anti-murine MASP-2 ab (mAbM11) | 18 hr prior to irradiation only |
| 3 | 20 | 6.5 | anti-murine MASP-2 ab (mAbM11) | 18 hr prior to irradiation, 2 hr post irradiation, weekly booster |
| 4 | 20 | 6.5 | anti-murine MASP-2 ab (mAbM11) | 2 hr post irradiation, weekly booster |
| 5 | 20 | 6.5 | anti-human MASP-2 ab (mAbOMS646) | 18 hr prior to irradiation, 2 hr post irradiation, weekly booster |
| 6 | 20 | 7.0 | Vehicle | 18 hr prior to irradiation, 2 hr post irradiation, weekly booster |
| 7 | 5 | 7.0 | Vehicle | 2 hr post irradiation only |
| 8 | 20 | 7.0 | anti-murine MASP-2 ab (mAbM11) | 18 hr prior to irradiation only |
| 9 | 20 | 7.0 | anti-murine MASP-2 ab (mAbM11) | 18 hr prior to irradiation, 2 hr post irradiation, weekly booster |
| 10 | 20 | 7.0 | anti-murine MASP-2 ab (mAbM11) | 2 hr post irradiation, weekly booster |
| 11 | 5 | 7.0 | anti-murine MASP-2 ab (mAbM11) | 2 hr post irradiation only |
| 12 | 20 | 7.0 | anti-human MASP-2 ab (mAbOMS646) | 18 hr prior to irradiation, 2 hr post irradiation, weekly booster |
| 13 | 10 | 8.0 | anti-human MASP-2 ab (mAbOMS646) | 18 hr prior to irradiation, 2 hr post irradiation, weekly booster |
| 14 | 5 | 8.0 | Vehicle | 2 hr post irradiation only |
| 15 | 5 | None | None | None |

Statistical Analysis. Kaplan-Meier survival curves were generated and used to compare mean survival time between treatment groups using log-Rank and Wilcoxon methods. Averages with standard deviations, or means with standard error of the mean are reported. Statistical comparisons were made using a two-tailed unpaired t-test between controlled irradiated animals and individual treatment groups.

Results of Study #1

Figure 18A:
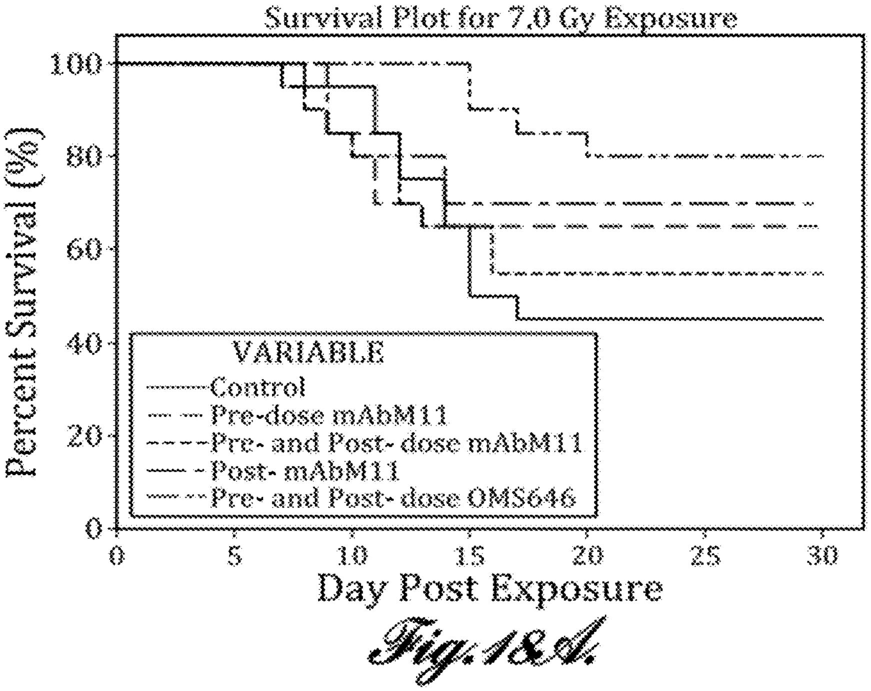
FIG. 18A is a Kaplan-Meier survival plot showing the percent survival over time after exposure to 7.0 Gy radiation in control mice and in mice treated with anti-murine MASP-2 antibody (mAbM11) or anti-human MASP-2 antibody (mAbOMS646) as described in Example 11.
Figure 18B:
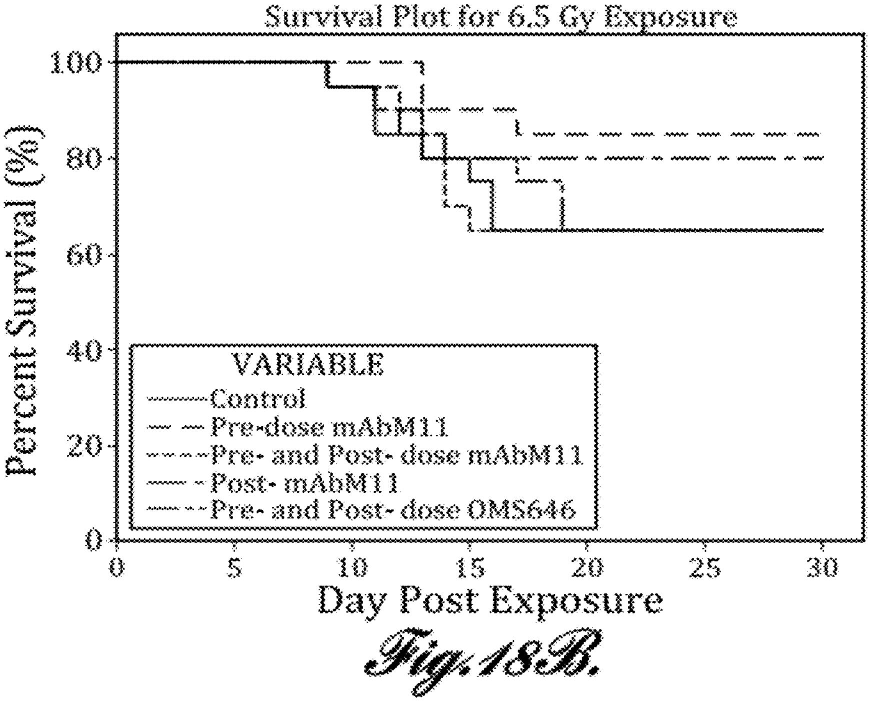
FIG. 18B is a Kaplan-Meier survival plot showing the percent survival over time after exposure to 6.5 Gy radiation in control mice and in mice treated with anti-murine MASP-2 antibody (mAbM11) or anti-human MASP-2 antibody (mAbOMS646), as described in Example 11.
Figure 18C:
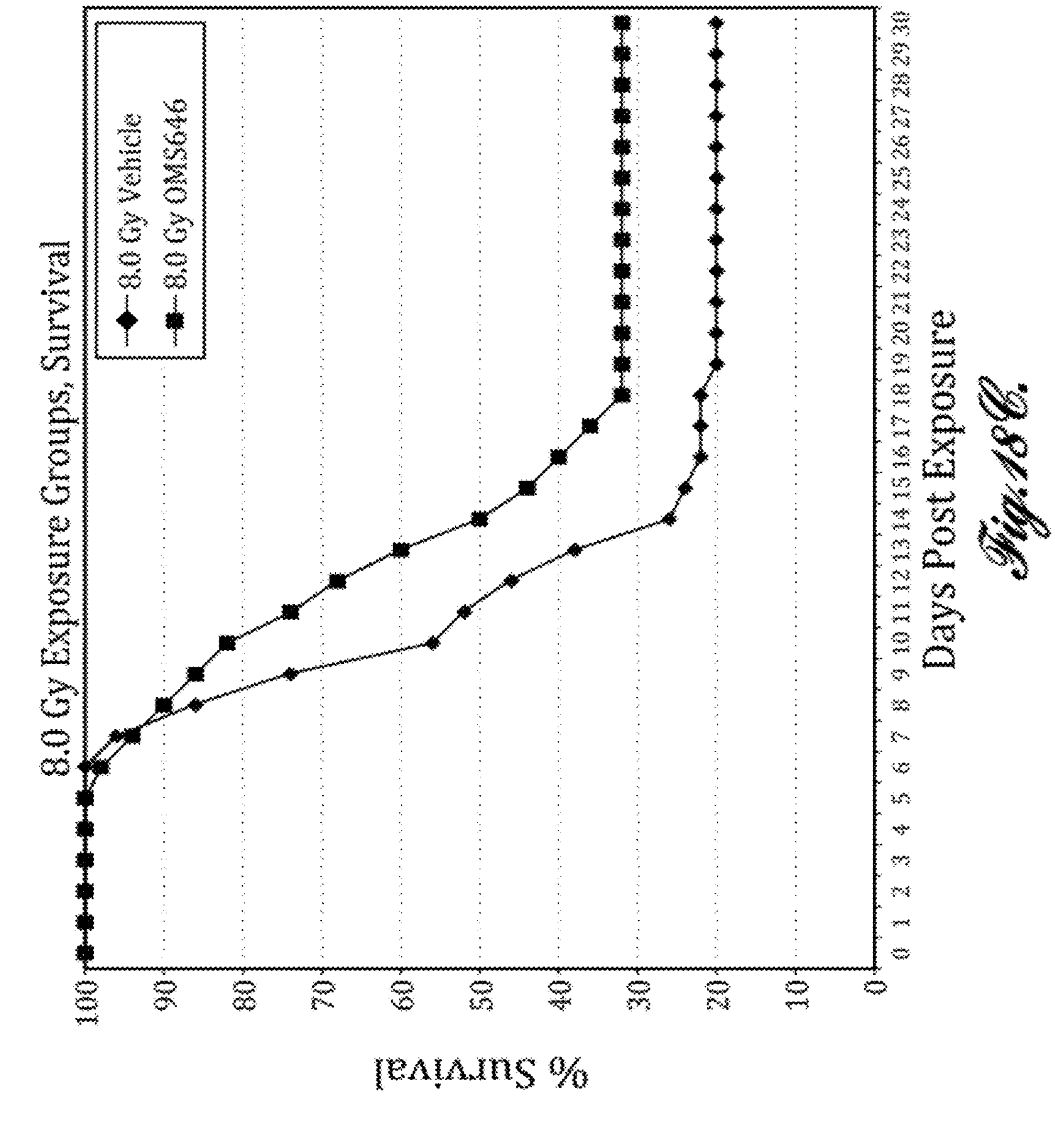
FIG. 18C is a Kaplan-Meier survival plot showing the percent survival over time after exposure to 8.0 Gy radiation in control mice and in mice treated with anti-human MASP-2 antibody (mAbOMS646), as described in Example 11.

Kaplan-Meier survival plots for 6.5, 7.0 and 8.0 Gy exposure groups are provided in FIGS. 18A, 18B and 18C, respectively, and summarized below in Table 29. Overall, treatment with anti-murine MASP-2 ab (mAbM11) pre-irradiation increased the survival of irradiated mice compared to vehicle treated irradiated control animals at both 6.5 (20% increase) and 7.0 Gy (30% increase) exposure levels. At the 6.5 Gy exposure level, post-irradiation treatment with anti-murine MASP-2 ab resulted in a modest increase in survival (15%) compared to vehicle control irradiated animals.

In comparison, all treated animals at the 7.0 Gy and 8.0 Gy exposure level showed an increase in survival compared to vehicle treated irradiated control animals. The greatest change in survival occurred in animals receiving mAbOMS646, with a 45% increase in survival compared to control animals at the 7.0 Gy exposure level, and a 12% increase in survival at the 8.0 Gy exposure level. Further, at the 7.0 Gy exposure level, mortalities in the mAbOMS646 treated group first occurred at post-irradiation day 15 compared to post-irradiation day 8 for vehicle treated irradiated control animals, an increase of 7 days over control animals. Mean time to mortality for mice receiving mAbOMS646 (27.3±1.3 days) was significantly increased (p=0.0087) compared to control animals (20.7±2.0 days) at the 7.0 Gy exposure level.

The percent change in body weight compared to pre-irradiation day (day −1) was recorded throughout the study. A transient weight loss occurred in all irradiated animals, with no evidence of differential changes due to mAbM11 or mAbOMS646 treatment compared to controls (data not shown). At study termination, all surviving animals showed an increase in body weight from starting (day −1) body weight.

TABLE 29

Survival rates of test animals exposed to radiation

| Test Group | Exposure Level | Survival (%) | Time to Death (Mean ± SEM, Day) | First/Last Death (Day) |
|---|---|---|---|---|
| Control Irradiation | 6.5 Gy | 65% | 24.0 ± 2.0 | 9/16 |
| mAbM11 pre-exposure | 6.5 Gy | 85% | 27.7 ± 1.5 | 13/17 |
| mAbM11 pre + post-exposure | 6.5 Gy | 65% | 24.0 ± 2.0 | 9/15 |
| mAbM11 post-exposure | 6.5 Gy | 80% | 26.3 ± 1.9 | 9/13 |
| mAbOMS646 pre + post-exposure | 6.5 Gy | 65% | 24.6 ± 1.9 | 9/19 |
| Control irradiation | 7.0 Gy | 35% | 20.7 ± 2.0 | 8/17 |
| mAbM11 pre-exposure | 7.0 Gy | 65% | 23.0 ± 2.3 | 7/13 |
| mAbM11 pre + post-exposure | 7.0 Gy | 55% | 21.6 ± 2.2 | 7/16 |
| mAbM11 post-exposure | 7.0 Gy | 70% | 24.3 ± 2.1 | 9/14 |
| mAbOMS646 pre + post-exposure | 7.0 Gy | 80% | 27.3 ± 1.3* | 15/20 |
| mAb OMS646 pre + post-exposure | 8.0 Gy | 32% | | |
| control irradiation | 8.0 Gy | 20% | | |

*p = 0.0087 by two-tailed unpaired t-test between controlled irradiated animals and treatment group at the same irradiation exposure level.

Discussion

Acute radiation syndrome consists of three defined subsyndromes: hematopoietic, gastrointestinal, and cerebrovascular. The syndrome observed depends on the radiation dose, with the hematopoietic effects observed in humans with significant partial or whole-body radiation exposures exceeding 1 Gy. The hematopoietic syndrome is characterized by severe depression of bone-marrow function leading to pancytopenia with changes in blood counts, red and white blood cells, and platelets occurring concomitant with damage to the immune system. As nadir occurs, with few neutrophils and platelets present in peripheral blood, neutropenia, fever, complications of sepsis and uncontrollable hemorrhage lead to death.

In the present study, administration of mAbH6 was found to increase survivability of whole-body x-ray irradiation in Swiss-Webster male mice irradiated at 7.0 Gy. Notably, at the 7.0 Gy exposure level, 80% of the animals receiving mAbOMS646 survived to 30 days compared to 35% of vehicle treated control irradiated animals. Importantly, the first day of death in this treated group did not occur until post-irradiation day 15, a 7-day increase over that observed in vehicle treated control irradiated animals. Curiously, at the lower X-ray exposure (6.5 Gy), administration of mAbOMS646 did not appear to impact survivability or delay in mortality compared to vehicle treated control irradiated animals. There could be multiple reasons for this difference in response between exposure levels, although verification of any hypothesis may require additional studies, including interim sample collection for microbiological culture and hematological parameters. One explanation may simply be that the number of animals assigned to groups may have precluded seeing any subtle treatment-related differences. For example, with groups sizes of n=20, the difference in survival between 65% (mAbOMS646 at 6.5 Gy exposure) and 80% (mAbH6 at 7.0 Gy exposure) is 3 animals. On the other hand, the difference between 35% (vehicle control at 7.0 Gy exposure) and 80% (mAbOMS646 at 7.0 Gy exposure) is 9 animals, and provides sound evidence of a treatment-related difference.

These results demonstrate that anti-MASP-2 antibodies are effective in treating a mammalian subject at risk for, or suffering from, the detrimental effects of acute radiation syndrome.

Study #2

Swiss Webster mice (n=50) were exposed to ionizing radiation (8.0 Gy). The effect of anti-MASP-2 antibody therapy (OMS646 5 mg/kg), administered 18 hours before and 2 hours after radiation exposure, and weekly thereafter, on mortality was assessed.

Results of Study #2

It was determined that administration of anti-MASP-2 antibody OMS646 increased survival in mice exposed to 8.0 Gy, with an adjusted median survival rate from 4 to 6 days as compared to mice that received vehicle control, and a mortality reduced by 12% when compared to mice that received vehicle control (log-rank test, p=0.040).

Study #3

Swiss Webster mice (n=50) were exposed to ionizing radiation (8.0 Gy) in the following groups: (I: vehicle) saline control; (II: low) anti-MASP-2 antibody OMS646 (5 mg/kg) administered 18 hours before irradiation and 2 hours after irradiation, (III: high) OMS646 (10 mg/kg) administered 18 hours before irradiation and 2 hours post irradiation; and (IV: high post) OMS646 (10 mg/kg) administered 2 hours post irradiation only.

Results of Study #3

It was determined that administration of anti-MASP-2 antibody pre- and post-irradiation adjusted the mean survival from 4 to 5 days in comparison to animals that received vehicle control. Mortality in the anti-MASP-2 antibody-treated mice was reduced by 6-12% in comparison to vehicle control mice. It was further noted that no significant detrimental treatment effects were observed.

In summary, the results in this Example demonstrate that anti-MASP-2 antibodies of the invention are effective in treating a mammalian subject at risk for, or suffering from the detrimental effects of acute radiation syndrome.

EXAMPLE 12

This Example describes further characterization of the OMS646 antibody (17D20m_d3521N11), fully human anti-human MASP-2 IgG4 antibody with a mutation in the hinge region).

Methods:

OMS646 (17D20m_d3521N11), fully human anti-human MASP-2 IgG4 antibody with a mutation in the hinge region) was generated as described above in Examples 2-8. OMS646 antibody was purified from culture supernatants of a CHO expression cell line stably transfected with expression constructs encoding the heavy and light chains of OMS646. Cells were grown in PF-CHO media for 16 to 20 days and cell free supernatant was collected when cell viability dropped below 50%. OMS646 was purified by Protein A affinity chromatograph followed by ion exchange, concentration and buffer exchange into PBS.

1. OMS646 Binds to Human MASP-2 with High Affinity

Surface Plasmon Resonance (Biocore) Analysis of Immobilized OMS646 Binding to Recombinant Human MASP-2

Methods:

OMS646 was immobilized at various densities by amine coupling to a CM5 chip and the association and disassociation of recombinant human MASP-2 dissolved at 9 nM, 3 nM, 1 nM or 0.3 nM was recorded over time to determine the association ($K_{on}$) and dissociation ($K_{off}$) rate constants. The equilibrium binding constant ($K_D$) was calculated based on experimental $K_{on}$ and $K_{off}$ values.

Figure 19:
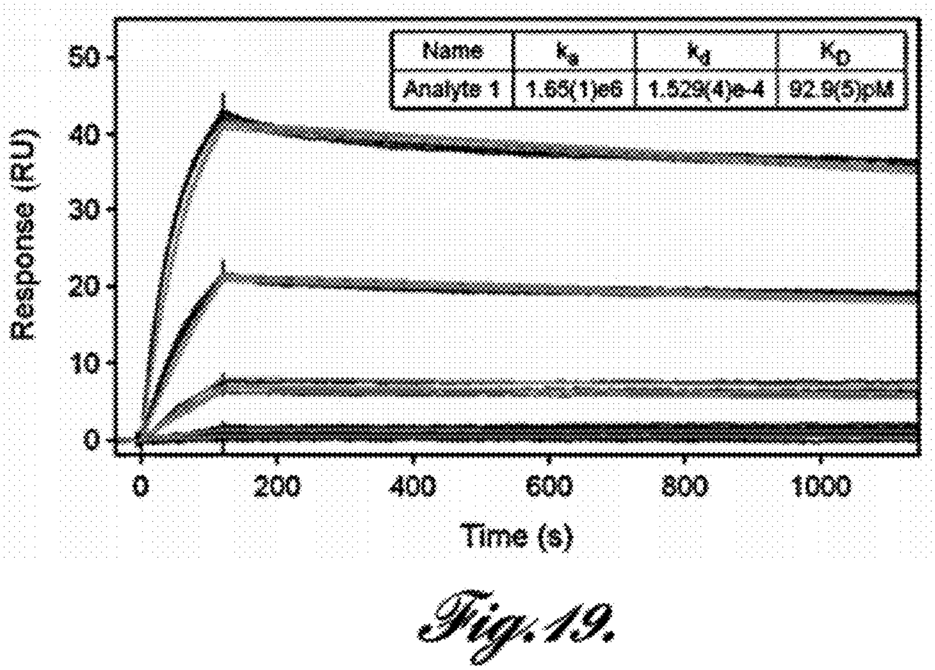
FIG. 19 graphically illustrates the results of surface plasmon resonance (Biacore) analysis on anti-MASP-2 antibody OMS646 (response units (binding) versus time in seconds), showing that immobilized OMS646 binds to recombinant MASP-2 with a $K_{off}$ rate of about 1-3×$10^{-4}S^{-1}$ and a $K_{on}$ rate of about 1.6-3×$10^{6}M^{-1}S^{-1}$, as described in Example 12.

Results:

FIG. 19 graphically illustrates the results of the surface plasmon resonance (Biocore) analysis on OMS646, showing that immobilized OMS646 binds to recombinant MASP-2 with a $K_{off}$ rate of about 1-3×$10^{-4}$ $S^{-1}$ and a $K_{on}$ rate of about 1.6-3×$10^{6}M^{-}S^{-1}$, implying an affinity ($K_D$ of about 92 μM) under these experimental conditions. Depending on the density of OMS646 immobilized and the concentration of MASP-2 in solution, experimental $K_D$ values in the range of 50 to 250 μM were determined.

ELISA Assay of 0M5646 Binding to Immobilized Recombinant Human MASP-2

Methods: An ELISA assay was carried out to assess the dose-response of OMS646 binding to immobilized recombinant MASP-2. Recombinant human MASP-2 (50 ng/well) was immobilized on maxisorp ELISA plates (Nunc) in PBS overnight at 4° C. The next day, the plates were blocked by washing three times with PBS-Tween (0.05%). A serial dilution series of OMS646 in blocking buffer (concentration range from 0.001 to 10 nM) was then added to the MASP-2 coated wells. After a 1 hour incubation to allow OMS646 binding to immobilized antigen, the wells were washed to remove unbound OMS646. Bound OMS646 was detected using HRP-labeled goat anti-human IgG antibody (Qualex; diluted 1:5000 in blocking buffer) followed by development with TMB peroxidase substrate (Kirkegaard & Perry Laboratories). The peroxidase reaction was stopped by adding 100 μl/well of 1.0 M $H_3PO_4$, and substrate conversion was quantified photometrically at 450 nM using a 96 well plate reader (Spectramax). A single binding site curve fitting algorithm (Graphpad) was used to calculate $K_D$ values.

Figure 20:
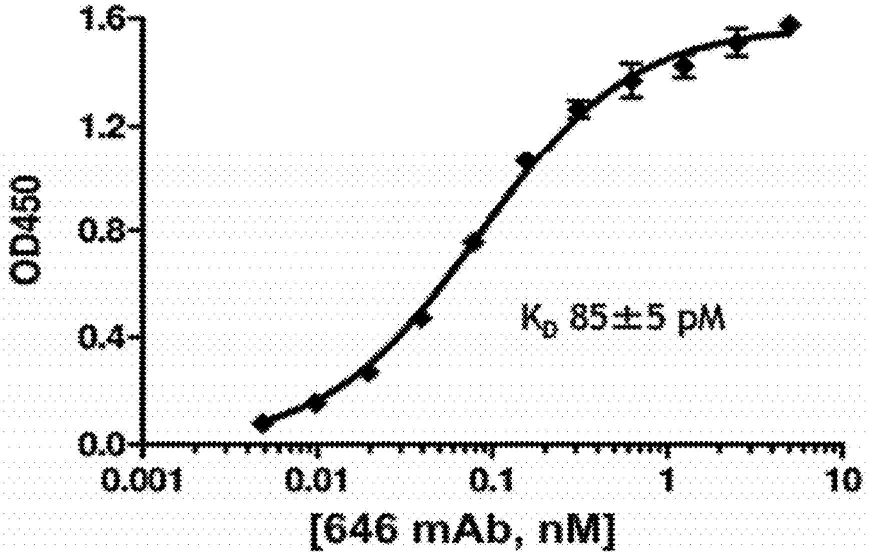
FIG. 20 graphically illustrates the results of an ELISA assay to determine the binding affinity of anti-MASP-2 antibody OMS646 to immobilized human MASP-2, showing that OMS646 binds to immobilized recombinant human MASP-2 with a $K_D$ of approximately 100 pM, as described in Example 12.

Results:

FIG. 20 graphically illustrates the results of the ELISA assay to determine the binding affinity of OMS646 to immobilized human MASP-2. As shown in FIG. 20, it was determined that OMS646 binds to immobilized recombinant human MASP-2 with a $K_D$ of 85±5 pM, which is consistent with the results obtained in the Biocore analysis, as shown in FIG. 19. These results demonstrate that OMS646 has high affinity to human MASP-2, with a $K_D$ of approximately 100 μM.

2. OMS646 Inhibits C4 Activation on a Mannan-Coated Surface, but not on an Immune Complex-Coated Surface Methods:

C4 activation was measured on a mannan-coated surface or an immune complex-coated surface in the presence or absence of OMS646 over the concentration range shown in FIGS. 21A and 21B, respectively as follows.

In the following method to measure the C4 cleavage activity of MASP-2, plastic wells coated with mannan were incubated for 60 minutes at 37° C. with 1% human serum to activate the lectin pathway. The wells were then washed and assayed for human C4b immobilized onto the wells using standard ELISA methods. The amount of C4b generated in this assay is a measure of MASP-2 dependent C4 cleavage activity. Anti-MASP-2 antibodies at selected concentrations were tested in this assay for their ability to inhibit C4 cleavage.

Methods:

C4 Activation on Mannan-Coated Surfaces:

In order to determine the effect of OMS646 on the lectin-pathway, 96-well Costar Medium Binding plates were coated with mannan by overnight incubation at 5° C. with 50 μL of a 40 μg/mL solution of mannan diluted in 50 mM carbonate buffer, pH 9.5. Each well was washed 3× with 200 μL PBS. The wells were then blocked with 100 μL/well of 1% bovine serum albumin in PBS and incubated for one hour at room temperature with gentle mixing. Each well was washed 3× with 200 μL of PBS. In a separate 96 well plate, serial dilutions of MASP-2 antibody (0MS646) were preincubated with 1% human serum in $Ca^{++}$ and $Mg^{++}$ containing GVB buffer (4.0 mM barbital, 141 mM NaCl, 1.0 mM $MgCl_2$, 2.0 mM $CaCl_2$, 0.1% gelatin, pH 7.4) for 1 hour at 5° C. These antibody-serum preincubation mixtures were subsequently transferred into the corresponding wells of the mannan-coated assay plate. Complement activation was initiated by transfer of the assay plate to a 37° C. water bath. Following a 60 minute incubation, the reaction was stopped by adding EDTA to the reaction mixture. Each well was washed 5×200 μL with PBS-Tween 20 (0.05% Tween 20 in PBS), then each well was washed with 2× with 200 μL PBS. 100 μL/well of 1:100 dilution of biotin-conjugated chicken anti-human C4c (Immunsystem AB, Uppsala, Sweden) was added in PBS containing 2.0 mg/ml bovine serum albumin (BSA) and incubated one hour at room temperature with gentle mixing. Each well was washed 5×200 μL PBS. 100 μL/well of 0.1 μg/ml of peroxidase-conjugated streptavidin (Pierce Chemical #21126) was added in PBS containing 2.0 mg/ml BSA and incubated for one hour at room temperature on a shaker with gentle mixing. Each well was washed 5×200 μL with PBS. 100 μL/well of the peroxidase substrate TMB (Kirkegaard & Perry Laboratories) was added and incubated at room temperature for 10 minutes. The peroxidase reaction was stopped by adding 100 μL/well of 1.0 M $H_3PO_4$ and the $OD_{450}$ was measured.

C4 Activation on Immune-Complex Coated Surfaces

In order to measure the effect of OMS646 on the classical pathway, the assay described above was modified to use immune-complex coated plates. The assay was carried out as detailed for the lectin pathway above, with the difference that wells were coated with purified sheep IgG used to stimulate C4 activation via the classical pathway.

Figure 21A:
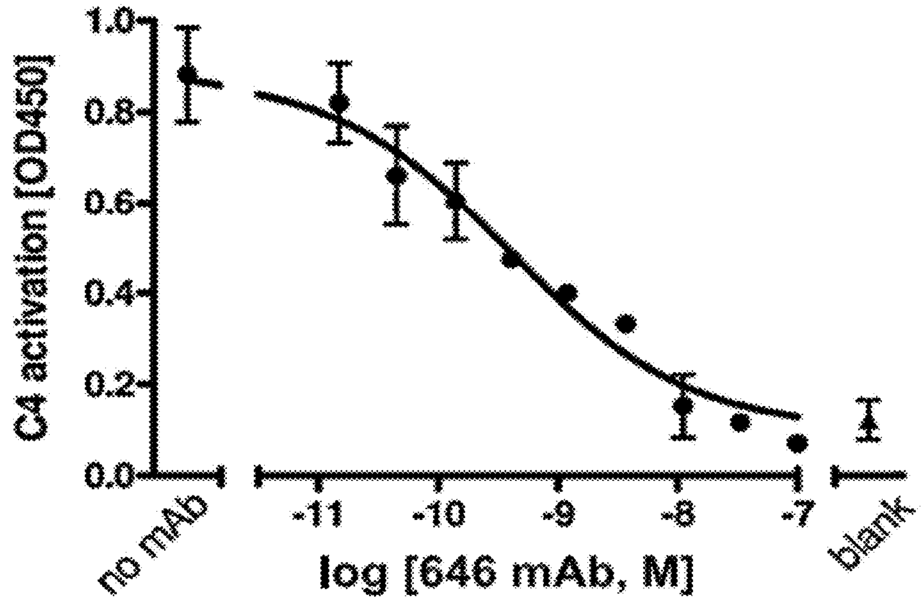
FIG. 21A graphically illustrates the level of C4 activation on a mannan-coated surface in the presence or absence of anti-MASP-2 antibody (OMS646), demonstrating that OMS646 inhibits C4 activation on a mannan-coated surface with an $IC_{50}$ of approximately 0.5 nM in 1% human serum, as described in Example 12.
Figure 21B:
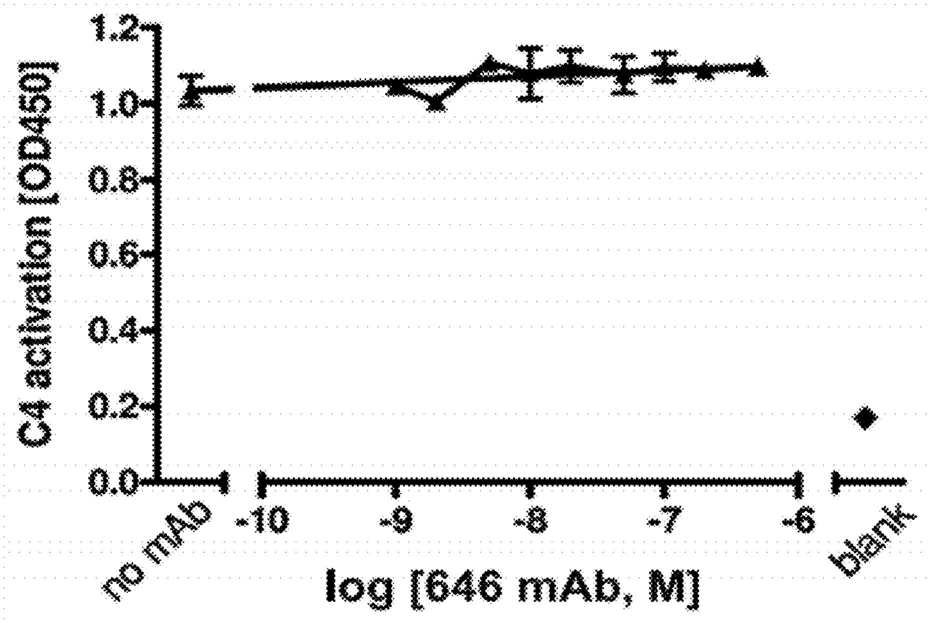
FIG. 21B graphically illustrates the level of C4 activation on an IgG-coated surface in the presence or absence of anti-MASP-2 antibody (OMS646), showing that OMS646 does not inhibit classical pathway-dependent activation of complement component C4, as described in Example 12.

Results:

FIG. 21A graphically illustrates the level of C4 activation on a mannan-coated surface in the presence or absence of OMS646. FIG. 21B graphically illustrates the level of C4 activation on an IgG-coated surface in the presence or absence of OMS646. As shown in FIG. 21A, OMS646 inhibits C4 activation on mannan-coated surface with an $IC_{50}$ of approximately 0.5 nM in 1% human serum. The $IC_{50}$ value obtained in 10 independent experiments was 0.52±0.28 nM (average±SD). In contrast, as shown in FIG. 21B, OMS646 did not inhibit C4 activation on an IgG-coated surface. These results demonstrate that OMS646 blocks lectin-dependent, but not classical pathway-dependent activation of complement component C4.

3. OMS646 Specifically Blocks Lectin-Dependent Activation of Terminal Complement Components Methods:

The effect of OMS646 on membrane attack complex (MAC) deposition was analyzed using pathway-specific conditions for the lectin pathway, the classical pathway and the alternative pathway. For this purpose, the Wieslab Comp300 complement screening kit (Wieslab, Lund, Sweden) was used following the manufacturer's instructions.

Figure 22A:
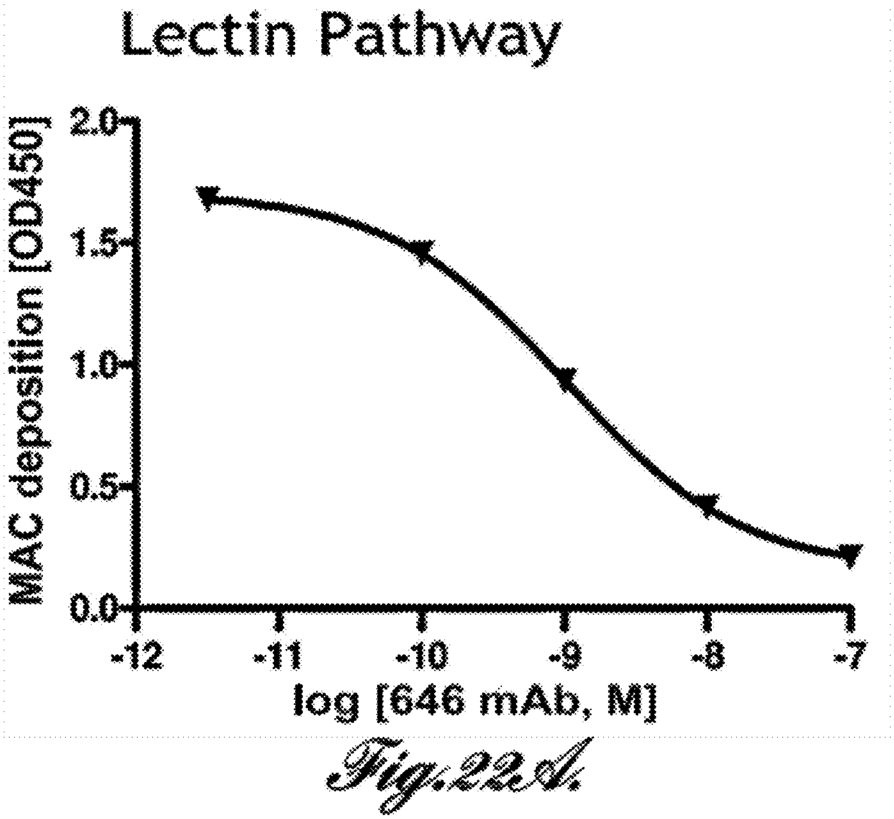
FIG. 22A graphically illustrates the level of MAC deposition in the presence or absence of anti-MASP-2 antibody (OMS646) under lectin pathway-specific assay conditions, demonstrating that OMS646 inhibits lectin-mediated MAC deposition with an $IC_{50}$ value of approximately 1 nM, as described in Example 12.
Figure 22B:
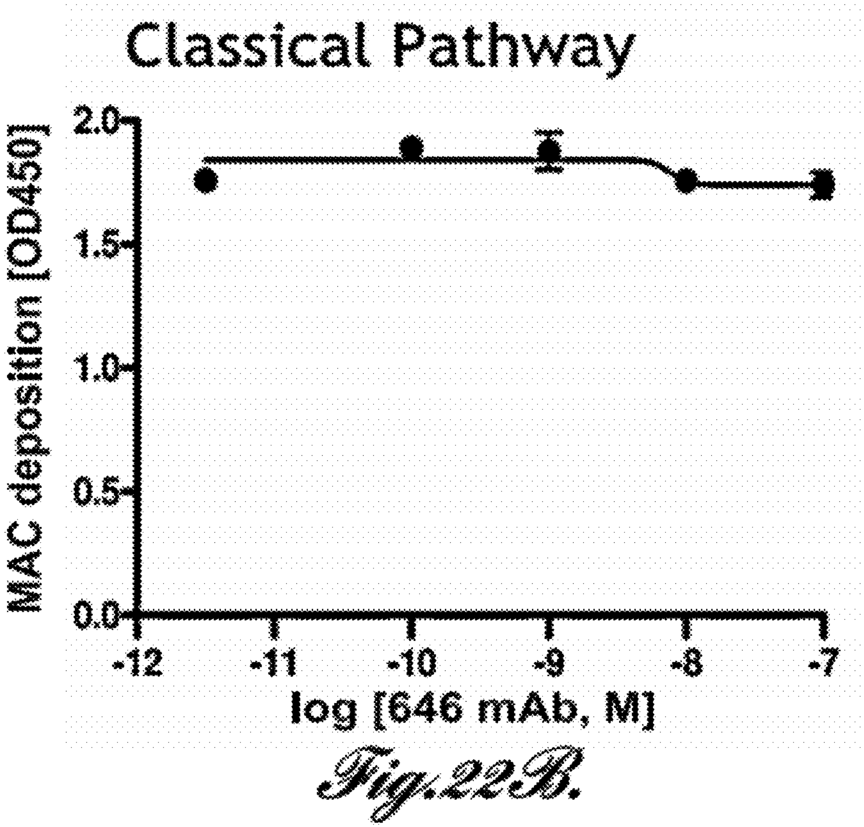
FIG. 22B graphically illustrates the level of MAC deposition in the presence or absence of anti-MASP-2 antibody (OMS646) under classical pathway-specific assay conditions, demonstrating that OMS646 does not inhibit classical pathway-mediated MAC deposition, as described in Example 12.
Figure 22C:
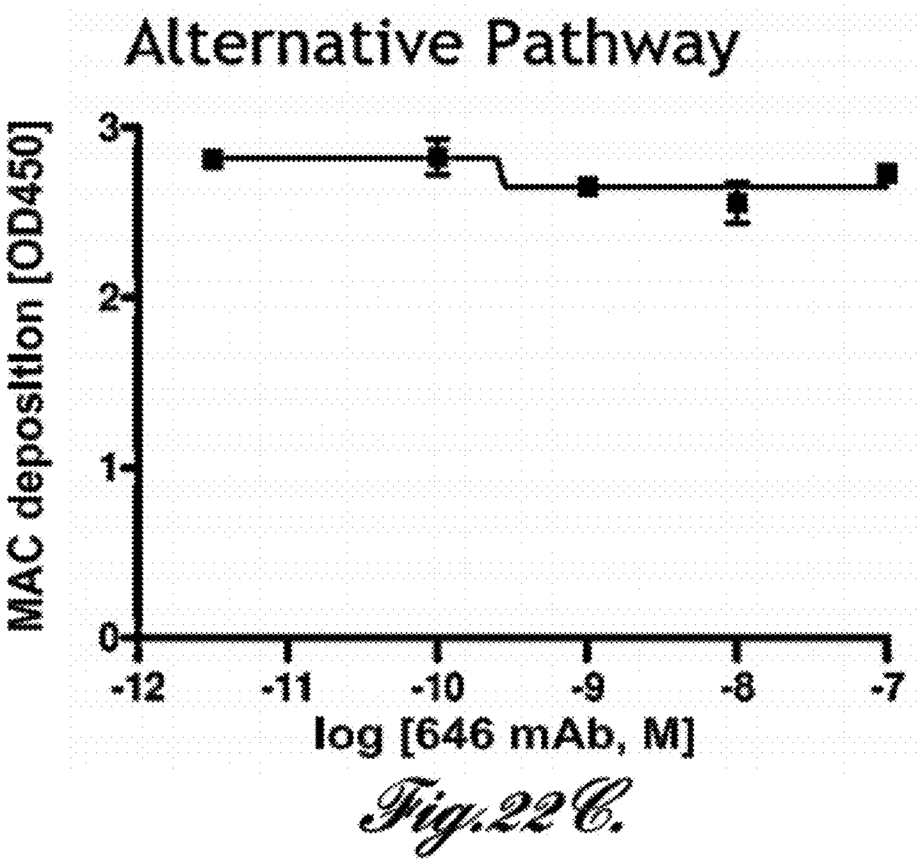
FIG. 22C graphically illustrates the level of MAC deposition in the presence or absence of anti-MASP-2 antibody (OMS646) under alternative pathway-specific assay conditions, demonstrating that OMS646 does not inhibit alternative pathway-mediated MAC deposition, as described in Example 12.
Figure 22A:
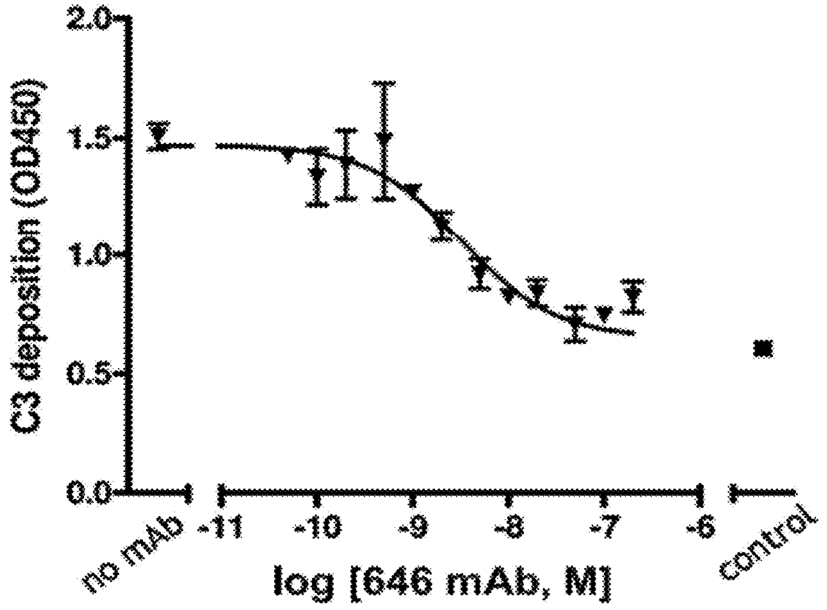

Results:

FIG. 22A graphically illustrates the level of MAC deposition in the presence or absence of anti-MASP-2 antibody (OMS646) under lectin pathway-specific assay conditions. FIG. 22B graphically illustrates the level of MAC deposition in the presence or absence of anti-MASP-2 antibody (OMS646) under classical pathway-specific assay conditions. FIG. 22C graphically illustrates the level of MAC deposition in the presence or absence of anti-MASP-2 antibody (OMS646) under alternative pathway-specific assay conditions.

As shown in FIG. 22A, OMS646 blocks lectin pathway-mediated activation of MAC deposition with an $IC_{50}$ value of approximately 1 nM. However, OMS646 had no effect on MAC deposition generated from classical pathway-mediated activation (FIG. 22B) or from alternative pathway-mediated activation (FIG. 22C).

4. OMS646 Effectively Inhibits Lectin Pathway Activation Under Physiologic Conditions Methods:

The lectin dependent C3 and C4 activation was assessed in 90% human serum in the absence and in the presence of various concentrations of OMS646 as follows:

C4 Activation Assay

To assess the effect of OMS646 on lectin-dependent C4 activation, 96-well Costar medium binding plates were coated overnight at 5° C. with 2 μg of mannan (50 μl of a 40 μg/mL solution in 50 mM carbonate buffer, pH 9.5. Plates were then washed three times with 200 μl PBS and blocked with 100 μL/well of 1% bovine serum albumin in PBS for one hour at room temperature with gentle mixing. In a separate preincubation plate, select concentrations of OMS646 were mixed with 90% human serum and incubated for 1 hour on ice. These antibody-serum preincubation mixtures were then transferred into the mannan-coated wells of the assay plates on ice. The assay plates were then incubated for 90 minutes in an ice water bath to allow complement activation. The reaction was stopped by adding EDTA to the reaction mixture. Each well was washed 5 times with 200 μL of PBS-Tween 20 (0.05% Tween 20 in PBS), then each well was washed two times with 200 μL PBS. 100 μL/well of 1:1000 dilution of biotin-conjugated chicken anti-human C4c (Immunsystem AB, Uppsala, Sweden) was added in PBS containing 2.0 mg/ml bovine serum albumin (BSA) and incubated 1 hour at room temperature with gentle mixing. Each well was washed 5 times with 200 μL PBS. 100 μL/well of 0.1 μg/mL of peroxidase-conjugated streptavidin (Pierce Chemical #21126) was added in PBS containing 2.0 mg/ml BSA and incubated for 1 hour at room temperature on a shaker with gentle mixing. Each well was washed five times with 200 μL PBS. 100 μL/well of the peroxidase substrate TMB (Kirdegaard & Perry Laboratories) was added and incubated at room temperature for 16 minutes. The peroxidase reaction was stopped by adding 100 μL/well of 1.0M $H_3PO_4$ and the $OD_{450}$ was measured.

C3 Activation Assay

To assess the effect of OMS646 on lectin-dependent C3 activation, assays were carried out in an identical manner to the C4 activation assay described above, except that C3 deposition was assessed as the endpoint. C3 deposition was quantified as follows. At the end of the complement deposition reaction, plates were washed as described above and subsequently incubated for 1 hour with 100 μL/well of 1:5000 dilution of rabbit anti-human C3c antibody (Dako) in PBS containing 2.0 mg/mL bovine serum albumin (BSA). Each plate was washed five times with 200 μL PBS, and then incubated for 1 hour at room temperature with 100 μL/well of HRP-labeled goat anti-rabbit IgG (American Qualex Antibodies) in PBS containing 2.0 mg/mL BSA. Plates were washed five times with 200 μL PBS and then 100 μL/well of the peroxidase substrate TMB (Kirkegaard & Perry Laboratories) was added and incubated at room temperature for 10 minutes. The peroxidase reaction was stopped by adding 100 μL/well of 1.0M $H_3PO_4$ and the $OD_{450}$ was measured. $IC_{50}$ values were derived by applying a sigmoidal dose-response curve fitting algorithm (GraphPad) to the experimental data sets.

Figure 23B:
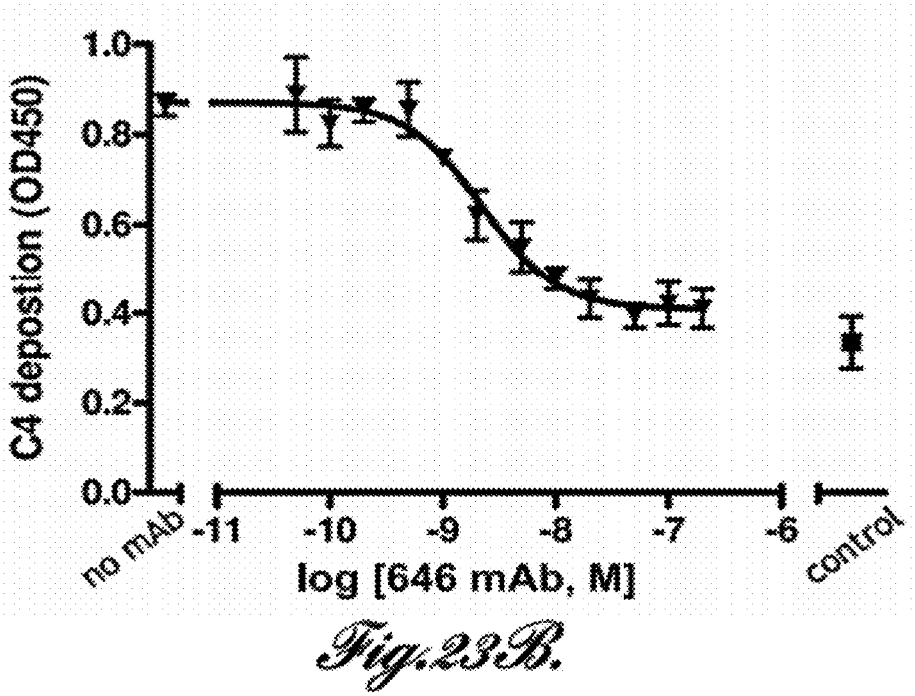
FIG. 23B graphically illustrates the level of C4 deposition in the presence or absence of anti-MASP-2 antibody (OMS646) over a range of concentrations in 90% human serum under lectin pathway-specific conditions, demonstrating that OMS646 blocks C4 deposition under physiological conditions, as described in Example 12.

Results:

FIG. 23A graphically illustrates the level of C3 deposition in the presence or absence of anti-MASP-2 antibody (OMS646) over a range of concentrations in 90% human serum under lectin pathway specific conditions. FIG. 23B graphically illustrates the level of C4 deposition in the presence or absence of anti-MASP-2 antibody (OMS646) over a range of concentrations in 90% human serum under lectin pathway specific conditions. As shown in FIG. 23A, OMS646 blocked C3 deposition in 90% human serum with an $IC_{50}$=3±1.5 nM (n=6). As shown in FIG. 23B, OMS646 blocked C4 deposition with an $IC_{50}$=2.8±1.3 nM (n=6).

These results demonstrate that OMS646 provides potent, effective blockade of lectin pathway activation under physiological conditions, thereby providing support for the use of low therapeutic doses of OMS646. Based on these data, it is expected that OMS646 will block >90% of the lectin pathway in the circulation of a patient at a plasma concentration of 20 nM (3 μg/mL) or less. Based on a plasma volume of a typical human of approximately 3 L, and the knowledge that the bulk of antibody material administered is retained in plasma (Lin Y. S. et al., JPET 288:371 (1999)), it is expected that a dose of OMS646 as low as 10 mg administered intravenously will be effective at blocking the lectin pathway during an acute time period (i.e., a transient time period, such as from 1 to 3 days). In the context of a chronic illness, it may be advantageous to block the lectin pathway for an extended period of time to achieve maximal treatment benefit. Thus, for such chronic conditions, an OMS646 dose of 100 mg may be preferred, which is expected to be effective at blocking the lectin pathway in an adult human subject for at least one week or longer. Given the slow clearance and long half-life that is commonly observed for antibodies in humans, it is possible that a 100 mg dose of OMS646 may be effective for longer than one week, such as for 2 weeks, or even 4 weeks. It is expected that a higher dose of antibody (i.e., greater than 100 mg, such as 200 mg, 500 mg or greater, such as 700 mg or 1000 mg), with have a longer duration of action (e.g., greater than 2 weeks).

5. OMS646 Blocks Lectin Pathway Activation in Monkeys

As described above in Example 10 and shown in FIG. 17, it was determined that OMS646 ablates systemic lectin pathway activity for a time period of about 72 hours following intravenous administration of OMS646 (3 mg/kg) into African Green monkeys, followed by recovery of lectin pathway activity.

This Example describes a follow up study in which lectin dependent C4 activation was assessed in 90% African Green monkey serum or in 90% Cynomoglus monkey serum over a range of concentrations of OMS646 and in the absence of OMS646, as follows:

To assess the effect of OMS646 on lectin-dependent C4 activation in different non-human primate species, 96-well Costar medium binding plates were coated overnight at 5° C. with 2 μg of mannan (50 μl of a 40 μg/mL solution in 50 mM carbonate buffer, pH 9.5). Plates were then washed three times with 200 μL PBS and blocked with 100 μL/well of 1% bovine serum albumin in PBS for 1 hour at room temperature with gentle mixing. In a separate preincubation plate, select concentrations of OMS646 were mixed with 90% serum collected from African Green Monkeys or Cynomoglus Monkeys, and incubated with 1 hour on ice. These antibody-serum preincubation mixtures were then transferred into the mannan-coated wells of the assay plates on ice. The assay plates were then incubated for 90 minutes in an ice water bath to allow complement activation. The reaction was stopped by adding EDTA to the reaction mixture. Each well was washed five times with 200 μL PBS-Tween 20 (0.05% Tween 20 in PBS), then each well was washed two times with 200 μL PBS. 100 μL/well of 1:1000 dilution of biotin-conjugated chicken anti-human C4c (Immunosystem AB, Uppsala, Sweden) was added in PBS containing 2.0 mg/mL BSA and incubated one hour at room temperature with gentle mixing. Each well was washed five times with 200 μL PBS. 100 μL/well of 0.1 μg/mL of peroxidase-conjugated streptavidin (Pierce Chemical #21126) was added in PBS containing 2.0 mg/mL BSA and incubated for one hour at room temperature on a shaker with gentle mixing. Each well was washed five times with 200 μL PBS. 100 μL/well of the peroxidase substrate TMB (Kirkegaard & Perry Laboratories) was added and incubated at room temperature for 10 minutes. The peroxidase reaction was stopped by adding 100 μL/well of 1.0 M $H_3PO_4$ and the $OD_{450}$ was measured. $IC_{50}$ values were derived by applying a sigmoidal dose-response curve fitting algorithm (GraphPad) to the experimental data sets.

Figure 24A:
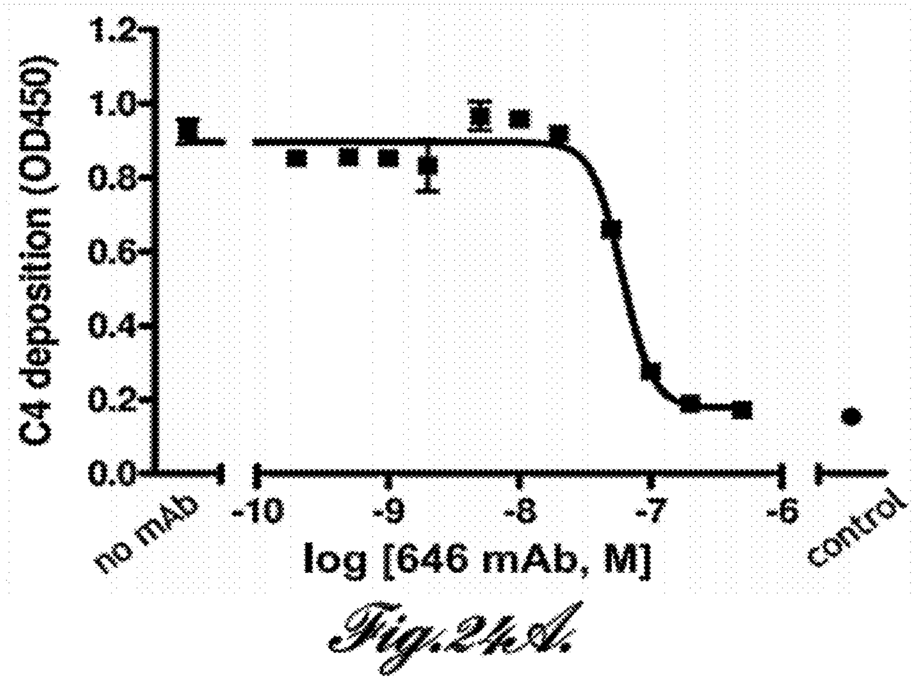
FIG. 24A graphically illustrates the level of C4 deposition in the absence or presence of anti-MASP-2 antibody (OMS646) in 90% Cynomuglus monkey serum under lectin pathway-specific conditions, demonstrating that OMS646 inhibits lectin pathway C4 deposition in Cynomuglus monkey serum in a dose-responsive manner with $IC_{50}$ values in the range of 30 to 50 nM, as described in Example 12.
Figure 24B:
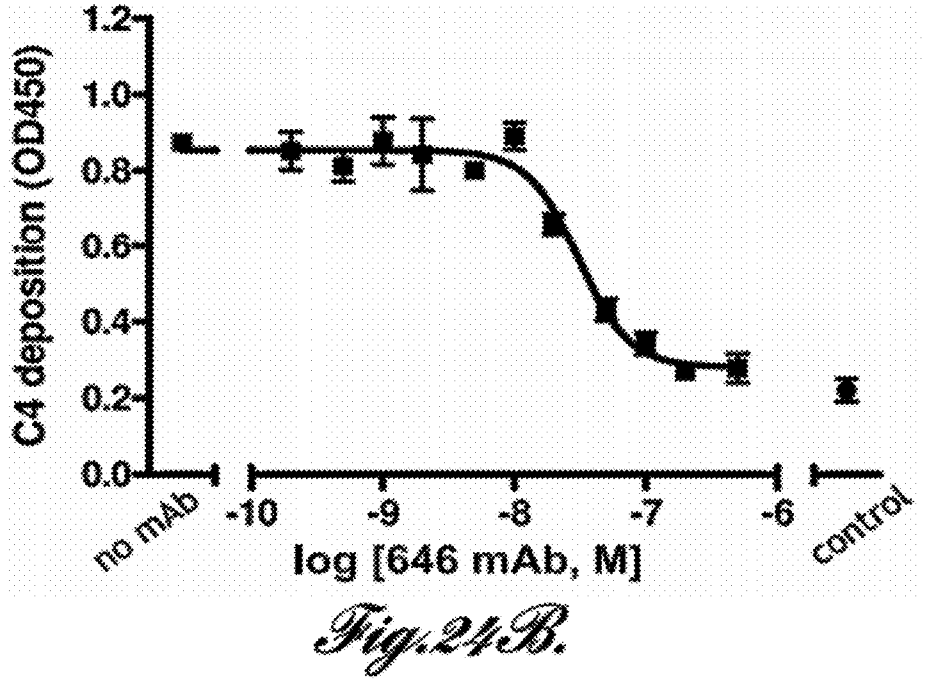
FIG. 24B graphically illustrates the level of C4 deposition in the absence or presence of anti-MASP-2 antibody (OMS646) in 90% African Green monkey serum under lectin pathway-specific conditions, demonstrating that OMS646 inhibits lectin pathway C4 deposition in African Green monkey serum in a dose-responsive manner with $IC_{50}$ values in the range of 15 to 30 nM, as described in Example 12.

Results:

A dose response of lectin pathway inhibition in 90% Cynomoglus monkey serum (FIG. 24A) and in 90% African Green monkey serum (FIG. 24B) was observed with $IC_{50}$ values in the range of 30 nM to 50 nM, and 15 nM to 30 nM, respectively.

In summary, OMS646, a fully human anti-human MASP-2 IgG4 antibody (with a mutation in the hinge region) was observed to have the following advantageous properties: high affinity binding to human MASP-2 ($K_D$ in the range of 50 to 250 pM, with a $K_{off}$ rate in the range of 1-3×$10^{-4}$ $S^{-1}$ and a $K_{on}$ rate in the range of 1.6-3×$10^6 M^{-1}S^{-1}$; functional potency in human serum with inhibition of C4 deposition with an $IC_{50}$ of 0.52±0.28 nM (n=10) in 1% human serum; and an $IC_{50}$ of 3±1.5 nM in 90% serum); and cross-reactivity in monkey showing inhibition of C4 deposition with an $IC_{50}$ in the range of 15 to 50 nM (90% monkey serum).

As described above, doses as low as 10 mg OMS646 (corresponding to 0.15 mg/kg for an average human) are expected to be effective at acutely blocking the lectin pathway in human circulation (e.g., for a period of at least 1 to 3 days), while doses of 100 mg OMS646 (corresponding to 1.5 mg/kg for an average human) are expected to block the lectin pathway in the circulation of a patient for at least one week or longer. Larger doses of OMS646 (e.g., doses greater than 100 mg, such as at least 200 mg, at least 300 mg, at least 400 mg, at least 500 mg, or greater), and preferably subcutaneous (sc) or intramuscular (im) routes of administration can be employed to further extend the time window of effective lectin pathway ablation to two weeks and preferably four weeks.

For example, as shown in the experimental data herein, in primates a dose of 1 mg/kg OMS646 resulted in inhibition of the lectin pathway for 1 day, and a 3 mg/kg dose of OMS646 resulted in inhibition of the lectin pathway for about 3 days (72 hours). It is therefore estimated that a larger dosage of 7 to 10 mg/kg would be effective to inhibit the lectin pathway for a time period of about 7 days. As shown herein, the OMS646 has a 5-10 fold greater potency against human MASP-2 as compared to monkey MASP-2. Assuming comparable pharmacokinetics, the expected dosages ranges to achieve effective lectin pathway ablation in humans is shown in TABLE 30 below.

TABLE 30

OMS646 dosing to inhibit the lectin pathway in vivo

| | 1 Day | 3 day | 7 day |
|---|---|---|---|
| Monkey | 1 mg/kg | 3 mg/kg | 10 mg/kg |
| Human (estimate) | 0.1 to 0.2 mg/kg | 0.3 to 0.6 mg/kg | 1-2 mg/kg |

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. An isolated human monoclonal antibody, or antigen binding fragment thereof, that binds to human MASP-2, comprising:

(i) a heavy chain variable region comprising three complementarity determining regions (CDRs), comprising a CDR-H1 comprising the amino acid sequence RGKMG (SEQ ID NO:28), a CDR-H2 comprising the amino acid sequence LAHIFSSDEKSYRTSI, (SEC ID NO: 32) and a CDR-H3 comprising the amino acid sequence YYCARIRX (SEQ ID NO:90:), wherein X at position 8 is A or R; and (ii) a light chain variable region comprising three CDRs, comprising a CDR-L1 comprising the amino acid sequence GXKLGDKXAYW (SEQ ID NO:91), wherein X at position 2 is D or E and wherein X at position 8 is F or Y, a CDR-L2 comprising the amino acid sequence DXXRPSG (SEQ ID NO:93), wherein X at position 2 is N or K and wherein X at position 3 K or Q, and CDR-L3 compromising the amino acid sequence AWDSSTAVF (SEQ ID NO: 51), and wherein the isolated antibody or antigen-binding fragment thereof binds to human MASP-2 and inhibits MASP-2 dependent complement activation.

2. The isolated antibody of claim 1, wherein the amino acid sequence set forth in SEQ ID NO:90 contains an R at position 8.

3. The isolated antibody of claim 1, wherein the amino acid sequence set forth in SEQ ID NO:91 contains an E at position 2.

4. The isolated antibody of claim 1, wherein the amino acid sequence set forth in SEQ ID NO:91 contains a Y at position 8.

5. The isolated antibody of claim 1, wherein CDR-L2 of the light chain variable region comprises SEQ ID NO:93, and wherein the amino acid sequence set forth in SEQ ID NO:93 contains a K at position 2.

6. The isolated antibody of claim 1, wherein CDR-L2 of the light chain variable region comprises SEQ ID NO: 93, and wherein the amino acid sequence set forth in SEQ ID NO:93 contains a Q at position 3.

7. The isolated antibody of claim 1, wherein the heavy chain variable region comprises a CDR-H1 comprising the amino acid sequence RGKMG (SEQ ID NO:28), a CDR-H2 comprising the amino acid sequence LAHIFSSDEKSYRTSL (SEQ ID NO: 32) and a CDR-H3 comprising the amino acid sequence YYCARIRX (SED ID NO:90), wherein X at position 8 is R; and wherein the light chain variable region comprises a CDR-L1 comprising the amino acid sequence GXKLGDKXAYW (SED ID NO:91), wherein X at position 2 is E and wherein X at position 8 is Y, a CDR-L2 comprising the amino acid sequence DXXRPSG (SEQ ID NO:93), wherein X at position 2 is K and wherein X at position 3 is Q, and CDR-L3 of the light chain variable region comprises SEQ ID NO:51.

8. The isolated antibody of claim 1, wherein the antibody or antigen-binding fragment thereof is selected from the group consisting of a Fab, a Fab' fragment, a $F(ab')_2$ fragment and a whole antibody.

9. The isolated antibody of claim 1, wherein the antibody or antigen-binding fragment thereof is selected from the group consisting of a single chain antibody, an ScFv, and a univalent antibody lacking a hinge region.

10. The isolated antibody of claim 1, wherein said antibody binds human MASP-2 with a $K_D$ of 10 nM or less.

11. The antibody of claim 1, wherein said antibody inhibits C4 activation in an in vitro assay in 1% human serum at an $IC_{50}$ of 10 nM or less.

12. The antibody of claim 1, wherein said antibody inhibits C4 activation in 90% human serum with an $IC_{50}$ of 30 nM or less.

13. The antibody of claim 1, wherein said antibody binds an epitope in the CCP1 domain of MASP-2.

14. The antibody of claim 1, wherein said antibody inhibits C3b deposition in an in vitro assay in 1% human serum at an $IC_{50}$ of 10 nM or less.

15. The antibody of claim 1, wherein said antibody inhibits C3b deposition in 90% human serum with an $IC_{50}$ of 30 nM or less.

16. The antibody of claim 1, wherein the antibody is a single chain molecule.

17. The antibody of claim 1, wherein the antibody does not substantially inhibit the classical pathway.

18. An isolated monoclonal antibody, or antigen-binding fragment thereof, that binds to human MASP-2, comprising a heavy chain variable region comprising the amino acid sequence set forth in SEQ ID NO:18, or SEQ ID NO:20 and a light chain variable region comarising the amino acid sequence set forth in SEQ ID NO:22 or SEQ ID NO:24.

19. The isolated monoclonal antibody, or antigen-binding fragment thereof of claim 18 comprising a heavy chain variable region comprising the amino acid sequence set forth in SEQ ID NO:20 and a light chain variable region comprising the amino acid sequence set forth in SEQ ID NO:24.

20. A composition comprising the fully human monoclonal anti-MASP-2 antibody, or fragment thereof, of claim 1, 18 or 19 and a pharmaceutically acceptable excipient.

21. The composition of claim 20, wherein the composition is formulated for systemic delivery.

22. The composition of claim 21, wherein the composition is formulated for intra-arterial, intravenous, intracranial, intramuscular, inhalational, nasal or subcutaneous administration.

23. The composition of claim 21, wherein the composition is formulated tor subcutaneous administration.

24. An article of manufacture comprising a unit dose of a human monoclonal anti-MASP-2 antibody of claim 1, 18 or 19 suitable for therapeutic administration to a human subject, wherein the unit dose is the range of from 1 mg to 1000 mg.

* * * * *

UNITED STATES PATENT AND TRADEMARK OFFICE

CERTIFICATE OF CORRECTION

PATENT NO. : 9,011,860 B2
APPLICATION NO. : 13/464334
DATED : April 21, 2015
INVENTOR(S) : Thomas Dudler et al.

It is certified that error appears in the above-identified patent and that said Letters Patent is hereby corrected as shown below:

IN THE SPECIFICATION

| COLUMN | LINE | ERROR |
|---|---|---|
| 1 | 25 | "20120504 ST25." should read --20120504_ST25.-- |
| 2 | 53 | "Luet" should read --Lu-- |
| 3 | 61 | "C lr/Cls" should read --Clr/Cls-- |
| 4 | 32 | "CUB1" should read --CUBI-- |
| 4 | 34 | "also associated" should read --also be associated-- |
| 8 | 7 | "an one" should read --any one-- |
| 9 | 9 | "NO:56)4D9" should read --NO:56), 4D9-- |
| 9 | 11 | "NO:61)" should read --NO:61),-- |
| 9 | 15 | "say" should read --scFv-- |
| 9 | 30 | "(SEQ ID NO: 59)" should read --(SEQ ID NO:59)-- |
| 9 | 31 | "(SEQ ID NO :66)" should read --(SEQ ID NO:66)-- |
| 9 | 32 | "has" should read --have-- |
| 9 | 44 | "mutagensis" should read --mutagenesis-- |
| 14 | 46 | "or only 4%, or only 4%, or only 3% or" should read --or only 4%, or only 3%, or-- |
| 15 | 48 | "and is not." should read --and is not-- |
| 16 | 20 | "by one or more by one or more" should read --by one or more-- |
| 22 | 34 | "CCP1 and CCP2" should read --CCPI and CCPII-- |
| 22 | 37 | "CUB1-EGF" should read --CUBI-EGF-- |
| 22 | 48 | "CUB1" should read --CUBI-- |
| 22 | 52 | "CUB1EGFCUBII" should read --CUBIEGFCUBII-- |
| 23 | 23 | "aa 278-671 aa" should read --aa 278-671-- |
| 23 | 47 | "CCP1" should read --CCPI-- |
| 23 | 50 | "CCP1" should read --CCPI-- |

Signed and Sealed this
Fifteenth Day of March, 2016

Michelle K. Lee

Michelle K. Lee
*Director of the United States Patent and Trademark Office*

IN THE SPECIFICATION

| COLUMN | LINE | ERROR |
|---|---|---|
| 31 | Table 3F Col. 102 | “A” should read --**A**--; “R” should read --**R**--; “D” should read --**D**--; and “D” should read --**D**-- |
| 33 | Table 5B Col. 32 | “**A**” should read --A-- |
| 42 | 15 | “CCP1” should read --CCPI-- |
| 54 | 26 | “CUB1” should read --CUBI-- |
| 54 | 29 | “CUB1/EGF” should read --CUBI/EGF-- |
| 65 | 30-31 | Remove the break between “non-human primate” and “(NHP) serum” |
| 69 | 13 | “($IC_{50}$ of 15 nM)” should read --($IC_{50}$ of ≈15 nM)-- |
| 71 | 5 | “affinity that the” should read --affinity than the-- |
| 71 | 36 | “is a amino” should read --is an amino-- |
| 74 | 28 | “potent that the” should read --potent than the-- |
| 78 | 20 | “CUB-EGF-CUB2” should read --CUBI-EGF-CUBII-- |
| 82 | 55 | “region)” should read --region-- |
| 83 | 14 | “$1.6\text{-}3\times10^6M^-S^{-1}$” should read --$1.6\text{-}3\times10^6M^{-1}S^{-1}$-- |
| 83 | 14 | “about 92μM” should read --about 92pM-- |
| 83 | 18 | “250μM” should read --250pM-- |
| 83 | 19 | “0M5646” should read --OMS646-- |
| 83 | 50 | “μM” should read --pM-- |
| 84 | 12 | “(0MS646)” should read --(OMS646)-- |
| 86 | 47 | “with” should read --will-- |
| 87 | 4 | “with” should read --for-- |

IN THE CLAIMS

| | | |
|---|---|---|
| 199 | 10 | “LAHIFSSDEKSYRTSI, (SEC” should read --LAHIFSSDEKSYRTSL (SEQ-- |
| 199 | 12 | “(SEQ ID NO:90:),” should read --(SEQ ID NO:90),-- |

SEQUENCE LISTING

```
<160> NUMBER OF SEQ ID NOS: 94

<210> SEQ ID NO 1
<211> LENGTH: 2460
<212> TYPE: DNA
<213> ORGANISM: Homo sapiens
<220> FEATURE:
<221> NAME/KEY: CDS
<222> LOCATION: (22)..(2082)

<400> SEQUENCE: 1

ggccagctgg acgggcacac c atg agg ctg ctg acc ctc ctg ggc ctt ctg       51
                        Met Arg Leu Leu Thr Leu Leu Gly Leu Leu
                        1               5                   10

tgt ggc tcg gtg gcc acc ccc ttg ggc ccg aag tgg cct gaa cct gtg       99
Cys Gly Ser Val Ala Thr Pro Leu Gly Pro Lys Trp Pro Glu Pro Val
                15                  20                  25

ttc ggg cgc ctg gca tcc ccc ggc ttt cca ggg gag tat gcc aat gac      147
Phe Gly Arg Leu Ala Ser Pro Gly Phe Pro Gly Glu Tyr Ala Asn Asp
            30                  35                  40

cag gag cgg cgc tgg acc ctg act gca ccc ccc ggc tac cgc ctg cgc      195
```

```
Gln Glu Arg Arg Trp Thr Leu Thr Ala Pro Pro Gly Tyr Arg Leu Arg
        45                  50                  55

ctc tac ttc acc cac ttc gac ctg gag ctc tcc cac ctc tgc gag tac      243
Leu Tyr Phe Thr His Phe Asp Leu Glu Leu Ser His Leu Cys Glu Tyr
    60                  65                  70

gac ttc gtc aag ctg agc tcg ggg gcc aag gtg ctg gcc acg ctg tgc      291
Asp Phe Val Lys Leu Ser Ser Gly Ala Lys Val Leu Ala Thr Leu Cys
75                  80                  85                  90

ggg cag gag agc aca gac acg gag cgg gcc cct ggc aag gac act ttc      339
Gly Gln Glu Ser Thr Asp Thr Glu Arg Ala Pro Gly Lys Asp Thr Phe
                95                  100                 105

tac tcg ctg ggc tcc agc ctg gac att acc ttc cgc tcc gac tac tcc      387
Tyr Ser Leu Gly Ser Ser Leu Asp Ile Thr Phe Arg Ser Asp Tyr Ser
            110                 115                 120

aac gag aag ccg ttc acg ggg ttc gag gcc ttc tat gca gcc gag gac      435
Asn Glu Lys Pro Phe Thr Gly Phe Glu Ala Phe Tyr Ala Ala Glu Asp
        125                 130                 135

att gac gag tgc cag gtg gcc ccg gga gag gcg ccc acc tgc gac cac      483
Ile Asp Glu Cys Gln Val Ala Pro Gly Glu Ala Pro Thr Cys Asp His
    140                 145                 150

cac tgc cac aac cac ctg ggc ggt ttc tac tgc tcc tgc cgc gca ggc      531
His Cys His Asn His Leu Gly Gly Phe Tyr Cys Ser Cys Arg Ala Gly
155                 160                 165                 170

tac gtc ctg cac cgt aac aag cgc acc tgc tca gcc ctg tgc tcc ggc      579
Tyr Val Leu His Arg Asn Lys Arg Thr Cys Ser Ala Leu Cys Ser Gly
            175                 180                 185

cag gtc ttc acc cag agg tct ggg gag ctc agc agc cct gaa tac cca      627
Gln Val Phe Thr Gln Arg Ser Gly Glu Leu Ser Ser Pro Glu Tyr Pro
            190                 195                 200

cgg ccg tat ccc aaa ctc tcc agt tgc act tac agc atc agc ctg gag      675
Arg Pro Tyr Pro Lys Leu Ser Ser Cys Thr Tyr Ser Ile Ser Leu Glu
        205                 210                 215

gag ggg ttc agt gtc att ctg gac ttt gtg gag tcc ttc gat gtg gag      723
Glu Gly Phe Ser Val Ile Leu Asp Phe Val Glu Ser Phe Asp Val Glu
    220                 225                 230

aca cac cct gaa acc ctg tgt ccc tac gac ttt ctc aag att caa aca      771
Thr His Pro Glu Thr Leu Cys Pro Tyr Asp Phe Leu Lys Ile Gln Thr
235                 240                 245                 250

gac aga gaa gaa cat ggc cca ttc tgt ggg aag aca ttg ccc cac agg      819
Asp Arg Glu Glu His Gly Pro Phe Cys Gly Lys Thr Leu Pro His Arg
                255                 260                 265

att gaa aca aaa agc aac acg gtg acc atc acc ttt gtc aca gat gaa      867
Ile Glu Thr Lys Ser Asn Thr Val Thr Ile Thr Phe Val Thr Asp Glu
            270                 275                 280

tca gga gac cac aca ggc tgg aag atc cac tac acg agc aca gcg cag      915
Ser Gly Asp His Thr Gly Trp Lys Ile His Tyr Thr Ser Thr Ala Gln
        285                 290                 295

cct tgc cct tat ccg atg gcg cca cct aat ggc cac gtt tca cct gtg      963
Pro Cys Pro Tyr Pro Met Ala Pro Pro Asn Gly His Val Ser Pro Val
    300                 305                 310

caa gcc aaa tac atc ctg aaa gac agc ttc tcc atc ttt tgc gag act     1011
Gln Ala Lys Tyr Ile Leu Lys Asp Ser Phe Ser Ile Phe Cys Glu Thr
315                 320                 325                 330

ggc tat gag ctt ctg caa ggt cac ttg ccc ctg aaa tcc ttt act gca     1059
Gly Tyr Glu Leu Leu Gln Gly His Leu Pro Leu Lys Ser Phe Thr Ala
                335                 340                 345

gtt tgt cag aaa gat gga tct tgg gac cgg cca atg ccc gcg tgc agc     1107
Val Cys Gln Lys Asp Gly Ser Trp Asp Arg Pro Met Pro Ala Cys Ser
            350                 355                 360
```

-continued

```
att gtt gac tgt ggc cct cct gat gat cta ccc agt ggc cga gtg gag      1155
Ile Val Asp Cys Gly Pro Pro Asp Asp Leu Pro Ser Gly Arg Val Glu
        365                 370                 375

tac atc aca ggt cct gga gtg acc acc tac aaa gct gtg att cag tac      1203
Tyr Ile Thr Gly Pro Gly Val Thr Thr Tyr Lys Ala Val Ile Gln Tyr
    380                 385                 390

agc tgt gaa gag acc ttc tac aca atg aaa gtg aat gat ggt aaa tat      1251
Ser Cys Glu Glu Thr Phe Tyr Thr Met Lys Val Asn Asp Gly Lys Tyr
395                 400                 405                 410

gtg tgt gag gct gat gga ttc tgg acg agc tcc aaa gga gaa aaa tca      1299
Val Cys Glu Ala Asp Gly Phe Trp Thr Ser Ser Lys Gly Glu Lys Ser
                415                 420                 425

ctc cca gtc tgt gag cct gtt tgt gga cta tca gcc cgc aca aca gga      1347
Leu Pro Val Cys Glu Pro Val Cys Gly Leu Ser Ala Arg Thr Thr Gly
            430                 435                 440

ggg cgt ata tat gga ggg caa aag gca aaa cct ggt gat ttt cct tgg      1395
Gly Arg Ile Tyr Gly Gly Gln Lys Ala Lys Pro Gly Asp Phe Pro Trp
        445                 450                 455

caa gtc ctg ata tta ggt gga acc aca gca gca ggt gca ctt tta tat      1443
Gln Val Leu Ile Leu Gly Gly Thr Thr Ala Ala Gly Ala Leu Leu Tyr
    460                 465                 470

gac aac tgg gtc cta aca gct gct cat gcc gtc tat gag caa aaa cat      1491
Asp Asn Trp Val Leu Thr Ala Ala His Ala Val Tyr Glu Gln Lys His
475                 480                 485                 490

gat gca tcc gcc ctg gac att cga atg ggc acc ctg aaa aga cta tca      1539
Asp Ala Ser Ala Leu Asp Ile Arg Met Gly Thr Leu Lys Arg Leu Ser
                495                 500                 505

cct cat tat aca caa gcc tgg tct gaa gct gtt ttt ata cat gaa ggt      1587
Pro His Tyr Thr Gln Ala Trp Ser Glu Ala Val Phe Ile His Glu Gly
            510                 515                 520

tat act cat gat gct ggc ttt gac aat gac ata gca ctg att aaa ttg      1635
Tyr Thr His Asp Ala Gly Phe Asp Asn Asp Ile Ala Leu Ile Lys Leu
        525                 530                 535

aat aac aaa gtt gta atc aat agc aac atc acg cct att tgt ctg cca      1683
Asn Asn Lys Val Val Ile Asn Ser Asn Ile Thr Pro Ile Cys Leu Pro
    540                 545                 550

aga aaa gaa gct gaa tcc ttt atg agg aca gat gac att gga act gca      1731
Arg Lys Glu Ala Glu Ser Phe Met Arg Thr Asp Asp Ile Gly Thr Ala
555                 560                 565                 570

tct gga tgg gga tta acc caa agg ggt ttt ctt gct aga aat cta atg      1779
Ser Gly Trp Gly Leu Thr Gln Arg Gly Phe Leu Ala Arg Asn Leu Met
                575                 580                 585

tat gtc gac ata ccg att gtt gac cat caa aaa tgt act gct gca tat      1827
Tyr Val Asp Ile Pro Ile Val Asp His Gln Lys Cys Thr Ala Ala Tyr
            590                 595                 600

gaa aag cca ccc tat cca agg gga agt gta act gct aac atg ctt tgt      1875
Glu Lys Pro Pro Tyr Pro Arg Gly Ser Val Thr Ala Asn Met Leu Cys
        605                 610                 615

gct ggc tta gaa agt ggg ggc aag gac agc tgc aga ggt gac agc gga      1923
Ala Gly Leu Glu Ser Gly Gly Lys Asp Ser Cys Arg Gly Asp Ser Gly
    620                 625                 630

ggg gca ctg gtg ttt cta gat agt gaa aca gag agg tgg ttt gtg gga      1971
Gly Ala Leu Val Phe Leu Asp Ser Glu Thr Glu Arg Trp Phe Val Gly
635                 640                 645                 650

gga ata gtg tcc tgg ggt tcc atg aat tgt ggg gaa gca ggt cag tat      2019
Gly Ile Val Ser Trp Gly Ser Met Asn Cys Gly Glu Ala Gly Gln Tyr
                655                 660                 665

gga gtc tac aca aaa gtt att aac tat att ccc tgg atc gag aac ata      2067
Gly Val Tyr Thr Lys Val Ile Asn Tyr Ile Pro Trp Ile Glu Asn Ile
            670                 675                 680
```

```
att agt gat ttt taa cttgcgtgtc tgcagtcaag gattcttcat ttttagaaat     2122
Ile Ser Asp Phe
        685

gcctgtgaag accttggcag cgacgtggct cgagaagcat tcatcattac tgtggacatg   2182

gcagttgttg ctccacccaa aaaaacagac tccaggtgag gctgctgtca tttctccact   2242

tgccagttta attccagcct tacccattga ctcaagggga cataaaccac gagagtgaca   2302

gtcatctttg cccacccagt gtaatgtcac tgctcaaatt acatttcatt accttaaaaa   2362

gccagtctct tttcatactg gctgttggca tttctgtaaa ctgcctgtcc atgctctttg   2422

tttttaaact tgttcttatt gaaaaaaaaa aaaaaaaa                          2460


<210> SEQ ID NO 2
<211> LENGTH: 686
<212> TYPE: PRT
<213> ORGANISM: Homo sapiens

<400> SEQUENCE: 2

Met Arg Leu Leu Thr Leu Leu Gly Leu Leu Cys Gly Ser Val Ala Thr
1               5                   10                  15

Pro Leu Gly Pro Lys Trp Pro Glu Pro Val Phe Gly Arg Leu Ala Ser
            20                  25                  30

Pro Gly Phe Pro Gly Glu Tyr Ala Asn Asp Gln Glu Arg Arg Trp Thr
        35                  40                  45

Leu Thr Ala Pro Pro Gly Tyr Arg Leu Arg Leu Tyr Phe Thr His Phe
    50                  55                  60

Asp Leu Glu Leu Ser His Leu Cys Glu Tyr Asp Phe Val Lys Leu Ser
65                  70                  75                  80

Ser Gly Ala Lys Val Leu Ala Thr Leu Cys Gly Gln Glu Ser Thr Asp
                85                  90                  95

Thr Glu Arg Ala Pro Gly Lys Asp Thr Phe Tyr Ser Leu Gly Ser Ser
            100                 105                 110

Leu Asp Ile Thr Phe Arg Ser Asp Tyr Ser Asn Glu Lys Pro Phe Thr
        115                 120                 125

Gly Phe Glu Ala Phe Tyr Ala Ala Glu Asp Ile Asp Glu Cys Gln Val
    130                 135                 140

Ala Pro Gly Glu Ala Pro Thr Cys Asp His His Cys His Asn His Leu
145                 150                 155                 160

Gly Gly Phe Tyr Cys Ser Cys Arg Ala Gly Tyr Val Leu His Arg Asn
                165                 170                 175

Lys Arg Thr Cys Ser Ala Leu Cys Ser Gly Gln Val Phe Thr Gln Arg
            180                 185                 190

Ser Gly Glu Leu Ser Ser Pro Glu Tyr Pro Arg Pro Tyr Pro Lys Leu
        195                 200                 205

Ser Ser Cys Thr Tyr Ser Ile Ser Leu Glu Glu Gly Phe Ser Val Ile
    210                 215                 220

Leu Asp Phe Val Glu Ser Phe Asp Val Glu Thr His Pro Glu Thr Leu
225                 230                 235                 240

Cys Pro Tyr Asp Phe Leu Lys Ile Gln Thr Asp Arg Glu Glu His Gly
                245                 250                 255

Pro Phe Cys Gly Lys Thr Leu Pro His Arg Ile Glu Thr Lys Ser Asn
            260                 265                 270

Thr Val Thr Ile Thr Phe Val Thr Asp Glu Ser Gly Asp His Thr Gly
        275                 280                 285
```

-continued

```
Trp Lys Ile His Tyr Thr Ser Thr Ala Gln Pro Cys Pro Tyr Pro Met
    290                 295                 300

Ala Pro Pro Asn Gly His Val Ser Pro Val Gln Ala Lys Tyr Ile Leu
305                 310                 315                 320

Lys Asp Ser Phe Ser Ile Phe Cys Glu Thr Gly Tyr Glu Leu Leu Gln
                325                 330                 335

Gly His Leu Pro Leu Lys Ser Phe Thr Ala Val Cys Gln Lys Asp Gly
            340                 345                 350

Ser Trp Asp Arg Pro Met Pro Ala Cys Ser Ile Val Asp Cys Gly Pro
        355                 360                 365

Pro Asp Asp Leu Pro Ser Gly Arg Val Glu Tyr Ile Thr Gly Pro Gly
    370                 375                 380

Val Thr Thr Tyr Lys Ala Val Ile Gln Tyr Ser Cys Glu Glu Thr Phe
385                 390                 395                 400

Tyr Thr Met Lys Val Asn Asp Gly Lys Tyr Val Cys Glu Ala Asp Gly
                405                 410                 415

Phe Trp Thr Ser Ser Lys Gly Glu Lys Ser Leu Pro Val Cys Glu Pro
            420                 425                 430

Val Cys Gly Leu Ser Ala Arg Thr Thr Gly Gly Arg Ile Tyr Gly Gly
        435                 440                 445

Gln Lys Ala Lys Pro Gly Asp Phe Pro Trp Gln Val Leu Ile Leu Gly
    450                 455                 460

Gly Thr Thr Ala Ala Gly Ala Leu Leu Tyr Asp Asn Trp Val Leu Thr
465                 470                 475                 480

Ala Ala His Ala Val Tyr Glu Gln Lys His Asp Ala Ser Ala Leu Asp
                485                 490                 495

Ile Arg Met Gly Thr Leu Lys Arg Leu Ser Pro His Tyr Thr Gln Ala
            500                 505                 510

Trp Ser Glu Ala Val Phe Ile His Glu Gly Tyr Thr His Asp Ala Gly
        515                 520                 525

Phe Asp Asn Asp Ile Ala Leu Ile Lys Leu Asn Asn Lys Val Val Ile
    530                 535                 540

Asn Ser Asn Ile Thr Pro Ile Cys Leu Pro Arg Lys Glu Ala Glu Ser
545                 550                 555                 560

Phe Met Arg Thr Asp Asp Ile Gly Thr Ala Ser Gly Trp Gly Leu Thr
                565                 570                 575

Gln Arg Gly Phe Leu Ala Arg Asn Leu Met Tyr Val Asp Ile Pro Ile
            580                 585                 590

Val Asp His Gln Lys Cys Thr Ala Ala Tyr Glu Lys Pro Pro Tyr Pro
        595                 600                 605

Arg Gly Ser Val Thr Ala Asn Met Leu Cys Ala Gly Leu Glu Ser Gly
    610                 615                 620

Gly Lys Asp Ser Cys Arg Gly Asp Ser Gly Gly Ala Leu Val Phe Leu
625                 630                 635                 640

Asp Ser Glu Thr Glu Arg Trp Phe Val Gly Gly Ile Val Ser Trp Gly
                645                 650                 655

Ser Met Asn Cys Gly Glu Ala Gly Gln Tyr Gly Val Tyr Thr Lys Val
            660                 665                 670

Ile Asn Tyr Ile Pro Trp Ile Glu Asn Ile Ile Ser Asp Phe
        675                 680                 685
```

<210> SEQ ID NO 3
<211> LENGTH: 671
<212> TYPE: PRT

<213> ORGANISM: Homo sapiens

<400> SEQUENCE: 3

```
Thr Pro Leu Gly Pro Lys Trp Pro Glu Pro Val Phe Gly Arg Leu Ala
1               5                   10                  15

Ser Pro Gly Phe Pro Gly Glu Tyr Ala Asn Asp Gln Glu Arg Arg Trp
            20                  25                  30

Thr Leu Thr Ala Pro Pro Gly Tyr Arg Leu Arg Leu Tyr Phe Thr His
        35                  40                  45

Phe Asp Leu Glu Leu Ser His Leu Cys Glu Tyr Asp Phe Val Lys Leu
    50                  55                  60

Ser Ser Gly Ala Lys Val Leu Ala Thr Leu Cys Gly Gln Glu Ser Thr
65                  70                  75                  80

Asp Thr Glu Arg Ala Pro Gly Lys Asp Thr Phe Tyr Ser Leu Gly Ser
                85                  90                  95

Ser Leu Asp Ile Thr Phe Arg Ser Asp Tyr Ser Asn Glu Lys Pro Phe
            100                 105                 110

Thr Gly Phe Glu Ala Phe Tyr Ala Ala Glu Asp Ile Asp Glu Cys Gln
        115                 120                 125

Val Ala Pro Gly Glu Ala Pro Thr Cys Asp His His Cys His Asn His
    130                 135                 140

Leu Gly Gly Phe Tyr Cys Ser Cys Arg Ala Gly Tyr Val Leu His Arg
145                 150                 155                 160

Asn Lys Arg Thr Cys Ser Ala Leu Cys Ser Gly Gln Val Phe Thr Gln
                165                 170                 175

Arg Ser Gly Glu Leu Ser Ser Pro Glu Tyr Pro Arg Pro Tyr Pro Lys
            180                 185                 190

Leu Ser Ser Cys Thr Tyr Ser Ile Ser Leu Glu Glu Gly Phe Ser Val
        195                 200                 205

Ile Leu Asp Phe Val Glu Ser Phe Asp Val Glu Thr His Pro Glu Thr
    210                 215                 220

Leu Cys Pro Tyr Asp Phe Leu Lys Ile Gln Thr Asp Arg Glu Glu His
225                 230                 235                 240

Gly Pro Phe Cys Gly Lys Thr Leu Pro His Arg Ile Glu Thr Lys Ser
                245                 250                 255

Asn Thr Val Thr Ile Thr Phe Val Thr Asp Glu Ser Gly Asp His Thr
            260                 265                 270

Gly Trp Lys Ile His Tyr Thr Ser Thr Ala Gln Pro Cys Pro Tyr Pro
        275                 280                 285

Met Ala Pro Pro Asn Gly His Val Ser Pro Val Gln Ala Lys Tyr Ile
    290                 295                 300

Leu Lys Asp Ser Phe Ser Ile Phe Cys Glu Thr Gly Tyr Glu Leu Leu
305                 310                 315                 320

Gln Gly His Leu Pro Leu Lys Ser Phe Thr Ala Val Cys Gln Lys Asp
                325                 330                 335

Gly Ser Trp Asp Arg Pro Met Pro Ala Cys Ser Ile Val Asp Cys Gly
            340                 345                 350

Pro Pro Asp Asp Leu Pro Ser Gly Arg Val Glu Tyr Ile Thr Gly Pro
        355                 360                 365

Gly Val Thr Thr Tyr Lys Ala Val Ile Gln Tyr Ser Cys Glu Glu Thr
    370                 375                 380

Phe Tyr Thr Met Lys Val Asn Asp Gly Lys Tyr Val Cys Glu Ala Asp
385                 390                 395                 400
```

-continued

```
Gly Phe Trp Thr Ser Ser Lys Gly Glu Lys Ser Leu Pro Val Cys Glu
                405                 410                 415

Pro Val Cys Gly Leu Ser Ala Arg Thr Thr Gly Gly Arg Ile Tyr Gly
            420                 425                 430

Gly Gln Lys Ala Lys Pro Gly Asp Phe Pro Trp Gln Val Leu Ile Leu
        435                 440                 445

Gly Gly Thr Thr Ala Ala Gly Ala Leu Leu Tyr Asp Asn Trp Val Leu
    450                 455                 460

Thr Ala Ala His Ala Val Tyr Glu Gln Lys His Asp Ala Ser Ala Leu
465                 470                 475                 480

Asp Ile Arg Met Gly Thr Leu Lys Arg Leu Ser Pro His Tyr Thr Gln
                485                 490                 495

Ala Trp Ser Glu Ala Val Phe Ile His Glu Gly Tyr Thr His Asp Ala
            500                 505                 510

Gly Phe Asp Asn Asp Ile Ala Leu Ile Lys Leu Asn Asn Lys Val Val
        515                 520                 525

Ile Asn Ser Asn Ile Thr Pro Ile Cys Leu Pro Arg Lys Glu Ala Glu
    530                 535                 540

Ser Phe Met Arg Thr Asp Asp Ile Gly Thr Ala Ser Gly Trp Gly Leu
545                 550                 555                 560

Thr Gln Arg Gly Phe Leu Ala Arg Asn Leu Met Tyr Val Asp Ile Pro
                565                 570                 575

Ile Val Asp His Gln Lys Cys Thr Ala Ala Tyr Glu Lys Pro Pro Tyr
            580                 585                 590

Pro Arg Gly Ser Val Thr Ala Asn Met Leu Cys Ala Gly Leu Glu Ser
        595                 600                 605

Gly Gly Lys Asp Ser Cys Arg Gly Asp Ser Gly Gly Ala Leu Val Phe
    610                 615                 620

Leu Asp Ser Glu Thr Glu Arg Trp Phe Val Gly Gly Ile Val Ser Trp
625                 630                 635                 640

Gly Ser Met Asn Cys Gly Glu Ala Gly Gln Tyr Gly Val Tyr Thr Lys
                645                 650                 655

Val Ile Asn Tyr Ile Pro Trp Ile Glu Asn Ile Ile Ser Asp Phe
            660                 665                 670


<210> SEQ ID NO 4
<211> LENGTH: 2091
<212> TYPE: DNA
<213> ORGANISM: Rat
<220> FEATURE:
<221> NAME/KEY: CDS
<222> LOCATION: (10)..(2067)

<400> SEQUENCE: 4

tggcacaca atg agg cta ctg atc gtc ctg ggt ctg ctt tgg agt ttg gtg      51
          Met Arg Leu Leu Ile Val Leu Gly Leu Leu Trp Ser Leu Val
          1               5                   10

gcc aca ctt ttg ggc tcc aag tgg cct gag cct gta ttc ggg cgc ctg        99
Ala Thr Leu Leu Gly Ser Lys Trp Pro Glu Pro Val Phe Gly Arg Leu
15                  20                  25                  30

gtg tcc ctg gcc ttc cca gag aag tat ggc aac cat cag gat cga tcc       147
Val Ser Leu Ala Phe Pro Glu Lys Tyr Gly Asn His Gln Asp Arg Ser
                35                  40                  45

tgg acg ctg act gca ccc cct ggc ttc cgc ctg cgc ctc tac ttc acc       195
Trp Thr Leu Thr Ala Pro Pro Gly Phe Arg Leu Arg Leu Tyr Phe Thr
            50                  55                  60

cac ttc aac ctg gaa ctc tct tac cgc tgc gag tat gac ttt gtc aag       243
```

-continued

```
His Phe Asn Leu Glu Leu Ser Tyr Arg Cys Glu Tyr Asp Phe Val Lys
        65                  70                  75

ttg acc tca ggg acc aag gtg cta gcc acg ctg tgt ggg cag gag agt      291
Leu Thr Ser Gly Thr Lys Val Leu Ala Thr Leu Cys Gly Gln Glu Ser
    80                  85                  90

aca gat act gag cgg gca cct ggc aat gac acc ttc tac tca ctg ggt      339
Thr Asp Thr Glu Arg Ala Pro Gly Asn Asp Thr Phe Tyr Ser Leu Gly
95                  100                 105                 110

ccc agc cta aag gtc acc ttc cac tcc gac tac tcc aat gag aag cca      387
Pro Ser Leu Lys Val Thr Phe His Ser Asp Tyr Ser Asn Glu Lys Pro
                115                 120                 125

ttc aca gga ttt gag gcc ttc tat gca gcg gag gat gtg gat gaa tgc      435
Phe Thr Gly Phe Glu Ala Phe Tyr Ala Ala Glu Asp Val Asp Glu Cys
            130                 135                 140

aga aca tcc ctg gga gac tca gtc cct tgt gac cat tat tgc cac aac      483
Arg Thr Ser Leu Gly Asp Ser Val Pro Cys Asp His Tyr Cys His Asn
        145                 150                 155

tac ctg ggc ggc tac tac tgc tcc tgc cga gtg ggc tac att ctg cac      531
Tyr Leu Gly Gly Tyr Tyr Cys Ser Cys Arg Val Gly Tyr Ile Leu His
    160                 165                 170

cag aac aag cat acc tgc tca gcc ctt tgt tca ggc cag gtg ttc act      579
Gln Asn Lys His Thr Cys Ser Ala Leu Cys Ser Gly Gln Val Phe Thr
175                 180                 185                 190

ggg agg tct ggc ttt ctc agt agc cct gag tac cca cag cca tac ccc      627
Gly Arg Ser Gly Phe Leu Ser Ser Pro Glu Tyr Pro Gln Pro Tyr Pro
                195                 200                 205

aaa ctc tcc agc tgc gcc tac aac atc cgc ctg gag gaa ggc ttc agt      675
Lys Leu Ser Ser Cys Ala Tyr Asn Ile Arg Leu Glu Glu Gly Phe Ser
            210                 215                 220

atc acc ctg gac ttc gtg gag tcc ttt gat gtg gag atg cac cct gaa      723
Ile Thr Leu Asp Phe Val Glu Ser Phe Asp Val Glu Met His Pro Glu
        225                 230                 235

gcc cag tgc ccc tac gac tcc ctc aag att caa aca gac aag agg gaa      771
Ala Gln Cys Pro Tyr Asp Ser Leu Lys Ile Gln Thr Asp Lys Arg Glu
    240                 245                 250

tac ggc ccg ttt tgt ggg aag acg ctg ccc ccc agg att gaa act gac      819
Tyr Gly Pro Phe Cys Gly Lys Thr Leu Pro Pro Arg Ile Glu Thr Asp
255                 260                 265                 270

agc aac aag gtg acc att acc ttt acc acc gac gag tca ggg aac cac      867
Ser Asn Lys Val Thr Ile Thr Phe Thr Thr Asp Glu Ser Gly Asn His
                275                 280                 285

aca ggc tgg aag ata cac tac aca agc aca gca cag ccc tgc cct gat      915
Thr Gly Trp Lys Ile His Tyr Thr Ser Thr Ala Gln Pro Cys Pro Asp
            290                 295                 300

cca acg gcg cca cct aat ggt cac att tca cct gtg caa gcc acg tat      963
Pro Thr Ala Pro Pro Asn Gly His Ile Ser Pro Val Gln Ala Thr Tyr
        305                 310                 315

gtc ctg aag gac agc ttt tct gtc ttc tgc aag act ggc ttc gag ctt     1011
Val Leu Lys Asp Ser Phe Ser Val Phe Cys Lys Thr Gly Phe Glu Leu
    320                 325                 330

ctg caa ggt tct gtc ccc ctg aag tca ttc act gct gtc tgt cag aaa     1059
Leu Gln Gly Ser Val Pro Leu Lys Ser Phe Thr Ala Val Cys Gln Lys
335                 340                 345                 350

gat gga tct tgg gac cgg ccg ata cca gag tgc agc att att gac tgt     1107
Asp Gly Ser Trp Asp Arg Pro Ile Pro Glu Cys Ser Ile Ile Asp Cys
                355                 360                 365

ggc cct ccc gat gac cta ccc aat ggc cac gtg gac tat atc aca ggc     1155
Gly Pro Pro Asp Asp Leu Pro Asn Gly His Val Asp Tyr Ile Thr Gly
            370                 375                 380
```

-continued

```
cct gaa gtg acc acc tac aaa gct gtg att cag tac agc tgt gaa gag      1203
Pro Glu Val Thr Thr Tyr Lys Ala Val Ile Gln Tyr Ser Cys Glu Glu
        385                 390                 395

act ttc tac aca atg agc agc aat ggt aaa tat gtg tgt gag gct gat      1251
Thr Phe Tyr Thr Met Ser Ser Asn Gly Lys Tyr Val Cys Glu Ala Asp
    400                 405                 410

gga ttc tgg acg agc tcc aaa gga gaa aaa tcc ctc ccg gtt tgc aag      1299
Gly Phe Trp Thr Ser Ser Lys Gly Glu Lys Ser Leu Pro Val Cys Lys
415                 420                 425                 430

cct gtc tgt gga ctg tcc aca cac act tca gga ggc cgt ata att gga      1347
Pro Val Cys Gly Leu Ser Thr His Thr Ser Gly Gly Arg Ile Ile Gly
                435                 440                 445

gga cag cct gca aag cct ggt gac ttt cct tgg caa gtc ttg tta ctg      1395
Gly Gln Pro Ala Lys Pro Gly Asp Phe Pro Trp Gln Val Leu Leu Leu
            450                 455                 460

ggt gaa act aca gca gca ggt gct ctt ata cat gac gac tgg gtc cta      1443
Gly Glu Thr Thr Ala Ala Gly Ala Leu Ile His Asp Asp Trp Val Leu
        465                 470                 475

aca gcg gct cat gct gta tat ggg aaa aca gag gcg atg tcc tcc ctg      1491
Thr Ala Ala His Ala Val Tyr Gly Lys Thr Glu Ala Met Ser Ser Leu
    480                 485                 490

gac atc cgc atg ggc atc ctc aaa agg ctc tcc ctc att tac act caa      1539
Asp Ile Arg Met Gly Ile Leu Lys Arg Leu Ser Leu Ile Tyr Thr Gln
495                 500                 505                 510

gcc tgg cca gag gct gtc ttt atc cat gaa ggc tac act cac gga gct      1587
Ala Trp Pro Glu Ala Val Phe Ile His Glu Gly Tyr Thr His Gly Ala
                515                 520                 525

ggt ttt gac aat gat ata gca ctg att aaa ctc aag aac aaa gtc aca      1635
Gly Phe Asp Asn Asp Ile Ala Leu Ile Lys Leu Lys Asn Lys Val Thr
            530                 535                 540

atc aac aga aac atc atg ccg att tgt cta cca aga aaa gaa gct gca      1683
Ile Asn Arg Asn Ile Met Pro Ile Cys Leu Pro Arg Lys Glu Ala Ala
        545                 550                 555

tcc tta atg aaa aca gac ttc gtt gga act gtg gct ggc tgg ggg tta      1731
Ser Leu Met Lys Thr Asp Phe Val Gly Thr Val Ala Gly Trp Gly Leu
    560                 565                 570

acc cag aag ggg ttt ctt gct aga aac cta atg ttt gtg gac ata cca      1779
Thr Gln Lys Gly Phe Leu Ala Arg Asn Leu Met Phe Val Asp Ile Pro
575                 580                 585                 590

att gtt gac cac caa aaa tgt gct act gcg tat aca aag cag ccc tac      1827
Ile Val Asp His Gln Lys Cys Ala Thr Ala Tyr Thr Lys Gln Pro Tyr
                595                 600                 605

cca gga gca aaa gtg act gtt aac atg ctc tgt gct ggc cta gac cgc      1875
Pro Gly Ala Lys Val Thr Val Asn Met Leu Cys Ala Gly Leu Asp Arg
            610                 615                 620

ggt ggc aag gac agc tgc aga ggt gac agc gga ggg gca tta gtg ttt      1923
Gly Gly Lys Asp Ser Cys Arg Gly Asp Ser Gly Gly Ala Leu Val Phe
        625                 630                 635

cta gac aat gaa aca cag aga tgg ttt gtg gga gga ata gtt tcc tgg      1971
Leu Asp Asn Glu Thr Gln Arg Trp Phe Val Gly Gly Ile Val Ser Trp
    640                 645                 650

ggt tct att aac tgt ggg ggg tca gaa cag tat ggg gtc tac acg aaa      2019
Gly Ser Ile Asn Cys Gly Gly Ser Glu Gln Tyr Gly Val Tyr Thr Lys
655                 660                 665                 670

gtc acg aac tat att ccc tgg att gag aac ata ata aat aat ttc taa      2067
Val Thr Asn Tyr Ile Pro Trp Ile Glu Asn Ile Ile Asn Asn Phe
                675                 680                 685

tttgcaaaaa aaaaaaaaaa aaaa                                           2091
```

-continued

```
<210> SEQ ID NO 5
<211> LENGTH: 685
<212> TYPE: PRT
<213> ORGANISM: Rat

<400> SEQUENCE: 5

Met Arg Leu Leu Ile Val Leu Gly Leu Leu Trp Ser Leu Val Ala Thr
1               5                   10                  15

Leu Leu Gly Ser Lys Trp Pro Glu Pro Val Phe Gly Arg Leu Val Ser
            20                  25                  30

Leu Ala Phe Pro Glu Lys Tyr Gly Asn His Gln Asp Arg Ser Trp Thr
        35                  40                  45

Leu Thr Ala Pro Pro Gly Phe Arg Leu Arg Leu Tyr Phe Thr His Phe
    50                  55                  60

Asn Leu Glu Leu Ser Tyr Arg Cys Glu Tyr Asp Phe Val Lys Leu Thr
65                  70                  75                  80

Ser Gly Thr Lys Val Leu Ala Thr Leu Cys Gly Gln Glu Ser Thr Asp
                85                  90                  95

Thr Glu Arg Ala Pro Gly Asn Asp Thr Phe Tyr Ser Leu Gly Pro Ser
            100                 105                 110

Leu Lys Val Thr Phe His Ser Asp Tyr Ser Asn Glu Lys Pro Phe Thr
        115                 120                 125

Gly Phe Glu Ala Phe Tyr Ala Ala Glu Asp Val Asp Glu Cys Arg Thr
    130                 135                 140

Ser Leu Gly Asp Ser Val Pro Cys Asp His Tyr Cys His Asn Tyr Leu
145                 150                 155                 160

Gly Gly Tyr Tyr Cys Ser Cys Arg Val Gly Tyr Ile Leu His Gln Asn
                165                 170                 175

Lys His Thr Cys Ser Ala Leu Cys Ser Gly Gln Val Phe Thr Gly Arg
            180                 185                 190

Ser Gly Phe Leu Ser Ser Pro Glu Tyr Pro Gln Pro Tyr Pro Lys Leu
        195                 200                 205

Ser Ser Cys Ala Tyr Asn Ile Arg Leu Glu Glu Gly Phe Ser Ile Thr
    210                 215                 220

Leu Asp Phe Val Glu Ser Phe Asp Val Glu Met His Pro Glu Ala Gln
225                 230                 235                 240

Cys Pro Tyr Asp Ser Leu Lys Ile Gln Thr Asp Lys Arg Glu Tyr Gly
                245                 250                 255

Pro Phe Cys Gly Lys Thr Leu Pro Pro Arg Ile Glu Thr Asp Ser Asn
            260                 265                 270

Lys Val Thr Ile Thr Phe Thr Thr Asp Glu Ser Gly Asn His Thr Gly
        275                 280                 285

Trp Lys Ile His Tyr Thr Ser Thr Ala Gln Pro Cys Pro Asp Pro Thr
    290                 295                 300

Ala Pro Pro Asn Gly His Ile Ser Pro Val Gln Ala Thr Tyr Val Leu
305                 310                 315                 320

Lys Asp Ser Phe Ser Val Phe Cys Lys Thr Gly Phe Glu Leu Leu Gln
                325                 330                 335

Gly Ser Val Pro Leu Lys Ser Phe Thr Ala Val Cys Gln Lys Asp Gly
            340                 345                 350

Ser Trp Asp Arg Pro Ile Pro Glu Cys Ser Ile Ile Asp Cys Gly Pro
        355                 360                 365

Pro Asp Asp Leu Pro Asn Gly His Val Asp Tyr Ile Thr Gly Pro Glu
    370                 375                 380
```

```
Val Thr Thr Tyr Lys Ala Val Ile Gln Tyr Ser Cys Glu Glu Thr Phe
385                 390                 395                 400

Tyr Thr Met Ser Ser Asn Gly Lys Tyr Val Cys Glu Ala Asp Gly Phe
                405                 410                 415

Trp Thr Ser Ser Lys Gly Glu Lys Ser Leu Pro Val Cys Lys Pro Val
            420                 425                 430

Cys Gly Leu Ser Thr His Thr Ser Gly Gly Arg Ile Ile Gly Gly Gln
        435                 440                 445

Pro Ala Lys Pro Gly Asp Phe Pro Trp Gln Val Leu Leu Leu Gly Glu
    450                 455                 460

Thr Thr Ala Ala Gly Ala Leu Ile His Asp Asp Trp Val Leu Thr Ala
465                 470                 475                 480

Ala His Ala Val Tyr Gly Lys Thr Glu Ala Met Ser Ser Leu Asp Ile
                485                 490                 495

Arg Met Gly Ile Leu Lys Arg Leu Ser Leu Ile Tyr Thr Gln Ala Trp
            500                 505                 510

Pro Glu Ala Val Phe Ile His Glu Gly Tyr Thr His Gly Ala Gly Phe
        515                 520                 525

Asp Asn Asp Ile Ala Leu Ile Lys Leu Lys Asn Lys Val Thr Ile Asn
    530                 535                 540

Arg Asn Ile Met Pro Ile Cys Leu Pro Arg Lys Glu Ala Ala Ser Leu
545                 550                 555                 560

Met Lys Thr Asp Phe Val Gly Thr Val Ala Gly Trp Gly Leu Thr Gln
                565                 570                 575

Lys Gly Phe Leu Ala Arg Asn Leu Met Phe Val Asp Ile Pro Ile Val
            580                 585                 590

Asp His Gln Lys Cys Ala Thr Ala Tyr Thr Lys Gln Pro Tyr Pro Gly
        595                 600                 605

Ala Lys Val Thr Val Asn Met Leu Cys Ala Gly Leu Asp Arg Gly Gly
    610                 615                 620

Lys Asp Ser Cys Arg Gly Asp Ser Gly Gly Ala Leu Val Phe Leu Asp
625                 630                 635                 640

Asn Glu Thr Gln Arg Trp Phe Val Gly Gly Ile Val Ser Trp Gly Ser
                645                 650                 655

Ile Asn Cys Gly Gly Ser Glu Gln Tyr Gly Val Tyr Thr Lys Val Thr
            660                 665                 670

Asn Tyr Ile Pro Trp Ile Glu Asn Ile Ile Asn Asn Phe
        675                 680                 685


<210> SEQ ID NO 6
<211> LENGTH: 670
<212> TYPE: PRT
<213> ORGANISM: Rat

<400> SEQUENCE: 6

Thr Leu Leu Gly Ser Lys Trp Pro Glu Pro Val Phe Gly Arg Leu Val
1               5                   10                  15

Ser Leu Ala Phe Pro Glu Lys Tyr Gly Asn His Gln Asp Arg Ser Trp
            20                  25                  30

Thr Leu Thr Ala Pro Pro Gly Phe Arg Leu Arg Leu Tyr Phe Thr His
        35                  40                  45

Phe Asn Leu Glu Leu Ser Tyr Arg Cys Glu Tyr Asp Phe Val Lys Leu
    50                  55                  60

Thr Ser Gly Thr Lys Val Leu Ala Thr Leu Cys Gly Gln Glu Ser Thr
65                  70                  75                  80
```

```
Asp Thr Glu Arg Ala Pro Gly Asn Asp Thr Phe Tyr Ser Leu Gly Pro
                85                  90                  95

Ser Leu Lys Val Thr Phe His Ser Asp Tyr Ser Asn Glu Lys Pro Phe
            100                 105                 110

Thr Gly Phe Glu Ala Phe Tyr Ala Ala Glu Asp Val Asp Glu Cys Arg
        115                 120                 125

Thr Ser Leu Gly Asp Ser Val Pro Cys Asp His Tyr Cys His Asn Tyr
    130                 135                 140

Leu Gly Gly Tyr Tyr Cys Ser Cys Arg Val Gly Tyr Ile Leu His Gln
145                 150                 155                 160

Asn Lys His Thr Cys Ser Ala Leu Cys Ser Gly Gln Val Phe Thr Gly
                165                 170                 175

Arg Ser Gly Phe Leu Ser Ser Pro Glu Tyr Pro Gln Pro Tyr Pro Lys
            180                 185                 190

Leu Ser Ser Cys Ala Tyr Asn Ile Arg Leu Glu Glu Gly Phe Ser Ile
        195                 200                 205

Thr Leu Asp Phe Val Glu Ser Phe Asp Val Glu Met His Pro Glu Ala
    210                 215                 220

Gln Cys Pro Tyr Asp Ser Leu Lys Ile Gln Thr Asp Lys Arg Glu Tyr
225                 230                 235                 240

Gly Pro Phe Cys Gly Lys Thr Leu Pro Pro Arg Ile Glu Thr Asp Ser
                245                 250                 255

Asn Lys Val Thr Ile Thr Phe Thr Thr Asp Glu Ser Gly Asn His Thr
            260                 265                 270

Gly Trp Lys Ile His Tyr Thr Ser Thr Ala Gln Pro Cys Pro Asp Pro
        275                 280                 285

Thr Ala Pro Pro Asn Gly His Ile Ser Pro Val Gln Ala Thr Tyr Val
    290                 295                 300

Leu Lys Asp Ser Phe Ser Val Phe Cys Lys Thr Gly Phe Glu Leu Leu
305                 310                 315                 320

Gln Gly Ser Val Pro Leu Lys Ser Phe Thr Ala Val Cys Gln Lys Asp
                325                 330                 335

Gly Ser Trp Asp Arg Pro Ile Pro Glu Cys Ser Ile Ile Asp Cys Gly
            340                 345                 350

Pro Pro Asp Asp Leu Pro Asn Gly His Val Asp Tyr Ile Thr Gly Pro
        355                 360                 365

Glu Val Thr Thr Tyr Lys Ala Val Ile Gln Tyr Ser Cys Glu Glu Thr
    370                 375                 380

Phe Tyr Thr Met Ser Ser Asn Gly Lys Tyr Val Cys Glu Ala Asp Gly
385                 390                 395                 400

Phe Trp Thr Ser Ser Lys Gly Glu Lys Ser Leu Pro Val Cys Lys Pro
                405                 410                 415

Val Cys Gly Leu Ser Thr His Thr Ser Gly Gly Arg Ile Ile Gly Gly
            420                 425                 430

Gln Pro Ala Lys Pro Gly Asp Phe Pro Trp Gln Val Leu Leu Leu Gly
        435                 440                 445

Glu Thr Thr Ala Ala Gly Ala Leu Ile His Asp Asp Trp Val Leu Thr
    450                 455                 460

Ala Ala His Ala Val Tyr Gly Lys Thr Glu Ala Met Ser Ser Leu Asp
465                 470                 475                 480

Ile Arg Met Gly Ile Leu Lys Arg Leu Ser Leu Ile Tyr Thr Gln Ala
                485                 490                 495
```

```
Trp Pro Glu Ala Val Phe Ile His Glu Gly Tyr Thr His Gly Ala Gly
            500                 505                 510

Phe Asp Asn Asp Ile Ala Leu Ile Lys Leu Lys Asn Lys Val Thr Ile
        515                 520                 525

Asn Arg Asn Ile Met Pro Ile Cys Leu Pro Arg Lys Glu Ala Ala Ser
    530                 535                 540

Leu Met Lys Thr Asp Phe Val Gly Thr Val Ala Gly Trp Gly Leu Thr
545                 550                 555                 560

Gln Lys Gly Phe Leu Ala Arg Asn Leu Met Phe Val Asp Ile Pro Ile
                565                 570                 575

Val Asp His Gln Lys Cys Ala Thr Ala Tyr Thr Lys Gln Pro Tyr Pro
            580                 585                 590

Gly Ala Lys Val Thr Val Asn Met Leu Cys Ala Gly Leu Asp Arg Gly
        595                 600                 605

Gly Lys Asp Ser Cys Arg Gly Asp Ser Gly Gly Ala Leu Val Phe Leu
    610                 615                 620

Asp Asn Glu Thr Gln Arg Trp Phe Val Gly Gly Ile Val Ser Trp Gly
625                 630                 635                 640

Ser Ile Asn Cys Gly Gly Ser Glu Gln Tyr Gly Val Tyr Thr Lys Val
                645                 650                 655

Thr Asn Tyr Ile Pro Trp Ile Glu Asn Ile Ile Asn Asn Phe
            660                 665                 670


<210> SEQ ID NO 7
<211> LENGTH: 136
<212> TYPE: PRT
<213> ORGANISM: Artificial sequence
<220> FEATURE:
<223> OTHER INFORMATION: Synthetic

<400> SEQUENCE: 7

Met Arg Leu Leu Thr Leu Leu Gly Leu Leu Cys Gly Ser Val Ala Thr
1               5                   10                  15

Pro Leu Gly Pro Lys Trp Pro Glu Pro Val Phe Gly Arg Leu Ala Ser
            20                  25                  30

Pro Gly Phe Pro Gly Glu Tyr Ala Asn Asp Gln Glu Arg Arg Trp Thr
        35                  40                  45

Leu Thr Ala Pro Pro Gly Tyr Arg Leu Arg Leu Tyr Phe Thr His Phe
    50                  55                  60

Asp Leu Glu Leu Ser His Leu Cys Glu Tyr Asp Phe Val Lys Leu Ser
65                  70                  75                  80

Ser Gly Ala Lys Val Leu Ala Thr Leu Cys Gly Gln Glu Ser Thr Asp
                85                  90                  95

Thr Glu Arg Ala Pro Gly Lys Asp Thr Phe Tyr Ser Leu Gly Ser Ser
            100                 105                 110

Leu Asp Ile Thr Phe Arg Ser Asp Tyr Ser Asn Glu Lys Pro Phe Thr
        115                 120                 125

Gly Phe Glu Ala Phe Tyr Ala Ala
    130                 135


<210> SEQ ID NO 8
<211> LENGTH: 181
<212> TYPE: PRT
<213> ORGANISM: Artificial sequence
<220> FEATURE:
<223> OTHER INFORMATION: Synthetic

<400> SEQUENCE: 8
```

```
Met Arg Leu Leu Thr Leu Leu Gly Leu Leu Cys Gly Ser Val Ala Thr
1               5                   10                  15

Pro Leu Gly Pro Lys Trp Pro Glu Pro Val Phe Gly Arg Leu Ala Ser
            20                  25                  30

Pro Gly Phe Pro Gly Glu Tyr Ala Asn Asp Gln Glu Arg Arg Trp Thr
        35                  40                  45

Leu Thr Ala Pro Pro Gly Tyr Arg Leu Arg Leu Tyr Phe Thr His Phe
    50                  55                  60

Asp Leu Glu Leu Ser His Leu Cys Glu Tyr Asp Phe Val Lys Leu Ser
65                  70                  75                  80

Ser Gly Ala Lys Val Leu Ala Thr Leu Cys Gly Gln Glu Ser Thr Asp
                85                  90                  95

Thr Glu Arg Ala Pro Gly Lys Asp Thr Phe Tyr Ser Leu Gly Ser Ser
            100                 105                 110

Leu Asp Ile Thr Phe Arg Ser Asp Tyr Ser Asn Glu Lys Pro Phe Thr
        115                 120                 125

Gly Phe Glu Ala Phe Tyr Ala Ala Glu Asp Ile Asp Glu Cys Gln Val
    130                 135                 140

Ala Pro Gly Glu Ala Pro Thr Cys Asp His His Cys His Asn His Leu
145                 150                 155                 160

Gly Gly Phe Tyr Cys Ser Cys Arg Ala Gly Tyr Val Leu His Arg Asn
                165                 170                 175

Lys Arg Thr Cys Ser
            180


<210> SEQ ID NO 9
<211> LENGTH: 277
<212> TYPE: PRT
<213> ORGANISM: Artificial sequence
<220> FEATURE:
<223> OTHER INFORMATION: Synthetic

<400> SEQUENCE: 9

Thr Pro Leu Gly Pro Lys Trp Pro Glu Pro Val Phe Gly Arg Leu Ala
1               5                   10                  15

Ser Pro Gly Phe Pro Gly Glu Tyr Ala Asn Asp Gln Glu Arg Arg Trp
            20                  25                  30

Thr Leu Thr Ala Pro Pro Gly Tyr Arg Leu Arg Leu Tyr Phe Thr His
        35                  40                  45

Phe Asp Leu Glu Leu Ser His Leu Cys Glu Tyr Asp Phe Val Lys Leu
    50                  55                  60

Ser Ser Gly Ala Lys Val Leu Ala Thr Leu Cys Gly Gln Glu Ser Thr
65                  70                  75                  80

Asp Thr Glu Arg Ala Pro Gly Lys Asp Thr Phe Tyr Ser Leu Gly Ser
                85                  90                  95

Ser Leu Asp Ile Thr Phe Arg Ser Asp Tyr Ser Asn Glu Lys Pro Phe
            100                 105                 110

Thr Gly Phe Glu Ala Phe Tyr Ala Ala Glu Asp Ile Asp Glu Cys Gln
        115                 120                 125

Val Ala Pro Gly Glu Ala Pro Thr Cys Asp His His Cys His Asn His
    130                 135                 140

Leu Gly Gly Phe Tyr Cys Ser Cys Arg Ala Gly Tyr Val Leu His Arg
145                 150                 155                 160

Asn Lys Arg Thr Cys Ser Ala Leu Cys Ser Gly Gln Val Phe Thr Gln
                165                 170                 175
```

```
Arg Ser Gly Glu Leu Ser Ser Pro Glu Tyr Pro Arg Pro Tyr Pro Lys
            180                 185                 190

Leu Ser Ser Cys Thr Tyr Ser Ile Ser Leu Glu Glu Gly Phe Ser Val
        195                 200                 205

Ile Leu Asp Phe Val Glu Ser Phe Asp Val Glu Thr His Pro Glu Thr
    210                 215                 220

Leu Cys Pro Tyr Asp Phe Leu Lys Ile Gln Thr Asp Arg Glu Glu His
225                 230                 235                 240

Gly Pro Phe Cys Gly Lys Thr Leu Pro His Arg Ile Glu Thr Lys Ser
                245                 250                 255

Asn Thr Val Thr Ile Thr Phe Val Thr Asp Glu Ser Gly Asp His Thr
            260                 265                 270

Gly Trp Lys Ile His
        275


<210> SEQ ID NO 10
<211> LENGTH: 41
<212> TYPE: PRT
<213> ORGANISM: Artificial sequence
<220> FEATURE:
<223> OTHER INFORMATION: Synthetic

<400> SEQUENCE: 10

Glu Asp Ile Asp Glu Cys Gln Val Ala Pro Gly Glu Ala Pro Thr Cys
1               5                   10                  15

Asp His His Cys His Asn His Leu Gly Gly Phe Tyr Cys Ser Cys Arg
            20                  25                  30

Ala Gly Tyr Val Leu His Arg Asn Lys
        35                  40


<210> SEQ ID NO 11
<211> LENGTH: 394
<212> TYPE: PRT
<213> ORGANISM: Artificial sequence
<220> FEATURE:
<223> OTHER INFORMATION: Synthetic

<400> SEQUENCE: 11

Tyr Thr Ser Thr Ala Gln Pro Cys Pro Tyr Pro Met Ala Pro Pro Asn
1               5                   10                  15

Gly His Val Ser Pro Val Gln Ala Lys Tyr Ile Leu Lys Asp Ser Phe
            20                  25                  30

Ser Ile Phe Cys Glu Thr Gly Tyr Glu Leu Leu Gln Gly His Leu Pro
        35                  40                  45

Leu Lys Ser Phe Thr Ala Val Cys Gln Lys Asp Gly Ser Trp Asp Arg
    50                  55                  60

Pro Met Pro Ala Cys Ser Ile Val Asp Cys Gly Pro Pro Asp Asp Leu
65                  70                  75                  80

Pro Ser Gly Arg Val Glu Tyr Ile Thr Gly Pro Gly Val Thr Thr Tyr
                85                  90                  95

Lys Ala Val Ile Gln Tyr Ser Cys Glu Glu Thr Phe Tyr Thr Met Lys
            100                 105                 110

Val Asn Asp Gly Lys Tyr Val Cys Glu Ala Asp Gly Phe Trp Thr Ser
        115                 120                 125

Ser Lys Gly Glu Lys Ser Leu Pro Val Cys Glu Pro Val Cys Gly Leu
    130                 135                 140

Ser Ala Arg Thr Thr Gly Gly Arg Ile Tyr Gly Gly Gln Lys Ala Lys
```

```
145                 150                 155                 160

Pro Gly Asp Phe Pro Trp Gln Val Leu Ile Leu Gly Gly Thr Thr Ala
                165                 170                 175

Ala Gly Ala Leu Leu Tyr Asp Asn Trp Val Leu Thr Ala Ala His Ala
            180                 185                 190

Val Tyr Glu Gln Lys His Asp Ala Ser Ala Leu Asp Ile Arg Met Gly
        195                 200                 205

Thr Leu Lys Arg Leu Ser Pro His Tyr Thr Gln Ala Trp Ser Glu Ala
    210                 215                 220

Val Phe Ile His Glu Gly Tyr Thr His Asp Ala Gly Phe Asp Asn Asp
225                 230                 235                 240

Ile Ala Leu Ile Lys Leu Asn Asn Lys Val Val Ile Asn Ser Asn Ile
                245                 250                 255

Thr Pro Ile Cys Leu Pro Arg Lys Glu Ala Glu Ser Phe Met Arg Thr
            260                 265                 270

Asp Asp Ile Gly Thr Ala Ser Gly Trp Gly Leu Thr Gln Arg Gly Phe
        275                 280                 285

Leu Ala Arg Asn Leu Met Tyr Val Asp Ile Pro Ile Val Asp His Gln
    290                 295                 300

Lys Cys Thr Ala Ala Tyr Glu Lys Pro Pro Tyr Pro Arg Gly Ser Val
305                 310                 315                 320

Thr Ala Asn Met Leu Cys Ala Gly Leu Glu Ser Gly Gly Lys Asp Ser
                325                 330                 335

Cys Arg Gly Asp Ser Gly Gly Ala Leu Val Phe Leu Asp Ser Glu Thr
            340                 345                 350

Glu Arg Trp Phe Val Gly Gly Ile Val Ser Trp Gly Ser Met Asn Cys
        355                 360                 365

Gly Glu Ala Gly Gln Tyr Gly Val Tyr Thr Lys Val Ile Asn Tyr Ile
    370                 375                 380

Pro Trp Ile Glu Asn Ile Ile Ser Asp Phe
385                 390


<210> SEQ ID NO 12
<211> LENGTH: 152
<212> TYPE: PRT
<213> ORGANISM: Artificial sequence
<220> FEATURE:
<223> OTHER INFORMATION: Synthetic

<400> SEQUENCE: 12

Tyr Thr Ser Thr Ala Gln Pro Cys Pro Tyr Pro Met Ala Pro Pro Asn
1               5                   10                  15

Gly His Val Ser Pro Val Gln Ala Lys Tyr Ile Leu Lys Asp Ser Phe
            20                  25                  30

Ser Ile Phe Cys Glu Thr Gly Tyr Glu Leu Leu Gln Gly His Leu Pro
        35                  40                  45

Leu Lys Ser Phe Thr Ala Val Cys Gln Lys Asp Gly Ser Trp Asp Arg
    50                  55                  60

Pro Met Pro Ala Cys Ser Ile Val Asp Cys Gly Pro Pro Asp Asp Leu
65                  70                  75                  80

Pro Ser Gly Arg Val Glu Tyr Ile Thr Gly Pro Gly Val Thr Thr Tyr
                85                  90                  95

Lys Ala Val Ile Gln Tyr Ser Cys Glu Glu Thr Phe Tyr Thr Met Lys
            100                 105                 110

Val Asn Asp Gly Lys Tyr Val Cys Glu Ala Asp Gly Phe Trp Thr Ser
```

```
        115                 120                 125

Ser Lys Gly Glu Lys Ser Leu Pro Val Cys Glu Pro Val Cys Gly Leu
    130                 135                 140

Ser Ala Arg Thr Thr Gly Gly Arg
145                 150


<210> SEQ ID NO 13
<211> LENGTH: 70
<212> TYPE: PRT
<213> ORGANISM: Artificial sequence
<220> FEATURE:
<223> OTHER INFORMATION: Synthetic

<400> SEQUENCE: 13

Tyr Thr Ser Thr Ala Gln Pro Cys Pro Tyr Pro Met Ala Pro Pro Asn
1               5                   10                  15

Gly His Val Ser Pro Val Gln Ala Lys Tyr Ile Leu Lys Asp Ser Phe
            20                  25                  30

Ser Ile Phe Cys Glu Thr Gly Tyr Glu Leu Leu Gln Gly His Leu Pro
        35                  40                  45

Leu Lys Ser Phe Thr Ala Val Cys Gln Lys Asp Gly Ser Trp Asp Arg
    50                  55                  60

Pro Met Pro Ala Cys Ser
65                  70


<210> SEQ ID NO 14
<211> LENGTH: 324
<212> TYPE: PRT
<213> ORGANISM: Artificial sequence
<220> FEATURE:
<223> OTHER INFORMATION: Synthetic

<400> SEQUENCE: 14

Ile Val Asp Cys Gly Pro Pro Asp Asp Leu Pro Ser Gly Arg Val Glu
1               5                   10                  15

Tyr Ile Thr Gly Pro Gly Val Thr Thr Tyr Lys Ala Val Ile Gln Tyr
            20                  25                  30

Ser Cys Glu Glu Thr Phe Tyr Thr Met Lys Val Asn Asp Gly Lys Tyr
        35                  40                  45

Val Cys Glu Ala Asp Gly Phe Trp Thr Ser Ser Lys Gly Glu Lys Ser
    50                  55                  60

Leu Pro Val Cys Glu Pro Val Cys Gly Leu Ser Ala Arg Thr Thr Gly
65                  70                  75                  80

Gly Arg Ile Tyr Gly Gly Gln Lys Ala Lys Pro Gly Asp Phe Pro Trp
                85                  90                  95

Gln Val Leu Ile Leu Gly Gly Thr Thr Ala Ala Gly Ala Leu Leu Tyr
            100                 105                 110

Asp Asn Trp Val Leu Thr Ala Ala His Ala Val Tyr Glu Gln Lys His
        115                 120                 125

Asp Ala Ser Ala Leu Asp Ile Arg Met Gly Thr Leu Lys Arg Leu Ser
    130                 135                 140

Pro His Tyr Thr Gln Ala Trp Ser Glu Ala Val Phe Ile His Glu Gly
145                 150                 155                 160

Tyr Thr His Asp Ala Gly Phe Asp Asn Asp Ile Ala Leu Ile Lys Leu
                165                 170                 175

Asn Asn Lys Val Val Ile Asn Ser Asn Ile Thr Pro Ile Cys Leu Pro
            180                 185                 190
```

```
Arg Lys Glu Ala Glu Ser Phe Met Arg Thr Asp Asp Ile Gly Thr Ala
        195                 200                 205

Ser Gly Trp Gly Leu Thr Gln Arg Gly Phe Leu Ala Arg Asn Leu Met
    210                 215                 220

Tyr Val Asp Ile Pro Ile Val Asp His Gln Lys Cys Thr Ala Ala Tyr
225                 230                 235                 240

Glu Lys Pro Pro Tyr Pro Arg Gly Ser Val Thr Ala Asn Met Leu Cys
                245                 250                 255

Ala Gly Leu Glu Ser Gly Gly Lys Asp Ser Cys Arg Gly Asp Ser Gly
            260                 265                 270

Gly Ala Leu Val Phe Leu Asp Ser Glu Thr Glu Arg Trp Phe Val Gly
        275                 280                 285

Gly Ile Val Ser Trp Gly Ser Met Asn Cys Gly Glu Ala Gly Gln Tyr
    290                 295                 300

Gly Val Tyr Thr Lys Val Ile Asn Tyr Ile Pro Trp Ile Glu Asn Ile
305                 310                 315                 320

Ile Ser Asp Phe


<210> SEQ ID NO 15
<211> LENGTH: 82
<212> TYPE: PRT
<213> ORGANISM: Artificial sequence
<220> FEATURE:
<223> OTHER INFORMATION: Synthetic

<400> SEQUENCE: 15

Ile Val Asp Cys Gly Pro Pro Asp Asp Leu Pro Ser Gly Arg Val Glu
1               5                   10                  15

Tyr Ile Thr Gly Pro Gly Val Thr Thr Tyr Lys Ala Val Ile Gln Tyr
            20                  25                  30

Ser Cys Glu Glu Thr Phe Tyr Thr Met Lys Val Asn Asp Gly Lys Tyr
        35                  40                  45

Val Cys Glu Ala Asp Gly Phe Trp Thr Ser Ser Lys Gly Glu Lys Ser
    50                  55                  60

Leu Pro Val Cys Glu Pro Val Cys Gly Leu Ser Ala Arg Thr Thr Gly
65                  70                  75                  80

Gly Arg


<210> SEQ ID NO 16
<211> LENGTH: 242
<212> TYPE: PRT
<213> ORGANISM: Artificial sequence
<220> FEATURE:
<223> OTHER INFORMATION: Synthetic

<400> SEQUENCE: 16

Ile Tyr Gly Gly Gln Lys Ala Lys Pro Gly Asp Phe Pro Trp Gln Val
1               5                   10                  15

Leu Ile Leu Gly Gly Thr Thr Ala Ala Gly Ala Leu Leu Tyr Asp Asn
            20                  25                  30

Trp Val Leu Thr Ala Ala His Ala Val Tyr Glu Gln Lys His Asp Ala
        35                  40                  45

Ser Ala Leu Asp Ile Arg Met Gly Thr Leu Lys Arg Leu Ser Pro His
    50                  55                  60

Tyr Thr Gln Ala Trp Ser Glu Ala Val Phe Ile His Glu Gly Tyr Thr
65                  70                  75                  80

His Asp Ala Gly Phe Asp Asn Asp Ile Ala Leu Ile Lys Leu Asn Asn
```

```
                85                  90                  95

Lys Val Val Ile Asn Ser Asn Ile Thr Pro Ile Cys Leu Pro Arg Lys
            100                 105                 110

Glu Ala Glu Ser Phe Met Arg Thr Asp Asp Ile Gly Thr Ala Ser Gly
        115                 120                 125

Trp Gly Leu Thr Gln Arg Gly Phe Leu Ala Arg Asn Leu Met Tyr Val
    130                 135                 140

Asp Ile Pro Ile Val Asp His Gln Lys Cys Thr Ala Ala Tyr Glu Lys
145                 150                 155                 160

Pro Pro Tyr Pro Arg Gly Ser Val Thr Ala Asn Met Leu Cys Ala Gly
                165                 170                 175

Leu Glu Ser Gly Gly Lys Asp Ser Cys Arg Gly Asp Ser Gly Gly Ala
            180                 185                 190

Leu Val Phe Leu Asp Ser Glu Thr Glu Arg Trp Phe Val Gly Gly Ile
        195                 200                 205

Val Ser Trp Gly Ser Met Asn Cys Gly Glu Ala Gly Gln Tyr Gly Val
    210                 215                 220

Tyr Thr Lys Val Ile Asn Tyr Ile Pro Trp Ile Glu Asn Ile Ile Ser
225                 230                 235                 240

Asp Phe


<210> SEQ ID NO 17
<211> LENGTH: 16
<212> TYPE: PRT
<213> ORGANISM: Artificial sequence
<220> FEATURE:
<223> OTHER INFORMATION: Synthetic

<400> SEQUENCE: 17

Gly Lys Asp Ser Cys Arg Gly Asp Ala Gly Gly Ala Leu Val Phe Leu
1               5                   10                  15


<210> SEQ ID NO 18
<211> LENGTH: 118
<212> TYPE: PRT
<213> ORGANISM: Artificial sequence
<220> FEATURE:
<223> OTHER INFORMATION: Synthetic

<400> SEQUENCE: 18

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Arg Gly
            20                  25                  30

Lys Met Gly Val Ser Trp Ile Arg Gln Pro Pro Gly Lys Ala Leu Glu
        35                  40                  45

Trp Leu Ala His Ile Phe Ser Ser Asp Glu Lys Ser Tyr Arg Thr Ser
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile Arg Ala Gly Gly Ile Asp Tyr Trp Gly Gln Gly Thr
            100                 105                 110

Leu Val Thr Val Ser Ser
        115
```

<210> SEQ ID NO 19
<211> LENGTH: 354
<212> TYPE: DNA
<213> ORGANISM: Artificial sequence
<220> FEATURE:
<223> OTHER INFORMATION: Synthetic

<400> SEQUENCE: 19
caggtcacct tgaaggagtc tggtcctgtg ctggtgaaac ccacagagac cctcacgctg 60
acctgcaccg tctctgggtt ctcactcagc aggggtaaaa tgggtgtgag ctggatccgt 120
cagcccccag ggaaggccct ggagtggctt gcacacattt tttcgagtga cgaaaaatcc 180
tacaggacat cgctgaagag caggctcacc atctccaagg acacctccaa aaaccaggtg 240
gtccttacaa tgaccaacat ggaccctgtg gacacagcca cgtattactg tgcacggata 300
cgacgtggag gaattgacta ctggggccag ggaaccctgg tcactgtctc ctca 354

<210> SEQ ID NO 20
<211> LENGTH: 118
<212> TYPE: PRT
<213> ORGANISM: Artificial sequence
<220> FEATURE:
<223> OTHER INFORMATION: Synthetic

<400> SEQUENCE: 20

Gln Val Thr Leu Lys Glu Ser Gly Pro Val Leu Val Lys Pro Thr Glu
1 5 10 15

Thr Leu Thr Leu Thr Cys Thr Val Ser Gly Phe Ser Leu Ser Arg Gly
20 25 30

Lys Met Gly Val Ser Trp Ile Arg Gln Pro Pro Gly Lys Ala Leu Glu
35 40 45

Trp Leu Ala His Ile Phe Ser Ser Asp Glu Lys Ser Tyr Arg Thr Ser
50 55 60

Leu Lys Ser Arg Leu Thr Ile Ser Lys Asp Thr Ser Lys Asn Gln Val
65 70 75 80

Val Leu Thr Met Thr Asn Met Asp Pro Val Asp Thr Ala Thr Tyr Tyr
85 90 95

Cys Ala Arg Ile Arg Arg Gly Gly Ile Asp Tyr Trp Gly Gln Gly Thr
100 105 110

Leu Val Thr Val Ser Ser
115

<210> SEQ ID NO 21
<211> LENGTH: 121
<212> TYPE: PRT
<213> ORGANISM: Artificial sequence
<220> FEATURE:
<223> OTHER INFORMATION: Synthetic

<400> SEQUENCE: 21

Gln Val Gln Leu Gln Gln Ser Gly Pro Gly Leu Val Lys Pro Ser Gln
1 5 10 15

Thr Leu Ser Leu Thr Cys Ala Ile Ser Gly Asp Ser Val Ser Ser Thr
20 25 30

Ser Ala Ala Trp Asn Trp Ile Arg Gln Ser Pro Ser Arg Gly Leu Glu
35 40 45

Trp Leu Gly Arg Thr Tyr Tyr Arg Ser Lys Trp Tyr Asn Asp Tyr Ala
50 55 60

Val Ser Val Lys Ser Arg Ile Thr Ile Asn Pro Asp Thr Ser Lys Asn
65 70 75 80

Gln Phe Ser Leu Gln Leu Asn Ser Val Thr Pro Glu Asp Thr Ala Val
85 90 95

Tyr Tyr Cys Ala Arg Asp Pro Phe Gly Val Pro Phe Asp Ile Trp Gly
100 105 110

Gln Gly Thr Met Val Thr Val Ser Ser
115 120

<210> SEQ ID NO 22
<211> LENGTH: 107
<212> TYPE: PRT
<213> ORGANISM: Artificial sequence
<220> FEATURE:
<223> OTHER INFORMATION: Synthetic

<400> SEQUENCE: 22

Gln Pro Val Leu Thr Gln Pro Pro Ser Val Ser Val Ser Pro Gly Gln
1 5 10 15

Thr Ala Ser Ile Thr Cys Ser Gly Asp Lys Leu Gly Asp Lys Phe Ala
20 25 30

Tyr Trp Tyr Gln Gln Lys Pro Gly His Ser Pro Val Leu Val Ile Tyr
35 40 45

Gln Asp Asn Lys Arg Pro Ser Gly Ile Pro Gly Arg Phe Ser Gly Ser
50 55 60

Asn Ser Gly Asn Thr Ala Thr Leu Thr Ile Ser Gly Thr Gln Ala Met
65 70 75 80

Asp Glu Ala Asp Tyr Tyr Cys Gln Ala Trp Asp Ser Ser Thr Ala Val
85 90 95

Phe Gly Thr Gly Thr Lys Val Thr Val Leu Ala
100 105

<210> SEQ ID NO 23
<211> LENGTH: 318
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (246)..(246)
<223> OTHER INFORMATION: n is a, c, g, or t

<400> SEQUENCE: 23
cagccagtgc tgactcagcc cccctcactg tccgtgtccc caggacagac agccagcatc 60
acctgctctg gagagaaatt gggggataaa tatgcttact ggtatcagca gaagccaggc 120
cagtcccctg tgttggtcat gtatcaagat aaacagcggc cctcagggat ccctgagcga 180
ttctctggct ccaactctgg gaacacagcc actctgacca tcagcgggac ccaggctatg 240
gatgangctg actattactg tcaggcgtgg gacagcagca ctgcggtatt cggcggaggg 300
accaagctga ccgtccta 318

<210> SEQ ID NO 24
<211> LENGTH: 106
<212> TYPE: PRT
<213> ORGANISM: Artificial sequence
<220> FEATURE:
<223> OTHER INFORMATION: Synthetic

<400> SEQUENCE: 24

Gln Pro Val Leu Thr Gln Pro Pro Ser Leu Ser Val Ser Pro Gly Gln
1 5 10 15

-continued

```
Thr Ala Ser Ile Thr Cys Ser Gly Glu Lys Leu Gly Asp Lys Tyr Ala
            20                  25                  30

Tyr Trp Tyr Gln Gln Lys Pro Gly Gln Ser Pro Val Leu Val Met Tyr
        35                  40                  45

Gln Asp Lys Gln Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Ala Val
                85                  90                  95

Phe Gly Gly Gly Thr Lys Leu Thr Val Leu
            100                 105


<210> SEQ ID NO 25
<211> LENGTH: 120
<212> TYPE: PRT
<213> ORGANISM: Artificial sequence
<220> FEATURE:
<223> OTHER INFORMATION: Synthetic

<400> SEQUENCE: 25

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Asn Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Val Ser Arg Val Glu Ala Gly
65                  70                  75                  80

Asp Glu Ala Asp Tyr Tyr Cys Gln Val Trp Asp Thr Thr Thr Asp His
                85                  90                  95

Val Val Phe Gly Gly Gly Thr Lys Leu Thr Val Leu Ala Ala Ala Gly
            100                 105                 110

Ser Glu Gln Lys Leu Ile Ser Glu
        115                 120


<210> SEQ ID NO 26
<211> LENGTH: 324
<212> TYPE: DNA
<213> ORGANISM: Artificial sequence
<220> FEATURE:
<223> OTHER INFORMATION: Synthetic

<400> SEQUENCE: 26

tcctatgagc tgatacagcc accctcggtg tcagtggccc caggacagac ggccaccatt      60

acctgtgcgg gagacaacct tgggaagaaa cgtgtgcact ggtaccagca gaggccaggc     120

caggcccctg tgttggtcat ctatgatgat agcgaccggc cctcagggat ccctgaccga     180

ttctctgcct ccaactctgg gaacacggcc accctgacca tcactagggg cgaagccggg     240

gatgaggccg actattattg tcaggtgtgg gacattgcta ctgatcatgt ggtcttcggc     300

ggagggacca agctcaccgt ccta                                            324


<210> SEQ ID NO 27
<211> LENGTH: 120
<212> TYPE: PRT
```

-continued

```
<213> ORGANISM: Artificial sequence
<220> FEATURE:
<223> OTHER INFORMATION: Synthetic

<400> SEQUENCE: 27

Ser Tyr Glu Leu Ile Gln Pro Pro Ser Val Ser Val Ala Pro Gly Gln
1               5                   10                  15

Thr Ala Thr Ile Thr Cys Ala Gly Asp Asn Leu Gly Lys Lys Arg Val
            20                  25                  30

His Trp Tyr Gln Gln Arg Pro Gly Gln Ala Pro Val Leu Val Ile Tyr
        35                  40                  45

Asp Asp Ser Asp Arg Pro Ser Gly Ile Pro Asp Arg Phe Ser Ala Ser
    50                  55                  60

Asn Ser Gly Asn Thr Ala Thr Leu Thr Ile Thr Arg Gly Glu Ala Gly
65                  70                  75                  80

Asp Glu Ala Asp Tyr Tyr Cys Gln Val Trp Asp Ile Ala Thr Asp His
                85                  90                  95

Val Val Phe Gly Gly Gly Thr Lys Leu Thr Val Leu Ala Ala Ala Gly
            100                 105                 110

Ser Glu Gln Lys Leu Ile Ser Glu
        115                 120


<210> SEQ ID NO 28
<211> LENGTH: 5
<212> TYPE: PRT
<213> ORGANISM: Artificial sequence
<220> FEATURE:
<223> OTHER INFORMATION: Synthetic

<400> SEQUENCE: 28

Arg Gly Lys Met Gly
1               5


<210> SEQ ID NO 29
<211> LENGTH: 5
<212> TYPE: PRT
<213> ORGANISM: Artificial sequence
<220> FEATURE:
<223> OTHER INFORMATION: Synthetic

<400> SEQUENCE: 29

Ser Thr Ser Ala Ala
1               5


<210> SEQ ID NO 30
<211> LENGTH: 7
<212> TYPE: PRT
<213> ORGANISM: Artificial sequence
<220> FEATURE:
<223> OTHER INFORMATION: Synthetic

<400> SEQUENCE: 30

Gly Phe Ser Leu Ser Arg Gly
1               5


<210> SEQ ID NO 31
<211> LENGTH: 7
<212> TYPE: PRT
<213> ORGANISM: Artificial sequence
<220> FEATURE:
<223> OTHER INFORMATION: Synthetic

<400> SEQUENCE: 31
```

-continued

```
Gly Asp Ser Val Ser Ser Thr
1               5


<210> SEQ ID NO 32
<211> LENGTH: 16
<212> TYPE: PRT
<213> ORGANISM: Artificial sequence
<220> FEATURE:
<223> OTHER INFORMATION: Synthetic

<400> SEQUENCE: 32

Leu Ala His Ile Phe Ser Ser Asp Glu Lys Ser Tyr Arg Thr Ser Leu
1               5                   10                  15


<210> SEQ ID NO 33
<211> LENGTH: 16
<212> TYPE: PRT
<213> ORGANISM: Artificial sequence
<220> FEATURE:
<223> OTHER INFORMATION: Synthetic

<400> SEQUENCE: 33

Leu Gly Arg Thr Tyr Tyr Arg Ser Lys Trp Tyr Asn Asp Tyr Ala Val
1               5                   10                  15


<210> SEQ ID NO 34
<211> LENGTH: 5
<212> TYPE: PRT
<213> ORGANISM: Artificial sequence
<220> FEATURE:
<223> OTHER INFORMATION: Synthetic

<400> SEQUENCE: 34

His Ile Phe Ser Ser
1               5


<210> SEQ ID NO 35
<211> LENGTH: 5
<212> TYPE: PRT
<213> ORGANISM: Artificial sequence
<220> FEATURE:
<223> OTHER INFORMATION: Synthetic

<400> SEQUENCE: 35

Arg Thr Tyr Tyr Arg
1               5


<210> SEQ ID NO 36
<211> LENGTH: 8
<212> TYPE: PRT
<213> ORGANISM: Artificial sequence
<220> FEATURE:
<223> OTHER INFORMATION: Synthetic

<400> SEQUENCE: 36

Tyr Tyr Cys Ala Arg Ile Arg Ala
1               5


<210> SEQ ID NO 37
<211> LENGTH: 8
<212> TYPE: PRT
<213> ORGANISM: Artificial sequence
<220> FEATURE:
<223> OTHER INFORMATION: Synthetic

<400> SEQUENCE: 37

Tyr Tyr Cys Ala Arg Ile Arg Arg
```

1 5

<210> SEQ ID NO 38
<211> LENGTH: 8
<212> TYPE: PRT
<213> ORGANISM: Artificial sequence
<220> FEATURE:
<223> OTHER INFORMATION: Synthetic

<400> SEQUENCE: 38

Ala Val Tyr Tyr Cys Ala Arg Asp
1 5

<210> SEQ ID NO 39
<211> LENGTH: 7
<212> TYPE: PRT
<213> ORGANISM: Artificial sequence
<220> FEATURE:
<223> OTHER INFORMATION: Synthetic

<400> SEQUENCE: 39

Tyr Tyr Cys Ala Arg Ile Arg
1 5

<210> SEQ ID NO 40
<211> LENGTH: 7
<212> TYPE: PRT
<213> ORGANISM: Artificial sequence
<220> FEATURE:
<223> OTHER INFORMATION: Synthetic

<400> SEQUENCE: 40

Ala Val Tyr Tyr Cys Ala Arg
1 5

<210> SEQ ID NO 41
<211> LENGTH: 11
<212> TYPE: PRT
<213> ORGANISM: Artificial sequence
<220> FEATURE:
<223> OTHER INFORMATION: Synthetic

<400> SEQUENCE: 41

Gly Asp Lys Leu Gly Asp Lys Phe Ala Tyr Trp
1 5 10

<210> SEQ ID NO 42
<211> LENGTH: 11
<212> TYPE: PRT
<213> ORGANISM: Artificial sequence
<220> FEATURE:
<223> OTHER INFORMATION: Synthetic

<400> SEQUENCE: 42

Gly Glu Lys Leu Gly Asp Lys Tyr Ala Tyr Trp
1 5 10

<210> SEQ ID NO 43
<211> LENGTH: 11
<212> TYPE: PRT
<213> ORGANISM: Artificial sequence
<220> FEATURE:
<223> OTHER INFORMATION: Synthetic

<400> SEQUENCE: 43

Gly Asn Asn Ile Gly Ser Lys Asn Val His Trp
1 5 10

<210> SEQ ID NO 44
<211> LENGTH: 11
<212> TYPE: PRT
<213> ORGANISM: Artificial sequence
<220> FEATURE:
<223> OTHER INFORMATION: Synthetic

<400> SEQUENCE: 44

Gly Asp Asn Leu Gly Lys Lys Arg Val His Trp
1 5 10

<210> SEQ ID NO 45
<211> LENGTH: 16
<212> TYPE: PRT
<213> ORGANISM: Artificial sequence
<220> FEATURE:
<223> OTHER INFORMATION: Synthetic

<400> SEQUENCE: 45

Ala Gly Asp Asn Leu Gly Lys Lys Arg Val His Trp Tyr Gln Gln Arg
1 5 10 15

<210> SEQ ID NO 46
<211> LENGTH: 7
<212> TYPE: PRT
<213> ORGANISM: Artificial sequence
<220> FEATURE:
<223> OTHER INFORMATION: Synthetic

<400> SEQUENCE: 46

Asp Asn Lys Arg Pro Ser Gly
1 5

<210> SEQ ID NO 47
<211> LENGTH: 7
<212> TYPE: PRT
<213> ORGANISM: Artificial sequence
<220> FEATURE:
<223> OTHER INFORMATION: Synthetic

<400> SEQUENCE: 47

Asp Lys Gln Arg Pro Ser Gly
1 5

<210> SEQ ID NO 48
<211> LENGTH: 11
<212> TYPE: PRT
<213> ORGANISM: Artificial sequence
<220> FEATURE:
<223> OTHER INFORMATION: Synthetic

<400> SEQUENCE: 48

Asp Lys Gln Arg Pro Ser Gly Ile Pro Glu Arg
1 5 10

<210> SEQ ID NO 49
<211> LENGTH: 7
<212> TYPE: PRT
<213> ORGANISM: Artificial sequence
<220> FEATURE:
<223> OTHER INFORMATION: Synthetic

<400> SEQUENCE: 49

Asp Ser Asp Arg Pro Ser Gly
1 5

<210> SEQ ID NO 50
<211> LENGTH: 14
<212> TYPE: PRT
<213> ORGANISM: Artificial sequence
<220> FEATURE:
<223> OTHER INFORMATION: Synthetic

<400> SEQUENCE: 50

Asp Ser Asp Arg Pro Ser Gly Ile Pro Asp Arg Phe Ser Ala
1 5 10

<210> SEQ ID NO 51
<211> LENGTH: 9
<212> TYPE: PRT
<213> ORGANISM: Artificial sequence
<220> FEATURE:
<223> OTHER INFORMATION: Synthetic

<400> SEQUENCE: 51

Ala Trp Asp Ser Ser Thr Ala Val Phe
1 5

<210> SEQ ID NO 52
<211> LENGTH: 16
<212> TYPE: PRT
<213> ORGANISM: Artificial sequence
<220> FEATURE:
<223> OTHER INFORMATION: Synthetic

<400> SEQUENCE: 52

Ala Trp Asp Ser Ser Thr Ala Val Phe Gly Gly Gly Thr Lys Leu Thr
1 5 10 15

<210> SEQ ID NO 53
<211> LENGTH: 9
<212> TYPE: PRT
<213> ORGANISM: Artificial sequence
<220> FEATURE:
<223> OTHER INFORMATION: Synthetic

<400> SEQUENCE: 53

Val Trp Asp Thr Thr Thr Asp His Val
1 5

<210> SEQ ID NO 54
<211> LENGTH: 9
<212> TYPE: PRT
<213> ORGANISM: Artificial sequence
<220> FEATURE:
<223> OTHER INFORMATION: Synthetic

<400> SEQUENCE: 54

Val Trp Asp Ile Ala Thr Asp His Val
1 5

<210> SEQ ID NO 55
<211> LENGTH: 268
<212> TYPE: PRT
<213> ORGANISM: Artificial sequence
<220> FEATURE:
<223> OTHER INFORMATION: Synthetic

<400> SEQUENCE: 55

Gln Val Thr Leu Lys Glu Ser Gly Pro Val Leu Val Lys Pro Thr Glu
1 5 10 15

Thr Leu Thr Leu Thr Cys Thr Val Ser Gly Phe Ser Leu Ser Arg Gly

```
            20                  25                  30

Lys Met Gly Val Ser Trp Ile Arg Gln Pro Pro Gly Lys Ala Leu Glu
        35                  40                  45

Trp Leu Ala His Ile Phe Ser Ser Asp Glu Lys Ser Tyr Arg Thr Ser
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile Arg Ala Gly Gly Ile Asp Tyr Trp Gly Gln Gly Thr
            100                 105                 110

Leu Val Thr Val Ser Ser Lys Leu Ser Gly Ser Ala Ser Ala Pro Lys
        115                 120                 125

Leu Glu Glu Gly Glu Phe Ser Glu Ala Arg Val Gln Pro Val Leu Thr
    130                 135                 140

Gln Pro Pro Ser Val Ser Val Ser Pro Gly Gln Thr Ala Ser Ile Thr
145                 150                 155                 160

Cys Ser Gly Asp Lys Leu Gly Asp Lys Phe Ala Tyr Trp Tyr Gln Gln
                165                 170                 175

Lys Pro Gly His Ser Pro Val Leu Val Ile Tyr Gln Asp Asn Lys Arg
            180                 185                 190

Pro Ser Gly Ile Pro Gly Arg Phe Ser Gly Ser Asn Ser Gly Asn Thr
        195                 200                 205

Ala Thr Leu Thr Ile Ser Gly Thr Gln Ala Met Asp Glu Ala Asp Tyr
    210                 215                 220

Tyr Cys Gln Ala Trp Asp Ser Ser Thr Ala Val Phe Gly Thr Gly Thr
225                 230                 235                 240

Lys Val Thr Val Leu Ala Ala Ala Gly Ser Glu Gln Lys Leu Ile Ser
                245                 250                 255

Glu Glu Asp Leu Asn Ser His His His His His His
            260                 265


<210> SEQ ID NO 56
<211> LENGTH: 271
<212> TYPE: PRT
<213> ORGANISM: Artificial sequence
<220> FEATURE:
<223> OTHER INFORMATION: Synthetic

<400> SEQUENCE: 56

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Asn Ala
            20                  25                  30

Arg Met Gly Val Ser Trp Ile Arg Gln Pro Pro Gly Lys Ala Leu Glu
        35                  40                  45

Trp Leu Ala His Ile Phe Ser Asn Asp Glu Lys Ser Tyr Ser Thr Ser
    50                  55                  60

Leu Lys Ser Arg Leu Thr Ile Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

Cys Ala Arg Met Ala Ile Leu Thr Ala Gly Gly Met Asp Val Trp Gly
            100                 105                 110

Gln Gly Thr Thr Val Thr Val Ser Ser Lys Leu Ser Gly Ser Ala Ser
```

```
        115                 120                 125

Ala Pro Lys Leu Glu Glu Gly Glu Phe Ser Glu Ala Arg Val Ser Tyr
    130                 135                 140

Val Leu Thr Gln Pro Pro Ser Val Ser Ala Ser Pro Gly Gln Thr Ala
145                 150                 155                 160

Ser Ile Thr Cys Ser Gly Asp Lys Leu Gly Asp Lys Tyr Val Ser Trp
                165                 170                 175

Tyr Gln Gln Lys Pro Gly Arg Ser Pro Val Leu Val Ile Tyr Arg Asp
            180                 185                 190

Thr Lys Arg Pro Ser Gly Ile Pro Glu Arg Phe Ser Gly Ser Asn Tyr
        195                 200                 205

Gly Asn Thr Ala Thr Leu Thr Ile Ser Gly Thr Gln Ala Val Asp Glu
    210                 215                 220

Ala Asp Tyr Tyr Cys Gln Ala Trp Asp Ser Gly Ser Gly Val Phe Gly
225                 230                 235                 240

Gly Gly Thr Lys Val Thr Val Leu Ala Ala Ala Gly Ser Glu Gln Lys
                245                 250                 255

Leu Ile Ser Glu Glu Asp Leu Asn Ser His His His His His His
            260                 265                 270


<210> SEQ ID NO 57
<211> LENGTH: 272
<212> TYPE: PRT
<213> ORGANISM: Artificial sequence
<220> FEATURE:
<223> OTHER INFORMATION: Synthetic

<400> SEQUENCE: 57

Gln Ile Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Asn Ala
            20                  25                  30

Arg Met Gly Val Ser Trp Ile Arg Gln Pro Pro Gly Lys Ala Leu Glu
        35                  40                  45

Trp Leu Ala His Ile Phe Ser Asn Asp Glu Lys Ser Tyr Ser Thr Ser
    50                  55                  60

Leu Lys Ser Arg Leu Thr Ile Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

Cys Ala Arg Met Arg Tyr Ser Ser Ser Leu Tyr Gly Met Asp Val Trp
            100                 105                 110

Gly Gln Gly Thr Arg Val Thr Val Ser Ser Lys Leu Ser Gly Ser Ala
        115                 120                 125

Ser Ala Pro Lys Leu Glu Glu Gly Glu Phe Ser Glu Ala Arg Val Ser
    130                 135                 140

Tyr Glu Leu Ile Gln Pro Pro Ser Val Ser Val Ser Pro Gly Gln Thr
145                 150                 155                 160

Ala Ser Ile Thr Cys Ser Gly Asp Lys Leu Gly Asp Lys Tyr Val Ser
                165                 170                 175

Trp Tyr Gln Gln Lys Pro Gly Arg Ser Pro Val Leu Val Ile Tyr Arg
            180                 185                 190

Asp Thr Lys Arg Pro Ser Gly Ile Pro Glu Arg Phe Ser Gly Ser Asn
        195                 200                 205

Ser Gly Asn Thr Ala Thr Leu Thr Ile Ser Gly Thr Gln Ala Met Asp
```

```
    210                 215                 220

Glu Ala Asp Tyr Tyr Cys Gln Ala Trp Asp Ser Ser Thr Val Val Phe
225                 230                 235                 240

Gly Gly Gly Thr Lys Leu Thr Val Leu Ala Ala Ala Gly Ser Glu Gln
                245                 250                 255

Lys Leu Ile Ser Glu Glu Asp Leu Asn Ser His His His His His His
            260                 265                 270


<210> SEQ ID NO 58
<211> LENGTH: 273
<212> TYPE: PRT
<213> ORGANISM: Artificial sequence
<220> FEATURE:
<223> OTHER INFORMATION: Synthetic

<400> SEQUENCE: 58

Glu Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Lys
            20                  25                  30

Arg Ala Ala Trp Asp Trp Ile Arg Gln Ser Pro Ser Arg Gly Leu Glu
        35                  40                  45

Trp Leu Gly Arg Thr Tyr Tyr Arg Ser Lys Trp Phe Asn Asp Tyr Ala
    50                  55                  60

Ile Ser Val Lys Ser Arg Ile Thr Ile Asn Ala Asp Thr Ser Arg Asn
65                  70                  75                  80

Gln Phe Ser Leu Gln Leu Asn Ser Val Thr Pro Glu Asp Thr Ala Val
                85                  90                  95

Tyr Tyr Cys Val Lys Ser Asn Ser Gly Thr Gly Ala Phe Asp Ser Trp
            100                 105                 110

Gly Gln Gly Thr Leu Val Thr Val Ser Ser Lys Leu Ser Gly Ser Ala
        115                 120                 125

Ser Ala Pro Lys Leu Glu Glu Gly Glu Phe Ser Glu Ala Arg Val Gln
    130                 135                 140

Pro Gly Leu Thr Gln Pro Pro Ser Val Ser Val Ser Pro Gly Gln Thr
145                 150                 155                 160

Ala Arg Ile Thr Cys Ser Arg Asp Lys Leu Gly Asp Lys Tyr Val Ser
                165                 170                 175

Trp Tyr Gln Gln Lys Pro Gly Gln Ser Pro Val Val Val Met Tyr Lys
            180                 185                 190

Asp Asn Lys Arg Pro Ser Gly Ile Pro Glu Arg Phe Ser Gly Ser Asn
        195                 200                 205

Ser Gly Asn Thr Ala Thr Leu Thr Ile Ser Gly Thr Gln Ala Met Asp
    210                 215                 220

Glu Ala Asp Tyr Tyr Cys Gln Ala Trp Asp Ser Ser Thr Ala Gly Val
225                 230                 235                 240

Phe Gly Gly Gly Thr Lys Leu Thr Val Leu Ala Ala Ala Gly Ser Glu
                245                 250                 255

Gln Lys Leu Ile Ser Glu Glu Asp Leu Asn Ser His His His His His
            260                 265                 270

His


<210> SEQ ID NO 59
<211> LENGTH: 273
<212> TYPE: PRT
<213> ORGANISM: Artificial sequence
```

<220> FEATURE:
<223> OTHER INFORMATION: Synthetic

<400> SEQUENCE: 59

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Thr
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Pro Phe Gly Val Pro Phe Asp Ile Trp Gly
            100                 105                 110

Gln Gly Thr Met Val Thr Val Ser Ser Lys Leu Ser Gly Ser Ala Ser
        115                 120                 125

Ala Pro Lys Leu Glu Glu Gly Glu Phe Ser Glu Ala Arg Val Ser Tyr
    130                 135                 140

Val Leu Thr Gln Pro Pro Ser Val Ser Val Ala Pro Gly Gln Thr Ala
145                 150                 155                 160

Arg Ile Thr Cys Gly Gly Asn Asn Ile Gly Ser Lys Asn Val His Trp
                165                 170                 175

Tyr Gln Gln Lys Pro Gly Gln Ala Pro Val Leu Val Val Tyr Asp Asp
            180                 185                 190

Ser Asp Arg Pro Ser Gly Ile Pro Glu Arg Phe Ser Gly Ser Asn Ser
        195                 200                 205

Gly Asn Thr Ala Thr Leu Thr Val Ser Arg Val Glu Ala Gly Asp Glu
    210                 215                 220

Ala Asp Tyr Tyr Cys Gln Val Trp Asp Thr Thr Thr Asp His Val Val
225                 230                 235                 240

Phe Gly Gly Gly Thr Lys Leu Thr Val Leu Ala Ala Ala Gly Ser Glu
                245                 250                 255

Gln Lys Leu Ile Ser Glu Glu Asp Leu Asn Ser His His His His His
            260                 265                 270

His
```

<210> SEQ ID NO 60
<211> LENGTH: 273
<212> TYPE: PRT
<213> ORGANISM: Artificial sequence
<220> FEATURE:
<223> OTHER INFORMATION: Synthetic

<400> SEQUENCE: 60

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60
```

Val Ser Val Lys Ser Arg Ile Thr Ile Asn Pro Asp Thr Ser Lys Asn
65 70 75 80

Gln Phe Ser Leu Gln Leu Asn Ser Val Thr Pro Glu Asp Thr Ala Val
85 90 95

Tyr Tyr Cys Ala Arg Asp Pro Phe Gly Val Pro Phe Asp Ile Trp Gly
100 105 110

Gln Gly Thr Met Val Thr Val Ser Ser Lys Leu Ser Gly Ser Ala Ser
115 120 125

Ala Pro Lys Leu Glu Glu Gly Glu Phe Ser Glu Ala Arg Val Ser Tyr
130 135 140

Val Leu Thr Gln Pro Pro Ser Val Ser Val Ala Pro Gly Gln Thr Ala
145 150 155 160

Arg Val Thr Cys Gly Gly Asn Asn Ile Arg Ser Lys Asn Val His Trp
165 170 175

Tyr Gln Gln Lys Pro Gly Gln Ala Pro Val Leu Val Val Tyr Asp Asp
180 185 190

Thr Asp Arg Pro Ser Gly Ile Pro Glu Arg Phe Ser Gly Ser Asn Ser
195 200 205

Gly Asn Thr Ala Thr Leu Thr Val Ser Arg Val Glu Ala Gly Asp Glu
210 215 220

Ala Asp Tyr Tyr Cys Gln Val Trp Asp Thr Thr Thr Asp His Val Val
225 230 235 240

Phe Gly Gly Gly Thr Lys Leu Thr Val Leu Ala Ala Ala Gly Ser Glu
245 250 255

Gln Lys Leu Ile Ser Glu Glu Asp Leu Asn Ser His His His His His
260 265 270

His

<210> SEQ ID NO 61
<211> LENGTH: 273
<212> TYPE: PRT
<213> ORGANISM: Artificial sequence
<220> FEATURE:
<223> OTHER INFORMATION: Synthetic

<400> SEQUENCE: 61

Gln Val Gln Leu Gln Gln Ser Gly Pro Gly Leu Val Lys Pro Ser Gln
1 5 10 15

Thr Leu Ser Leu Thr Cys Ala Ile Ser Gly Asp Ser Val Ser Ser Asn
20 25 30

Ser Ala Ala Trp Asn Trp Ile Arg Gln Ser Pro Ser Arg Gly Leu Glu
35 40 45

Trp Leu Gly Arg Thr Tyr Tyr Arg Ser Lys Trp Tyr Asn Asp Tyr Ala
50 55 60

Val Ser Val Lys Ser Arg Ile Thr Ile Asn Pro Asp Thr Ser Lys Asn
65 70 75 80

Gln Phe Ser Leu Gln Leu Asn Ser Val Thr Pro Glu Asp Thr Ala Val
85 90 95

Tyr Tyr Cys Ala Arg Asp Pro Phe Gly Val Pro Phe Asp Ile Trp Gly
100 105 110

Gln Gly Thr Met Val Thr Val Ser Ser Lys Leu Ser Gly Ser Ala Ser
115 120 125

Ala Pro Lys Leu Glu Glu Gly Glu Phe Ser Glu Ala Arg Val Ser Tyr
130 135 140

```
Glu Leu Thr Gln Leu Pro Ser Val Ser Val Ala Pro Gly Gln Thr Ala
145                 150                 155                 160

Arg Val Thr Cys Gly Gly Asn Asn Ile Arg Ser Lys Asn Val His Trp
                165                 170                 175

Tyr Gln Gln Lys Pro Gly Gln Ala Pro Val Leu Val Val Tyr Asp Asp
            180                 185                 190

Thr Asp Arg Pro Ser Gly Ile Pro Glu Arg Phe Ser Gly Ser Asn Ser
        195                 200                 205

Gly Asn Thr Ala Thr Leu Thr Val Ser Arg Val Glu Ala Gly Asp Glu
    210                 215                 220

Ala Asp Tyr Tyr Cys Gln Val Trp Asp Thr Thr Thr Asp His Val Val
225                 230                 235                 240

Phe Gly Gly Gly Thr Lys Val Thr Val Leu Ala Ala Ala Gly Ser Glu
                245                 250                 255

Gln Lys Leu Ile Ser Glu Glu Asp Leu Asn Ser His His His His His
            260                 265                 270

His
```

<210> SEQ ID NO 62
<211> LENGTH: 984
<212> TYPE: DNA
<213> ORGANISM: Homo sapiens

<400> SEQUENCE: 62

```
gcctccacca agggcccatc cgtcttcccc ctggcgccct gctccaggag cacctccgag     60

agcacagccg ccctgggctg cctggtcaag gactacttcc ccgaaccggt gacggtgtcg    120

tggaactcag gcgccctgac cagcggcgtg cacaccttcc cggctgtcct acagtcctca    180

ggactctact ccctcagcag cgtggtgacc gtgccctcca gcagcttggg cacgaagacc    240

tacacctgca acgtagatca caagcccagc aacaccaagg tggacaagag agttgagtcc    300

aaatatggtc ccccatgccc atcatgccca gcacctgagt tcctgggggg accatcagtc    360

ttcctgttcc ccccaaaacc caaggacact ctcatgatct cccggacccc tgaggtcacg    420

tgcgtggtgg tggacgtgag ccaggaagac cccgaggtcc agttcaactg gtacgtggat    480

ggcgtggagg tgcataatgc caagacaaag ccgcgggagg agcagttcaa cagcacgtac    540

cgtgtggtca gcgtcctcac cgtcctgcac caggactggc tgaacggcaa ggagtacaag    600

tgcaaggtct ccaacaaagg cctcccgtcc tccatcgaga aaaccatctc caaagccaaa    660

gggcagcccc gagagccaca ggtgtacacc ctgcccccat cccaggagga gatgaccaag    720

aaccaggtca gcctgacctg cctggtcaaa ggcttctacc ccagcgacat cgccgtggag    780

tgggagagca atgggcagcc ggagaacaac tacaagacca cgcctcccgt gctggactcc    840

gacggctcct tcttcctcta cagcaggcta accgtggaca agagcaggtg gcaggagggg    900

aatgtcttct catgctccgt gatgcatgag gctctgcaca accactacac acagaagagc    960

ctctccctgt ctctcgggaa atga                                           984
```

<210> SEQ ID NO 63
<211> LENGTH: 327
<212> TYPE: PRT
<213> ORGANISM: Homo sapiens

<400> SEQUENCE: 63

```
Ala Ser Thr Lys Gly Pro Ser Val Phe Pro Leu Ala Pro Cys Ser Arg
1               5                   10                  15
```

-continued

```
Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325


<210> SEQ ID NO 64
<211> LENGTH: 984
<212> TYPE: DNA
<213> ORGANISM: Artificial sequence
<220> FEATURE:
<223> OTHER INFORMATION: Synthetic

<400> SEQUENCE: 64

gcctccacca agggcccatc cgtcttcccc ctggcgccct gctccaggag cacctccgag      60

agcacagccg ccctgggctg cctggtcaag gactacttcc ccgaaccggt gacggtgtcg     120

tggaactcag gcgccctgac cagcggcgtg cacaccttcc cggctgtcct acagtcctca     180

ggactctact ccctcagcag cgtggtgacc gtgccctcca gcagcttggg cacgaagacc     240

tacacctgca acgtagatca caagcccagc aacaccaagg tggacaagag agttgagtcc     300
```

-continued

```
aaatatggtc ccccatgccc accatgccca gcacctgagt tcctgggggg accatcagtc    360

ttcctgttcc ccccaaaacc caaggacact ctcatgatct cccggacccc tgaggtcacg    420

tgcgtggtgg tggacgtgag ccaggaagac cccgaggtcc agttcaactg gtacgtggat    480

ggcgtggagg tgcataatgc caagacaaag ccgcgggagg agcagttcaa cagcacgtac    540

cgtgtggtca gcgtcctcac cgtcctgcac caggactggc tgaacggcaa ggagtacaag    600

tgcaaggtct ccaacaaagg cctcccgtcc tccatcgaga aaaccatctc caaagccaaa    660

gggcagcccc gagagccaca ggtgtacacc ctgcccccat cccaggagga gatgaccaag    720

aaccaggtca gcctgacctg cctggtcaaa ggcttctacc ccagcgacat cgccgtggag    780

tgggagagca atgggcagcc ggagaacaac tacaagacca cgcctcccgt gctggactcc    840

gacggctcct tcttcctcta cagcaggcta accgtggaca agagcaggtg gcaggagggg    900

aatgtcttct catgctccgt gatgcatgag gctctgcaca accactacac acagaagagc    960

ctctccctgt ctctcgggaa atga                                           984


<210> SEQ ID NO 65
<211> LENGTH: 327
<212> TYPE: PRT
<213> ORGANISM: Artificial sequence
<220> FEATURE:
<223> OTHER INFORMATION: Synthetic

<400> SEQUENCE: 65

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240
```

-continued

```
Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325


<210> SEQ ID NO 66
<211> LENGTH: 262
<212> TYPE: PRT
<213> ORGANISM: Artificial sequence
<220> FEATURE:
<223> OTHER INFORMATION: Synthetic

<400> SEQUENCE: 66

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Thr
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Pro Phe Gly Val Pro Phe Asp Ile Trp Gly
            100                 105                 110

Gln Gly Thr Met Val Thr Val Ser Ser Lys Leu Ser Gly Ser Ala Ser
        115                 120                 125

Ala Pro Lys Leu Glu Glu Gly Glu Phe Ser Glu Ala Arg Val Ser Tyr
    130                 135                 140

Glu Leu Ile Gln Pro Pro Ser Val Ser Val Ala Pro Gly Gln Thr Ala
145                 150                 155                 160

Thr Ile Thr Cys Ala Gly Asp Asn Leu Gly Lys Lys Arg Val His Trp
                165                 170                 175

Tyr Gln Gln Arg Pro Gly Gln Ala Pro Val Leu Val Ile Tyr Asp Asp
            180                 185                 190

Ser Asp Arg Pro Ser Gly Ile Pro Asp Arg Phe Ser Ala Ser Asn Ser
        195                 200                 205

Gly Asn Thr Ala Thr Leu Thr Ile Thr Arg Gly Glu Ala Gly Asp Glu
    210                 215                 220

Ala Asp Tyr Tyr Cys Gln Val Trp Asp Ile Ala Thr Asp His Val Val
225                 230                 235                 240

Phe Gly Gly Gly Thr Lys Leu Thr Val Leu Ala Ala Ala Gly Ser Glu
                245                 250                 255

Gln Lys Leu Ile Ser Glu
            260
```

<210> SEQ ID NO 67
<211> LENGTH: 245
<212> TYPE: PRT
<213> ORGANISM: Artificial sequence
<220> FEATURE:
<223> OTHER INFORMATION: Synthetic

<400> SEQUENCE: 67

```
Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Arg Gly
            20                  25                  30

Lys Met Gly Val Ser Trp Ile Arg Gln Pro Pro Gly Lys Ala Leu Glu
        35                  40                  45

Trp Leu Ala His Ile Phe Ser Ser Asp Glu Lys Ser Tyr Arg Thr Ser
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile Arg Ala Gly Gly Ile Asp Tyr Trp Gly Gln Gly Thr
            100                 105                 110

Leu Val Thr Val Ser Ser Lys Leu Ser Gly Ser Ala Ser Ala Pro Lys
        115                 120                 125

Leu Glu Glu Gly Glu Phe Ser Glu Ala Arg Val Gln Pro Val Leu Thr
    130                 135                 140

Gln Pro Pro Ser Leu Ser Val Ser Pro Gly Gln Thr Ala Ser Ile Thr
145                 150                 155                 160

Cys Ser Gly Glu Lys Leu Gly Asp Lys Tyr Ala Tyr Trp Tyr Gln Gln
                165                 170                 175

Lys Pro Gly Gln Ser Pro Val Leu Val Met Tyr Gln Asp Lys Gln Arg
            180                 185                 190

Pro Ser Gly Ile Pro Glu Arg Phe Ser Gly Ser Asn Ser Gly Asn Thr
        195                 200                 205

Ala Thr Leu Thr Ile Ser Gly Thr Gln Ala Met Asp Glu Ala Asp Tyr
    210                 215                 220

Tyr Cys Gln Ala Trp Asp Ser Ser Thr Ala Val Phe Gly Gly Gly Thr
225                 230                 235                 240

Lys Leu Thr Val Leu
                245
```

<210> SEQ ID NO 68
<211> LENGTH: 245
<212> TYPE: PRT
<213> ORGANISM: Artificial sequence
<220> FEATURE:
<223> OTHER INFORMATION: Synthetic

<400> SEQUENCE: 68

```
Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Arg Gly
            20                  25                  30

Lys Met Gly Val Ser Trp Ile Arg Gln Pro Pro Gly Lys Ala Leu Glu
        35                  40                  45

Trp Leu Ala His Ile Phe Ser Ser Asp Glu Lys Ser Tyr Arg Thr Ser
```

-continued

```
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile Arg Arg Gly Gly Ile Asp Tyr Trp Gly Gln Gly Thr
            100                 105                 110

Leu Val Thr Val Ser Ser Lys Leu Ser Gly Ser Ala Ser Ala Pro Lys
        115                 120                 125

Leu Glu Glu Gly Glu Phe Ser Glu Ala Arg Val Gln Pro Val Leu Thr
    130                 135                 140

Gln Pro Pro Ser Leu Ser Val Ser Pro Gly Gln Thr Ala Ser Ile Thr
145                 150                 155                 160

Cys Ser Gly Glu Lys Leu Gly Asp Lys Tyr Ala Tyr Trp Tyr Gln Gln
                165                 170                 175

Lys Pro Gly Gln Ser Pro Val Leu Val Met Tyr Gln Asp Lys Gln Arg
            180                 185                 190

Pro Ser Gly Ile Pro Glu Arg Phe Ser Gly Ser Asn Ser Gly Asn Thr
        195                 200                 205

Ala Thr Leu Thr Ile Ser Gly Thr Gln Ala Met Asp Glu Ala Asp Tyr
    210                 215                 220

Tyr Cys Gln Ala Trp Asp Ser Ser Thr Ala Val Phe Gly Gly Gly Thr
225                 230                 235                 240

Lys Leu Thr Val Leu
                245


<210> SEQ ID NO 69
<211> LENGTH: 981
<212> TYPE: DNA
<213> ORGANISM: Homo sapiens

<400> SEQUENCE: 69

gcctccacca agggcccatc ggtcttcccc ctggcgccct gctccaggag cacctccgag      60

agcacagcgg ccctgggctg cctggtcaag gactacttcc ccgaaccggt gacggtgtcg     120

tggaactcag gcgctctgac cagcggcgtg cacaccttcc cagctgtcct acagtcctca     180

ggactctact ccctcagcag cgtggtgacc gtgccctcca gcaacttcgg cacccagacc     240

tacacctgca acgtagatca caagcccagc aacaccaagg tggacaagac agttgagcgc     300

aaatgttgtg tcgagtgccc accgtgccca gcaccacctg tggcaggacc gtcagtcttc     360

ctcttccccc caaaacccaa ggacaccctc atgatctccc ggacccctga ggtcacgtgc     420

gtggtggtgg acgtgagcca cgaagacccc gaggtccagt tcaactggta cgtggacggc     480

gtggaggtgc ataatgccaa gacaaagcca cgggaggagc agttcaacag cacgttccgt     540

gtggtcagcg tcctcaccgt tgtgcaccag gactggctga acggcaagga gtacaagtgc     600

aaggtctcca acaaaggcct cccagccccc atcgagaaaa ccatctccaa aaccaaaggg     660

cagccccgag aaccacaggt gtacaccctg cccccatccc gggaggagat gaccaagaac     720

caggtcagcc tgacctgcct ggtcaaaggc ttctacccca gcgacatcgc cgtagagtgg     780

gagagcaatg ggcagccgga gaacaactac aagaccacac ctcccatgct ggactccgac     840

ggctccttct tcctctacag caagctcacc gtggacaaga gcaggtggca gcaggggaac     900

gtcttctcat gctccgtgat gcatgaggct ctgcacaacc actacacgca gaagagcctc     960

tccctgtctc ccgggaaatg a                                               981
```

<210> SEQ ID NO 70
<211> LENGTH: 326
<212> TYPE: PRT
<213> ORGANISM: Homo sapiens

<400> SEQUENCE: 70

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325
```

<210> SEQ ID NO 71
<211> LENGTH: 702
<212> TYPE: DNA
<213> ORGANISM: Artificial sequence
<220> FEATURE:
<223> OTHER INFORMATION: Synthetic

<400> SEQUENCE: 71

```
atgatgtcct ttgtctctct gctcctggtt ggcatcctat tccatgccac ccaggcctcc     60

tatgagctga tacagccacc ctcggtgtca gtggccccag gacagacggc caccattacc    120

tgtgcgggag acaaccttgg gaagaaacgt gtgcactggt accagcagag gccaggccag    180

gcccctgtgt tggtcatcta tgatgatagc gaccggccct cagggatccc tgaccgattc    240

tctgcctcca actctgggaa cacggccacc ctgaccatca ctaggggcga agccggggat    300

gaggccgact attattgtca ggtgtgggac attgctactg atcatgtggt cttcggcgga    360

gggaccaagc tcaccgtcct aggccagcct aaggcggcgc cctcggtcac cctgttcccg    420

ccctcctctg aggagcttca agccaacaag gccacactgg tgtgtctcat aagtgacttc    480

tacccgggag ccgtgacagt ggcctggaag gcagatagca gccccgtcaa ggcgggagtg    540

gagaccacca caccctccaa acaaagcaac aacaagtacg cggccagcag ctatctgagc    600

ctgacgcctg agcagtggaa gtcccacaga agctacagct gccaggtcac gcatgaaggg    660

agcaccgtgg agaagacagt ggcccctaca gaatgttcat ag                       702
```

<210> SEQ ID NO 72
<211> LENGTH: 233
<212> TYPE: PRT
<213> ORGANISM: Artificial sequence
<220> FEATURE:
<223> OTHER INFORMATION: Synthetic

<400> SEQUENCE: 72

```
Met Met Ser Phe Val Ser Leu Leu Leu Val Gly Ile Leu Phe His Ala
1               5                   10                  15

Thr Gln Ala Ser Tyr Glu Leu Ile Gln Pro Pro Ser Val Ser Val Ala
            20                  25                  30

Pro Gly Gln Thr Ala Thr Ile Thr Cys Ala Gly Asp Asn Leu Gly Lys
        35                  40                  45

Lys Arg Val His Trp Tyr Gln Gln Arg Pro Gly Gln Ala Pro Val Leu
    50                  55                  60

Val Ile Tyr Asp Asp Ser Asp Arg Pro Ser Gly Ile Pro Asp Arg Phe
65                  70                  75                  80

Ser Ala Ser Asn Ser Gly Asn Thr Ala Thr Leu Thr Ile Thr Arg Gly
                85                  90                  95

Glu Ala Gly Asp Glu Ala Asp Tyr Tyr Cys Gln Val Trp Asp Ile Ala
            100                 105                 110

Thr Asp His Val Val Phe Gly Gly Gly Thr Lys Leu Thr Val Leu Gly
        115                 120                 125

Gln Pro Lys Ala Ala Pro Ser Val Thr Leu Phe Pro Pro Ser Ser Glu
    130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                165                 170                 175

Lys Ala Gly Val Glu Thr Thr Thr Pro Ser Lys Gln Ser Asn Asn Lys
            180                 185                 190

Tyr Ala Ala Ser Ser Tyr Leu Ser Leu Thr Pro Glu Gln Trp Lys Ser
        195                 200                 205

His Arg Ser Tyr Ser Cys Gln Val Thr His Glu Gly Ser Thr Val Glu
    210                 215                 220
```

Lys Thr Val Ala Pro Thr Glu Cys Ser
225 230

<210> SEQ ID NO 73
<211> LENGTH: 1401
<212> TYPE: DNA
<213> ORGANISM: Artificial sequence
<220> FEATURE:
<223> OTHER INFORMATION: Synthetic

<400> SEQUENCE: 73
atgatgtcct ttgtctctct gctcctggtt ggcatcctat tccatgccac ccaggcccag 60
gtacagctgc agcagtcagg tccaggactg gtgaagccct cgcagaccct ctcactcacc 120
tgtgccatct ccggggacag tgtctctagc accagtgctg cttggaactg gatcaggcag 180
tccccatcga gaggccttga gtggctggga aggacatact acaggtccaa gtggtataat 240
gattatgcag tatctgtgaa aagtcgaata accatcaacc cagacacatc caagaaccag 300
ttctccctgc agctgaactc tgtgactccc gaggacacgg ctgtgtatta ctgtgcaaga 360
gatcctttcg ggtacctttt tgatatctgg ggccaaggga caatggtcac cgtctcttca 420
gcctccacca agggcccatc ggtcttcccc ctggcgccct gctccaggag cacctccgag 480
agcacagcgg ccctgggctg cctggtcaag gactacttcc ccgaaccggt gacggtgtcg 540
tggaactcag gcgctctgac cagcggcgtg cacaccttcc cagctgtcct acagtcctca 600
ggactctact ccctcagcag cgtggtgacc gtgccctcca gcaacttcgg cacccagacc 660
tacacctgca acgtagatca caagcccagc aacaccaagg tggacaagac agttgagcgc 720
aaatgttgtg tcgagtgccc accgtgccca gcaccacctg tggcaggacc gtcagtcttc 780
ctcttccccc caaaacccaa ggacaccctc atgatctccc ggacccctga ggtcacgtgc 840
gtggtggtgg acgtgagcca cgaagacccc gaggtccagt tcaactggta cgtggacggc 900
gtggaggtgc ataatgccaa gacaaagcca cgggaggagc agttcaacag cacgttccgt 960
gtggtcagcg tcctcaccgt tgtgcaccag gactggctga acggcaagga gtacaagtgc 1020
aaggtctcca acaaaggcct cccagccccc atcgagaaaa ccatctccaa aaccaaaggg 1080
cagccccgag aaccacaggt gtacaccctg cccccatccc gggaggagat gaccaagaac 1140
caggtcagcc tgacctgcct ggtcaaaggc ttctacccca gcgacatcgc cgtagagtgg 1200
gagagcaatg ggcagccgga gaacaactac aagaccacac ctcccatgct ggactccgac 1260
ggctccttct tcctctacag caagctcacc gtggacaaga gcaggtggca gcaggggaac 1320
gtcttctcat gctccgtgat gcatgaggct ctgcacaacc actacacgca gaagagcctc 1380
tccctgtctc ccgggaaatg a 1401

<210> SEQ ID NO 74
<211> LENGTH: 466
<212> TYPE: PRT
<213> ORGANISM: Artificial sequence
<220> FEATURE:
<223> OTHER INFORMATION: Synthetic

<400> SEQUENCE: 74

Met Met Ser Phe Val Ser Leu Leu Leu Val Gly Ile Leu Phe His Ala
1 5 10 15

Thr Gln Ala Gln Val Gln Leu Gln Gln Ser Gly Pro Gly Leu Val Lys
20 25 30

Pro Ser Gln Thr Leu Ser Leu Thr Cys Ala Ile Ser Gly Asp Ser Val
35 40 45

```
Ser Ser Thr Ser Ala Ala Trp Asn Trp Ile Arg Gln Ser Pro Ser Arg
    50                  55                  60

Gly Leu Glu Trp Leu Gly Arg Thr Tyr Tyr Arg Ser Lys Trp Tyr Asn
65                  70                  75                  80

Asp Tyr Ala Val Ser Val Lys Ser Arg Ile Thr Ile Asn Pro Asp Thr
                85                  90                  95

Ser Lys Asn Gln Phe Ser Leu Gln Leu Asn Ser Val Thr Pro Glu Asp
            100                 105                 110

Thr Ala Val Tyr Tyr Cys Ala Arg Asp Pro Phe Gly Val Pro Phe Asp
        115                 120                 125

Ile Trp Gly Gln Gly Thr Met Val Thr Val Ser Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Asn Phe Gly Thr Gln Thr Tyr Thr Cys Asn
    210                 215                 220

Val Asp His Lys Pro Ser Asn Thr Lys Val Asp Lys Thr Val Glu Arg
225                 230                 235                 240

Lys Cys Cys Val Glu Cys Pro Pro Cys Pro Ala Pro Pro Val Ala Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Gln Phe Asn Trp Tyr Val Asp Gly Val Glu Val His
    290                 295                 300

Asn Ala Lys Thr Lys Pro Arg Glu Glu Gln Phe Asn Ser Thr Phe Arg
305                 310                 315                 320

Val Val Ser Val Leu Thr Val Val His Gln Asp Trp Leu Asn Gly Lys
                325                 330                 335

Glu Tyr Lys Cys Lys Val Ser Asn Lys Gly Leu Pro Ala Pro Ile Glu
            340                 345                 350

Lys Thr Ile Ser Lys Thr Lys Gly Gln Pro Arg Glu Pro Gln Val Tyr
        355                 360                 365

Thr Leu Pro Pro Ser Arg Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Met
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460
```

```
Gly Lys
465

<210> SEQ ID NO 75
<211> LENGTH: 1404
<212> TYPE: DNA
<213> ORGANISM: Artificial sequence
<220> FEATURE:
<223> OTHER INFORMATION: Synthetic

<400> SEQUENCE: 75

atgatgtcct ttgtctctct gctcctggtt ggcatcctat tccatgccac ccaggcccag      60

gtacagctgc agcagtcagg tccaggactg gtgaagccct cgcagaccct ctcactcacc     120

tgtgccatct ccggggacag tgtctctagc accagtgctg cttggaactg gatcaggcag     180

tccccatcga gaggccttga gtggctggga aggacatact acaggtccaa gtggtataat     240

gattatgcag tatctgtgaa aagtcgaata accatcaacc cagacacatc caagaaccag     300

ttctccctgc agctgaactc tgtgactccc gaggacacgg ctgtgtatta ctgtgcaaga     360

gatcctttcg ggtacctttt tgatatctgg ggccaaggga caatggtcac cgtctcttca     420

gcctccacca agggcccatc cgtcttcccc ctggcgccct gctccaggag cacctccgag     480

agcacagccg ccctgggctg cctggtcaag gactacttcc ccgaaccggt gacggtgtcg     540

tggaactcag gcgccctgac cagcggcgtg cacaccttcc cggctgtcct acagtcctca     600

ggactctact ccctcagcag cgtggtgacc gtgccctcca gcagcttggg cacgaagacc     660

tacacctgca acgtagatca caagcccagc aacaccaagg tggacaagag agttgagtcc     720

aaatatggtc ccccatgccc atcatgccca gcacctgagt tcctgggggg accatcagtc     780

ttcctgttcc ccccaaaacc caaggacact ctcatgatct cccggacccc tgaggtcacg     840

tgcgtggtgg tggacgtgag ccaggaagac cccgaggtcc agttcaactg gtacgtggat     900

ggcgtggagg tgcataatgc caagacaaag ccgcgggagg agcagttcaa cagcacgtac     960

cgtgtggtca gcgtcctcac cgtcctgcac caggactggc tgaacggcaa ggagtacaag    1020

tgcaaggtct ccaacaaagg cctcccgtcc tccatcgaga aaaccatctc caaagccaaa    1080

gggcagcccc gagagccaca ggtgtacacc ctgcccccat cccaggagga gatgaccaag    1140

aaccaggtca gcctgacctg cctggtcaaa ggcttctacc ccagcgacat cgccgtggag    1200

tgggagagca atgggcagcc ggagaacaac tacaagacca cgcctcccgt gctggactcc    1260

gacggctcct tcttcctcta cagcaggcta accgtggaca agagcaggtg gcaggagggg    1320

aatgtcttct catgctccgt gatgcatgag gctctgcaca accactacac acagaagagc    1380

ctctccctgt ctctcgggaa atga                                           1404

<210> SEQ ID NO 76
<211> LENGTH: 467
<212> TYPE: PRT
<213> ORGANISM: Artificial sequence
<220> FEATURE:
<223> OTHER INFORMATION: Synthetic

<400> SEQUENCE: 76

Met Met Ser Phe Val Ser Leu Leu Leu Val Gly Ile Leu Phe His Ala
1               5                   10                  15

Thr Gln Ala Gln Val Gln Leu Gln Gln Ser Gly Pro Gly Leu Val Lys
            20                  25                  30

Pro Ser Gln Thr Leu Ser Leu Thr Cys Ala Ile Ser Gly Asp Ser Val
        35                  40                  45
```

-continued

```
Ser Ser Thr Ser Ala Ala Trp Asn Trp Ile Arg Gln Ser Pro Ser Arg
    50                  55                  60

Gly Leu Glu Trp Leu Gly Arg Thr Tyr Tyr Arg Ser Lys Trp Tyr Asn
65                  70                  75                  80

Asp Tyr Ala Val Ser Val Lys Ser Arg Ile Thr Ile Asn Pro Asp Thr
                85                  90                  95

Ser Lys Asn Gln Phe Ser Leu Gln Leu Asn Ser Val Thr Pro Glu Asp
            100                 105                 110

Thr Ala Val Tyr Tyr Cys Ala Arg Asp Pro Phe Gly Val Pro Phe Asp
        115                 120                 125

Ile Trp Gly Gln Gly Thr Met Val Thr Val Ser Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Lys Thr Tyr Thr Cys Asn
    210                 215                 220

Val Asp His Lys Pro Ser Asn Thr Lys Val Asp Lys Arg Val Glu Ser
225                 230                 235                 240

Lys Tyr Gly Pro Pro Cys Pro Ser Cys Pro Ala Pro Glu Phe Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser Gln
        275                 280                 285

Glu Asp Pro Glu Val Gln Phe Asn Trp Tyr Val Asp Gly Val Glu Val
    290                 295                 300

His Asn Ala Lys Thr Lys Pro Arg Glu Glu Gln Phe Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Gly Leu Pro Ser Ser Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Gln Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Arg Leu Thr Val
            420                 425                 430

Asp Lys Ser Arg Trp Gln Glu Gly Asn Val Phe Ser Cys Ser Val Met
        435                 440                 445

His Glu Ala Leu His Asn His Tyr Thr Gln Lys Ser Leu Ser Leu Ser
    450                 455                 460
```

Leu Gly Lys
465

<210> SEQ ID NO 77
<211> LENGTH: 1404
<212> TYPE: DNA
<213> ORGANISM: Artificial sequence
<220> FEATURE:
<223> OTHER INFORMATION: Synthetic

<400> SEQUENCE: 77
atgatgtcct ttgtctctct gctcctggtt ggcatcctat tccatgccac ccaggcccag 60
gtacagctgc agcagtcagg tccaggactg gtgaagccct cgcagaccct ctcactcacc 120
tgtgccatct ccggggacag tgtctctagc accagtgctg cttggaactg gatcaggcag 180
tccccatcga gaggccttga gtggctggga aggacatact acaggtccaa gtggtataat 240
gattatgcag tatctgtgaa aagtcgaata accatcaacc cagacacatc caagaaccag 300
ttctccctgc agctgaactc tgtgactccc gaggacacgg ctgtgtatta ctgtgcaaga 360
gatcctttcg ggtacctttt tgatatctgg ggccaaggga caatggtcac cgtctcttca 420
gcctccacca agggcccatc cgtcttcccc ctggcgccct gctccaggag cacctccgag 480
agcacagccg ccctgggctg cctggtcaag gactacttcc ccgaaccggt gacggtgtcg 540
tggaactcag gcgccctgac cagcggcgtg cacaccttcc cggctgtcct acagtcctca 600
ggactctact ccctcagcag cgtggtgacc gtgccctcca gcagcttggg cacgaagacc 660
tacacctgca acgtagatca caagcccagc aacaccaagg tggacaagag agttgagtcc 720
aaatatggtc ccccatgccc accatgccca gcacctgagt tcctgggggg accatcagtc 780
ttcctgttcc ccccaaaacc caaggacact ctcatgatct cccggacccc tgaggtcacg 840
tgcgtggtgg tggacgtgag ccaggaagac cccgaggtcc agttcaactg gtacgtggat 900
ggcgtggagg tgcataatgc caagacaaag ccgcgggagg agcagttcaa cagcacgtac 960
cgtgtggtca gcgtcctcac cgtcctgcac caggactggc tgaacggcaa ggagtacaag 1020
tgcaaggtct ccaacaaagg cctcccgtcc tccatcgaga aaaccatctc caaagccaaa 1080
gggcagcccc gagagccaca ggtgtacacc ctgcccccat cccaggagga gatgaccaag 1140
aaccaggtca gcctgacctg cctggtcaaa ggcttctacc ccagcgacat cgccgtggag 1200
tgggagagca atgggcagcc ggagaacaac tacaagacca cgcctcccgt gctggactcc 1260
gacggctcct tcttcctcta cagcaggcta accgtggaca agagcaggtg gcaggagggg 1320
aatgtcttct catgctccgt gatgcatgag gctctgcaca accactacac acagaagagc 1380
ctctccctgt ctctcgggaa atga 1404

<210> SEQ ID NO 78
<211> LENGTH: 467
<212> TYPE: PRT
<213> ORGANISM: Artificial sequence
<220> FEATURE:
<223> OTHER INFORMATION: Synthetic

<400> SEQUENCE: 78

Met Met Ser Phe Val Ser Leu Leu Leu Val Gly Ile Leu Phe His Ala
1 5 10 15

Thr Gln Ala Gln Val Gln Leu Gln Gln Ser Gly Pro Gly Leu Val Lys
20 25 30

Pro Ser Gln Thr Leu Ser Leu Thr Cys Ala Ile Ser Gly Asp Ser Val
35 40 45

-continued

```
Ser Ser Thr Ser Ala Ala Trp Asn Trp Ile Arg Gln Ser Pro Ser Arg
    50                  55                  60

Gly Leu Glu Trp Leu Gly Arg Thr Tyr Tyr Arg Ser Lys Trp Tyr Asn
65                  70                  75                  80

Asp Tyr Ala Val Ser Val Lys Ser Arg Ile Thr Ile Asn Pro Asp Thr
                85                  90                  95

Ser Lys Asn Gln Phe Ser Leu Gln Leu Asn Ser Val Thr Pro Glu Asp
            100                 105                 110

Thr Ala Val Tyr Tyr Cys Ala Arg Asp Pro Phe Gly Val Pro Phe Asp
        115                 120                 125

Ile Trp Gly Gln Gly Thr Met Val Thr Val Ser Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Lys Thr Tyr Thr Cys Asn
    210                 215                 220

Val Asp His Lys Pro Ser Asn Thr Lys Val Asp Lys Arg Val Glu Ser
225                 230                 235                 240

Lys Tyr Gly Pro Pro Cys Pro Pro Cys Pro Ala Pro Glu Phe Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser Gln
        275                 280                 285

Glu Asp Pro Glu Val Gln Phe Asn Trp Tyr Val Asp Gly Val Glu Val
    290                 295                 300

His Asn Ala Lys Thr Lys Pro Arg Glu Glu Gln Phe Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Gly Leu Pro Ser Ser Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Gln Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Arg Leu Thr Val
            420                 425                 430

Asp Lys Ser Arg Trp Gln Glu Gly Asn Val Phe Ser Cys Ser Val Met
        435                 440                 445

His Glu Ala Leu His Asn His Tyr Thr Gln Lys Ser Leu Ser Leu Ser
    450                 455                 460
```

Leu Gly Lys
465

<210> SEQ ID NO 79
<211> LENGTH: 696
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (303)..(303)
<223> OTHER INFORMATION: n is a, c, g, or t

<400> SEQUENCE: 79
atgatgtcct ttgtctctct gctcctggtt ggcatcctat tccatgccac ccaggcccag 60
ccagtgctga ctcagccccc ctcactgtcc gtgtccccag gacagacagc cagcatcacc 120
tgctctggag agaaattggg ggataaatat gcttactggt atcagcagaa gccaggccag 180
tcccctgtgt tggtcatgta tcaagataaa cagcggccct cagggatccc tgagcgattc 240
tctggctcca actctgggaa cacagccact ctgaccatca gcgggaccca ggctatggat 300
gangctgact attactgtca ggcgtgggac agcagcactg cggtattcgg cggagggacc 360
aagctgaccg tcctaggcca gcctaaggcg gcgccctcgg tcaccctgtt cccgccctcc 420
tctgaggagc ttcaagccaa caaggccaca ctggtgtgtc tcataagtga cttctacccg 480
ggagccgtga cagtggcctg gaaggcagat agcagccccg tcaaggcggg agtggagacc 540
accacaccct ccaaacaaag caacaacaag tacgcggcca gcagctatct gagcctgacg 600
cctgagcagt ggaagtccca cagaagctac agctgccagg tcacgcatga agggagcacc 660
gtggagaaga cagtggcccc tacagaatgt tcatag 696

<210> SEQ ID NO 80
<211> LENGTH: 231
<212> TYPE: PRT
<213> ORGANISM: Artificial sequence
<220> FEATURE:
<223> OTHER INFORMATION: Synthetic

<400> SEQUENCE: 80

Met Met Ser Phe Val Ser Leu Leu Leu Val Gly Ile Leu Phe His Ala
1 5 10 15

Thr Gln Ala Gln Pro Val Leu Thr Gln Pro Pro Ser Leu Ser Val Ser
20 25 30

Pro Gly Gln Thr Ala Ser Ile Thr Cys Ser Gly Glu Lys Leu Gly Asp
35 40 45

Lys Tyr Ala Tyr Trp Tyr Gln Gln Lys Pro Gly Gln Ser Pro Val Leu
50 55 60

Val Met Tyr Gln Asp Lys Gln Arg Pro Ser Gly Ile Pro Glu Arg Phe
65 70 75 80

Ser Gly Ser Asn Ser Gly Asn Thr Ala Thr Leu Thr Ile Ser Gly Thr
85 90 95

Gln Ala Met Asp Glu Ala Asp Tyr Tyr Cys Gln Ala Trp Asp Ser Ser
100 105 110

Thr Ala Val Phe Gly Gly Gly Thr Lys Leu Thr Val Leu Gly Gln Pro
115 120 125

Lys Ala Ala Pro Ser Val Thr Leu Phe Pro Pro Ser Ser Glu Glu Leu
130 135 140

Gln Ala Asn Lys Ala Thr Leu Val Cys Leu Ile Ser Asp Phe Tyr Pro

-continued

```
145                 150                 155                 160

Gly Ala Val Thr Val Ala Trp Lys Ala Asp Ser Ser Pro Val Lys Ala
                165                 170                 175

Gly Val Glu Thr Thr Thr Pro Ser Lys Gln Ser Asn Asn Lys Tyr Ala
            180                 185                 190

Ala Ser Ser Tyr Leu Ser Leu Thr Pro Glu Gln Trp Lys Ser His Arg
        195                 200                 205

Ser Tyr Ser Cys Gln Val Thr His Glu Gly Ser Thr Val Glu Lys Thr
    210                 215                 220

Val Ala Pro Thr Glu Cys Ser
225                 230
```

<210> SEQ ID NO 81
<211> LENGTH: 1392
<212> TYPE: DNA
<213> ORGANISM: Artificial sequence
<220> FEATURE:
<223> OTHER INFORMATION: Synthetic

<400> SEQUENCE: 81

```
atgatgtcct ttgtctctct gctcctggtt ggcatcctat tccatgccac ccaggcccag      60

gtcaccttga aggagtctgg tcctgtgctg gtgaaaccca cagagaccct cacgctgacc     120

tgcaccgtct ctgggttctc actcagcagg ggtaaaatgg gtgtgagctg gatccgtcag     180

cccccaggga aggccctgga gtggcttgca cacatttttt cgagtgacga aaaatcctac     240

aggacatcgc tgaagagcag gctcaccatc tccaaggaca cctccaaaaa ccaggtggtc     300

cttacaatga ccaacatgga ccctgtggac acagccacgt attactgtgc acggatacga     360

cgtggaggaa ttgactactg gggccaggga accctggtca ctgtctcctc agcctccacc     420

aagggcccat cggtcttccc cctggcgccc tgctccagga gcacctccga gagcacagcg     480

gccctgggct gcctggtcaa ggactacttc cccgaaccgg tgacggtgtc gtggaactca     540

ggcgctctga ccagcggcgt gcacaccttc ccagctgtcc tacagtcctc aggactctac     600

tccctcagca gcgtggtgac cgtgccctcc agcaacttcg gcacccagac ctacacctgc     660

aacgtagatc acaagcccag caacaccaag gtggacaaga cagttgagcg caaatgttgt     720

gtcgagtgcc caccgtgccc agcaccacct gtggcaggac cgtcagtctt cctcttcccc     780

ccaaaaccca aggacaccct catgatctcc cggacccctg aggtcacgtg cgtggtggtg     840

gacgtgagcc acgaagaccc cgaggtccag ttcaactggt acgtggacgg cgtggaggtg     900

cataatgcca agacaaagcc acgggaggag cagttcaaca gcacgttccg tgtggtcagc     960

gtcctcaccg ttgtgcacca ggactggctg aacggcaagg agtacaagtg caaggtctcc    1020

aacaaaggcc tcccagcccc catcgagaaa accatctcca aaaccaaagg gcagccccga    1080

gaaccacagg tgtacaccct gcccccatcc cgggaggaga tgaccaagaa ccaggtcagc    1140

ctgacctgcc tggtcaaagg cttctacccc agcgacatcg ccgtagagtg ggagagcaat    1200

gggcagccgg agaacaacta caagaccaca cctcccatgc tggactccga cggctccttc    1260

ttcctctaca gcaagctcac cgtggacaag agcaggtggc agcaggggaa cgtcttctca    1320

tgctccgtga tgcatgaggc tctgcacaac cactacacgc agaagagcct ctccctgtct    1380

cccgggaaat ga                                                        1392
```

<210> SEQ ID NO 82
<211> LENGTH: 463
<212> TYPE: PRT

<213> ORGANISM: Artificial sequence
<220> FEATURE:
<223> OTHER INFORMATION: Synthetic

<400> SEQUENCE: 82

```
Met Met Ser Phe Val Ser Leu Leu Leu Val Gly Ile Leu Phe His Ala
1               5                   10                  15

Thr Gln Ala Gln Val Thr Leu Lys Glu Ser Gly Pro Val Leu Val Lys
            20                  25                  30

Pro Thr Glu Thr Leu Thr Leu Thr Cys Thr Val Ser Gly Phe Ser Leu
        35                  40                  45

Ser Arg Gly Lys Met Gly Val Ser Trp Ile Arg Gln Pro Pro Gly Lys
    50                  55                  60

Ala Leu Glu Trp Leu Ala His Ile Phe Ser Ser Asp Glu Lys Ser Tyr
65                  70                  75                  80

Arg Thr Ser Leu Lys Ser Arg Leu Thr Ile Ser Lys Asp Thr Ser Lys
                85                  90                  95

Asn Gln Val Val Leu Thr Met Thr Asn Met Asp Pro Val Asp Thr Ala
            100                 105                 110

Thr Tyr Tyr Cys Ala Arg Ile Arg Arg Gly Gly Ile Asp Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Asn Phe Gly Thr Gln Thr Tyr Thr Cys Asn Val Asp His
    210                 215                 220

Lys Pro Ser Asn Thr Lys Val Asp Lys Thr Val Glu Arg Lys Cys Cys
225                 230                 235                 240

Val Glu Cys Pro Pro Cys Pro Ala Pro Pro Val Ala Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Gln Phe Asn Trp Tyr Val Asp Gly Val Glu Val His Asn Ala Lys
    290                 295                 300

Thr Lys Pro Arg Glu Glu Gln Phe Asn Ser Thr Phe Arg Val Val Ser
305                 310                 315                 320

Val Leu Thr Val Val His Gln Asp Trp Leu Asn Gly Lys Glu Tyr Lys
                325                 330                 335

Cys Lys Val Ser Asn Lys Gly Leu Pro Ala Pro Ile Glu Lys Thr Ile
            340                 345                 350

Ser Lys Thr Lys Gly Gln Pro Arg Glu Pro Gln Val Tyr Thr Leu Pro
        355                 360                 365

Pro Ser Arg Glu Glu Met Thr Lys Asn Gln Val Ser Leu Thr Cys Leu
    370                 375                 380

Val Lys Gly Phe Tyr Pro Ser Asp Ile Ala Val Glu Trp Glu Ser Asn
```

```
385                 390                 395                 400

Gly Gln Pro Glu Asn Asn Tyr Lys Thr Thr Pro Pro Met Leu Asp Ser
                405                 410                 415

Asp Gly Ser Phe Phe Leu Tyr Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn His Tyr Thr Gln Lys Ser Leu Ser Leu Ser Pro Gly Lys
    450                 455                 460


<210> SEQ ID NO 83
<211> LENGTH: 1395
<212> TYPE: DNA
<213> ORGANISM: Artificial sequence
<220> FEATURE:
<223> OTHER INFORMATION: Synthetic

<400> SEQUENCE: 83

atgatgtcct ttgtctctct gctcctggtt ggcatcctat tccatgccac ccaggcccag     60

gtcaccttga aggagtctgg tcctgtgctg gtgaaaccca cagagaccct cacgctgacc    120

tgcaccgtct ctgggttctc actcagcagg ggtaaaatgg gtgtgagctg gatccgtcag    180

cccccaggga aggccctgga gtggcttgca cacatttttt cgagtgacga aaaatcctac    240

aggacatcgc tgaagagcag gctcaccatc tccaaggaca cctccaaaaa ccaggtggtc    300

cttacaatga ccaacatgga ccctgtggac acagccacgt attactgtgc acggatacga    360

cgtggaggaa ttgactactg gggccaggga accctggtca ctgtctcctc agcctccacc    420

aagggcccat ccgtcttccc cctggcgccc tgctccagga gcacctccga gagcacagcc    480

gccctgggct gcctggtcaa ggactacttc cccgaaccgg tgacggtgtc gtggaactca    540

ggcgccctga ccagcggcgt gcacaccttc ccggctgtcc tacagtcctc aggactctac    600

tccctcagca gcgtggtgac cgtgccctcc agcagcttgg gcacgaagac ctacacctgc    660

aacgtagatc acaagcccag caacaccaag gtggacaaga gagttgagtc caaatatggt    720

cccccatgcc catcatgccc agcacctgag ttcctggggg gaccatcagt cttcctgttc    780

cccccaaaac ccaaggacac tctcatgatc tcccggaccc ctgaggtcac gtgcgtggtg    840

gtggacgtga gccaggaaga ccccgaggtc cagttcaact ggtacgtgga tggcgtggag    900

gtgcataatg ccaagacaaa gccgcgggag gagcagttca acagcacgta ccgtgtggtc    960

agcgtcctca ccgtcctgca ccaggactgg ctgaacggca aggagtacaa gtgcaaggtc   1020

tccaacaaag gcctcccgtc ctccatcgag aaaaccatct ccaaagccaa agggcagccc   1080

cgagagccac aggtgtacac cctgccccca tcccaggagg agatgaccaa gaaccaggtc   1140

agcctgacct gcctggtcaa aggcttctac cccagcgaca tcgccgtgga gtgggagagc   1200

aatgggcagc cggagaacaa ctacaagacc acgcctcccg tgctggactc cgacggctcc   1260

ttcttcctct acagcaggct aaccgtggac aagagcaggt ggcaggaggg gaatgtcttc   1320

tcatgctccg tgatgcatga ggctctgcac aaccactaca cacagaagag cctctccctg   1380

tctctcggga aatga                                                    1395


<210> SEQ ID NO 84
<211> LENGTH: 464
<212> TYPE: PRT
<213> ORGANISM: Artificial sequence
<220> FEATURE:
<223> OTHER INFORMATION: Synthetic
```

<400> SEQUENCE: 84

Met Met Ser Phe Val Ser Leu Leu Leu Val Gly Ile Leu Phe His Ala
1               5                   10                  15

Thr Gln Ala Gln Val Thr Leu Lys Glu Ser Gly Pro Val Leu Val Lys
            20                  25                  30

Pro Thr Glu Thr Leu Thr Leu Thr Cys Thr Val Ser Gly Phe Ser Leu
        35                  40                  45

Ser Arg Gly Lys Met Gly Val Ser Trp Ile Arg Gln Pro Pro Gly Lys
    50                  55                  60

Ala Leu Glu Trp Leu Ala His Ile Phe Ser Ser Asp Glu Lys Ser Tyr
65                  70                  75                  80

Arg Thr Ser Leu Lys Ser Arg Leu Thr Ile Ser Lys Asp Thr Ser Lys
                85                  90                  95

Asn Gln Val Val Leu Thr Met Thr Asn Met Asp Pro Val Asp Thr Ala
            100                 105                 110

Thr Tyr Tyr Cys Ala Arg Ile Arg Arg Gly Gly Ile Asp Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Lys Thr Tyr Thr Cys Asn Val Asp His
    210                 215                 220

Lys Pro Ser Asn Thr Lys Val Asp Lys Arg Val Glu Ser Lys Tyr Gly
225                 230                 235                 240

Pro Pro Cys Pro Ser Cys Pro Ala Pro Glu Phe Leu Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser Gln Glu Asp Pro
        275                 280                 285

Glu Val Gln Phe Asn Trp Tyr Val Asp Gly Val Glu Val His Asn Ala
    290                 295                 300

Lys Thr Lys Pro Arg Glu Glu Gln Phe Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Gly Leu Pro Ser Ser Ile Glu Lys Thr
            340                 345                 350

Ile Ser Lys Ala Lys Gly Gln Pro Arg Glu Pro Gln Val Tyr Thr Leu
        355                 360                 365

Pro Pro Ser Gln Glu Glu Met Thr Lys Asn Gln Val Ser Leu Thr Cys
    370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp

```
                405                 410                 415

Ser Asp Gly Ser Phe Phe Leu Tyr Ser Arg Leu Thr Val Asp Lys Ser
            420                 425                 430

Arg Trp Gln Glu Gly Asn Val Phe Ser Cys Ser Val Met His Glu Ala
        435                 440                 445

Leu His Asn His Tyr Thr Gln Lys Ser Leu Ser Leu Ser Leu Gly Lys
    450                 455                 460
```

<210> SEQ ID NO 85
<211> LENGTH: 1395
<212> TYPE: DNA
<213> ORGANISM: Artificial sequence
<220> FEATURE:
<223> OTHER INFORMATION: Synthetic

<400> SEQUENCE: 85

```
atgatgtcct ttgtctctct gctcctggtt ggcatcctat tccatgccac ccaggcccag      60

gtcaccttga aggagtctgg tcctgtgctg gtgaaaccca cagagaccct cacgctgacc     120

tgcaccgtct ctgggttctc actcagcagg ggtaaaatgg gtgtgagctg gatccgtcag     180

cccccaggga aggccctgga gtggcttgca cacatttttt cgagtgacga aaaatcctac     240

aggacatcgc tgaagagcag gctcaccatc tccaaggaca cctccaaaaa ccaggtggtc     300

cttacaatga ccaacatgga ccctgtggac acagccacgt attactgtgc acggatacga     360

cgtggaggaa ttgactactg gggccaggga accctggtca ctgtctcctc agcctccacc     420

aagggcccat ccgtcttccc cctggcgccc tgctccagga gcacctccga gagcacagcc     480

gccctgggct gcctggtcaa ggactacttc cccgaaccgg tgacggtgtc gtggaactca     540

ggcgccctga ccagcggcgt gcacaccttc ccggctgtcc tacagtcctc aggactctac     600

tccctcagca gcgtggtgac cgtgccctcc agcagcttgg gcacgaagac ctacacctgc     660

aacgtagatc acaagcccag caacaccaag gtggacaaga gagttgagtc caaatatggt     720

cccccatgcc caccatgccc agcacctgag ttcctggggg gaccatcagt cttcctgttc     780

cccccaaaac ccaaggacac tctcatgatc tcccggaccc ctgaggtcac gtgcgtggtg     840

gtggacgtga gccaggaaga ccccgaggtc cagttcaact ggtacgtgga tggcgtggag     900

gtgcataatg ccaagacaaa gccgcgggag gagcagttca acagcacgta ccgtgtggtc     960

agcgtcctca ccgtcctgca ccaggactgg ctgaacggca aggagtacaa gtgcaaggtc    1020

tccaacaaag gcctcccgtc ctccatcgag aaaaccatct ccaaagccaa agggcagccc    1080

cgagagccac aggtgtacac cctgccccca tcccaggagg agatgaccaa gaaccaggtc    1140

agcctgacct gcctggtcaa aggcttctac cccagcgaca tcgccgtgga gtgggagagc    1200

aatgggcagc cggagaacaa ctacaagacc acgcctcccg tgctggactc cgacggctcc    1260

ttcttcctct acagcaggct aaccgtggac aagagcaggt ggcaggaggg gaatgtcttc    1320

tcatgctccg tgatgcatga ggctctgcac aaccactaca cacagaagag cctctccctg    1380

tctctcggga aatga                                                     1395
```

<210> SEQ ID NO 86
<211> LENGTH: 464
<212> TYPE: PRT
<213> ORGANISM: Artificial sequence
<220> FEATURE:
<223> OTHER INFORMATION: Synthetic

<400> SEQUENCE: 86

-continued

```
Met Met Ser Phe Val Ser Leu Leu Leu Val Gly Ile Leu Phe His Ala
1               5                   10                  15

Thr Gln Ala Gln Val Thr Leu Lys Glu Ser Gly Pro Val Leu Val Lys
            20                  25                  30

Pro Thr Glu Thr Leu Thr Leu Thr Cys Thr Val Ser Gly Phe Ser Leu
        35                  40                  45

Ser Arg Gly Lys Met Gly Val Ser Trp Ile Arg Gln Pro Pro Gly Lys
    50                  55                  60

Ala Leu Glu Trp Leu Ala His Ile Phe Ser Ser Asp Glu Lys Ser Tyr
65                  70                  75                  80

Arg Thr Ser Leu Lys Ser Arg Leu Thr Ile Ser Lys Asp Thr Ser Lys
                85                  90                  95

Asn Gln Val Val Leu Thr Met Thr Asn Met Asp Pro Val Asp Thr Ala
            100                 105                 110

Thr Tyr Tyr Cys Ala Arg Ile Arg Arg Gly Gly Ile Asp Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Lys Thr Tyr Thr Cys Asn Val Asp His
    210                 215                 220

Lys Pro Ser Asn Thr Lys Val Asp Lys Arg Val Glu Ser Lys Tyr Gly
225                 230                 235                 240

Pro Pro Cys Pro Pro Cys Pro Ala Pro Glu Phe Leu Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser Gln Glu Asp Pro
        275                 280                 285

Glu Val Gln Phe Asn Trp Tyr Val Asp Gly Val Glu Val His Asn Ala
    290                 295                 300

Lys Thr Lys Pro Arg Glu Glu Gln Phe Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Gly Leu Pro Ser Ser Ile Glu Lys Thr
            340                 345                 350

Ile Ser Lys Ala Lys Gly Gln Pro Arg Glu Pro Gln Val Tyr Thr Leu
        355                 360                 365

Pro Pro Ser Gln Glu Glu Met Thr Lys Asn Gln Val Ser Leu Thr Cys
    370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Tyr Ser Arg Leu Thr Val Asp Lys Ser
```

```
        420                 425                 430

Arg Trp Gln Glu Gly Asn Val Phe Ser Cys Ser Val Met His Glu Ala
    435                 440                 445

Leu His Asn His Tyr Thr Gln Lys Ser Leu Ser Leu Ser Leu Gly Lys
    450                 455                 460


<210> SEQ ID NO 87
<211> LENGTH: 750
<212> TYPE: DNA
<213> ORGANISM: Artificial sequence
<220> FEATURE:
<223> OTHER INFORMATION: Synthetic

<400> SEQUENCE: 87

caggtacagc tgcagcagtc aggtccagga ctggtgaagc cctcgcagac cctctcactc      60

acctgtgcca tctccgggga cagtgtctct agcaccagtg ctgcttggaa ctggatcagg     120

cagtccccat cgagaggcct tgagtggctg ggaaggacat actacaggtc caagtggtat     180

aatgattatg cagtatctgt gaaaagtcga ataaccatca acccagacac atccaagaac     240

cagttctccc tgcagctgaa ctctgtgact cccgaggaca cggctgtgta ttactgtgca     300

agagatcctt tcggggtacc ttttgatatc tggggccaag ggacaatggt caccgtctct     360

tcaaagcttt cagggagtgc atccgcccca aaacttgaag aaggtgaatt ttcagaagca     420

cgcgtatcct atgagctgat acagccaccc tcggtgtcag tggccccagg acagacggcc     480

accattacct gtgcgggaga caaccttggg aagaaacgtg tgcactggta ccagcagagg     540

ccaggccagg cccctgtgtt ggtcatctat gatgatagcg accggccctc agggatccct     600

gaccgattct ctgcctccaa ctctgggaac acggccaccc tgaccatcac taggggcgaa     660

gccggggatg aggccgacta ttattgtcag gtgtgggaca ttgctactga tcatgtggtc     720

ttcggcggag ggaccaagct caccgtccta                                      750


<210> SEQ ID NO 88
<211> LENGTH: 735
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (663)..(663)
<223> OTHER INFORMATION: n is a, c, g, or t

<400> SEQUENCE: 88

caggtcacct tgaaggagtc tggtcctgtg ctggtgaaac ccacagagac cctcacgctg      60

acctgcaccg tctctgggtt ctcactcagc aggggtaaaa tgggtgtgag ctggatccgt     120

cagcccccag ggaaggccct ggagtggctt gcacacattt tttcgagtga cgaaaaatcc     180

tacaggacat cgctgaagag caggctcacc atctccaagg acacctccaa aaaccaggtg     240

gtccttacaa tgaccaacat ggaccctgtg gacacagcca cgtattactg tgcacggata     300

cgagcgggag gaattgacta ctggggccag ggaaccctgg tcactgtctc ctcaaagctt     360

tcagggagtg catccgcccc aaaacttgaa gaaggtgaat tttcagaagc acgcgtacag     420

ccagtgctga ctcagccccc ctcactgtcc gtgtccccag gacagacagc cagcatcacc     480

tgctctggag agaaattggg ggataaatat gcttactggt atcagcagaa gccaggccag     540

tcccctgtgt tggtcatgta tcaagataaa cagcggccct cagggatccc tgagcgattc     600

tctggctcca actctgggaa cacagccact ctgaccatca gcgggaccca ggctatggat     660
```

gangctgact attactgtca ggcgtgggac agcagcactg cggtattcgg cggagggacc 720
aagctgaccg tccta 735

<210> SEQ ID NO 89
<211> LENGTH: 735
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (663)..(663)
<223> OTHER INFORMATION: n is a, c, g, or t

<400> SEQUENCE: 89
caggtcacct tgaaggagtc tggtcctgtg ctggtgaaac ccacagagac cctcacgctg 60
acctgcaccg tctctgggtt ctcactcagc aggggtaaaa tgggtgtgag ctggatccgt 120
cagcccccag ggaaggccct ggagtggctt gcacacattt tttcgagtga cgaaaaatcc 180
tacaggacat cgctgaagag caggctcacc atctccaagg acacctccaa aaaccaggtg 240
gtccttacaa tgaccaacat ggaccctgtg gacacagcca cgtattactg tgcacggata 300
cgacgtggag gaattgacta ctggggccag ggaaccctgg tcactgtctc ctcaaagctt 360
tcagggagtg catccgcccc aaaacttgaa gaaggtgaat tttcagaagc acgcgtacag 420
ccagtgctga ctcagccccc ctcactgtcc gtgtccccag gacagacagc cagcatcacc 480
tgctctggag agaaattggg ggataaatat gcttactggt atcagcagaa gccaggccag 540
tcccctgtgt tggtcatgta tcaagataaa cagcggccct cagggatccc tgagcgattc 600
tctggctcca actctgggaa cacagccact ctgaccatca gcgggaccca ggctatggat 660
gangctgact attactgtca ggcgtgggac agcagcactg cggtattcgg cggagggacc 720
aagctgaccg tccta 735

<210> SEQ ID NO 90
<211> LENGTH: 8
<212> TYPE: PRT
<213> ORGANISM: Artificial Sequence
<220> FEATURE:
<223> OTHER INFORMATION: consensus CDRH3 of 17D20m and d3521N11
<220> FEATURE:
<221> NAME/KEY: VARIANT
<222> LOCATION: (8)..(8)
<223> OTHER INFORMATION: wherein Xaa at position 8 is Ala or Arg

<400> SEQUENCE: 90

Tyr Tyr Cys Ala Arg Ile Arg Xaa
1 5

<210> SEQ ID NO 91
<211> LENGTH: 11
<212> TYPE: PRT
<213> ORGANISM: Artificial sequence
<220> FEATURE:
<223> OTHER INFORMATION: consensus of CDRL1 of 17D20m and d3521N11
<220> FEATURE:
<221> NAME/KEY: VARIANT
<222> LOCATION: (2)..(2)
<223> OTHER INFORMATION: wherein Xaa at position 2 is Asp or Glu
<220> FEATURE:
<221> NAME/KEY: VARIANT
<222> LOCATION: (8)..(8)
<223> OTHER INFORMATION: wherein Xaa at position 8 is Phe or Tyr

<400> SEQUENCE: 91

Gly Xaa Lys Leu Gly Asp Lys Xaa Ala Tyr Trp
1 5 10

<210> SEQ ID NO 92
<211> LENGTH: 11
<212> TYPE: PRT
<213> ORGANISM: Artificial sequence
<220> FEATURE:
<223> OTHER INFORMATION: consensus CDRL1 of 17N16m and d17N9
<220> FEATURE:
<221> NAME/KEY: VARIANT
<222> LOCATION: (2)..(2)
<223> OTHER INFORMATION: wherein Xaa at position 2 is Asn or Asp
<220> FEATURE:
<221> NAME/KEY: VARIANT
<222> LOCATION: (4)..(4)
<223> OTHER INFORMATION: wherein Xaa at position 4 is Ile or Leu
<220> FEATURE:
<221> NAME/KEY: VARIANT
<222> LOCATION: (6)..(6)
<223> OTHER INFORMATION: wherein Xaa at position 6 is Ser or Lys
<220> FEATURE:
<221> NAME/KEY: VARIANT
<222> LOCATION: (8)..(8)
<223> OTHER INFORMATION: wherein Xaa at position 8 is Asn or Arg

<400> SEQUENCE: 92

Gly Xaa Asn Xaa Gly Xaa Lys Xaa Val His Trp
1 5 10

<210> SEQ ID NO 93
<211> LENGTH: 7
<212> TYPE: PRT
<213> ORGANISM: Artificial sequence
<220> FEATURE:
<223> OTHER INFORMATION: consensus CDRL2 of 17D20m and d3521N11
<220> FEATURE:
<221> NAME/KEY: VARIANT
<222> LOCATION: (2)..(2)
<223> OTHER INFORMATION: wherein Xaa atposition 2 is Asn or Lys or Ser
<220> FEATURE:
<221> NAME/KEY: VARIANT
<222> LOCATION: (3)..(3)
<223> OTHER INFORMATION: wherein Xaa at position 3 is Lys or Gln or Asp

<400> SEQUENCE: 93

Asp Xaa Xaa Arg Pro Ser Gly
1 5

<210> SEQ ID NO 94
<211> LENGTH: 9
<212> TYPE: PRT
<213> ORGANISM: Artificial sequence
<220> FEATURE:
<223> OTHER INFORMATION: consensus CDRL3 of 17N16m and d17N9
<220> FEATURE:
<221> NAME/KEY: VARIANT
<222> LOCATION: (4)..(4)
<223> OTHER INFORMATION: wherein Xaa at position 4 is Thr or Ile
<220> FEATURE:
<221> NAME/KEY: VARIANT
<222> LOCATION: (5)..(5)
<223> OTHER INFORMATION: wherein Xaa at position 5 is Thr or Ala

<400> SEQUENCE: 94

Val Trp Asp Xaa Xaa Thr Asp His Val
1 5